(12) United States Patent
Rothberg et al.

(10) Patent No.: US 9,039,888 B2
(45) Date of Patent: May 26, 2015

(54) METHODS AND APPARATUS FOR DETECTING MOLECULAR INTERACTIONS USING FET ARRAYS

(71) Applicant: LIFE TECHNOLOGIES CORPORATION, Carlsbad, CA (US)

(72) Inventors: Jonathan Rothberg, Guilford, CT (US); Wolfgang Hinz, Killingworth, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/033,934

(22) Filed: Sep. 23, 2013

(65) Prior Publication Data

US 2014/0080719 A1   Mar. 20, 2014

Related U.S. Application Data

(63) Continuation of application No. 13/229,456, filed on Sep. 9, 2011, now Pat. No. 8,540,868, which is a continuation of application No. 12/492,844, filed on Jun. 26, 2009, now Pat. No. 8,349,167, said (Continued)

(51) Int. Cl.
  *G01N 27/414* (2006.01)
  *G01N 33/50* (2006.01)
  (Continued)

(52) U.S. Cl.
  CPC ........ *G01N 33/54373* (2013.01); *C12Q 1/6825* (2013.01); *C12Q 1/6869* (2013.01); *H01L 29/78* (2013.01); *H01L 2924/01006* (2013.01); *G01N 27/26* (2013.01); *G01N 33/6818* (2013.01); *G01N 27/4148* (2013.01); *C12Q 1/6874* (2013.01); *G01N 27/4145* (2013.01)

(58) Field of Classification Search
  USPC ........................ 257/235; 205/789, 792, 793.5; 422/82.01–82.03; 435/6, 285.1, 287.1, 435/287.2; 436/103–105; 506/1, 9
  See application file for complete search history.

(56) References Cited

U.S. PATENT DOCUMENTS 4,411,741 A   10/1983   Janata
4,437,969 A   3/1984    Covington et al.

(Continued)

FOREIGN PATENT DOCUMENTS

CN   1461350      12/2003
CN   102203282    9/2011

(Continued)

OTHER PUBLICATIONS

Fraden, J., Handbook of Modern Sensors—Physics, Designs, and Applications, 17.3.2 CHEMFET Sensors, 1996, p. 499-501.*

(Continued)

*Primary Examiner* — J. Christopher Ball

(57) ABSTRACT

Methods and apparatuses relating to large scale FET arrays for analyte detection and measurement are provided. Chem-FET (e.g., ISFET) arrays may be fabricated using conventional CMOS processing techniques based on improved FET pixel and array designs that increase measurement sensitivity and accuracy, and at the same time facilitate significantly small pixel sizes and dense arrays. Improved array control techniques provide for rapid data acquisition from large and dense arrays. Such arrays may be employed to detect a presence and/or concentration changes of various analyte types in a wide variety of chemical and/or biological processes.

20 Claims, 77 Drawing Sheets

Related U.S. Application Data application No. 13/229,456 is a continuation-in-part of application No. 12/002,781, filed on Dec. 17, 2007, now Pat. No. 8,262,900, and a continuation-in-part of application No. 12/002,291, filed on Dec. 14, 2007, now Pat. No. 7,948,015.

(60) Provisional application No. 61/133,204, filed on Jun. 26, 2008, provisional application No. 60/956,324, filed on Aug. 16, 2007, provisional application No. 60/948,748, filed on Jul. 10, 2007, provisional application No. 60/870,073, filed on Dec. 14, 2006.

(51) Int. Cl.
*G01N 33/543* (2006.01)
*C12Q 1/68* (2006.01)
*H01L 29/78* (2006.01)
*G01N 27/26* (2006.01)
*G01N 33/68* (2006.01)

(56) References Cited

U.S. PATENT DOCUMENTS

| | | |
|---|---|---|
| 4,438,354 A | 3/1984 | Haque et al. |
| 4,490,678 A | 12/1984 | Kuisl et al. |
| 4,722,830 A | 2/1988 | Urie et al. |
| 4,743,954 A | 5/1988 | Brown |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,038,192 A | 8/1991 | Bonneau et al. |
| 5,057,426 A | 10/1991 | Henco et al. |
| 5,110,441 A | 5/1992 | Kinlen et al. |
| 5,142,236 A | 8/1992 | Maloberti et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,478,893 A | 12/1995 | Ghosh et al. |
| 5,554,339 A | 9/1996 | Cozzette et al. |
| 5,593,838 A | 1/1997 | Zanzucchi et al. |
| 5,600,451 A | 2/1997 | Maki |
| 5,637,469 A | 6/1997 | Wilding et al. |
| 5,650,649 A | 7/1997 | Tsukiji |
| 5,702,964 A | 12/1997 | Lee |
| 5,793,230 A | 8/1998 | Chu et al. |
| 5,830,645 A | 11/1998 | Pinkel et al. |
| 5,846,708 A | 12/1998 | Hollis et al. |
| 5,894,284 A | 4/1999 | Garrity et al. |
| 5,911,873 A | 6/1999 | McCarron et al. |
| 5,922,591 A | 7/1999 | Anderson et al. |
| 5,923,421 A | 7/1999 | Rajic et al. |
| 5,926,064 A | 7/1999 | Hariton |
| 5,932,450 A | 8/1999 | Dattagupta et al. |
| 5,958,703 A | 9/1999 | Dower et al. |
| 5,965,452 A | 10/1999 | Kovacs |
| 6,090,935 A | 7/2000 | Breivik et al. |
| 6,107,032 A | 8/2000 | Kilger et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,280,586 B1 | 8/2001 | Wolf et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,537,881 B1 | 3/2003 | Rangarajan et al. |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,700,814 B1 | 3/2004 | Nahas et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,919,211 B1 | 7/2005 | Fodor et al. |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi et al. |
| 7,192,700 B2 | 3/2007 | McKeown |
| 7,192,745 B2 | 3/2007 | Jaeger |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,394,263 B2 | 7/2008 | Pechstein et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,470,352 B2 | 12/2008 | Eversmann et al. |
| 7,482,153 B2 | 1/2009 | Okada et al. |
| 7,575,865 B2 | 8/2009 | Leamon et al. |
| 7,595,883 B1 | 9/2009 | El Gamal et al. |
| 7,608,810 B2 | 10/2009 | Yamada |
| 7,667,501 B2 | 2/2010 | Surendranath et al. |
| 7,695,907 B2 | 4/2010 | Miyahara et al. |
| 7,785,790 B1 | 8/2010 | Church et al. |
| 7,815,868 B1 | 10/2010 | Jones et al. |
| 7,859,029 B2 | 12/2010 | Lee et al. |
| 7,888,013 B2 | 2/2011 | Miyahara et al. |
| 7,923,240 B2 | 4/2011 | Su |
| 7,932,034 B2 | 4/2011 | Esfandyarpour et al. |
| 7,948,015 B2 | 5/2011 | Rothberg et al. |

(56) References Cited

U.S. PATENT DOCUMENTS

| | | |
|---|---|---|
| 8,231,831 B2 | 7/2012 | Hartzell et al. |
| 8,262,900 B2 | 9/2012 | Rothberg et al. |
| 8,306,757 B2 | 11/2012 | Rothberg et al. |
| 8,349,167 B2 | 1/2013 | Rothberg et al. |
| 8,470,164 B2 | 6/2013 | Rothberg et al. |
| 8,540,865 B2 | 9/2013 | Rothberg et al. |
| 8,540,867 B2 | 9/2013 | Rothberg et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0108867 A1 | 6/2003 | Chee et al. |
| 2003/0124599 A1 | 7/2003 | Chen et al. |
| 2003/0138809 A1 | 7/2003 | Williams et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0162891 A1 | 8/2003 | Panattoni |
| 2003/0186262 A1 | 10/2003 | Cailloux et al. |
| 2003/0194740 A1 | 10/2003 | Williams |
| 2003/0211637 A1 | 11/2003 | Schoeniger et al. |
| 2003/0215857 A1 | 11/2003 | Kilger et al. |
| 2003/0224419 A1 | 12/2003 | Corcoran et al. |
| 2004/0002470 A1* | 1/2004 | Keith et al. ............... 514/44 |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0121354 A1 | 6/2004 | Yazawa et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0019842 A1 | 1/2005 | Prober et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0136414 A1 | 6/2005 | Gunderson et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230271 A1* | 10/2005 | Levon et al. ............... 205/789 |
| 2005/0233318 A1 | 10/2005 | Chee et al. |
| 2005/0239132 A1 | 10/2005 | Klapprith |
| 2005/0266456 A1 | 12/2005 | Williams et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1* | 6/2006 | Miyahara et al. ............... 435/6 |
| 2006/0154399 A1 | 7/2006 | Sauer et al. |
| 2006/0166203 A1 | 7/2006 | Tooke |
| 2006/0182664 A1 | 8/2006 | Peck et al. |
| 2006/0183145 A1 | 8/2006 | Turner |
| 2006/0197118 A1* | 9/2006 | Migliorato et al. ............ 257/253 |
| 2006/0199193 A1* | 9/2006 | Koo et al. ............... 435/6 |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber et al. |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0099208 A1 | 5/2007 | Drmanac et al. |
| 2007/0099351 A1* | 5/2007 | Peters et al. ............... 438/142 |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0096216 A1 | 4/2008 | Quake |
| 2008/0102466 A1 | 5/2008 | Macevicz |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0204048 A1 | 8/2008 | Stasiak et al. |
| 2008/0213770 A1 | 9/2008 | Williams et al. |
| 2008/0230386 A1 | 9/2008 | Srinivasan et al. |
| 2008/0242560 A1 | 10/2008 | Gunderson et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |

(56) References Cited

U.S. PATENT DOCUMENTS

| | | |
|---|---|---|
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0273386 A1 | 11/2009 | Korobeynikov et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0165557 A1 | 7/2011 | Ah et al. |
| 2011/0217697 A1 | 9/2011 | Rothberg et al. |
| 2011/0263463 A1 | 10/2011 | Rothberg et al. |
| 2011/0275522 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0022795 A1 | 1/2012 | Johnson et al. |
| 2012/0040844 A1 | 2/2012 | Rothberg et al. |
| 2012/0056248 A1 | 3/2012 | Fife |
| 2012/0129728 A1 | 5/2012 | Rothberg et al. |
| 2012/0129732 A1 | 5/2012 | Rothberg et al. |
| 2012/0168307 A1 | 7/2012 | Fife |
| 2012/0168784 A1 | 7/2012 | Fife et al. |

FOREIGN PATENT DOCUMENTS

| | | |
|---|---|---|
| EP | 0223618 | 5/1987 |
| EP | 1371974 | 12/2003 |
| EP | 1432818 | 6/2004 |
| EP | 1542009 | 6/2005 |
| EP | 2307577 | 4/2011 |
| GB | 2457851 | 9/2009 |
| GB | 2461127 B | 7/2010 |
| JP | 2002/272463 | 9/2002 |
| JP | 2005-518541 | 6/2005 |
| JP | 2011-525810 | 9/2011 |
| KR | 10-0442838 | 7/2004 |
| KR | 10-0455283 | 10/2004 |
| WO | 89/09283 | 10/1989 |
| WO | 98/13523 | 4/1998 |
| WO | 98/46797 | 10/1998 |
| WO | 01/42498 | 1/2001 |
| WO | 01/20039 | 3/2001 |
| WO | 01/81896 | 11/2001 |
| WO | 02/077287 | 10/2002 |
| WO | 02/086162 | 10/2002 |
| WO | 2003/073088 | 9/2003 |
| WO | 2004/040291 | 5/2004 |
| WO | 2005/047878 | 5/2005 |
| WO | 2005/084367 | 9/2005 |
| WO | 2005/095938 | 10/2005 |
| WO | 2006/022370 | 3/2006 |
| WO | 2007/086935 | 8/2007 |
| WO | 2008/007716 | 1/2008 |
| WO | 2008/058282 | 5/2008 |
| WO | 2008/076406 | 6/2008 |
| WO | 2008/107014 | 9/2008 |
| WO | 2009/012112 | 1/2009 |
| WO | 2009/158006 | 12/2009 |
| WO | 2009/158006 A3 | 12/2009 |
| WO | 2010/008480 | 1/2010 |
| WO | 2010/008480 A3 | 1/2010 |
| WO | 2010/047804 | 4/2010 |
| WO | 2010/138182 | 12/2010 |
| WO | 2010/138186 | 12/2010 |
| WO | 2010/138187 | 12/2010 |
| WO | 2010/138188 | 12/2010 |
| WO | 2010/138182 A3 | 1/2011 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/006222 | 1/2012 |

OTHER PUBLICATIONS

Chinese Patent Application 200980133783.8 First Office Action, Feb. 18, 2013.
[No Author Listed], "ISFET Wikipedia article", *Wikipedia*, Last modified Nov. 7, 2006.
09110396, Response to office action mailed Aug. 19, 2010, 133.
U.S. Appl. No. 12/002,781, Office Action mailed Jun. 13, 2011, 6.
U.S. Appl. No. 12/474,897, Office Action mailed May 20, 2011, 44 Pgs.
U.S. Appl. No. 12/475,311, Office Action mailed May 18, 2011, 7 Pgs.
U.S. Appl. No. 12/475,311, Response to May 18, 2010 Office Action mailed, 2.
12002291, Notice of Allowance mailed Jan. 21, 2011, 23.
U.S. Appl. No. 13/026,707, Office Action mailed Jun. 16, 2011, 3.
U.S. Appl. No. 13/026,759, Office Action mailed Jun. 16, 2011, 3.
U.S. Appl. No. 13/027,336, Office Action mailed Jun. 29, 2011, 50.
U.S. Appl. No. 13/029,566, Office Action mailed Jul. 12, 2011, 3.
U.S. Appl. No. 13/029,611, Office Action mailed on Jul. 14, 2011, 3 Pgs.
Ahmadian, A. et al., "Single-nucleotide polymorphism analysis by pyrosequencing", *Anal. Biochem.* vol. 280, 2000, pp. 103-110.
Akiyama, T et al., "Ion-Sensitive Field-Effect Transistors with Inorganic Gate Oxide for pH Sensing", *IEEE Transactions on Electron Devices, Vol ED-29*(12), 1982, pp. 1936-1941.
AU2011226767, Search Information Statement, Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical, vol. 118*, 2006, 41-46.
Bashford, G. et al., "Automated bead-trapping apparatus and control system for single-molecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, P, "ISFET, Theory and Practice", *IEEE Sensor Conference, Toronto, Oct. 2003* 2003, pp. 1-26.
Bergveld, P., "Thirty years of ISFETOLOGY What happened in the past 30 years and what may happen in the next 30 years", *Sensors and Actuators B*, vol. 88, 2003, pp. 1-20.
Besselink, G et al., "ISFET Affinity Sensor", *Methods in Biotechnology: vol. 7: Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.

(56) References Cited

OTHER PUBLICATIONS

Bousse, L. et al., "A process for the combined fabrication of ion sensors and CMOS circuits", *IEEE Electron Device Letters*, vol. 9(1), 1988, pp. 44-46.

Bousse, L. et al., "Zeta potential measurements of Ta2O5 and SiO2 thin films", *J. Colloid Interface Sci.*, vol. 147(1), 1991, pp. 22-32.

Brzozka, Z. et al., "Enhanced performance of potassium CHEMFETs by optimization of a polysiloxane membrane", *Sensors and Actuators B. Chemical*, 18-19, 1994, 38-41.

Chen, Y. et al., "Nanoscale field effect transistor for biomolecular signal amplification", *App Phys Letter*, vol. 91, 2007, pp. 243511-1-243511-3.

Chen, Y. et al., "Silicon-based nanoelectronic field-effect pH sensor with local gate control", *App Phys Letter*, vol. 89, 2006, pp. 223512-1-223512-3.

Chou, J. et al., "Letter to the Editor on Simulation of Ta2O5 gate ISFET temperature characteristics", *Sensors and Actuators B*, vol. 80, 2001, pp. 290-291.

Chou, J. et al., "Simulation of Ta2O5 gate ISFET temperature characteristics", *Sensor and Actuators B*, vol. 71, Letter to the Editor, 2000, pp. 73-76.

Chung, W-Y et al., "ISFET interface circuit embedded with noise rejection capability", *Electronics Letters*, vol. 40(18), e-pub; 2 pages, 2004,.

Chung, W-Y et al., "ISFET performance enhancement by using the improved circuit techniques", *Sensors and Actuators B*, vol. 113, 2006, pp. 555-562.

CN200780051353.2, Second Office Action, [English Translation of Office Action], Mar. 5, 2013, 7 pages.

Cobben, Peter et al., "Transduction of Selective Recognition of Heavy Metal Ions by Chemically Modified Field Effect Transistors (CHEMFETs)", *J. Am. Chem. Soc.*, vol. 114, No. 26, 1992, 10573-10582.

Eijkel, J. et al., "Measuring Donnan-related phenomena using a solid-state ion sensor and a concentration-step method", *J. Membrane Sci.*, vol. 127, 1997, pp. 203-221.

Eijkel, J., "Potentiometric detection and characterization of adsorbed protein using stimulus-response measurement techniques", *Thesis*- Sep. 3, 1955, pp. 1-147; 160-192.

Eltoukhy, H et al., "A 0.18um CMOS 10-6 lux Bioluminescence Detection System-on-Chip", *ISSCC 2004/Session12/Biomicrosystems/12.3*, 2004, pp. 1-3.

Eltoukhy, H. et al., "A. 0.18-um CMOS Bioluminescence Detection Lab-on-Chip" *IEEE JSolid-State Circuits*, vol. 41(3), 2006, pp. 651-662.

EP09770544.6, Extended European Search Report mailed Oct. 2, 2013, 15 pages.

EP7867780.4, Examination Report mailed Jul. 3, 2012.

Eriksson, J. et al., "Pyrosequencing technology at elevated temperature", *Electrophoresis*, vol. 25, 2004, pp. 20-27.

Esfandyarpour, H. et al., "Gate-controlled microfluidic chamber with magnetic bead for DNA sequencing-by-synthesis technology" *Proc 5th Intl Conf Nanochannels, Microchannels, Minnichannels*, Puebla, Mexico, Jun. 18, 2007, pp. 1-5.

Eversmann, B. et al., "A 128 x 128 CMOS Biosensor Array for Extracellular Recording of Neural Activity", *IEEE J. Solid-State Circ.*, vol. 38(12), Dec. 12, 2003, pp. 2306-2317.

Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.

Finn, A et al., "Towards an Optimization of FET-Based Bio-Sensors", *European Cells and Materials*, vol. 4, Sup 2, 2002, pp. 21-23.

Fraden, J. , "Handbook of Modern Sensors—Physics, Designs, and Applications . . .", *17.3.2. CHEMFET Sensors*, 1996, pp. 499-501.

Fritz, J. et al., "Electronic detection of DNA by its intrinsic molecular charge", PNAS, vol. 99, No. 22, Oct. 2002, 14142-14146 .

GB0811656.8, Search and Examination Report, Mar. 12, 2010.

GB0811656.8, Search Report, Sep. 21, 2009.

GB0811657.6, Examination Report, Jun. 30, 2010.

GB0811657.6, Search Report under Section 17, Oct. 26, 2009.

Gracia, I. et al., "Test Structures for ISFET Chemical Sensors", *Proc IEEE 1992 Intl Conf Microelec Test Struct*, vol. 5, 1992, pp. 156-159 .

Hammond, P. et al., "A System-on-Chip Digital pH Meter for Use in a Wireless Diagnostic Capsule", *IEEE Transactons on Biomedical Engineering*, vol. 52(4), 2005, pp. 687-694.

Hammond, P. et al., "Design of a Single-Chip pH Sensor Using a Conventional 0.6—μm CMOS Process", *IEEE Sensors Journal*, vol. 4(6), 2004, 706-712.

Hammond, P. et al., "Encapsulation of a liquid-sensing microchip using SU-8 photoresist", *MicoElectronic Engineering*, vol. 73-74, 2004, pp. 893-897.

Hammond, S. et al., "Genomic sequencing and analysis of a Chinese Hamster ovary cell line using Illumina sequencing technology", *BMC Genomics*, vol. 12:67, 2011, pp. 1-8.

Han, Y, "Label-free detection of biomolecules by a field-effect transistor microarray biosensor with bio-functionalized gate surfaces", Masters Dissertation, 2006, pp. 1-63.

Han, Y. et al., "Detection of DNA hybridization by a field-effect transistor with covalently attached catcher molecules", *Surface and Interface Analysis*, 38:, 2006, 176-181.

Hara, H. et al., "Dynamic response of a Ta2O5-gate pH-sensitive field-effect transistor", *Sensors Actuators B*, vol. 32, 1996, pp. 115-119.

Hermon, Z. et al., "Miniaturized bio-electronic hybrid for chemical sensing applications", *Tech Connect News*, Apr. 22, 2008, pp. 1.

Hideshima, S. et al., "Detection of tumor marker in blood serum using antibody-modified field effect transistor with optimized BSA blocking", *Sensors and Actuations B: Chemical*, vol. 161, 2012, pp. 146-150 .

Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.

Hizawa, T et al., "Fabrication of a two-dimensional pH image sensor using a charge transfer technique", *Sensors and Actuators B Chemical vol.* 117 2006, 509-515.

Hizawa, T. et al., "32 x 32 pH Image Sensors for Real Time Observation of Biochemical Phenomena", *Transducers & Eurosensors'07*, 14th Intl. Conf. on Solid-State, Actuators and Microsystems, Lyon, France, Jun. 10-14, 2007, 2007, pp. 1311-1312.

Jakobson, C. et al., "Low frequency noise and drift in Ion Senstive Field Effect Transistors", *Sensors Actuators B*, vol. 68, 2000, pp. 134-139.

Ji, H. et al., "A CMOS contact imager for locating individual cells", *ISCAS*, 2006, pp. 3357-3360 .

Ji, H. et al., "Contact Imaging: Simulation and Experiment", *IEEE Trans Circuits Systems-I:Regular Papers*, vol. 54(8), 2007, pp. 1698-1710.

Kim, D. et al., "An FET-type charger sensor for highly sensitive detection of DNA sequence", *Biosens Bioelectron*, vol. 20(1), 2004, pp. 69-74.

Klein, M., "Time effects of ion-sensitive field-effect transistors", *Sens Act B*, vol. 17, 1989, pp. 203-208.

Koch, S et al., "Protein detection with a novel ISFET-based zeta potential analyzer", *Biosensors & Bioelectronics*, vol. 14, 1999, pp. 413-421.

Kruise, J. et al., "Detection of protein concentrations using a pH-step titration method", *Sensors Actuators B*, vol. 44, 1997, pp. 297-303.

Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.

Leamon, J. et al., "Cramming More Sequencing Reactions onto Microreactor Chips", *Chemical Reviews*, vol. 107, 2007, pp. 3367-3376.

Lee, C-S et al., "Ion-sensitive Field-Effect Transistor for Biological Sensing", *Sensors*, vol. 9, 2009, pp. 7111-7131.

Li, et al., "Sequence-Specific Label-Free DNA Sensors Based on Silico Nanowires", *Nano Letters*, vol. 4(2), 2004, pp. 245-247.

Lohrengel, M. et al., "A new microcell or microreactor for material surface investigations at large current densities", *Electrochimica Acta*, vol. 49, 2004, pp. 2863-2870.

(56) References Cited

OTHER PUBLICATIONS

Lui, A. et al., "A Test Chip for ISFET/CMNOS Technology Development" *Proc. of the 1996 IEEE Intl. Conf. On Microelectronic Test Structures*, vol. 9, 1996, pp. 123-128.
Margulies, et al., "Genome sequencing in microfabricated high-density picolitre reactors", *Nature* vol. 437 (15), Jul. 31, 2005, 376-380.
Marshall, A. et al., "DNA chips: an array of possibilities", *Nature Biotechnology*, vol. 16, 1998, pp. 27-31.
Martel, R. et al., "Single-and multi-wall carbon nanotube field-effect transistors" *Applied Physics Letters*, vol. 73, No. 17, 1998, 2447-2449.
Martinoia, S. et al., "A behavioral macromodel of the ISFET in SPICE", *Sensors Actuators B*, vol. 62, 2000, pp. 182-189.
Martinoia, S. et al., "Development of ISFET Array-Based Microsystems for Bioelectrochemical measurements of cell populations", *Biosensors & Bioelectronics, vol. 16* , 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), 2006, pp. 1037-1044.
Milgrew, M. et al., "A 16 x 16 CMOS proton camera array for direct extracellular imaging of hydrogen-ion activity", *IEEE Intl Solid-State Circuits Conf*, Session 32:24, 2008, pp. 590-591;638.
Milgrew, M. et al., "A large transistor based sensor array chip for direct extracellular imaging", *Sensors and Actuators B Chemical, vol. 111-112*, 2005, 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B, vol. 103*, 2004, 37-42.
Milgrew, M. et al., "The fabrication of scalable multi-sensor arrays using standard CMOS technology", *2003 IEEE Custom Integrated Circuits Conference*, 2003, pp. 513-516.
Miyahara, Y. et al., "Biochip Using Micromachining Technology", *J. Institute of Electrostatics, Japan*, vol. 27(6), 2003, pp. 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305 .
Miyahara, Y. et al., "Potentiometric Detection of DNA Molecules Using Field Effect Transistor ", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348 .
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), 2006, pp. 4261-4269
PCT/JP2005/001987, International Search Report, Apr. 5, 2005.
PCT/JP2005/015522, International Search Report, (includes English translation), Sep. 27, 2005.
PCT/US/2009/05745, International Preliminary Report on Patentability, Issued Apr. 26, 2011, 2009.
PCT/US/2009/05745, International Search Report, Dec. 11, 2009.
PCT/US/2009/05745, Written Opinion, Dec. 11, 2009.
PCT/US10/01547, International Search Report and Written Opinion, Aug. 5, 2010.
PCT/US2007/025721, Declaration of Non-Establishment of International Search Report, Jul. 15, 2008.
PCT/US2007/025721, International Preliminary Report on Patentability, Jun. 16, 2009.
PCT/US2007/025721, Written Opinion, Jun. 16, 2009.
PCT/US2009/003766, International Preliminary Report on Patentability, Jan. 5, 2011.
PCT/US2009/003766, International Search Report, Apr. 8, 2010.
PCT/US2009/003766, Written Opinion, Apr. 8, 2010.
PCT/US2009/003797, International Search Report, Mar. 12, 2010.
PCT/US2009/003797, Written Opinion, Mar. 12, 2010.
PCT/US2010/001543, International Preliminary Report on Patentability, Nov. 29, 2011, pp. 1-8.
PCT/US2010/001543, International Search Report and Written Opinion, Oct. 13, 2010, pp. 1-12.
PCT/US2010/001549, International Preliminary Report on Patentability, 2011, pp. 1-8.
PCT/US2010/001549, International Search Report, Sep. 10, 2010.
PCT/US2010/001549, Written Opinion, Sep. 17, 2010.
PCT/US2010/001553, International Preliminary Report on Patentability, Dec. 8, 2011, pp. 1-10.
PCT/US2010/001553, International Search Report, Jul. 28, 2010, pp. 1-2.
PCT/US2010/001553, Written Opinion, Jul. 14, 2010, pp. 1-6.
PCT/US2010/01547, International Preliminary Report on Patentability, Nov. 29, 2011, pp. 1-8.
PCT/US2010/48835, International Search Report and Written Opinion, Dec. 16, 2010, pp. 1-12.
PCT/US2011/042655, International Search Report mailed Oct. 21, 2011, 2011, pp. 1-2.
PCT/US2011/042660, International Search Report, Nov. 2, 2011.
PCT/US2011/042665, International Search Report mailed Nov. 2, 2011.
PCT/US2011/042669, International Search Report, Jan. 9, 2012, pp. 1-5.
PCT/US2011/042669, Written Opinion, Jan. 9, 2012, pp. 1-5.
PCT/US2011/042683, International Search Report, Feb. 16, 2012.
PCT/US2011/042683, Written Opinon, Feb. 16, 2012.
PCT/US2013/022140, International Search Report and Written Opinion, May 2, 2013, 15 pages.
Poghossian, a. et al., "Functional testing and characterization of ISFETs on wafer level by means of a micro-droplet cell", *Sensors*, vol. 6, 2006, pp. 397-404.
Pourmand, n. et al., "Direct electrical detection of DNA synthesis", *PNAS* vol. 103(17),2006, pp. 6466-6470.
Pouthas, F. et al., "Spatially resolved electronic detection of biopolymers", *Phys Rev*, vol.70, 2004, pp. 031906-1-031906-8
Premanode, B. et al., "A composite ISFET readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), 2006, 2 pages.
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rehman, F. et al., "Immobilization of Acrylamide-modified Oligonucleotides by Copolymerization", *Nucleic Acids Research, vol. 27, No. 2*, 1999, pp. 649-655.
Rodriguez-Villegas, E., "Solution to trapped charge in FGMOS transistors", *Electronics Letters* vol. 39(19), 2003.
Ronaghi, M. et al., "A Sequencing Method Based on Real-Time Pyrophosphate", *Science* vol. 281, 1998, 363-365.

(56) References Cited

OTHER PUBLICATIONS

Sakata, T. et al., "Cell-based field effect devices fo cell adhesion analysis", *Intl. Conf. On Microtechnologies in Medicine and Biology, May 9-12, 2006 Okinawa, Japan*, 2006, pp. 177-179.

Sakata, T. et al., "Detection of DNA recognition events using multi-well field effect transistor", *Biosensors and Bioelectronics vol. 21*, 2005, pp. 827-832.

Sakata, T. et al., "Detection sensitivity of genetic field effect transistor combined with charged nanoparticle-DNA conjugate", *Proc. of 2006 Intl. Conf. On Microtechnologies in Medicine and Biology, May. 9-12, 2005, Okinawa, Japan*, 2006, pp. 97-100.

Sakata, T. et al., "Direct detection of single nucleotide polymorphism using genetic field effect transistor", *Digest of Papers Microprocesses and Nanotechnology 2004, Osaka, Japan, 2004 International Microprocesses and Nanotechnology Conference*, 2004, pp. 226-227.

Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology, Kahuku, Oahu, HI, May 12-15, 2005*, 2005, pp. 219-222.

Sakata, T. et al., "Direct transduction of allele-specific primer extension into electrical signal using genetic field effect transistor", *Biosensors and Bioelectronics*, vol. 22, 2007, pp. 1311-1316.

Sakata, T. et al., "DNA Analysis Chip Based on Field-Effect Transistors", *Japanese Journal of Applied Physics*, vol. 44(4B), 2005, pp. 2854-2859.

Sakata, T. et al., "DNA Sequencing Based on Intrinsic Molecular Charges", *Angewandte Chemie International Edition 2006*, vol. 118, 2006, pp. 2283-2286.

Sakata, T. et al., "DNA Sequencing Based on Intrinsic Molecular Charges", *Angewandte Chemie International Edition 2006*, vol. 45, 2006, pp. 2225-2228.

Sakata, T. et al., "DNA Sequencing Using Genetic Field Effect Transistor", *13th Intl. Conf. on Solid-State Sensors, Actuators and Microsystems, Jun. 5-9, .2005, Seoul, Korea*, 2005, pp.1676-1679.

Sakata, T. et al., "Immobilization of oligonucleotide probes on Si3N4 surface and its application to genetic field effect transistor", *Materials Science and Engineering: C*, vol. 24, 2004, pp. 827-832.

Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.

Sakata, T. et al., "Potential Response of Genetic Field Effect Transistor to Charged Nanoparticle-DNA Conjugate", *Digest of Papers Microprocesses and Nanotechnology 2005, Tokyo, Japan, 2005 Intl Microprocesses and Nanotech Conference, Hotel Bellclassic*, 2005, pp.42-43.

Sakata, T. et al., "Potentiometric Detection of Allele Specific Oligonucleotide Hybridization Using Genetic Field Effect Transistor", *Micro Total Analysis Systems 2004, 8th Intl. Conf. on Miniaturized Systems for Chemistry and Life Sciences, Sep. 26-30, 2004, Malmo, Sweden*, 2004, pp. 300-302.

Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.

Sakata, T. et al., "Potentiometric Detection of DNA Using Genetic Transistor", *Denki Gakkai Kenkyukai Shiryo Chemical Sensor Kenkyukai, CHS-03-51-55*, 2003, pp. 1-5.

Sakata, T. et al., "Potentiometric Detection of Single Nucleotide Polymorphism by Using a Genetic Field-effect transistor", *ChemBioChem*, vol. 6, 2005, pp. 703-710.

Sakurai, T. et al., "Real-Time Monitoring of DNA Polymerase Reactions by a Micro ISFET pH Sensor", *Anal Chem*, vol. 64(17), 1992, pp. 1996-1997.

Salama, K., "CMOS luminescence detection lab-on-chip: modeling, design, and characterization", *Thesis*, Presented at Stanford University, 2005, pp. ii - 78.

Salama, K., "Modeling and simulation of luminescence detection platforms", *Biosensors & Bioelectronics*, 2004, pp. 1377-1386.

Sawada, K. et al., "A novel fused sensor for photo- and ion-sensing", *Sensors Actuators B*, vol. 106, 2005, pp. 614-618.

Sawada, K. et al., "Highly sensitive ion sensors using charge transfer technique", *Sensors Actuators B*, vol. 98, 2004, pp. 69-72.

Schasfoort, R. et al., "A new approach to immunoFET operation", *Biosensors & Bioelectronics*, vol. 5, 1990, pp. 103-124.

Schasfoort, R. et al., "Field-effect flow control for microfabricated fluidic networks", *Science*, vol. 286(5441), 1999, pp. 942-945.

Schoning, M. et al., "Bio FEDs (Field-Effect Devices): State-of-the-Art and New Directions", *Electroanalysis*, vol. 18(19-20), 2006, pp. 1893-1900.

Schoning, Michael et al., "Recent advances in biologically sensitive field-effect transistors (BioFETs)", *Analyst*, vol. 127(9), 2002, pp. 1137-1151.

SG200903992-6, Search and Examination Report (Favourable) mailed Jan. 20, 2011, 12.

Shah, N., "Microfabrication of a parellel-array DNA pyrosequencing chip", *NNIN REU Research Accomplishments*, 2005, pp. 130-131.

Shepherd, L et al., "Towards Direct Biochemical Analysis with Weak Inversion ISFETS", *IEEE International Workshop on Biomedical Circuits & Systems*, 2004, pp. S1.5-5-S1.5.8.

Shepherd, L. et al., "A biochemical translinear principle with weak inversion ISFETs", *IEEE Trans Circuits Syst-I*, vol. 52(12), Dec. 2005, pp. 2614-2619.

Shepherd, L. et al. "A novel voltage-clamped CMOS ISFET senser interface", *IEEE*, 2007, pp. 3331-3334.

Shepherd, L. et al., "Weak inversion ISFETs for ultra-low power biochemical sensing and real-time analysis", *Sensors Actuators B*, vol. 107, 2005, pp. 468-473.

Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Sibbald, A. et al., "A miniature flowthrough cell with a four-function ChemFET integrated circuit for simultaneous measurements of potassium, hydrogen, calcium and sodium ions", *Analytica chimica acta.*, 159, 1984, 47-62.

Simonian, A. L. et al., "FET based biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenlnaphthalene Dimide as the Electrochemically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemicalcomposition in lab on . . .", *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J et al., "The ISFET based heparin sensor with a monolayer of protamine as affinity ligand", *Biosensors & Bioelectronics*, vol. 10(3), 1995, pp. 269-282.

Van Kerkhof, J. et al., "ISFET Responses on a stepwise change in electrolyte concentration at constant pH", *Sensors Actuators B: Chemical*, vol. 18-19, 1994, pp. 56-59.

VAn Kerkhof, J., "The Development of an ISFET-based Heparin Sensor", *Thesis*, 1994.

(56) References Cited

OTHER PUBLICATIONS

Wagner, T et al., "'All-in-one' solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad. Of Sciences (PNAS)*, vol. 102(9), 2005, pp. 3208-3212.

Woias, P, "Modeling the short time response of ISFET sensors", *Sensors and Actuators B*, vol. 24-25, 1995, pp. 211-217.

Woias, P. et al., "Slow pH response effects of silicon nitride ISFET sensors", *Sensors and Actuators B*, vol. 48, 1998, pp. 501-504.

Wu, P. et al., "DNA and protein microarray printing on silicon nitride waveguide surfaces", *Biosenses Bioelectron*, vol. 21(7), 2006, pp. 1252-1263.

Xu, J-J et al., "Analytical Aspects of FET-Based Biosensors", *Frontiers in Bioscience*, vol. 10, 2005, pp. 420-430.

Yeow, T.C.W. et al., "A very large integrated pH-ISFET sensor array chip compatible with standard CMOS processes", *Sensor and Actuators B*, vol. 44, 1997, 434-440.

Yuqing, M. et al., "Ion sensitive field effect trnasducer-based biosensors", *Biotechnology Advances*, vol. 21, 2003, pp. 527-534.

Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", Nuc. Acids Res., vol. 29(19), e93, 2001, pp. 1-11.

\* cited by examiner

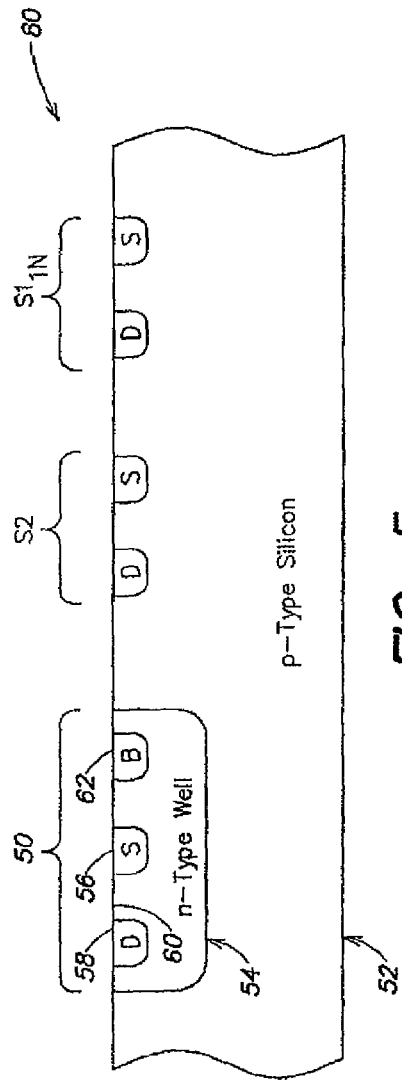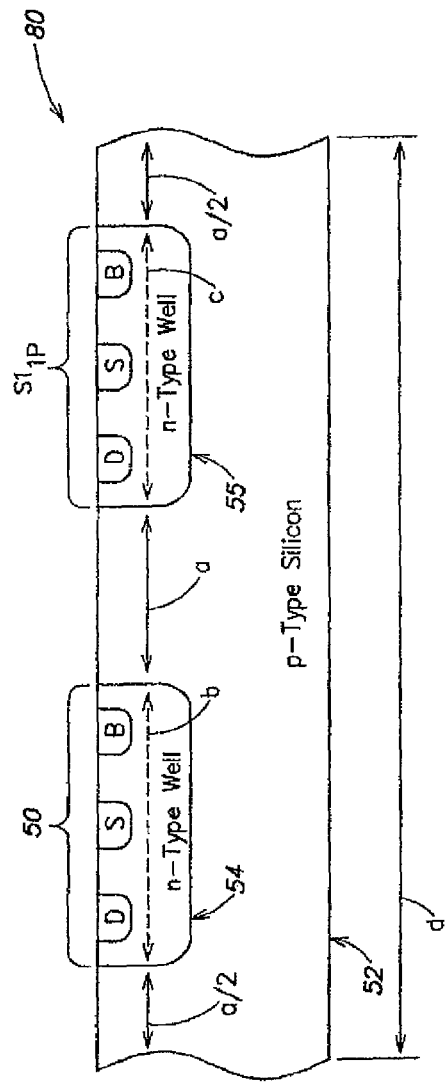

FIG. 11A

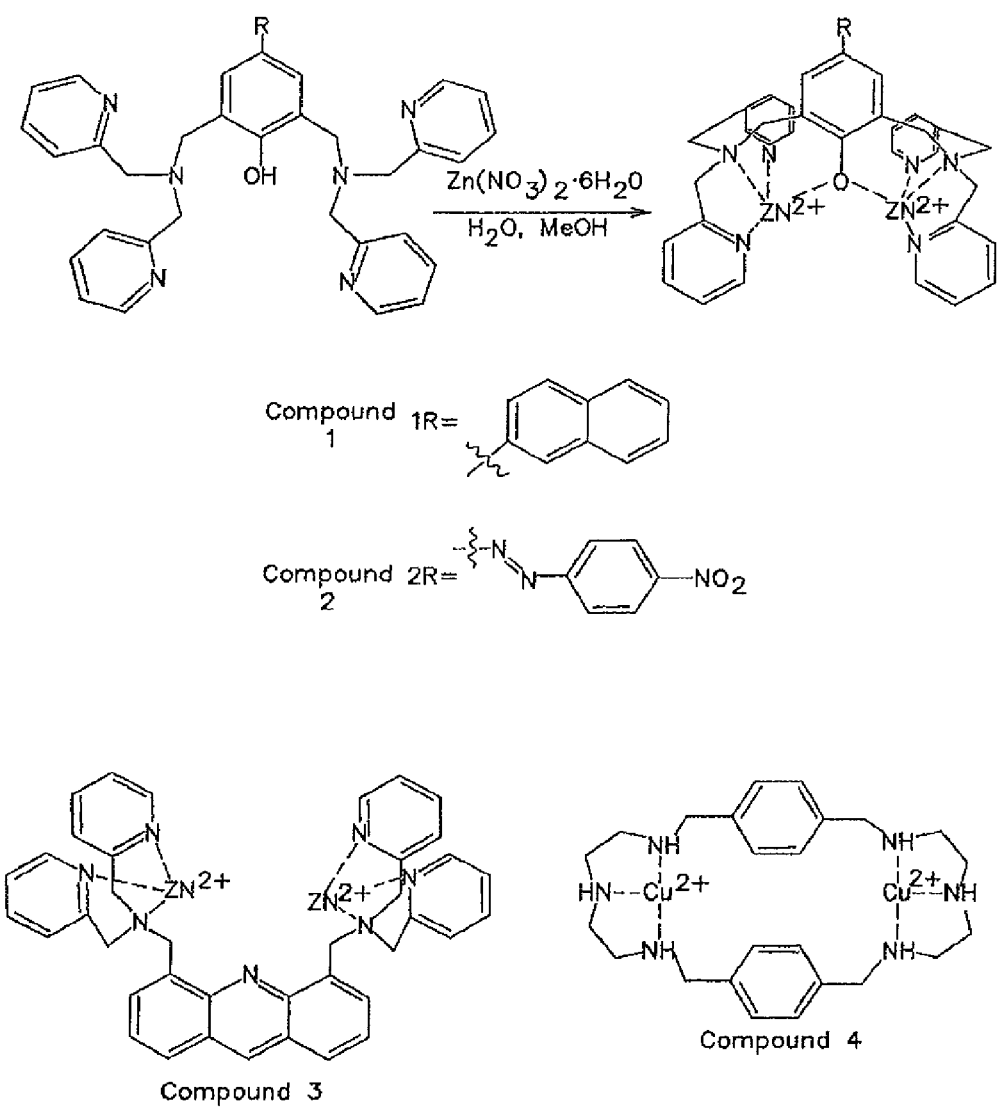
FIG. 11B(1)

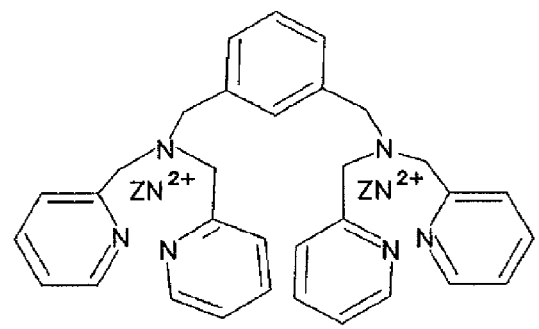
ZN²⁺-dipicolylamine
Compound 5
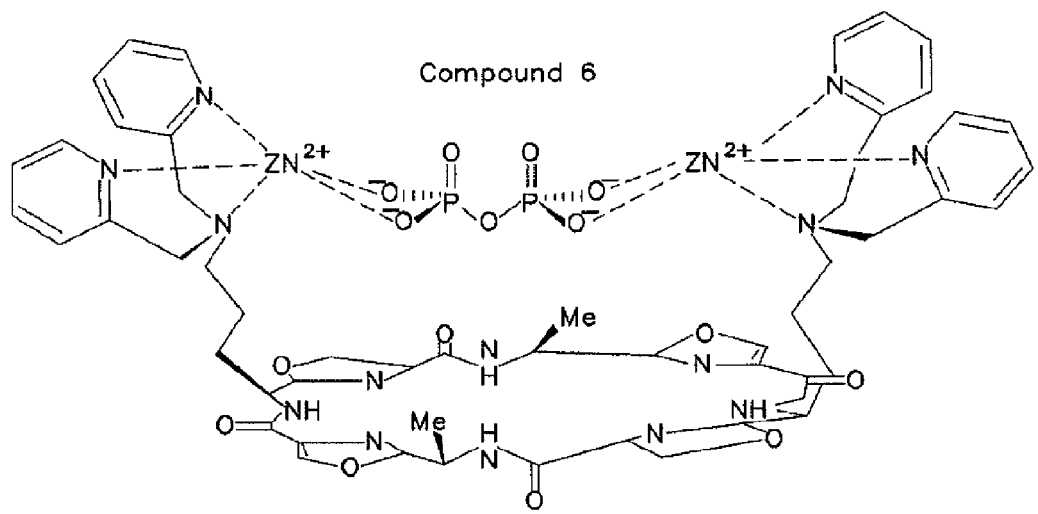
Compound 6
FIG. 11B(2)

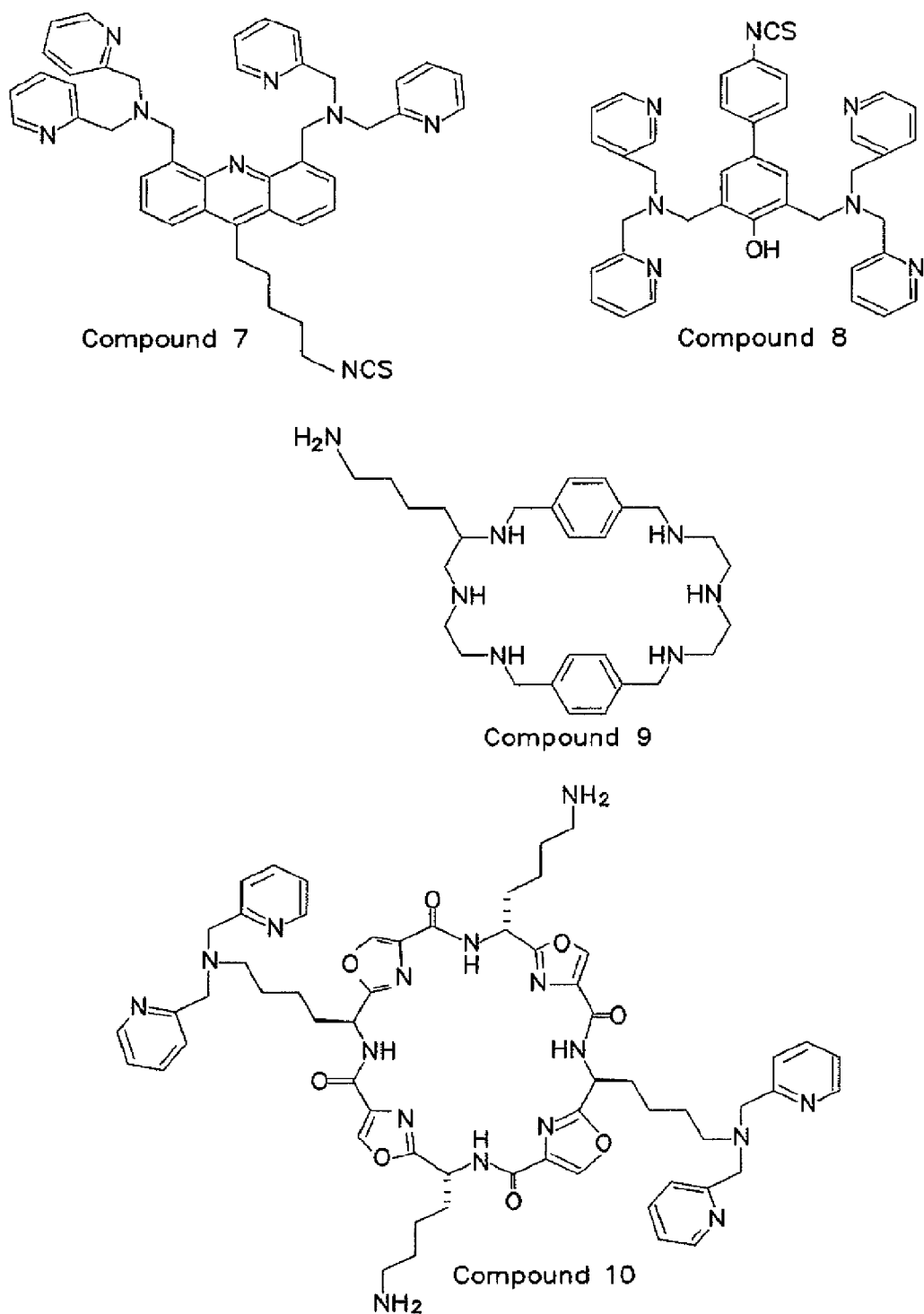
FIG. 11B(3)

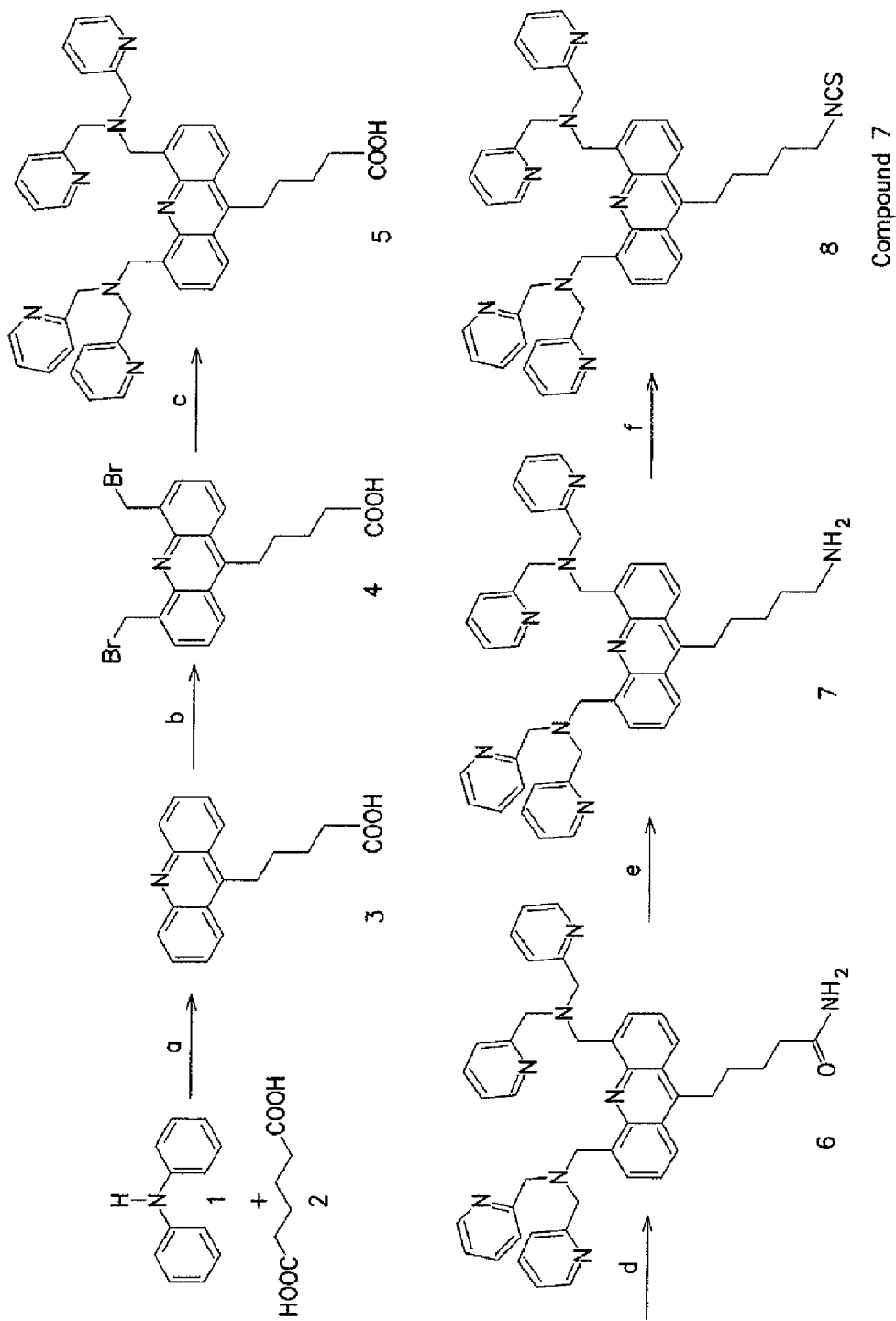
FIG. 11C(1)-1

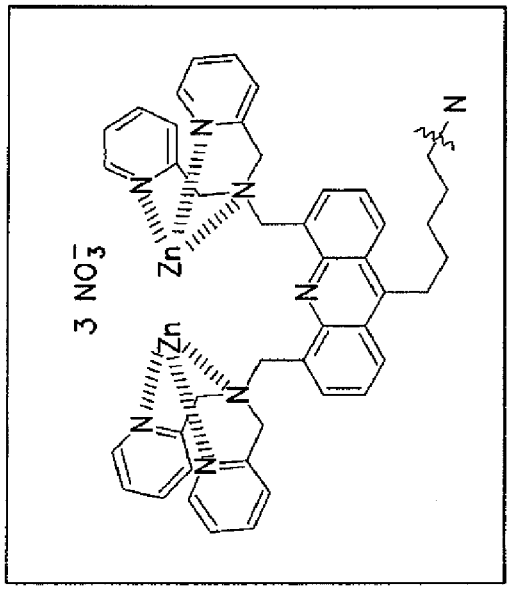
a. ZnCl$_2$; 20% H$_2$SO$_4$
b. BrCH$_2$OCH$_3$, H$_2$SO$_4$, 50°C, 18%
c. dipicorylamine, K$_2$CO$_3$, CH$_2$Cl$_2$, 66%
d. NH$_2$CONH$_2$, heat
e. LiAlH$_4$, Et$_2$O or BH$_3$
di-2-pyridyl thiocarbonate,CH$_2$Cl$_2$, 46%
Note: Zn ion are added post covalent linking to surface.
FIG. 11C(1)-2

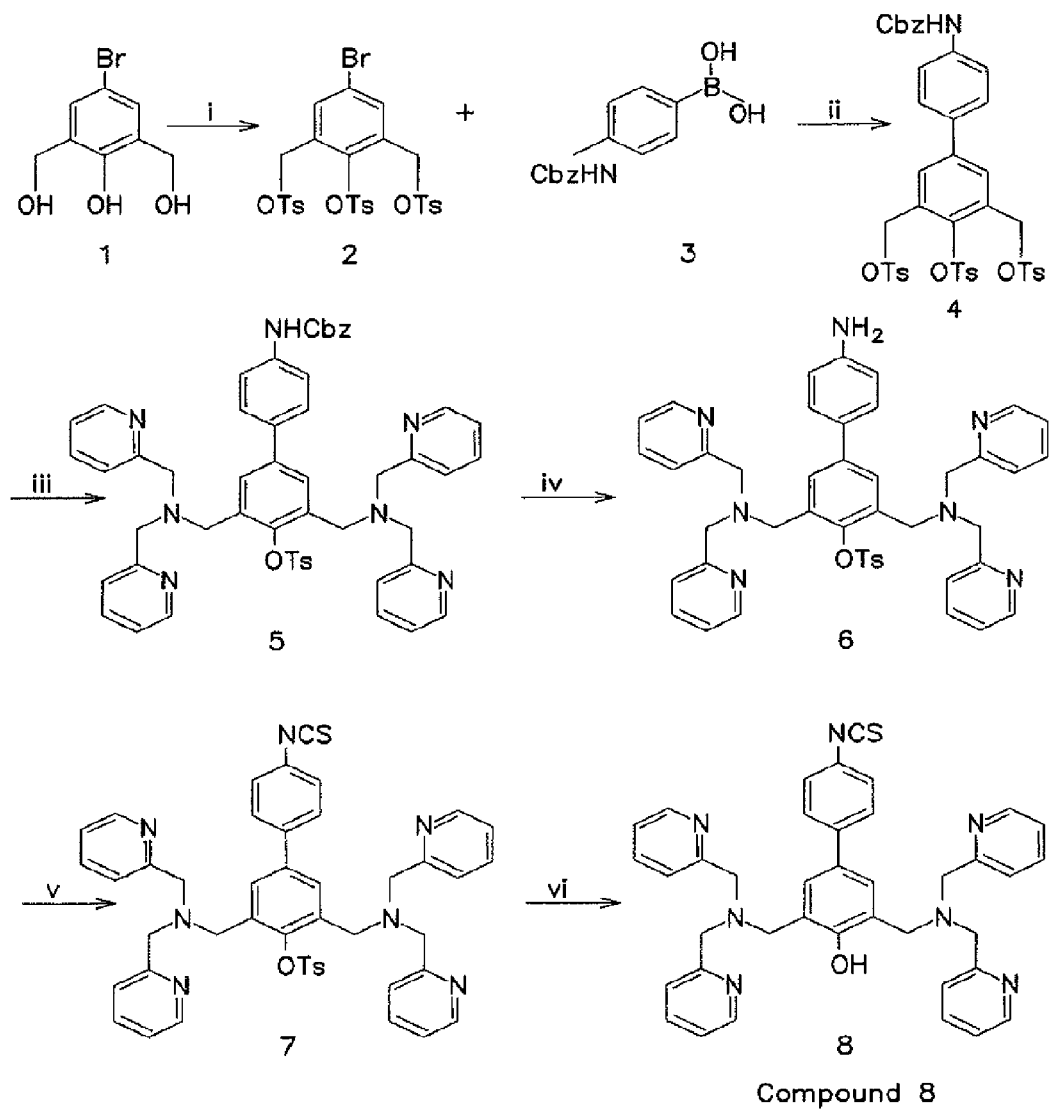
i. TsCl, TEA, 4-DMAP, THF
ii. Pd(PPh₃)₄, aq Na₂CO₃, EtOH/benzene
iii. dipicoylamine, K₂CO₃, KI, MeCN
iv. H₂, Pd/C, MeOH
v. DPT, MeCN, r.t.
vi. NaOH, MeOH, THF
FIG. 11C(2)

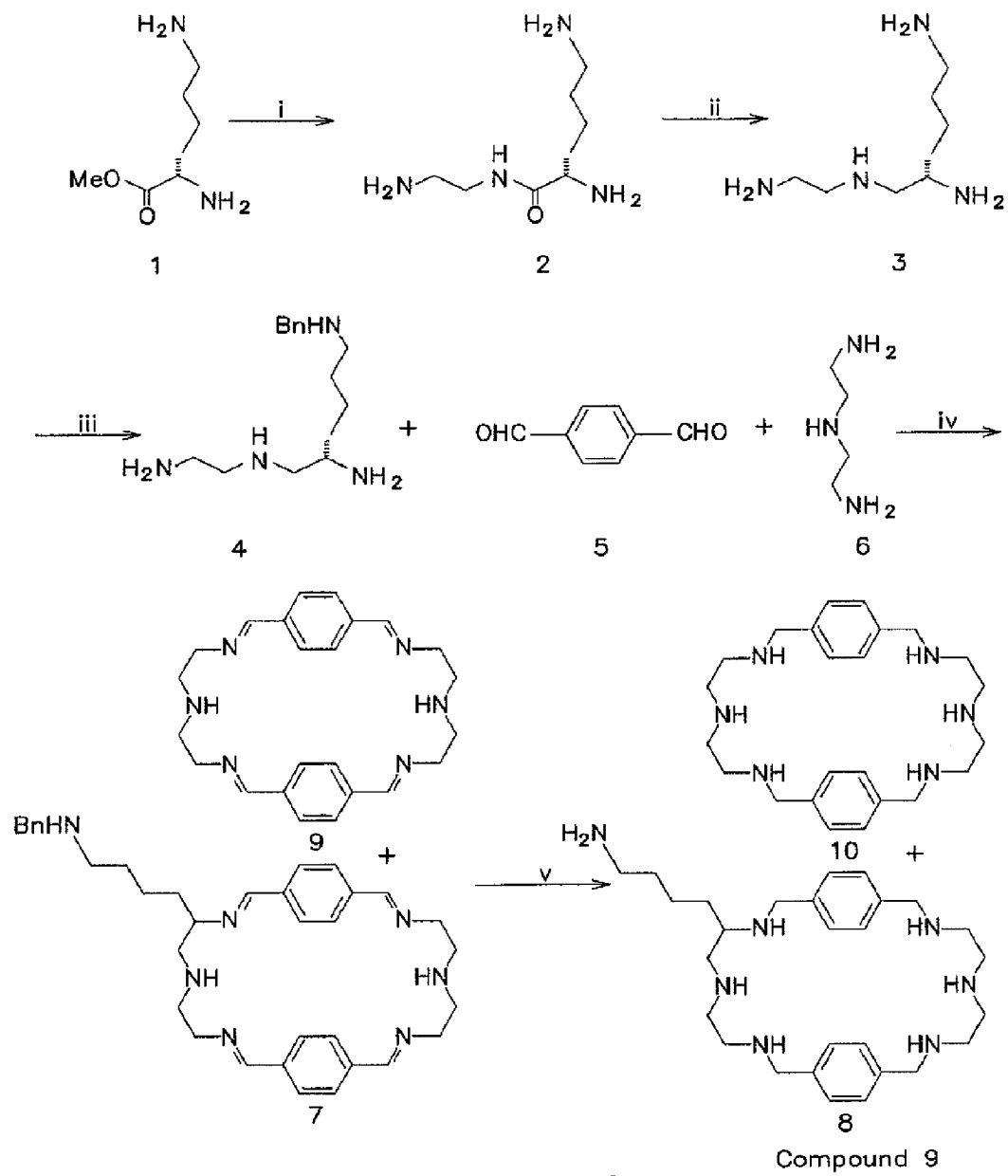
FIG. 11C(3)

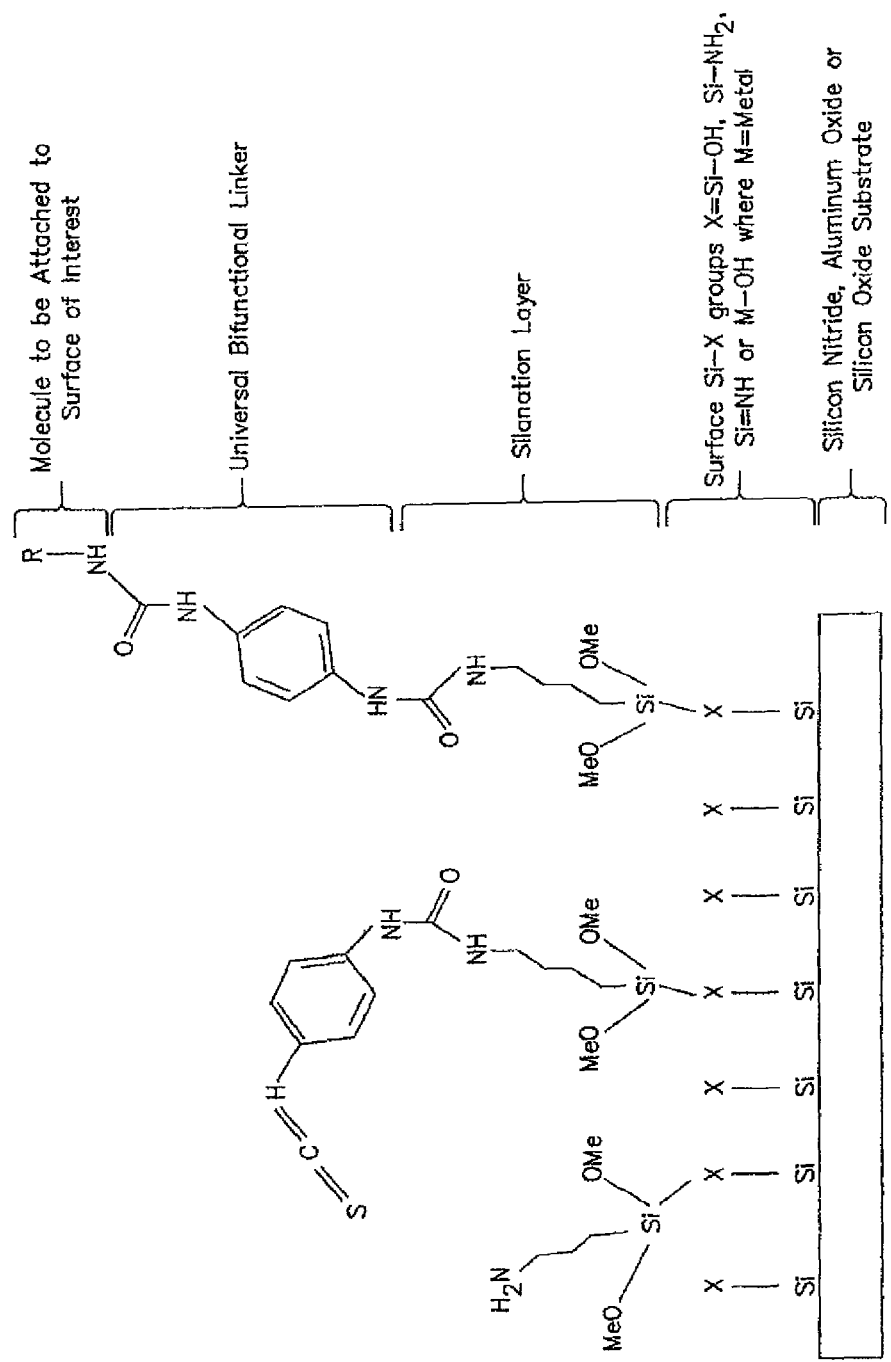
FIG. 11D(1)

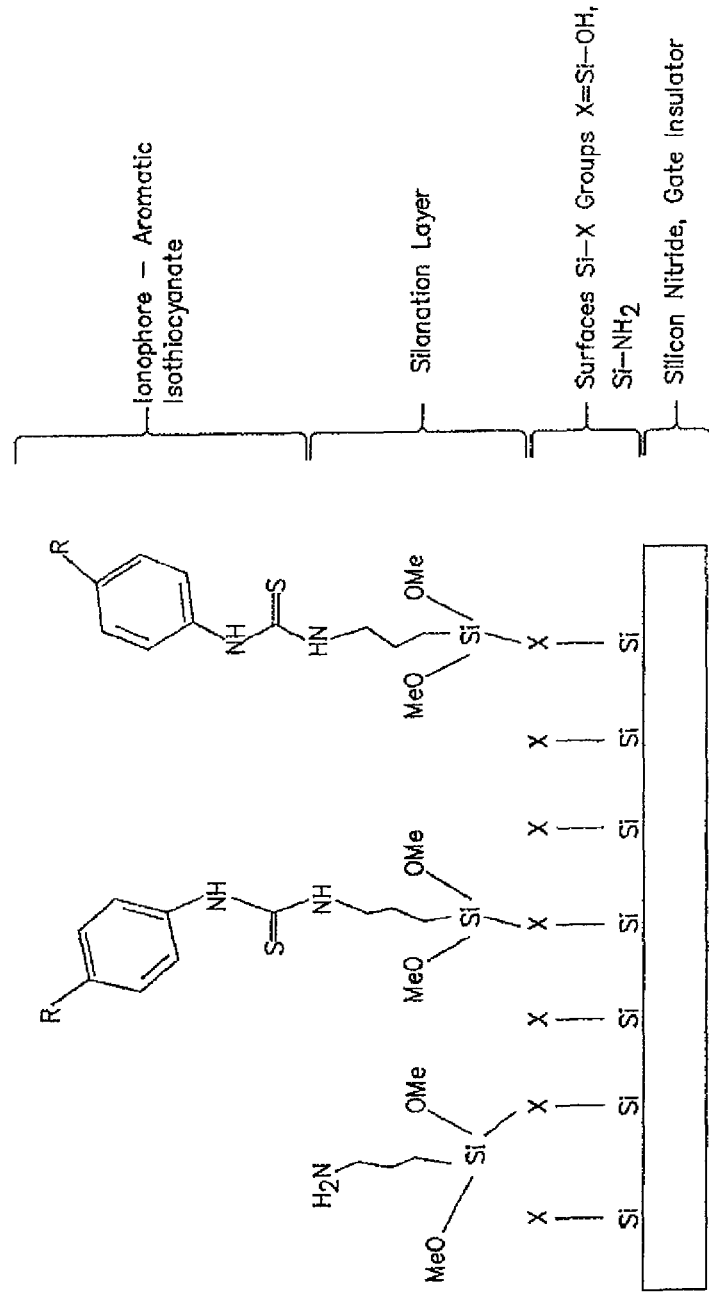
FIG. 11D(2)

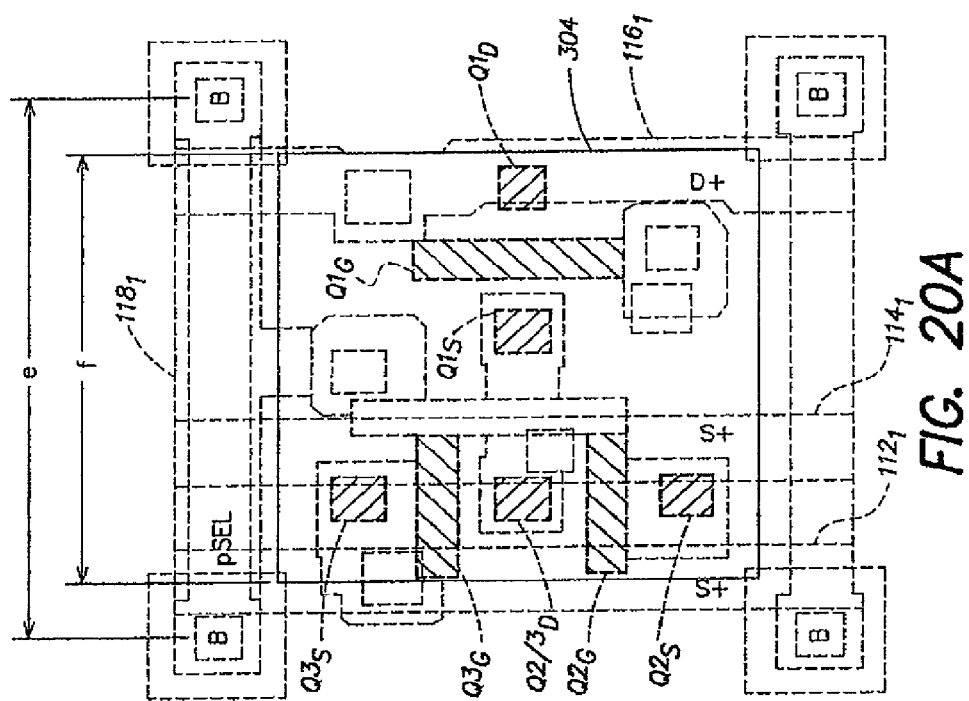

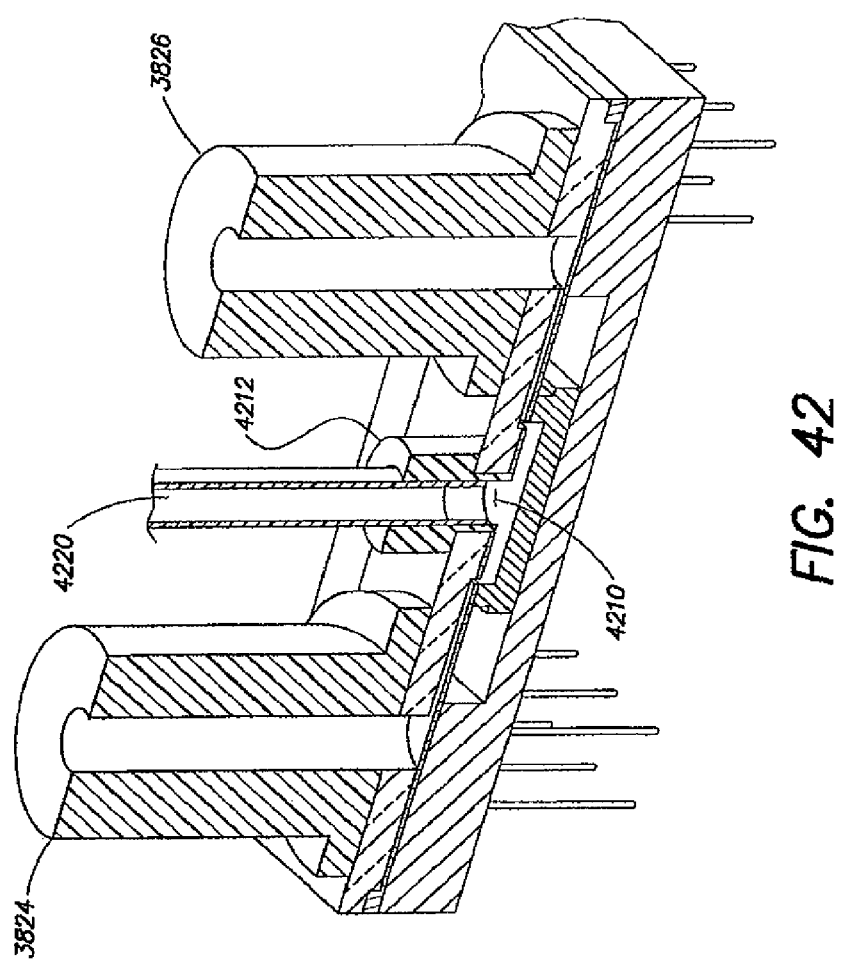

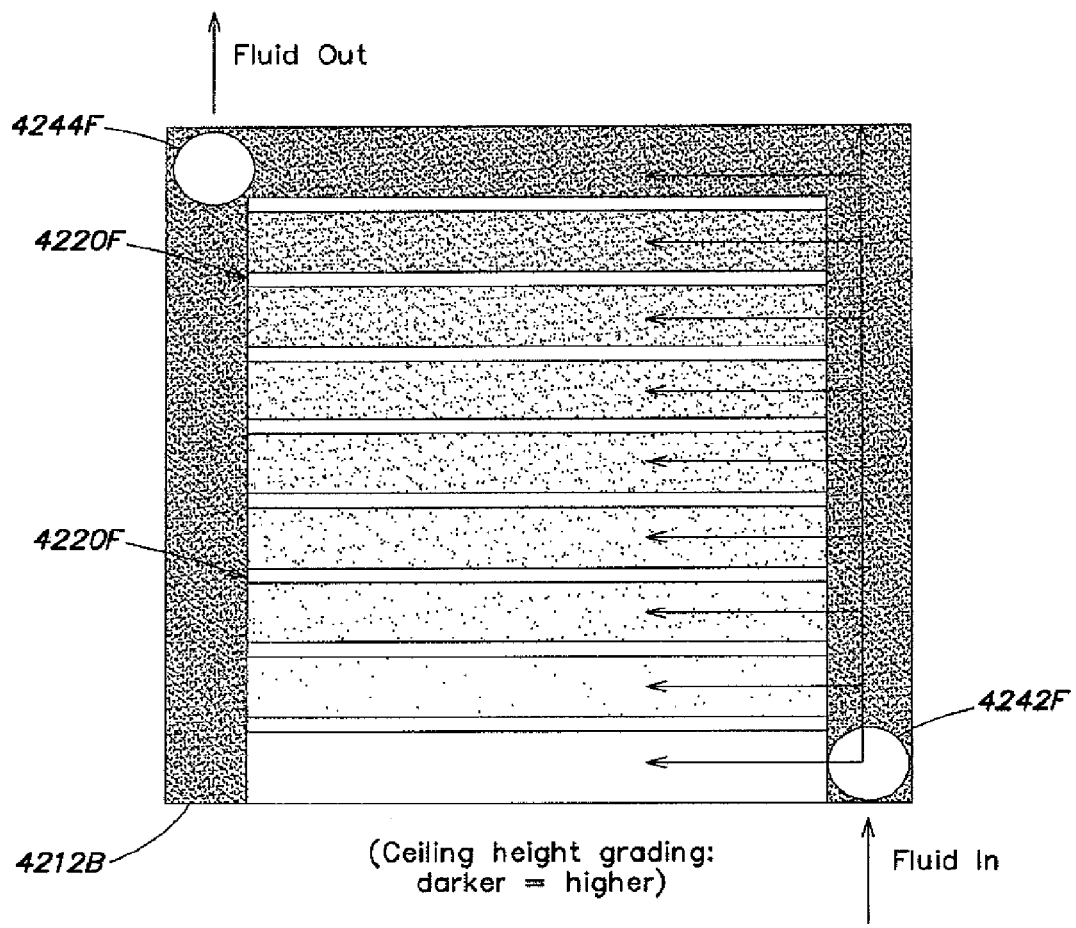
FIG. 42F1

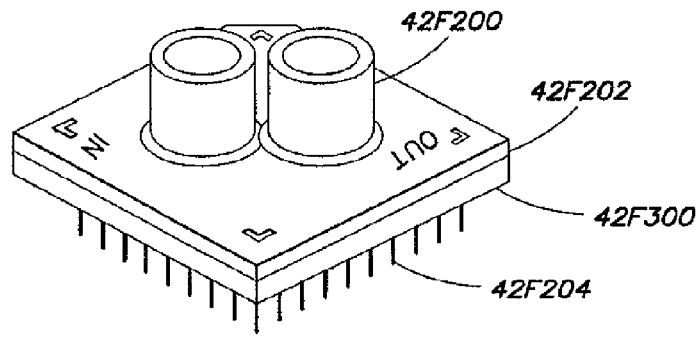
FIG. 42F2
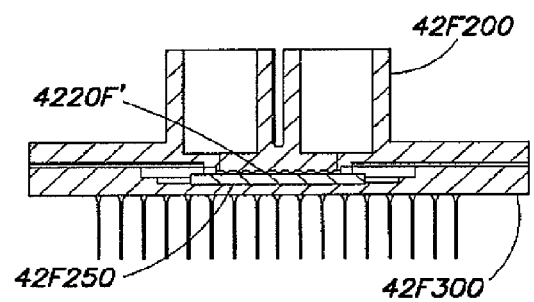
FIG. 42F3
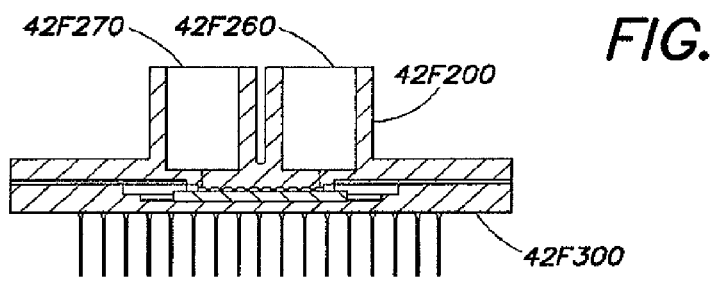
FIG. 42F4
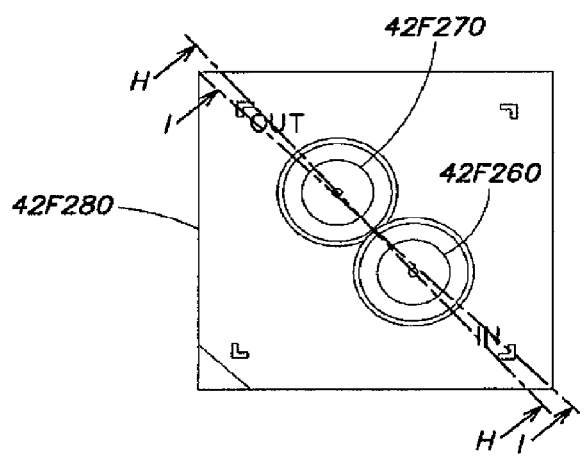
FIG. 42F5

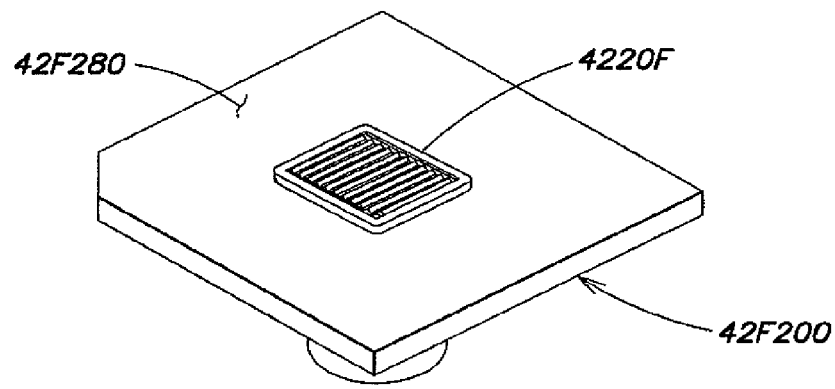
FIG. 42F6
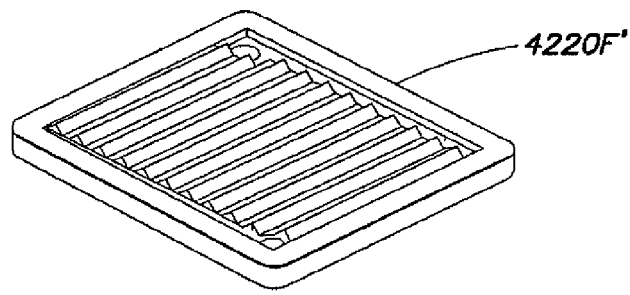
FIG. 42F7
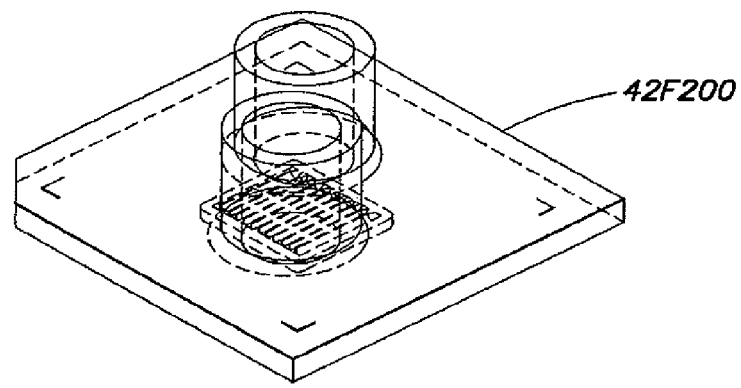
FIG. 42F8

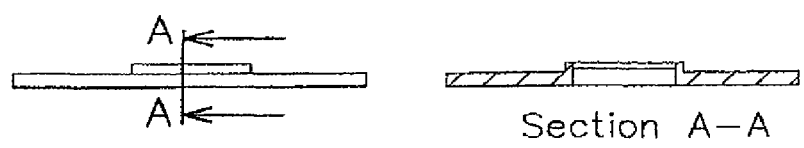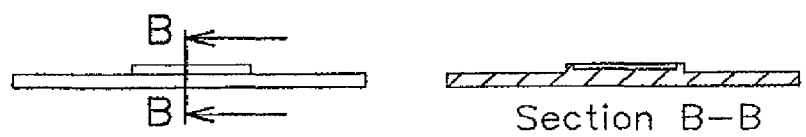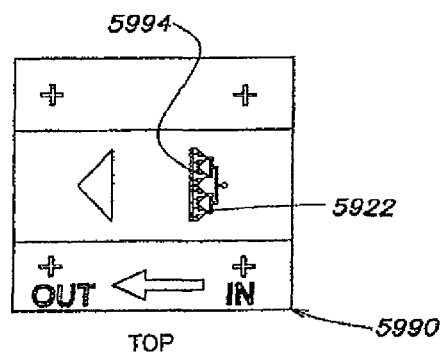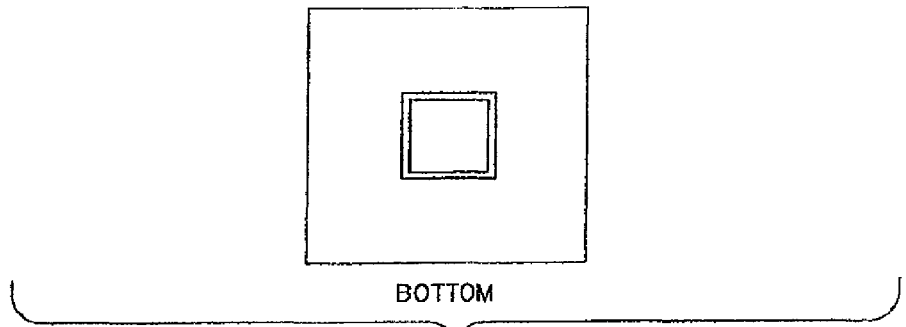
FIG. 59C

METHODS AND APPARATUS FOR DETECTING MOLECULAR INTERACTIONS USING FET ARRAYS

RELATED APPLICATIONS

This application is a continuation of U.S. application Ser. No. 13/229,456 filed Sep. 9, 2011, which is a continuation of U.S. application Ser. No. 12/492,844 (now Issued U.S. Pat. No. 8,349,167) filed Jun. 26, 2009, which claims priority to U.S. provisional application No. 61/133,204 filed Jun. 26, 2008; said application Ser. No. 13/229,456 is a continuation-in-part of U.S. application Ser. No. 12/002,781 (now Issued U.S. Pat. No. 8,262,900) filed Dec. 17, 2007, and claims priority to and is a continuation-in-part of U.S. application Ser. No. 12/002,291 filed Dec. 14, 2007 (now Issued U.S. Pat. No. 7,948,015), both of which claim priority to U.S. provisional application No. 60/870,073 filed Dec. 14, 2006, U.S. provisional application No. 60/948,748 filed Jul. 10, 2007, and U.S. provisional application No. 60/956,324 filed Aug. 16, 2007, all of which disclosures are herein incorporated by reference in their entirety.

FIELD OF THE DISCLOSURE

The present disclosure is directed generally to inventive methods and apparatus relating to detection and measurement of one or more analytes.

BACKGROUND OF THE INVENTION

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as ISFET (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20, which publication is hereby incorporated herein by reference (hereinafter referred to as "Bergveld").

FIG. 1 illustrates a cross-section of a p-type (p-channel) ISFET 50 fabricated using a conventional CMOS (Complimentary Metal Oxide Semiconductor) process. However, biCMOS (i.e., bipolar and CMOS) processing may also be used, such as a process that would include a PMOS FET array with bipolar structures on the periphery. Taking the CMOS example, P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate 64 is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

Like a MOSFET, the operation of an ISFET is based on the modulation of charge concentration caused by a MOS (Metal-Oxide-Semiconductor) capacitance constituted by the polysilicon gate 64, the gate oxide 65 and the region 60 of the n-type well 54 between the source and the drain. When a negative voltage is applied across the gate and source regions ($V_{GS}$<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential $V_{GS}$ is negative enough to attract holes from the source into the channel. The gate-source potential at which the channel 63 begins to conduct current is referred to as the transistor's threshold voltage $V_{TH}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

In the ISFET 50 of FIG. 1, the n-type well 54 (transistor body), via the body connection 62, is forced to be biased at a same potential as the source 56 (i.e., $V_{SB}$=0 Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a non-linear relationship, and is commonly referred to as the "body effect," which in many applications is undesirable.

As also shown in FIG. 1, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device; i.e., the presence of—analytes such as ions in an "analyte solution" 74 (i.e., a solution containing analytes (including ions) of interest or being tested for the presence of analytes of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in the analyte solution 74, whereas passivation layers comprising polyvinyl chloride containing valinomycin provide sensitivity to potassium ion concentration in the analyte solution 74. Materials suitable for passivation layers and sensitive to other ions such as sodium, silver, iron, bromine, iodine, calcium, and nitrate, for example, are known.

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution 74 in proximity to the sensitive area 78). This surface potential in turn affects the threshold voltage $V_{TH}$ of the ISFET; thus, it is the threshold voltage $V_{TH}$ of the ISFET that varies with changes in ion concentration in the analyte solution 74 in proximity to the sensitive area 78.

FIG. 2 illustrates an electric circuit representation of the p-channel ISFET 50 shown in FIG. 1. With reference again to FIG. 1, a reference electrode 76 (a conventional Ag/AgCl electrode) in the analyte solution 74 determines the electric potential of the bulk of the analyte solution 74 itself and is analogous to the gate terminal of a conventional MOSFET, as shown in FIG. 2. In a linear or non-saturated operating region of the ISFET, the drain current $I_D$ is given as:

$$I_D = \beta\left(V_{GS} - V_{TH} - \frac{1}{2}V_{DS}\right)V_{DS}, \quad (1)$$

where $V_{DS}$ is the voltage between the drain and the source, and $\beta$ is a transconductance parameter (in units of Amps/Volts$^2$) given by:

$$\beta = \mu C_{ox}\left(\frac{W}{L}\right), \quad (2)$$

where $\mu$ represents the carrier mobility, $C_{ox}$ is the gate oxide capacitance per unit area, and the ratio W/L is the width to length ratio of the channel 63. If the reference electrode 76 provides an electrical reference or ground ($V_G=0$ Volts), and the drain current $I_D$ and the drain-to-source voltage $V_{DS}$ are kept constant, variations of the source voltage $V_S$ of the ISFET directly track variations of the threshold voltage $V_{TH}$, according to Eq. (1); this may be observed by rearranging Eq. (1) as:

$$V_S = -V_{TH} - \left(\frac{I_D}{\beta V_{DS}} + \frac{V_{DS}}{2}\right). \quad (3)$$

Since the threshold voltage $V_{TH}$ of the ISFET is sensitive to ion concentration as discussed above, according to Eq. (3) the source voltage $V_S$ provides a signal that is directly related to the ion concentration in the analyte solution 74 in proximity to the sensitive area 78 of the ISFET. More specifically, the threshold voltage $V_{TH}$ is given by:

$$V_{TH} = V_{FB} - \frac{Q_B}{C_{ox}} + 2\phi_F, \quad (4)$$

where $V_{FB}$ is the flatband voltage, $Q_B$ is the depletion charge in the silicon and $\phi_F$ is the Fermi-potential. The flatband voltage in turn is related to material properties such as workfunctions and charge accumulation. In the case of an ISFET, with reference to FIGS. 1 and 2, the flatband voltage contains terms that reflect interfaces between 1) the reference electrode 76 (acting as the transistor gate G) and the analyte solution 74; and 2) the analyte solution 74 and the passivation layer 72 in the sensitive area 78 (which in turn mimics the interface between the polysilicon gate 64 of the floating gate structure 70 and the gate oxide 65). The flatband voltage $V_{FB}$ is thus given by:

$$V_{FB} = E_{ref} - \Psi_0 + \chi_{sol} - \frac{\Phi_{Si}}{q} - \frac{Q_{ss} + Q_{ox}}{C_{ox}}, \quad (5)$$

where $E_{ref}$ is the reference electrode potential relative to vacuum, $\Psi_0$ is the surface potential that results from chemical reactions at the analyte solution/passivation layer interface (e.g., dissociation of surface groups in the passivation layer), and $\chi_{sol}$ is the surface dipole potential of the analyte solution 74. The fourth term in Eq. (5) relates to the silicon workfunction (q is the electron charge), and the last term relates to charge densities at the silicon surface and in the gate oxide. The only term in Eq. (5) sensitive to ion concentration in the analyte solution 74 is $\Psi_0$, as the ion concentration in the analyte solution 74 controls the chemical reactions (dissociation of surface groups) at the analyte solution/passivation layer interface. Thus, substituting Eq. (5) into Eq. (4), it may be readily observed that it is the surface potential $\Psi_0$ that renders the threshold voltage $V_{TH}$ sensitive to ion concentration in the analyte solution 74.

Regarding the chemical reactions at the analyte solution/passivation layer interface, the surface of a given material employed for the passivation layer 72 may include chemical groups that may donate protons to or accept protons from the analyte solution 74, leaving at any given time negatively charged, positively charged, and neutral sites on the surface of the passivation layer 72 at the interface with the analyte solution 74. A model for this proton donation/acceptance process at the analyte solution/passivation layer interface is referred to in the relevant literature as the "Site-Dissociation Model" or the "Site-Binding Model," and the concepts underlying such a process may be applied generally to characterize surface activity of passivation layers comprising various materials (e.g., metal oxides, metal nitrides, metal oxynitrides).

Using the example of a metal oxide for purposes of illustration, the surface of any metal oxide contains hydroxyl groups that may donate a proton to or accept a proton from the analyte to leave negatively or positively charged sites, respectively, on the surface. The equilibrium reactions at these sites may be described by:

$$AOH \leftrightarrows AO^- + H_s^+ \quad (6)$$

$$AOH_2^+ \leftrightarrows AOH + H_s^+ \quad (7)$$

where A denotes an exemplary metal, $H_s^+$ represents a proton in the analyte solution 74, Eq. (6) describes proton donation by a surface group, and Eq. (7) describes proton acceptance by a surface group. It should be appreciated that the reactions given in Eqs. (6) and (7) also are present and need to be considered in the analysis of a passivation layer comprising metal nitrides, together with the equilibrium reaction:

$$ANH_3^+ \leftrightarrows ANH_2 + H^+, \quad (7b)$$

wherein Eq. (7b) describes another proton acceptance equilibrium reaction. For purposes of the present discussion however, again only the proton donation and acceptance reactions given in Eqs. (6) and (7) are initially considered to illustrate the relevant concepts.

Based on the respective forward and backward reaction rate constants for each equilibrium reaction, intrinsic dissociation constants $K_a$ (for the reaction of Eq. (6)) and $K_b$ (for the reaction of Eq. (7)) may be calculated that describe the equilibrium reactions. These intrinsic dissociation constants in turn may be used to determine a surface charge density $\sigma_0$ (in units of Coulombs/unit area) of the passivation layer 72 according to:

$$\sigma_0 = -qB, \qquad (8)$$

where the term B denotes the number of negatively charged surface groups minus the number of positively charged surface groups per unit area, which in turn depends on the total number of proton donor/acceptor sites per unit area $N_S$ on the passivation layer surface, multiplied by a factor relating to the intrinsic dissociation constants $K_a$ and $K_b$ of the respective proton donation and acceptance equilibrium reactions and the surface proton activity (or $pH_S$). The effect of a small change in surface proton activity ($pH_S$) on the surface charge density is given by:

$$\frac{\partial \sigma_0}{\partial pH_S} = -q \frac{\partial B}{\partial pH_S} = -q\beta_{int}, \qquad (19)$$

where $\beta_{int}$ is referred to as the "intrinsic buffering capacity" of the surface. It should be appreciated that since the values of $N_S$, $K_a$ and $K_b$ are material dependent, the intrinsic buffering capacity $\beta_{int}$ of the surface similarly is material dependent.

The fact that ionic species in the analyte solution 74 have a finite size and cannot approach the passivation layer surface any closer than the ionic radius results in a phenomenon referred to as a "double layer capacitance" proximate to the analyte solution/passivation layer interface. In the Gouy-Chapman-Stern model for the double layer capacitance as described in Bergveld, the surface charge density $\sigma_0$ is balanced by an equal but opposite charge density in the analyte solution 74 at some position from the surface of the passivation layer 72. These two parallel opposite charges form a so-called "double layer capacitance" $C_{dl}$ (per unit area), and the potential difference across the capacitance $C_{dl}$ is defined as the surface potential $\Psi_0$, according to:

$$\sigma_0 = C_{dl}\Psi_0 = -\sigma_{dl} \qquad (10)$$

where $\sigma_{dl}$ is the charge density on the analyte solution side of the double layer capacitance. This charge density $\sigma_{dl}$ in turn is a function of the concentration of all ion species or other analyte species (i.e., not just protons) in the bulk analyte solution 74; in particular, the surface charge density can be balanced not only by hydrogen ions but other ion species (e.g., Na$^+$, K$^+$) in the bulk analyte solution.

In the regime of relatively lower ionic strengths (e.g., <1 mole/liter), the Debye theory may be used to describe the double layer capacitance $C_{dl}$ according to:

$$C_{dl} = \frac{k\varepsilon_0}{\lambda} \qquad (11)$$

where k is the dielectric constant $\in/\in_0$ (for relatively lower ionic strengths, the dielectric constant of water may be used), and $\lambda$ is the Debye screening length (i.e., the distance over which significant charge separation can occur). The Debye length $\lambda$ is in turn inversely proportional to the square root of the strength of the ionic species in the analyte solution, and in water at room temperature is given by:

$$\lambda = \frac{0.3 \text{ nm}}{\sqrt{I}}. \qquad (12)$$

The ionic strength I of the bulk analyte is a function of the concentration of all ionic species present, and is given by:

$$I = \frac{1}{2}\sum_s z_s^2 c_s, \qquad (13)$$

where $z_s$ is the charge number of ionic species s and $c_s$ is the molar concentration of ionic species s. Accordingly, from Eqs. (10) through (13), it may be observed that the surface potential is larger for larger Debye screening lengths (i.e., smaller ionic strengths).

The relation between pH values present at the analyte solution/passivation layer interface and in the bulk solution is expressed in the relevant literature by Boltzman statistics with the surface potential $\Psi_0$ as a parameter:

$$(pH_s - pH_B) = \frac{q\Psi_0}{kT}. \qquad (14)$$

From Eqs. (9), (10) and (14), the sensitivity of the surface potential $\Psi_0$ particularly to changes in the bulk pH of the analyte solution (i.e., "pH sensitivity") is given by:

$$\frac{\Delta \Psi_0}{\Delta pH} = -2.3 \frac{kT}{q}\alpha, \qquad (15)$$

where the parameter $\alpha$ is a dimensionless sensitivity factor that varies between zero and one and depends on the double layer capacitance $C_{dl}$ and the intrinsic buffering capacity of the surface $\beta_{int}$ as discussed above in connection with Eq. (9). In general, passivation layer materials with a high intrinsic buffering capacity $\beta_{int}$ render the surface potential $\Psi_0$ less sensitive to concentration in the analyte solution 74 of ionic species other than protons (e.g., $\alpha$ is maximized by a large $\beta_{int}$). From Eq. (15), at a temperature T of 298 degrees Kelvin, it may be appreciated that a theoretical maximum pH sensitivity of 59.2 mV/pH may be achieved at $\alpha$=1. From Eqs. (4) and (5), as noted above, changes in the ISFET threshold voltage $V_{TH}$ directly track changes in the surface potential $\Psi_0$; accordingly, the pH sensitivity of an ISFET given by Eq. (15) also may be denoted and referred to herein as $\Delta V_{TH}$ for convenience. In exemplary conventional ISFETs employing a silicon nitride or silicon oxynitride passivation layer 72 for pH-sensitivity, pH sensitivities $\Delta V_{TH}$ (i.e., a change in threshold voltage with change in pH of the analyte solution 74) over a range of approximately 30 mV/pH to 60 mV/pH have been observed experimentally.

Another noteworthy metric in connection with ISFET pH sensitivity relates to the bulk pH of the analyte solution 74 at which there is no net surface charge density $\sigma_0$ and, accordingly, a surface potential $\Psi_0$ of zero volts. This pH is referred to as the "point of zero charge" and denoted as $pH_{pzc}$. With reference again to Eqs. (8) and (9), like the intrinsic buffering capacity $\beta_{int}$, $pH_{pzc}$ is a material dependent parameter. From the foregoing, it may be appreciated that the surface potential at any given bulk $pH_B$ of the analyte solution 74 may be calculated according to:

$$\Psi_0(pH_B) = (pH_B - pH_{pzc})\frac{\Delta\Psi_0}{\Delta pH}. \quad (16)$$

Table 1 below lists various metal oxides and metal nitrides and their corresponding points of zero charge ($pH_{pzc}$), pH sensitivities ($\Delta V_{TH}$), and theoretical maximum surface potential at a pH of 9:

TABLE 1

| Metal | Oxide/Nitride | $pH_{pzc}$ | $\Delta V_{TH}$ (mV/pH) | Theoretical $\Psi_0$ (mV) @ pH = 9 |
|---|---|---|---|---|
| Al | Al$_2$O$_3$ | 9.2 | 54.5 (35° C.) | −11 |
| Zr | ZrO$_2$ | 5.1 | 50 | 150 |
| Ti | TiO$_2$ | 5.5 | 57.4-62.3 (32° C., pH 3-11) | 201 |
| Ta | Ta$_2$O$_5$ | 2.9, 2.8 | 62.87 (35° C.) | 384 |
| Si | Si$_3$N$_4$ | 4.6, 6-7 | 56.94 (25° C.) | 251 |
| Si | SiO$_2$ | 2.1 | 43 | 297 |
| Mo | MoO$_3$ | 1.8-2.1 | 48-59 | 396 |
| W | WO$_2$ | 0.3, 0.43, 0.5 | 50 | 435 |

Prior research efforts to fabricate ISFETs for pH measurements based on conventional CMOS processing techniques typically have aimed to achieve high signal linearity over a pH range from 1-14. Using an exemplary threshold sensitivity of approximately 50 mV/pH, and considering Eq. (3) above, this requires a linear operating range of approximately 700 mV for the source voltage $V_S$. As discussed above in connection with FIG. 1, the threshold voltage $V_{TH}$ of ISFETs (as well as MOSFETs) is affected by any voltage $V_{SB}$ between the source and the body (n-type well 54). More specifically, the threshold voltage $V_{TH}$ is a nonlinear function of a nonzero source-to-body voltage $V_{SB}$. Accordingly, so as to avoid compromising linearity due to a difference between the source and body voltage potentials (i.e., to mitigate the "body effect"), as shown in FIG. 1 the source 56 and body connection 62 of the ISFET 50 often are coupled to a common potential via the metal contact 68. This body-source coupling also is shown in the electric circuit representation of the ISFET 50 shown in FIG. 2.

While the foregoing discussion relates primarily to a steady state analysis of ISFET response based on the equilibrium reactions given in Eqs. (6) and (7), the transient or dynamic response of a conventional ISFET to an essentially instantaneous change in ionic strength of the analyte solution 74 (e.g., a stepwise change in proton or other ionic species concentration) has been explored in some research efforts. One exemplary treatment of ISFET transient or dynamic response is found in "ISFET responses on a stepwise change in electrolyte concentration at constant pH," J. C. van Kerkof, J. C. T. Eijkel and P. Bergveld, *Sensors and Actuators* 8, 18-19 (1994), pp. 56-59, which is incorporated herein by reference.

For ISFET transient response, a stepwise change in the concentration of one or more ionic species in the analyte solution in turn essentially instantaneously changes the charge density $\sigma_{dl}$ on the analyte solution side of the double layer capacitance $C_{dl}$. Because the instantaneous change in charge density $\sigma_{dl}$ is faster than the reaction kinetics at the surface of the passivation layer 72, the surface charge density $\sigma_0$ initially remains constant, and the change in ion concentration effectively results in a sudden change in the double layer capacitance $C_{dl}$. From Eq. (10), it may be appreciated that such a sudden change in the capacitance $C_{dl}$ at a constant surface charge density $\sigma_0$ results in a corresponding sudden change in the surface potential $\Psi_0$. FIG. 2A illustrates this phenomenon, in which an essentially instantaneous or stepwise increase in ion concentration in the analyte solution, as shown in the top graph, results in a corresponding change in the surface potential $\Psi_0$, as shown in the bottom graph of FIG. 2A. After some time, as the passivation layer surface groups react to the stimulus (i.e., as the surface charge density adjusts), the system returns to some equilibrium point, as illustrated by the decay of the ISFET response "pulse" 79 shown in the bottom graph of FIG. 2A. The foregoing phenomenon is referred to in the relevant literature (and hereafter in this disclosure) as an "ion-step" response.

As indicated in the bottom graph of FIG. 2A, an amplitude $\Delta\Psi_0$ of the ion-step response 79 may be characterized by:

$$\Delta\Psi_0 = \Psi_1 - \Psi_2 = \frac{\sigma_0}{C_{dl,1}} - \frac{\sigma_0}{C_{dl,2}} = \Psi_1\left(1 - \frac{C_{dl,1}}{C_{dl,2}}\right), \quad (17)$$

where $\Psi_1$ is an equilibrium surface potential at an initial ion concentration in the analyte solution, $C_{dl,1}$ is the double layer capacitance per unit area at the initial ion concentration, $\Psi_2$ is the surface potential corresponding to the ion-step stimulus, and $C_{dl,2}$ is the double layer capacitance per unit area based on the ion-step stimulus. The time decay profile 81 associated with the response 79 is determined at least in part by the kinetics of the equilibrium reactions at the analyte solution/passivation layer interface (e.g., as given by Eqs. (6) and (7) for metal oxides, and also Eq. (7b) for metal nitrides). One instructive treatment in this regard is provided by "Modeling the short-time response of ISFET sensors," P. Woias et al., *Sensors and Actuators B*, 24-25 (1995) 211-217 (hereinafter referred to as "Woias"), which publication is incorporated herein by reference.

In the Woias publication, an exemplary ISFET having a silicon nitride passivation layer is considered. A system of coupled non-linear differential equations based on the equilibrium reactions given by Eqs. (6), (7), and (7a) is formulated to describe the dynamic response of the ISFET to a step (essentially instantaneous) change in pH; more specifically, these equations describe the change in concentration over time of the various surface species involved in the equilibrium reactions, based on the forward and backward rate constants for the involved proton acceptance and proton donation reactions and how changes in analyte pH affect one or more of the reaction rate constants. Exemplary solutions, some of which include multiple exponential functions and associated time constants, are provided for the concentration of each of the surface ion species as a function of time. In one example provided by Woias, it is assumed that the proton donation reaction given by Eq. (6) dominates the transient response of the silicon nitride passivation layer surface for relatively small step changes in pH, thereby facilitating a mono-exponential approximation for the time decay profile 81 of the response 79 according to:

$$\Psi_0(t) = \Delta\Psi_0 e^{t/\tau}, \quad (18)$$

where the exponential function essentially represents the change in surface charge density as a function of time. In Eq. (16), the time constant $\tau$ is both a function of the bulk pH and material parameters of the passivation layer, according to:

$$\tau = \tau_0 \times 10^{pH/2}, \quad (19)$$

where $\tau_0$ denotes a theoretical minimum response time that only depends on material parameters. For silicon nitride, Woias provides exemplary values for $\tau_0$ on the order of 60 microseconds to 200 microseconds. For purposes of providing an illustrative example, using $\tau_0$=60 microseconds and a bulk pH of 9, the time constant $\tau$ given by Eq. (19) is 1.9 seconds. Exemplary values for other types of passivation materials may be found in the relevant literature and/or determined empirically.

Previous efforts to fabricate two-dimensional arrays of ISFETs based on the ISFET design of FIG. 1 have resulted in a maximum of 256 ISFET sensor elements (or "pixels") in an array (i.e., a 16 pixel by 16 pixel array). Exemplary research in ISFET array fabrication is reported in the publications "A large transistor-based sensor array chip for direct extracellular imaging," M. J. Milgrew, M. O. Riehle, and D. R. S. Cumming, *Sensors and Actuators, B: Chemical,* 111-112, (2005), pp. 347-353, and "The development of scalable sensor arrays using standard CMOS technology," M. J. Milgrew, P. A. Hammond, and D. R. S. Cumming, *Sensors and Actuators, B: Chemical,* 103, (2004), pp. 37-42, which publications are incorporated herein by reference and collectively referred to hereafter as "Milgrew et al." Other research efforts relating to the realization of ISFET arrays are reported in the publications "A very large integrated pH-ISFET sensor array chip compatible with standard CMOS processes," T. C. W. Yeow, M. R. Haskard, D. E. Mulcahy, H. I. Seo and D. H. Kwon, *Sensors and Actuators B: Chemical,* 44, (1997), pp. 434-440 and "Fabrication of a two-dimensional pH image sensor using a charge transfer technique," Ilizawa, T., Sawada, K., Takao, H., Ishida, M., *Sensors and Actuators, B: Chemical* 117 (2), 2006, pp. 509-515, which publications also are incorporated herein by reference.

FIG. 3 illustrates one column $85_j$ of a two-dimensional ISFET array according to the design of Milgrew et al. The column $85_j$ includes sixteen (16) pixels $80_1$ through $80_{16}$ and, as discussed further below in connection with FIG. 7, a complete two-dimensional array includes sixteen (16) such columns $85_j$ (j=1, 2, 3, . . . 16) arranged side by side. As shown in FIG. 3, a given column $85_j$ includes a current source $I_{SOURCEj}$ that is shared by all pixels of the column, and ISFET bias/readout circuitry $82_j$ (including current sink $I_{SINKj}$) that is also shared by all pixels of the column. Each ISFET pixel $80_1$ through $80_{16}$ includes a p-channel ISFET 50 having an electrically coupled source and body (as shown in FIGS. 1 and 2), plus two switches S1 and S2 that are responsive to one of sixteen row select signals ($RSEL_1$ through $RSEL_{16}$, and their complements). As discussed below in connection with FIG. 7, a row select signal and its complement are generated simultaneously to "enable" or select a given pixel of the column $85_j$, and such signal pairs are generated in some sequence to successively enable different pixels of the column one at a time.

As shown in FIG. 3, the switch S2 of each pixel 80 in the design of Milgrew et al. is implemented as a conventional n-channel MOSFET that couples the current source $I_{SOURCEj}$ to the source of the ISFET 50 upon receipt of the corresponding row select signal. The switch S1 of each pixel 80 is implemented as a transmission gate, i.e., a CMOS pair including an n-channel MOSFET and a p-channel MOSFET, that couples the source of the ISFET 50 to the bias/readout circuitry $82_j$ upon receipt of the corresponding row select signal and its complement. An example of the switch $S1_1$ of the pixel $80_1$ is shown in FIG. 4, in which the p-channel MOSFET of the transmission gate is indicated as $S1_{1P}$ and the n-channel MOSFET is indicated as $S1_{1N}$. In the design of Milgrew et al., a transmission gate is employed for the switch S1 of each pixel so that, for an enabled pixel, any ISFET source voltage within the power supply range $V_{DD}$ to $V_{SS}$ may be applied to the bias/readout circuitry $82_j$ and output by the column as the signal $V_{Sj}$. From the foregoing, it should be appreciated that each pixel 80 in the ISFET sensor array design of Milgrew et al. includes four transistors, i.e., a p-channel ISFET, a CMOS-pair transmission gate including an n-channel MOSFET and a p-channel MOSFET for switch S1, and an n-channel MOSFET for switch S2.

As also shown in FIG. 3, the bias/readout circuitry $82_j$ employs a source-drain follower configuration in the form of a Kelvin bridge to maintain a constant drain-source voltage $V_{DSj}$ and isolate the measurement of the source voltage $V_{Sj}$ from the constant drain current $I_{SOURCEj}$ for the ISFET of an enabled pixel in the column $85_j$. To this end, the bias/readout circuitry $82_j$ includes two operational amplifiers A1 and A2, a current sink $I_{SINKj}$, and a resistor $R_{SDj}$. The voltage developed across the resistor $R_{SDj}$ due to the current $I_{SINKj}$ flowing through the resistor is forced by the operational amplifiers to appear across the drain and source of the ISFET of an enabled pixel as a constant drain-source voltage $V_{DSj}$. Thus, with reference again to Eq. (3), due to the constant $V_{DSj}$ and the constant $I_{SOURCEj}$, the source voltage $V_{Sj}$ of the ISFET of the enabled pixel provides a signal corresponding to the ISFETs threshold voltage $V_{TH}$, and hence a measurement of pH in proximity to the ISFETs sensitive area (see FIG. 1). The wide dynamic range for the source voltage $V_{Sj}$ provided by the transmission gate S1 ensures that a full range of pH values from 1-14 may be measured, and the source-body connection of each ISFET ensures sufficient linearity of the ISFETs threshold voltage over the full pH measurement range.

In the column design of Milgrew et al. shown in FIG. 3, it should be appreciated that for the Kelvin bridge configuration of the column bias/readout circuitry $82_j$ to function properly, a p-channel ISFET 50 as shown in FIG. 1 must be employed in each pixel; more specifically, an alternative implementation based on the Kelvin bridge configuration is not possible using an n-channel ISFET. With reference again to FIG. 1, for an n-channel ISFET based on a conventional CMOS process, the n-type well 54 would not be required, and highly doped n-type regions for the drain and source would be formed directly in the p-type silicon substrate 52 (which would constitute the transistor body). For n-channel FET devices, the transistor body typically is coupled to electrical ground. Given the requirement that the source and body of an ISFET in the design of Milgrew et al. are electrically coupled together to mitigate nonlinear performance due to the body effect, this would result in the source of an n-channel ISFET also being connected to electrical ground (i.e., $V_S=V_B=0$ Volts), thereby precluding any useful output signal from an enabled pixel. Accordingly, the column design of Milgrew et al. shown in FIG. 3 requires p-channel ISFETs for proper operation.

It should also be appreciated that in the column design of Milgrew et al. shown in FIG. 3, the two n-channel MOSFETs required to implement the switches S1 and S2 in each pixel cannot be formed in the n-type well 54 shown in FIG. 1, in which the p-channel ISFET for the pixel is formed; rather, the n-channel MOSFETs are formed directly in the p-type silicon substrate 52, beyond the confines of the n-type well 54 for the ISFET. FIG. 5 is a diagram similar to FIG. 1, illustrating a wider cross-section of a portion of the p-type silicon substrate 52 corresponding to one pixel 80 of the column 85j shown in FIG. 3, in which the n-type well 54 containing the drain 58, source 56 and body connection 62 of the ISFET 50 is shown alongside a first n-channel MOSFET corresponding to the switch S2 and a second n-channel MOSFET S1$_{1N}$ constituting one of the two transistors of the transmission gate S1$_1$ shown in FIG. 4.

Furthermore, in the design of Milgrew et al., the p-channel MOSFET required to implement the transmission gate S1 in each pixel (e.g., see S1$_{1P}$ in FIG. 4) cannot be formed in the same n-type well in which the p-channel ISFET 50 for the pixel is formed. In particular, because the body and source of the p-channel ISFET are electrically coupled together, implementing the p-channel MOSFET S1$_{1P}$ in the same n-well as the p-channel ISFET 50 would lead to unpredictable operation of the transmission gate, or preclude operation entirely. Accordingly, two separate n-type wells are required to implement each pixel in the design of Milgrew et al. FIG. 6 is a diagram similar to FIG. 5, showing a cross-section of another portion of the p-type silicon substrate 52 corresponding to one pixel 80, in which the n-type well 54 corresponding to the ISFET 50 is shown alongside a second n-type well 55 in which is formed the p-channel MOSFET S1$_{1P}$ constituting one of the two transistors of the transmission gate S1$_1$ shown in FIG. 4. It should be appreciated that the drawings in FIGS. 5 and 6 are not to scale and may not exactly represent the actual layout of a particular pixel in the design of Milgrew et al.; rather these figures are conceptual in nature and are provided primarily to illustrate the requirements of multiple n-wells, and separate n-channel MOSFETs fabricated outside of the n-wells, in the design of Milgrew et al.

The array design of Milgrew et al. was implemented using a 0.35 micrometer (μm) conventional CMOS fabrication process. In this process, various design rules dictate minimum separation distances between features. For example, according to the 0.35 μm CMOS design rules, with reference to FIG. 6, a distance "a" between neighboring n-wells must be at least three (3) micrometers. A distance "a/2" also is indicated in FIG. 6 to the left of the n-well 54 and to the right of the n-well 55 to indicate the minimum distance required to separate the pixel 80 shown in FIG. 6 from neighboring pixels in other columns to the left and right, respectively. Additionally, according to typical 0.35 μm CMOS design rules, a distance "b" shown in FIG. 6 representing the width in cross-section of the n-type well 54 and a distance "c" representing the width in cross-section of the n-type well 55 are each on the order of approximately 3 μm to 4 μm (within the n-type well, an allowance of 1.2 μm is made between the edge of the n-well and each of the source and drain, and the source and drain themselves have a width on the order of 0.7 μm). Accordingly, a total distance "d" shown in FIG. 6 representing the width of the pixel 80 in cross-section is on the order of approximately 12 μm to 14 μm. In one implementation, Milgrew et al. report an array based on the column/pixel design shown in FIG. 3 comprising geometrically square pixels each having a dimension of 12.8 μm by 12.8 μm.

In sum, the ISFET pixel design of Milgrew et al. is aimed at ensuring accurate hydrogen ion concentration measurements over a pH range of 1-14. To ensure measurement linearity, the source and body of each pixel's ISFET are electrically coupled together. To ensure a full range of pH measurements, a transmission gate S1 is employed in each pixel to transmit the source voltage of an enabled pixel. Thus, each pixel of Milgrew's array requires four transistors (p-channel ISFET, p-channel MOSFET, and two n-channel MOSFETs) and two separate n-wells (FIG. 6). Based on a 0.35 micrometer conventional CMOS fabrication process and corresponding design rules, the pixels of such an array have a minimum size appreciably greater than 10 μm, i.e., on the order of approximately 12 μm to 14 μm.

FIG. 7 illustrates a complete two-dimensional pixel array 95 according to the design of Milgrew et al., together with accompanying row and column decoder circuitry and measurement readout circuitry. The array 95 includes sixteen columns 85$_1$ through 85$_{16}$ of pixels, each column having sixteen pixels as discussed above in connection with FIG. 3 (i.e., a 16 pixel by 16 pixel array). A row decoder 92 provides sixteen pairs of complementary row select signals, wherein each pair of row select signals simultaneously enables one pixel in each column 85$_1$ through 85$_{16}$ to provide a set of column output signals from the array 95 based on the respective source voltages V$_{S1}$ through V$_{S16}$ of the enabled row of ISFETs. The row decoder 92 is implemented as a conventional four-to-sixteen decoder (i.e., a four-bit binary input ROW$_1$-ROW$_4$ to select one of $2^4$ outputs). The set of column output signals V$_{S1}$ through V$_{S16}$ for an enabled row of the array is applied to switching logic 96, which includes sixteen transmission gates S1 through S16 (one transmission gate for each output signal). As above, each transmission gate of the switching logic 96 is implemented using a p-channel MOSFET and an n-channel MOSFET to ensure a sufficient dynamic range for each of the output signals V$_{S1}$ through V$_{S16}$. The column decoder 94, like the row decoder 92, is implemented as a conventional four-to-sixteen decoder and is controlled via the four-bit binary input COL$_1$-COL$_4$ to enable one of the transmission gates S1 through S16 of the switching logic 96 at any given time, so as to provide a single output signal V$_S$ from the switching logic 96. This output signal V$_S$ is applied to a 10-bit analog to digital converter (ADC) 98 to provide a digital representation D$_1$-D$_{10}$ of the output signal V$_S$ corresponding to a given pixel of the array.

As noted earlier, individual ISFETs and arrays of ISFETs similar to those discussed above have been employed as sensing devices in a variety of chemical and biological applications. In particular, ISFETs have been employed as pH sensors in the monitoring of various processes involving nucleic acids such as DNA. Some examples of employing ISFETs in various life-science related applications are given in the following publications, each of which is incorporated herein by reference: Massimo Barbaro, Annalisa Bonfiglio, Luigi Raffo, Andrea Alessandrini, Paolo Facci and Imrich Barák, "Fully electronic DNA hybridization detection by a standard CMOS biochip," *Sensors and Actuators B: Chemical*, Volume 118, Issues 1-2, 2006, pp. 41-46; Toshinari Sakurai and Yuzuru Husimi, "Real-time monitoring of DNA polymerase reactions by a micro ISFET pH sensor," *Anal. Chem.*, 64(17), 1992, pp 1996-1997; S. Purushothaman, C. Toumazou, J. Georgiou, "Towards fast solid state DNA sequencing," *Circuits and Systems*, vol. 4, 2002, pp. IV-169 to IV-172; S. Purushothaman, C. Toumazou, C. P. Ou, "Protons and single nucleotide polymorphism detection: A simple use for the Ion Sensitive Field Effect Transistor," *Sensors and Actuators B: Chemical*, Vol. 114, no. 2, 2006, pp. 964-968; A. L. Simonian, A. W. Flounders, J. R. Wild, "FET-Based Biosensors for The Direct Detection of Organophosphate Neurotoxins," *Electroanalysis*, Vol. 16, No. 22, 2004, pp. 1896-1906; C. Toumazou, S. Purushothaman, "Sensing Apparatus and Method," United States Patent Application 2004-0134798, published Jul. 15, 2004; and T. W. Koo, S. Chan, X. Su, Z. Jingwu, M. Yamakawa, V. M. Dubin, "Sensor Arrays and Nucleic Acid Sequencing Applications," United States Patent Application 2006-0199193, published Sep. 7, 2006.

SUMMARY OF THE INVENTION

The invention relates in part to the use of chemically-sensitive FETs (i.e., chemFETs), more particularly chemFET arrays, and even more particularly large chemFET arrays (e.g., those comprising 256 FETs or sensors) for monitoring biological and/or chemical processes or reactions, including without limitation molecular interactions for the purpose of detecting analytes in a sample. These sensors may be used to detect and measure static and/or dynamic levels or concentrations of a variety of analytes (e.g., hydrogen or other ions, non-ionic molecules or compounds, nucleic acids, proteins, polysaccharides, small chemical compounds such as chemical combinatorial library members, and the like). Analytes may be naturally occurring or non-naturally occurring, whether synthesized in vivo or in vitro. Analytes may be used as markers of a reaction or interaction, or progression thereof.

Reactions, processes or interactions that may be monitored according to the invention include without limitation those occurring in cell or tissue cultures, those occurring between molecular entities such as receptor-ligand interactions, antibody-antigen interactions, nucleic acid-nucleic acid interactions, neural cell stimulation and/or triggering, interactions of cells or tissues with agents such as pharmaceutical candidate agents, and the like.

Samples may also be monitored according to the invention for the presence of analytes. Such samples may be naturally occurring or non-naturally occurring, including without limitation bodily samples to be analyzed for diagnostic, prognostic and/or therapeutic purposes, chemical or biological libraries to be screened for the presence of agents with particular structural or functional attributes, etc. Samples are typically liquid (or are dissolved in a liquid) and of small volume, and therefore are amenable to high-speed, high-density analysis such as analyte detection.

Accordingly, various embodiments of the present disclosure are directed generally to inventive methods and apparatuses that employ chemFETs and chemFET arrays, including large chemFET arrays (e.g., those that comprise 256 FETs or sensors, as the terms are used interchangeably herein) for measuring one or more analytes. FET arrays by definition include at least two FETs. An ISFET, as discussed above, is a particular type of chemFET that is configured for ion detection. It is to be understood that ISFETs may be employed in various embodiments disclosed herein. Other types of chemFETs contemplated by the present disclosure include enzyme FETs (EnFETs) which employ enzymes to detect analytes. It should be appreciated, however, that the present disclosure is not limited to ISFETs and EnFETs, but more generally relates to any FET that is configured to detect one or more analytes or one or more interactions. Typically, in these arrays, one or more chemFET-containing elements or "pixels" constituting the sensors are configured to monitor one or more independent biological or chemical reactions or events occurring in proximity to the pixels of the array.

In some exemplary implementations, individual chemFETs or chemFET arrays may be coupled to one or more microfluidics structures that form one or more reaction chambers, or "wells" or "microwells," over individual sensors or groups of sensors (in the case of an array), and optionally to an apparatus that delivers samples to the reaction chambers and removes them from the reaction chambers between measurements. Even when reaction chambers are not employed (and therefore the volume above the sensors is continuous), the sensor array may be coupled to one or more microfluidics structures for the delivery of samples or agents to the pixels and for removal of samples, agents and/or analytes between measurements. Accordingly, inventive aspects of this disclosure, which are desired to be protected, include the various microfluidic structures which may be employed to flow samples and where appropriate other agents useful in for example the detection and measurement of analytes to and from the wells or pixels, methods and structures for coupling the arrayed wells with arrayed pixels, and the like.

Thus, in various aspects, the invention provides an apparatus comprising a chemFET array having disposed on its surface a biological array or a chemical array. The biological array may be a nucleic acid array, a protein array including but not limited to an enzyme array, an antibody array and an antibody fragment array, a cell array, and the like. The chemical array may be an organic molecule array, or an inorganic molecule array, and the like. The biological array or chemical array may be arranged into a plurality of "cells" or spatially defined regions, and each of these regions is situated over a different sensor in the chemFET array, in some embodiments.

In another aspect, the invention provides a method for detecting a nucleic acid comprising contacting a nucleic acid array disposed on a chemFET array with a sample, and detecting binding of a nucleic acid from the sample to one or more regions on the nucleic acid array.

In another aspect, the invention provides a method for detecting a protein comprising contacting a protein array disposed on a chemFET array with a sample, and detecting binding of a protein from the sample to one or more regions on the protein array.

In another aspect, the invention provides a method for detecting a nucleic acid comprising contacting a protein array disposed on a chemFET array with a sample, and detecting binding of a nucleic acid from the sample to one or more regions on the protein array.

In another aspect, the invention provides a method for detecting an antigen comprising contacting an antibody array disposed on a chemFET array with a sample, and detecting binding of an antigen from the sample to one or more regions on the antibody array.

In another aspect, the invention provides a method for detecting an enzyme substrate or inhibitor comprising contacting an enzyme array disposed on a chemFET array with a sample, and detecting binding of an entity from the sample to one or more regions on the enzyme array.

In another aspect, the invention provides a method for detecting an analyte in a sample comprising contacting a sample to a plurality of biological or chemical agents attached to a chemFET array, and analyzing electrical output from a plurality of chemFET sensors in the chemFET array after contact with the sample, wherein electrical output from a chemFET sensor after contact with the sample indicates binding of an analyte to the biological or chemical agent attached to the array.

As noted above, the sample may be from a naturally occurring source (e.g., a subject) and optionally it may be a bodily fluid. It may comprise cells, nucleic acids, proteins (including glycoproteins, antibodies, etc.), polysaccharides, and the like.

In various embodiments, the plurality of biological or chemical agents is a plurality of proteins, or a plurality of nucleic acids, or it may be a mixture of proteins and nucleic acids. The biological or chemical agents may be non-naturally occurring or naturally-occurring, and if naturally-occurring may be synthesized in vivo or in vitro. The plurality of biological or chemical agents may be a homogenous plurality of biological or chemical agents. In other embodiments, the plurality of biological or chemical agents is not homogeneous.

In one embodiment, the analyte is present in the sample. In another embodiment, the analyte is generated following contact of the sample with the chemFET array or with other reagents in the solution in contact with the chemFET array.

In still other embodiments, each chemFET sensor in the chemFET array is coupled to a reaction chamber.

In another aspect, the invention provides a method for monitoring a biological or chemical process comprising exposing a first agent to a second agent in proximity to a chemFET sensor, and measuring an electrical output at the chemFET sensor after exposure of the first agent to the second agent, wherein an electrical output at the chemFET sensor after exposure of the first agent to the second agent indicates an interaction between the first agent and the second agent, and wherein the chemFET sensor is present in a chemFET array having at least 2 chemFET sensors.

In another aspect, the invention provides a method for monitoring a biological or chemical process comprising exposing a first agent to a second agent in proximity to a chemFET sensor, and measuring an electrical output at the chemFET sensor after exposure of the first agent to the second agent, wherein an electrical output at the chemFET sensor after exposure of the first agent to the second agent indicates an interaction between the first agent and the second agent, wherein the chemFET sensor is present in a chemFET array having at least 2 chemFET sensors, and wherein each chemFET sensor is coupled to a separate reaction chamber.

In another aspect, the invention provides an apparatus comprising nucleic acids or a plurality of nucleic acids attached to a chemFET array comprising $10^4$ chemFETs.

In another aspect, the invention provides an apparatus comprising a protein or a plurality of proteins attached to a chemFET comprising $10^4$ chemFETs.

In another aspect, the invention provides an apparatus comprising a peptide or a plurality of peptides attached to a chemFET array comprising $10^4$ chemFET sensors.

In various embodiments, the chemFET is coupled to a reaction chamber array.

In still another aspect, the invention provides an apparatus comprising a cell culture disposed on a chemFET or a chemFET array.

In still another aspect, the invention provides an apparatus comprising a nucleic acid array disposed on a chemFET array, optionally comprising a coupled array of reaction chambers.

In still another aspect, the invention provides an apparatus comprising a nucleic acid array comprising a plurality of nucleic acids bound to physically defined regions of a solid support disposed on a chemFET array. In one embodiment, each of the physically defined regions is associated with at least one chemFET in the array. In one embodiment, the nucleic acid array comprises a plurality of reaction chambers. In one embodiment, each physically defined region is associated with a single reaction chamber.

It is to be understood that any of the chemFET arrays described herein may comprise 3, 4, 5, 6, 7, 8, 9, 10, 11, 12, 13, 14, 15, 16, 17, 18, 19, 20, 50, 100, 200, 300, 400, 500, $10^3$, $10^4$, $10^5$, $10^6$, $10^7$, or more chemFET sensors. In some embodiments, the chemFET array comprises 104 chemFET or more than 104 chemFET. When used, reaction chamber arrays that are in contact with or capacitively coupled to chemFET arrays similarly may comprise 3, 4, 5, 6, 7, 8, 9, 10, 11, 12, 13, 14, 15, 16, 17, 18, 19, 20, 50, 100, 200, 300, 400, 500, $10^3$, $10^4$, $10^5$, $10^6$, $10^7$, or more reaction chambers. It is also to be understood that, as used herein particularly with respect to arrays, an array that comprises, for example, 5 elements (such as sensors or reaction chambers) has at least 5 elements and may have more. An array that comprises more than, for example, 5 elements has at least 6 elements and may have more. It is further intended that aspects and embodiments described herein that "comprise" elements and/or steps also fully support and embrace aspects and embodiments that "consist of" or "consist essentially of" such elements and/or steps.

In some embodiments, the center-to-center distance between adjacent sensors and/or adjacent reaction chambers is about 1-10 µm, about 1-9 µm, or about 2-9 µm, about 1 µm, about 2 µm, about 3 µm, about 4 µm, about 5 µm, about 6 µm, about 7 µm, about 8 µm, or about 9 µm.

In one embodiment the plurality of nucleic acids is homogeneous, while in another embodiment the plurality of nucleic acids is not homogeneous. In one embodiment, the nucleic acid has a length of less than 1000 bases in length, or the plurality of nucleic acid has an average length of less than 1000 bases in length.

In one embodiment, the nucleic acid or the plurality of nucleic acids is single stranded. In another embodiment, the nucleic acid or the plurality of nucleic acids is double stranded.

In one embodiment, the nucleic acid or the plurality of nucleic acids is DNA, RNA, miRNA, or cDNA. In another embodiment, the nucleic acid or the plurality of nucleic acids is an aptamer.

In various embodiments, the protein is an antibody or an antigen-binding antibody fragment, a tyrosine kinase receptor, a transcription factor, a hormone, or an enzyme.

In one embodiment, the nucleic acid or the protein is attached covalently to the chemFET array. In another embodiment, the nucleic acid or the protein is attached non-covalently to the chemFET array.

In other embodiments, the analyte of interest is hydrogen ion, and/or the ISFET arrays are specifically configured to measure changes in $H^+$ concentration (i.e., changes in pH).

In other embodiments, biological or chemical reactions may be monitored, and the chemFET arrays may be specifically configured to measure hydrogen ions and/or one or more other analytes that provide relevant information relating to the occurrence and/or progress of a particular biological or chemical process of interest.

Various embodiments may be embraced in the various foregoing aspects of the invention and these are recited below once for convenience and brevity.

In various embodiments, the chemFET comprises a silicon nitride passivation layer. In some embodiments, the chemFET comprises a passivation layer attached to inorganic pyrophosphate (PPi) receptors. The chemFET may comprise a passivation layer that is or is not attached (whether covalently or non-covalently) to a nucleic acid or a protein or a polysaccharide.

In some embodiments, each reaction chamber is in contact or is capacitively coupled with a single chemFET.

In some embodiments, the reaction chamber has a volume of equal to or less than about 1 picoliter (pL), including less than 0.5 pL, less than 0.1 pL, less than 0.05 pL, less than 0.01 pL, less than 0.005 pL.

In some embodiments, the chemFET array comprises equal rows and columns of sensors such as 512 rows and 512 columns of sensors, although it not so limited.

The reaction chambers may have a square cross section, for example at their base or bottom. Examples include an 8 µm by 8 µm cross section, a 4 µm by 4 µm cross section, or a 1.5 µm by 1.5 µm cross section. Alternatively, they may have a rectangular cross section, for example at their base or bottom. Examples include an 8 µm by 12 µm cross section, a 4 µm by 6 µm cross section, or a 1.5 µm by 2.25 µm cross section.

In various aspects, the chemFET arrays may be fabricated using conventional CMOS (or biCMOS or other suitable) processing technologies, and are particularly configured to facilitate the rapid acquisition of data from the entire array (scanning all of the pixels to obtain corresponding pixel output signals).

With respect to analyte detection and measurement, it should be appreciated that in various embodiments discussed herein, one or more analytes measured by a chemFET array according to the present disclosure may include any of a variety of biological or chemical substances that provide relevant information regarding a biological or chemical process (e.g., binding events such as hybridization of nucleic acids to each other, antigen-antibody binding, receptor-ligand binding, enzyme-inhibitor binding, enzyme-substrate binding, and the like). In some aspects, the ability to measure absolute or relative as well as static and/or dynamic levels and/or concentrations of one or more analytes, in addition to merely determining the presence or absence of an analyte, provides valuable information in connection with biological and chemical processes. In other aspects, mere determination of the presence or absence of an analyte or analytes of interest may provide valuable information may be sufficient.

A chemFET array according to various inventive embodiments of the present disclosure may be configured for sensitivity to any one or more of a variety of analytes. In one embodiment, one or more chemFETs of an array may be particularly configured for sensitivity to one or more analytes, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one embodiment, the first and second analytes may be related to each other. As an example, the first and second analytes may be byproducts of the same biological or chemical reaction/process and therefore they may be detected concurrently to confirm the occurrence of a reaction (or lack thereof). Such redundancy is preferred in some analyte detection methods. Of course, it should be appreciated that more than two different types of chemFETs may be employed in any given array to detect and/or measure different types of analytes, and optionally to monitor biological or chemical processes such as binding events. In general, it should be appreciated in any of the embodiments of sensor arrays discussed herein that a given sensor array may be "homogeneous" and thereby consist of chemFETs of substantially similar or identical type that detect and/or measure the same analyte (e.g., pH or other ion concentration), or a sensor array may be "heterogeneous" and include chemFETs of different types to detect and/or measure different analytes. In another embodiment, the sensors in an array may be configured to detect and/or measure a single type (or class) of analyte even though the species of that type (or class) detected and/or measured may be different between sensors. As an example, all the sensors in an array may be configured to detect and/or measure nucleic acids, but each sensor detects and/or measures a different nucleic acid.

The invention has specifically improved upon the ISFET array design of Milgrew et al. discussed above in connection with FIGS. 1-7, as well as other conventional ISFET array designs, so as to significantly reduce pixel size, and thereby increase the number of pixels of a chemFET array for a given semiconductor die size (i.e., increase pixel density). In various embodiments, this increase in pixel density is accomplished while at the same time increasing the signal-to-noise ratio (SNR) of output signals corresponding to monitored biological and chemical processes, and the speed with which such output signals may be read from the array. In particular, it has been recognized and appreciated that by relaxing requirements for chemFET linearity and focusing on a more limited measurement output signal range (e.g., output signals corresponding to a pH range of from approximately 7 to 9 or smaller, rather than 1 to 14, as well as output signals that do not necessarily relate significantly to pH), individual pixel complexity and size may be significantly reduced, thereby facilitating the realization of very large scale dense chemFET arrays. It has also been recognized and appreciated that alternative less complex approaches to pixel selection in an chemFET array (e.g., alternatives to the row and column decoder approach employed in the design of Milgrew et al. as shown in FIG. 7, whose complexity scales with array size), as well as various data processing techniques involving ISFET response modeling and data extrapolation based on such modeling, facilitate rapid acquisition of data from significantly large and dense arrays.

With respect to chemFET array fabrication, it has been further recognized and appreciated that various techniques employed in a conventional CMOS fabrication process, as well as various post-fabrication processing steps (wafer handling, cleaning, dicing, packaging, etc.), may in some instances adversely affect performance of the resulting chemFET array. For example, with reference again to FIG. 1, one potential issue relates to trapped charge that may be induced in the gate oxide 65 during etching of metals associated with the floating gate structure 70, and how such trapped charge may affect chemFET threshold voltage $V_{TH}$. Another potential issue relates to the density/porosity of the chemFET passivation layer (e.g., see ISFET passivation layer 72 in FIG. 1) resulting from low-temperature material deposition processes commonly employed in aluminum metal-based CMOS fabrication. While such low-temperature processes generally provide an adequate passivation layer for conventional CMOS devices, they may result in a somewhat low-density and porous passivation layer which may be potentially problematic for chemFETs in contact with an analyte solution; in particular, a low-density porous passivation layer over time may absorb and become saturated with analytes or other substances in the solution, which may in turn cause an undesirable time-varying drift in the chemFETs threshold voltage $V_{TH}$. This phenomenon may in turn impede accurate measurements of one or more particular analytes of interest. In view of the foregoing, other inventive embodiments disclosed herein relate to methods and apparatuses which mitigate potentially adverse effects on chemFET performance that may arise from various aspects of fabrication and post-fabrication processing/handling of chemFET arrays.

Accordingly, one embodiment of the present invention is directed to an apparatus, comprising an array of CMOS-fabricated sensors, each sensor comprising one chemFET (and in some cases, consisting of one chemFET but optionally having other elements) and occupying an area on a surface of the array of 10 µm² or less.

Another embodiment is directed to a sensor array comprising a two-dimensional array of electronic sensors including at least 512 rows and at least 512 columns of the electronic sensors, each sensor comprising one chemFET (and in some cases, consisting of one chemFET but optionally having other elements) configured to provide at least one output signal representing a presence and/or concentration of an analyte proximate to a surface of the two-dimensional array.

Another embodiment is directed to an apparatus comprising an array of CMOS-fabricated sensors, each sensor comprising one chemFET (and in some cases, consisting of one chemFET but optionally having other elements). The array of CMOS-fabricated sensors includes more than 256 sensors, and a collection of chemFET output signals from all chemFETs of the array constitutes a frame of data. The apparatus further comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second.

Another embodiment is directed to an apparatus comprising an array of CMOS-fabricated sensors, each sensor comprising a chemFET (and in some cases, consisting of one chemFET but optionally having other elements). The chemFET comprises a floating gate structure, and a source and a drain having a first semiconductor type and fabricated in a region having a second semiconductor type, wherein there is no electrical conductor that electrically connects the region having the second semiconductor type to either the source or the drain.

Another embodiment is directed to an apparatus comprising an array of electronic sensors, each sensor consisting of three FETs including one chemFET.

Another embodiment is directed to an apparatus comprising an array of electronic sensors, each sensor comprising three or fewer FETs, wherein the three or fewer FETs includes one chemFET.

Another embodiment is directed to an apparatus comprising an array of electronic sensors, each sensor comprising a plurality of FETs including one chemFET, and a plurality of electrical conductors electrically connected to the plurality of FETs, wherein the plurality of FETs are arranged such that the plurality of electrical conductors includes no more than four conductors traversing an area occupied by each sensor and interconnecting multiple sensors of the array.

Another embodiment is directed to an apparatus comprising an array of CMOS-fabricated sensors, each sensor comprising a plurality of FETs including one chemFET, wherein all of the FETs in each sensor are of a same channel type and are implemented in a single semiconductor region of an array substrate.

Another embodiment is directed to a sensor array comprising a plurality of electronic sensors arranged in a plurality of rows and a plurality of columns. Each sensor comprises one chemFET configured to provide at least one and in some instances at least two output signals representing a presence and/or a concentration of an analyte proximate to a surface of the array. For each column of the plurality of columns, the array further comprises column circuitry configured to provide a constant drain current and a constant drain-to-source voltage to respective chemFETs in the column, the column circuitry including two operational amplifiers and a diode-connected FET arranged in a Kelvin bridge configuration with the respective chemFETs to provide the constant drain-to-source voltage.

Another embodiment is directed to a sensor array, comprising a plurality of electronic sensors arranged in a plurality of rows and a plurality of columns. Each sensor comprises one chemFET configured to provide at least one output signal and in some instances at least two output signals representing a concentration of ions in a solution proximate to a surface of the array. The array further comprises at least one row select shift register to enable respective rows of the plurality of rows, and at least one column select shift register to acquire chemFET output signals from respective columns of the plurality of columns.

Another embodiment is directed to an apparatus, comprising an array of CMOS-fabricated sensors, each sensor comprising a chemFET. The chemFET comprises a floating gate structure, and a source and a drain having a first semiconductor type and fabricated in a region having a second semiconductor type, wherein there is no electrical conductor that electrically connects the region having the second semiconductor type to either the source or the drain. The array includes a two-dimensional array of at least 512 rows and at least 512 columns of the CMOS-fabricated sensors. Each sensor consists of three FETs including the chemFET, and each sensor includes a plurality of electrical conductors electrically connected to the three FETs. The three FETs are arranged such that the plurality of electrical conductors includes no more than four conductors traversing an area occupied by each sensor and interconnecting multiple sensors of the array. All of the FETs in each sensor are of a same channel type and implemented in a single semiconductor region of an array substrate. A collection of chemFET output signals from all chemFETs of the array constitutes a frame of data. The apparatus further comprises control circuitry coupled to the array and configured to generate at least one array output signal to provide multiple frames of data from the array at a frame rate of at least 20 frames per second.

Another embodiment is directed to a method for processing an array of CMOS-fabricated sensors, each sensor comprising a chemFET. The method comprises a) dicing a semiconductor wafer including the array to form at least one diced portion including the array, and b) performing a forming gas anneal on the at least one diced portion.

Another embodiment is directed to a method for manufacturing an array of chemFETs. The method comprises fabricating an array of chemFETs, depositing on the array a dielectric material, applying a forming gas anneal to the array before a dicing step, dicing the array, and applying a forming gas anneal after the dicing step. The method may further comprise testing the semiconductor wafer between one or more deposition steps.

Another embodiment is directed to a method for processing an array of CMOS-fabricated sensors. Each sensor comprises a chemFET having a chemically-sensitive passivation layer of silicon nitride and/or silicon oxynitride deposited via plasma enhanced chemical vapor deposition (PECVD). The method comprises depositing at least one additional passivation material on the chemically-sensitive passivation layer so as to reduce a porosity and/or increase a density of the passivation layer.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

FIG. 5 is a diagram similar to FIG. 1, illustrating a wider cross-section of a portion of a substrate corresponding to one pixel of the array column shown in FIG. 3, in which the ISFET is shown alongside two n-channel MOSFETs also included in the pixel.

FIG. 6 is a diagram similar to FIG. 5, illustrating a cross-section of another portion of the substrate corresponding to one pixel of the array column shown in FIG. 3, in which the ISFET is shown alongside the p-channel MOSFET of the transmission gate shown in FIG. 4.

FIG. 11A-1 shows a composite cross-sectional view of multiple neighboring pixels, along the line I-I of one of the pixels shown in FIG. 10A, including additional elements of the pixel between the lines II-II, illustrating a layer-by-layer view of pixel fabrication according to another inventive embodiment of the present disclosure.

FIGS. 11B(1)-(3) provide the chemical structures of ten PPi receptors (compounds 1 through 10).

FIG. 11C(1) is a schematic of a synthesis protocol for compound 7 from FIG. 11B(3).

FIG. 11C(2) is a schematic of a synthesis protocol for compound 8 from FIG. 11B(3).

FIG. 11C(3) is a schematic of a synthesis protocol for compound 9 from FIG. 11B(3).

FIGS. 11D(1) and (2) are schematics illustrating a variety of chemistries that can be applied to the passivation layer in order to bind molecular recognition compounds (such as but not limited to PPi receptors).

FIGS. 12A1 through 12A12 provide top views of each of the fabrication layers shown in FIG. 11A, according to one inventive embodiment of the present disclosure.

FIGS. 12B1 through 12B12 provide top views of each of the fabrication layers shown in FIG. 11A-1, according to another inventive embodiment of the present disclosure.

FIG. 20A illustrates a top view of a chip layout design for a pixel of the chemFET array shown in FIG. 20, according to another inventive embodiment of the present disclosure.

FIG. 33B-1 is an image from a scanning electron microscope showing in cross-section a portion of an array architecture as taught herein, with microwells formed in a layer of silicon dioxide over ISFETs.

FIG. 33B-2 is a diagrammatic illustration of a microwell in cross-section, the microwell being produced as taught herein and having sloped sides, and showing how a bead of a correspondingly appropriate diameter larger than that of the well bottom can be spaced from the well bottom by interference with the well sidewalls.

FIG. 33B-3 is another diagrammatic illustration of such a microwell with beads of different diameters shown, and indicating optional use of packing beads below the nucleic acid-carrying bead such as a DNA-carrying bead FIGS. 34-37 diagrammatically illustrate a first example of a suitable experiment apparatus incorporating a fluidic interface with the sensor array, with FIG. 35 providing a cross-section through the FIG. 34 apparatus along section line 35-35' and FIG. 36 expanding part of FIG. 35, in perspective, and FIG. 37 further expanding a portion of the structure to make the fluid flow more visible.

FIGS. 42-54 (but not including FIGS. 42A-42L) and 57-58 are pairs of partly isometric, sectional views of example apparatus and enlargements, showing ways of introducing a reference electrode into, and forming, a flow cell and flow chamber, using materials such as plastic and PDMS.

FIG. 42F1 is a diagrammatic illustration of an example of a ceiling baffle arrangement for a flow cell in which fluid is introduced at one corner of the chip and exits at a diagonal corner, the baffle arrangement facilitating a desired fluid flow across the array.

FIGS. 42F2-42F8 comprise a set of illustrations of an exemplary flow cell member that may be manufactured by injection molding and may incorporate baffles to facilitate fluid flow, as well as a metalized surface for serving as a reference electrode, including an illustration of said member mounted to a sensor array package over a sensor array, to form a flow chamber thereover.

FIGS. 59A-59C are illustrations of the pieces for two examples of two-piece injection molded parts for forming a flow cell.

DETAILED DESCRIPTION OF THE INVENTION

Figure 1:
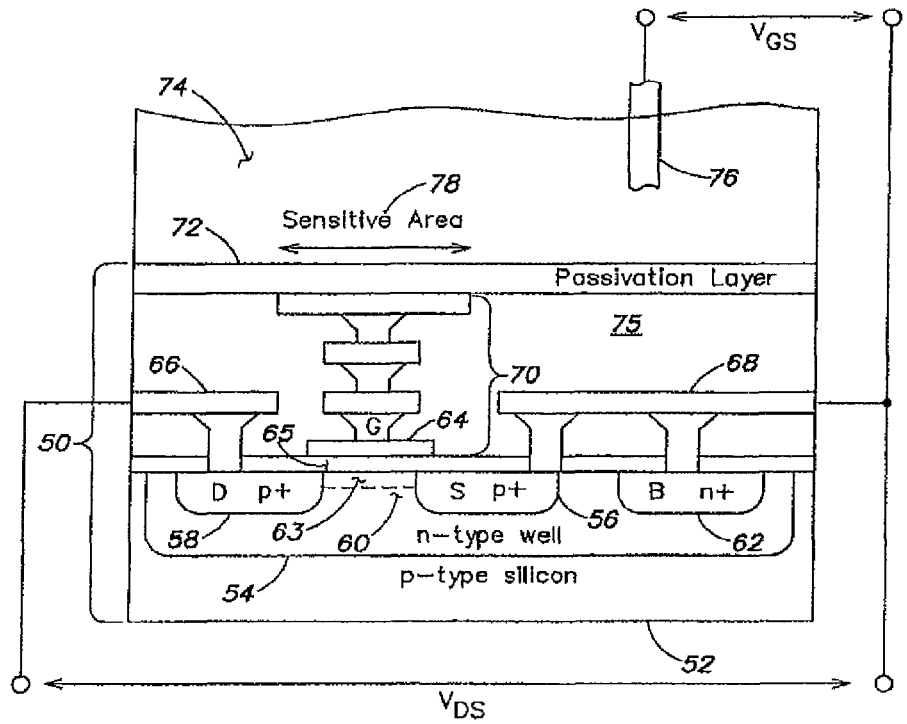
FIG. 1 illustrates a cross-section of a p-type (p-channel) ion-sensitive field effect transistor (ISFET) fabricated using a conventional CMOS process.

Following below are more detailed descriptions of various concepts related to, and embodiments of, inventive methods and apparatus relating to large scale chemFET arrays for detection and/or measurement or analytes. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Various inventive embodiments according to the present disclosure are directed at least in part to a semiconductor-based/microfluidic hybrid system that combines the power of microelectronics with the biocompatibility of a microfluidic system. In some examples below, the microelectronics portion of the hybrid system is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein.

One embodiment disclosed herein is directed to a large sensor array of chemFETs, wherein the individual chemFET sensor elements or "pixels" of the array are configured to detect analyte presence (or absence), analyte levels (or amounts), and/or analyte concentration in an unmanipulated sample, or as a result of chemical and/or biological processes (e.g., chemical reactions, cell cultures, neural activity, nucleic acid sequencing processes, etc.) occurring in proximity to the array. Examples of chemFETs contemplated by various embodiments discussed in greater detail below include, but are not limited to, ISFETs and EnFETs. In one exemplary implementation, one or more microfluidic structures is/are fabricated above the chemFET sensor array to provide for containment and/or confinement of a biological or chemical reaction in which an analyte of interest may be produced or consumed, as the case may be. For example, in one implementation, the microfluidic structure(s) may be configured as one or more "wells" (e.g., small reaction chambers or "reaction wells") disposed above one or more sensors of the array, such that the one or more sensors over which a given well is disposed detect and measure analyte presence, level, and/or concentration in the given well.

In important aspects and embodiments, the chemFET array comprises 104 chemFET and/or the center-to-center spacing between adjacent chemFETs is 1-10 μm.

In another exemplary implementation, the invention encompasses a system for high-throughput sequencing comprising at least one two-dimensional array of reaction chambers, wherein each reaction chamber is coupled to a chemFET and each reaction chamber is no greater than 10 μm$^3$ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least 100, 1,000, 10,000, 100,000, or 1,000,000 reaction chambers. The reaction chambers may be capacitively coupled to the chemFETs, and preferably are capacitively coupled to the chemFETs.

The device may comprise an array of chemFETs with an array of microfluidic reaction chambers and/or a semiconductor material coupled to a dielectric material.

The above-described method may be automated via robotics. In addition, the information obtained via the signal from the chemFET may be provided to a personal computer, a personal digital assistant, a cellular phone, a video game system, or a television so that a user can monitor the progress of reactions remotely.

In some embodiments, such a chemFET array/microfluidics hybrid structure may be used to analyze solution(s)/material(s) of interest potentially containing analytes such as nucleic acids. For example, such structures may be employed to monitor sequencing of nucleic acids. Detection and/or sequencing of analytes such as nucleic acids may be performed to determine partial or complete nucleotide sequence of a nucleic acid, to detect the presence and in some instances nature of a single nucleotide polymorphism in a nucleic acid, to determine what therapeutic regimen will be most effective to treat a subject having a particular condition as can be determined by the subject's genetic make-up, to determine and compare nucleic acid expression profiles of two or more states (e.g., comparing expression profiles of diseased and normal tissue, or comparing expression profiles of untreated tissue and tissue treated with drug, enzymes, radiation or chemical treatment), to haplotype a sample (e.g., comparing genes or variations in genes on each of the two alleles present in a human subject), to karyotype a sample (e.g., analyzing chromosomal make-up of a cell or a tissue such as an embryo, to detect gross chromosomal or other genomic abnormalities), and to genotype (e.g., analyzing one or more genetic loci to determine for example carrier status and/or species-genus relationships).

The systems described herein can also be used to aid in the identification and treatment of disease. For example, the system can be used for identifying a sequence associated with a particular disease or for identifying a sequence associated with a positive response to a particular active ingredient.

In one embodiment, the invention encompasses a method for identifying a sequence associated with a condition comprising delivering nucleic acids from a plurality of subjects having the condition to a sequencing apparatus comprising a two-dimensional array of reaction chambers, wherein each of the reaction chambers is capacitively coupled to a chemFET, determining sequences of the nucleic acids from signal from said chemFETs, and identifying a common sequence between the DNA from the plurality of subjects. Preferably, the subject is a mammal, and more preferably a human. Preferably, the condition is cancer, an immunosuppressant condition, a neurological condition, or a viral infection.

In another embodiment, the invention encompasses a method for identifying a sequence associated with a positive response to a particular active agent, comprising sequencing DNA from a plurality of subjects that have exhibited a positive response and from a plurality of subjects having a negative response to an active agent using one or more sequencing apparatuses, wherein each sequencing apparatus comprises an array of chemFETs; and identifying a common DNA sequence in the plurality of subjects that have exhibited a positive response or from the subjects that have exhibited a negative response that is not present in the other plurality of subjects. Preferably, the subject is a mammal, and more preferably a human.

It should be appreciated, however, that while some illustrative examples of the concepts disclosed herein focus on nucleic acid processing, the invention contemplates a broader application of these concepts and is not intended to be limited to these examples.

Figure 8:
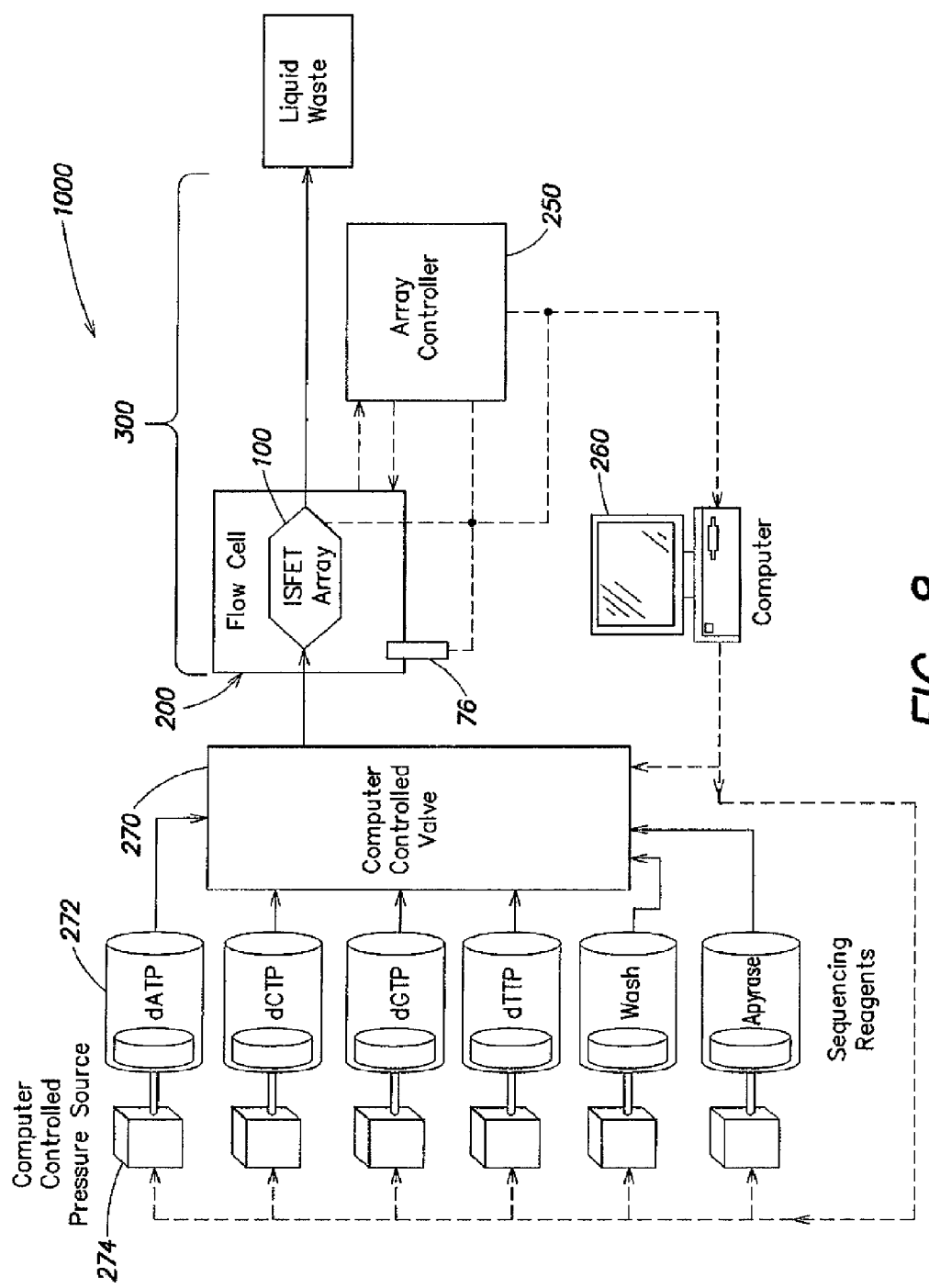
FIG. 8 generally illustrates a nucleic acid processing system comprising a large scale chemFET array, according to one inventive embodiment of the present disclosure.

FIG. 8 generally illustrates a nucleic acid processing system 1000 comprising a large scale chemFET array, according to one inventive embodiment of the present disclosure. An example of a nucleic acid processing system is a nucleic acid sequencing system. In the discussion that follows, the chemFET sensors of the array are described for purposes of illustration as ISFETs configured for sensitivity to static and/or dynamic ion concentration, including but not limited to hydrogen ion concentration and/or concentration of other ionic species involved in nucleic acid processing. However, it should be appreciated that the present disclosure is not limited in this respect, and that in any of the embodiments discussed herein in which ISFETs are employed as an illustrative example, other types of chemFETs may be similarly employed in alternative embodiments, as discussed in further detail below. Similarly it should be appreciated that various aspects and embodiments of the invention may employ ISFETs as sensors yet detect one or more ionic species that are not hydrogen ions.

The system 1000 includes a semiconductor/microfluidics hybrid structure 300 comprising an ISFET sensor array 100 and a microfluidics flow cell 200. In one aspect, the flow cell 200 may comprise a number of wells (not shown in FIG. 8) disposed above corresponding sensors of the ISFET array 100. In another aspect, the flow cell 200 is configured to facilitate the sequencing of one or more identical template nucleic acids disposed in the flow cell via the controlled and ordered admission (or introduction) to the flow cell of a number of sequencing reagents 272 (e.g., bases dATP, dCTP, dGTP, dTTP, generically referred to herein as dNTP, divalent cations such as but not limited to $Mg^{2+}$, wash solutions, and the like).

As illustrated in FIG. 8, the admission of the sequencing reagents to the flow cell 200 may be accomplished via one or more valves 270 and one or more pumps 274 that are controlled by computer 260. A number of techniques may be used to admit (i.e., introduce) the various processing materials (i.e., solutions, samples, reaction reagents, wash solutions, and the like) to the wells of such a flow cell. As illustrated in FIG. 8, reagents including bases may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100.

In still other embodiments, the wells can be coated with one or more nucleic acids, including for example a pair of primer nucleic acids, and a nucleic acid having adaptor nucleotide sequences complementary to the primer nucleotide sequence may be introduced into the wells. These and other agents useful in immobilizing nucleic acids may be provided to the sensor array, to individual dies as part of the chip packaging, or to wells immediately before the processing of a sample. Other methods involving solgels may be used to immobilize agents such as nucleic acids near the surface of the ISFET array.

As will be discussed in greater detail herein, in some aspects contemplated by the invention, nucleic acids may be amplified prior to or after placement in the well. Various methods exist to amplify nucleic acids. Thus, in one aspect, once a nucleic acid is loaded into a well, amplification may be performed in the well, and the resulting amplified product may be further analyzed. Amplification methods include but are not limited to bridge amplification, rolling circle amplification, or other strategies using isothermal or non-isothermal amplification techniques.

In sum, the flow cell 200 in the system of FIG. 8 may be configured in a variety of manners to provide one or more analytes (or one or more reaction solutions) in proximity to the ISFET array 100. For example, a nucleic acid may be directly attached or applied in suitable proximity to one or more pixels of the sensor array 100, or on a support material (e.g., one or more "beads") located above the sensor array. Processing reagents (e.g., enzymes such as polymerases) can also be placed on the sensors directly, or on one or more solid supports in proximity to the sensors. It is to be understood that the device may be used without wells or beads for a number of biosensor applications involving the detection and/or measurement of at least one sensor-detectable product (e.g., ion concentration change).

In the system 1000 of FIG. 8, according to one embodiment the ISFET sensor array 100 monitors ionic species, and in particular, changes in the levels/amounts and/or concentration of ionic species. In some embodiments, the species are those that result from a nucleic acid synthesis or sequencing reaction. One particularly important ionic species is the PPi that is released as a result of nucleotide incorporation. Another important species is excess nucleotides added to and remaining in the reaction chamber once a nucleic acid synthesis or sequencing reaction is complete. Such nucleotides are referred to herein as "unincorporated nucleotides."

As will be discussed in greater detail herein, various embodiments of the present invention may relate to monitoring/measurement techniques that involve the static and/or dynamic responses of an ISFET. In one embodiment relating to detection of nucleotide incorporation during a nucleic acid synthesis or sequencing reaction, detection/measurement techniques particularly rely on the transient or dynamic response of an ISFET (ion-step response, or "ion pulse" output), as discussed above in connection with FIG. 2A, to detect concentration changes of various ionic species relating to a nucleic acid synthesis or sequencing reaction. Although the particular example of a nucleic acid synthesis or sequencing reaction is provided to illustrate the transient or dynamic response of an ISFET, it should be appreciated that according to other embodiments, the transient or dynamic response of an ISFET as discussed below may be exploited for monitoring/sensing other types of chemical and/or biological activity beyond the specific example of a nucleic acid synthesis or sequencing reaction.

In one exemplary implementation, beyond the step-wise or essentially instantaneous pH changes in the analyte solution contemplated by prior research efforts, detection/measurement techniques relying on the dynamic response of an ISFET according to some embodiments of the present invention are based at least in part on the differential diffusion of various ionic species proximate to the analyte/passivation layer interface of the ISFET(s) (e.g., at the bottom of a reaction well over an ISFET). In particular, it has been recognized and appreciated that if a given stimulus constituted by a change in ionic strength proximate to the analyte/passivation layer interface, due to the appropriate diffusion of respective species of interest, occurs at a rate that is significantly faster than the ability of the passivation layer to adjust its surface charge density in response to the stimulus of the concentration change (e.g., faster than a characteristic response time constant τ associated with the passivation layer surface), a step-wise or essentially instantaneous change in ionic strength is not necessarily required to observe an ion pulse output from the ISFET. This principle is applicable not only to the example of DNA sequencing, but also to other types of chemical and chemical reaction sensing, as well.

As noted above, the ISFET may be employed to measure steady state pH values, since in some embodiments pH change is proportional to the number of nucleotides incorporated into the newly synthesized nucleic acid strand. In other embodiments discussed in greater detail below, the FET sensor array may be particularly configured for sensitivity to other analytes that may provide relevant information about the chemical reactions of interest. An example of such a modification or configuration is the use of analyte-specific receptors to bind the analytes of interest, as discussed in greater detail herein.

Via an array controller 250 (also under operation of the computer 260), the ISFET array may be controlled so as to acquire data (e.g., output signals of respective ISFETs of the array) relating to analyte detection and/or measurements, and collected data may be processed by the computer 260 to yield meaningful information associated with the processing (including sequencing) of the template nucleic acid.

With respect to the ISFET array 100 of the system 1000 shown in FIG. 8, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes and/or reactions. With reference again to FIG. 1, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a base line against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

The ISFET array 100 is not limited to any particular size, as one- or two-dimensional arrays, including but not limited to as few as two to 256 pixels (e.g., 16 by 16 pixels in a two-dimensional implementation) or as many as 54 mega-pixels (e.g., 7400 by 7400 pixels in a two-dimensional implementation) or even greater may be fabricated and employed for various chemical/biological analysis purposes pursuant to the concepts disclosed herein. In one embodiment of the exemplary system shown in FIG. 8, the individual ISFET sensors of the array may be configured for sensitivity to PPi, unincorporated nucleotides, hydrogen ions, and the like; however, it should also be appreciated that the present disclosure is not limited in this respect, as individual sensors of an ISFET sensor array may be particularly configured for sensitivity to other types of ion concentrations for a variety of applications (materials sensitive to other ions such as sodium, silver, iron, bromine, iodine, calcium, and nitrate, for example, are known).

More generally, a chemFET array according to various embodiments of the present disclosure may be configured for sensitivity to any one or more of a variety of analytes. In one embodiment, one or more chemFETs of an array may be particularly configured for sensitivity to one or more analytes and/or one or more binding events, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one exemplary implementation, both a first and a second analyte may indicate a particular reaction such as for example nucleotide incorporation in a sequencing-by-synthesis method. Of course, it should be appreciated that more than two different types of chemFETs may be employed in any given array to detect and/or measure different types of analytes and/or other reactions. In general, it should be appreciated in any of the embodiments of sensor arrays discussed herein that a given sensor array may be "homogeneous" and include chemFETs of substantially similar or identical types to detect and/or measure a same type of analyte (e.g., pH or other ion concentration), or a sensor array may be "heterogeneous" and include chemFETs of different types to detect and/or measure different analytes. For simplicity of discussion, again the example of an ISFET is discussed below in various embodiments of sensor arrays, but the present disclosure is not limited in this respect, and several other options for analyte sensitivity are discussed in further detail below (e.g., in connection with FIG. 11A).

The chemFET arrays configured for sensitivity to any one or more of a variety of analytes may be disposed in electronic chips, and each chip may be configured to perform one or more different biological reactions. The electronic chips can be connected to the portions of the above-described system which read the array output by means of pins coded in a manner such that the pins convey information to the system as to characteristics of the array and/or what kind of biological reaction(s) is(are) to be performed on the particular chip.

In one embodiment, the invention encompasses an electronic chip configured for conducting biological reactions thereon, comprising one or more pins for delivering information to a circuitry identifying a characteristic of the chip and/or a type of reaction to be performed on the chip. Such t may include, but are not limited to, a short nucleotide polymorphism detection, short tandem repeat detection, or sequencing.

In another embodiment, the invention encompasses a system adapted to performing more than one biological reaction on a chip comprising: a chip receiving module adapted for receiving the chip; and a receiver for detecting information from the electronic chip, wherein the information determines a biological reaction to be performed on the chip. Typically, the system further comprises one or more reagents to perform the selected biological reaction.

In another embodiment, the invention encompasses an apparatus for sequencing a polymer template comprising: at least one integrated circuit that is configured to relay information about spatial location of a reaction chamber, type of monomer added to the spatial location, time required to complete reaction of a reagent comprising a plurality of the monomers with an elongating polymer.

In exemplary implementations based on 0.35 micrometer CMOS processing techniques (or CMOS processing techniques capable of smaller feature sizes), each pixel of the ISFET array 100 may include an ISFET and accompanying enable/select components, and may occupy an area on a surface of the array of approximately ten micrometers by ten micrometers (i.e., 100 micrometers$^2$) or less; stated differently, arrays having a pitch (center of pixel-to-center of pixel spacing) on the order of 10 micrometers or less may be realized. An array pitch on the order of 10 micrometers or less using a 0.35 micrometer CMOS processing technique constitutes a significant improvement in terms of size reduction with respect to prior attempts to fabricate ISFET arrays, which resulted in pixel sizes on the order of at least 12 micrometers or greater.

More specifically, in some embodiments discussed further below based on the inventive concepts disclosed herein, an array pitch of approximately nine (9) micrometers allows an ISFET array including over 256,000 pixels (e.g., a 512 by 512 array), together with associated row and column select and bias/readout electronics, to be fabricated on a 7 millimeter by 7 millimeter semiconductor die, and a similar sensor array including over four million pixels (e.g., a 2048 by 2048 array yielding over 4 Mega-pixels) to be fabricated on a 21 millimeter by 21 millimeter die. In other examples, an array pitch of approximately 5 micrometers allows an ISFET array including approximately 1.55 Mega-pixels (e.g., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pitch significantly below 5 micrometers may be fabricated (e.g., array pitch of 2.6 micrometers or pixel area of less than 8 or 9 micrometers$^2$), providing for significantly dense ISFET arrays. Of course, it should be appreciated that pixel sizes greater than 10 micrometers (e.g., on the order of approximately 20, 50, 100 micrometers or greater) may be implemented in various embodiments of chemFET arrays according to the present disclosure also.

As will be understood by those of skill in the art, the ability to miniaturize sequencing reactions reduces the time, cost and labor involved in sequencing of large genomes (such as the human genome).

In other aspects of the system shown in FIG. 8, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

As used herein, an array is planar arrangement of elements such as sensors or wells. The array may be one or two dimensional. A one dimensional array is an array having one column (or row) of elements in the first dimension and a plurality of columns (or rows) in the second dimension. An example of a one dimensional array is a 1×5 array. A two dimensional array is an array having a plurality of columns (or rows) in both the first and the second dimension. The number of columns (or rows) in the first and second dimensions may or may not be the same. An example of a two dimensional array is a 5×10 array.

Having provided a general overview of the role of a chemFET (e.g., ISFET) array 100 in an exemplary system 1000 for measuring one or more analytes, following below are more detailed descriptions of exemplary chemFET arrays according to various inventive embodiments of the present disclosure that may be employed in a variety of applications. Again, for purposes of illustration, chemFET arrays according to the present disclosure are discussed below using the particular example of an ISFET array, but other types of chemFETs may be employed in alternative embodiments. Also, again, for purposes of illustration, chemFET arrays are discussed in the context of nucleic acid sequencing applications, however, the invention is not so limited and rather contemplates a variety of applications for the chemFET arrays described herein.

As noted above, various inventive embodiments disclosed herein specifically improve upon the ISFET array design of Milgrew et al. discussed above in connection with FIGS. 1-7, as well as other prior ISFET array designs, so as to significantly reduce pixel size and array pitch, and thereby increase the number of pixels of an ISFET array for a given semiconductor die size (i.e., increase pixel density). In some implementations, an increase in pixel density is accomplished while at the same time increasing the signal-to-noise ratio (SNR) of output signals corresponding to respective measurements relating to one or more analytes and the speed with which such output signals may be read from the array. In particular, Applicants have recognized and appreciated that by relaxing requirements for ISFET linearity and focusing on a more limited signal output/measurement range (e.g., signal outputs corresponding to a pH range of from approximately 7 to 9 or smaller rather than 1 to 14, as well as output signals that may not necessarily relate significantly to pH changes in sample), individual pixel complexity and size may be significantly reduced, thereby facilitating the realization of very large scale dense ISFET arrays.

Figure 9:
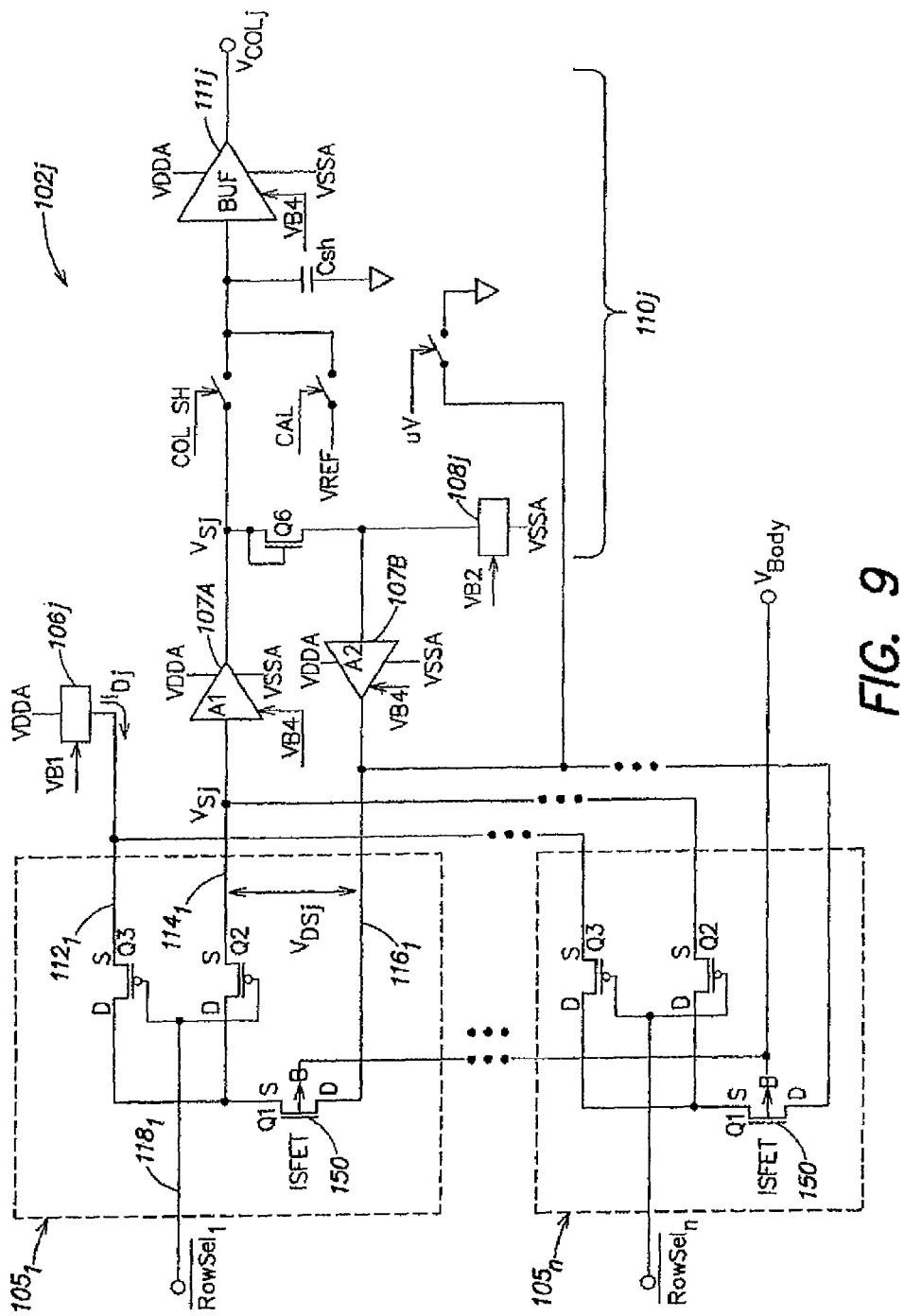
FIG. 9 illustrates one column of an chemFET array similar to that shown in FIG. 8, according to one inventive embodiment of the present disclosure.

To this end, FIG. 9 illustrates one column 102$_j$ of an ISFET array 100, according to one inventive embodiment of the present disclosure, in which ISFET pixel design is appreciably simplified to facilitate small pixel size. The column 102$_j$ includes n pixels, the first and last of which are shown in FIG. 9 as the pixels 105$_1$ and 105$_n$. As discussed further below in connection with FIG. 13, a complete two-dimensional ISFET array 100 based on the column design shown in FIG. 9 includes m such columns 102$_j$ (j=1, 2, 3, . . . m) with successive columns of pixels generally arranged side by side. Of course, the ISFETs may be arrayed in other than a row-column grid, such as in a honeycomb pattern.

In one aspect of the embodiment shown in FIG. 9, each pixel 105$_1$ through 105$_n$ of the column 102$_j$ includes only three components, namely, an ISFET 150 (also labeled as Q1) and two MOSFET switches Q2 and Q3. The MOSFET switches Q2 and Q3 are both responsive to one of n row select signals ($\overline{RowSel_1}$ through $\overline{RowSel_n}$, logic low active) so as to enable or select a given pixel of the column 102$_j$. Using pixel 105$_1$ as an example that applies to all pixels of the column, the transistor switch Q3 couples a controllable current source 106$_j$ via the line 112$_1$ to the source of the ISFET 150 upon receipt of the corresponding row select signal via the line 118$_1$. The transistor switch Q2 couples the source of the ISFET 150 to column bias/readout circuitry 110$_j$ via the line 114$_1$ upon receipt of the corresponding row select signal. The drain of the ISFET 150 is directly coupled via the line 116$_1$ to the bias/readout circuitry 110$_j$. Thus, only four signal lines per pixel, namely the lines 112$_1$, 114$_1$, 116$_1$ and 118$_1$, are required to operate the three components of the pixel 105$_1$. In an array of m columns, a given row select signal is applied simultaneously to one pixel of each column (e.g., at same positions in respective columns).

Figure 3:
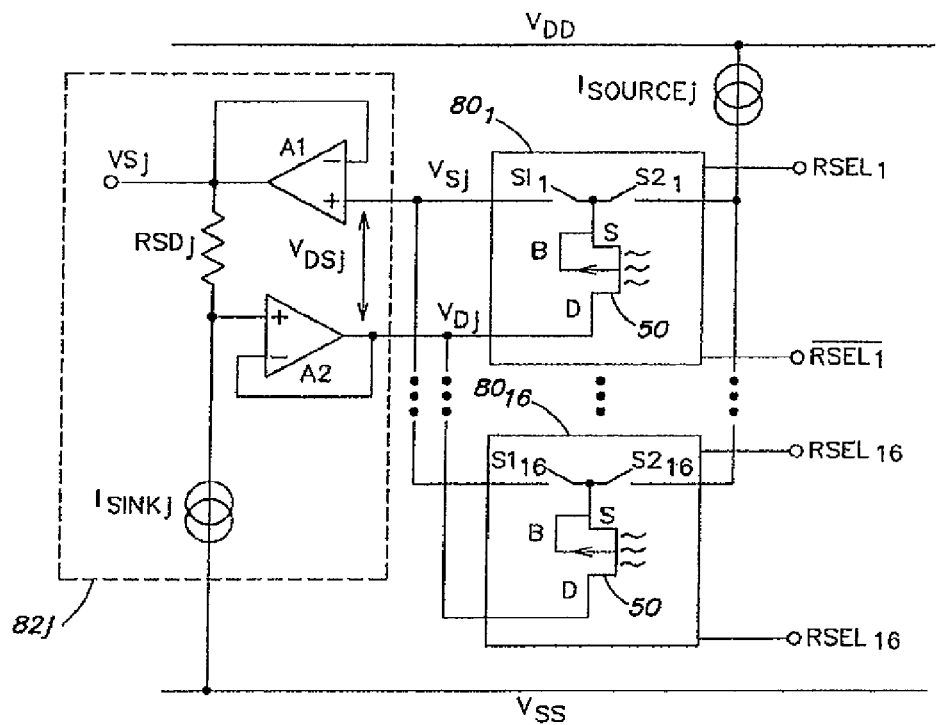
FIG. 3 illustrates one column of a two-dimensional ISFET array based on the ISFET shown in FIG. 1.

As illustrated in FIG. 9, the design for the column 102$_j$ according to one embodiment is based on general principles similar to those discussed above in connection with the column design of Milgrew et al. shown FIG. 3. In particular, the ISFET of each pixel, when enabled, is configured with a constant drain current $I_{Dj}$ and a constant drain-to-source voltage $V_{DSj}$ to obtain an output signal $V_{Sj}$ from an enabled pixel according to Eq. (3) above. To this end, the column 102$_j$ includes a controllable current source 106$_j$, coupled to an analog circuitry positive supply voltage VDDA and responsive to a bias voltage VB1, that is shared by all pixels of the column to provide a constant drain current $I_{Dj}$ to the ISFET of an enabled pixel. In one aspect, the current source 106$_j$ is implemented as a current mirror including two long-channel length and high output impedance MOSFETs. The column also includes bias/readout circuitry 110$_j$ that is also shared by all pixels of the column to provide a constant drain-to-source voltage to the ISFET of an enabled pixel. The bias/readout circuitry 110$_j$ is based on a Kelvin Bridge configuration and includes two operational amplifiers 107A (A1) and 107B (A2) configured as buffer amplifiers and coupled to analog circuitry positive supply voltage VDDA and the analog supply voltage ground VSSA. The bias/readout circuitry also includes a controllable current sink 108$_j$ (similar to the current source 106$j$) coupled to the analog ground VSSA and responsive to a bias voltage VB2, and a diode-connected MOSFET Q6. The bias voltages VB1 and VB2 are set/controlled in tandem to provide a complimentary source and sink current. The voltage developed across the diode-connected MOSFET Q6 as a result of the current drawn by the current sink 108$_j$ is forced by the operational amplifiers to appear across the drain and source of the ISFET of an enabled pixel as a constant drain-source voltage $V_{DSj}$.

By employing the diode-connected MOSFET Q6 in the bias/readout circuitry 110$_j$ of FIG. 9, rather than the resistor $R_{SDj}$ as shown in the design of Milgrew et al. illustrated in FIG. 3, a significant advantage is provided in a CMOS fabrication process; specifically, matching resistors can be fabricated with error tolerances generally on the order of ±20%, whereas MOSFET matching in a CMOS fabrication process is on the order of ±1% or better. The degree to which the component responsible for providing a constant ISFET drainto-source voltage $V_{DSj}$ can be matched from column to column significantly affects measurement accuracy (e.g., offset) from column to column. Thus, employing the MOSFET Q6 rather than a resistor appreciably mitigates measurement offsets from column-to-column. Furthermore, whereas the thermal drift characteristics of a resistor and an ISFET may be appreciably different, the thermal drift characteristics of a MOSFET and ISFET are substantially similar, if not virtually identical; hence, any thermal drift in MOSFET Q6 virtually cancels any thermal drift from ISFET Q1, resulting in greater measurement stability with changes in array temperature.

In FIG. 9, the column bias/readout circuitry 110*j* also includes sample/hold and buffer circuitry to provide an output signal $V_{COLj}$ from the column. In particular, after one of the pixels $105_1$ through $105_n$ is enabled or selected via the transistors Q2 and Q3 in each pixel, the output of the amplifier 107A (A1), i.e., a buffered $V_{Sj}$, is stored on a column sample and hold capacitor $C_{sh}$ via operation of a switch (e.g., a transmission gate) responsive to a column sample and hold signal COL SH. Examples of suitable capacitances for the sample and hold capacitor include, but are not limited to, a range of from approximately 500 fF to 2 pF. The sampled voltage is buffered via a column output buffer amplifier 111*j* (BUF) and provided as the column output signal $V_{COLj}$. As also shown in FIG. 9, a reference voltage VREF may be applied to the buffer amplifier 111*j*, via a switch responsive to a control signal CAL, to facilitate characterization of column-to-column non-uniformities due to the buffer amplifier 111*j* and thus allow post-read data correction.

Figure 9A:
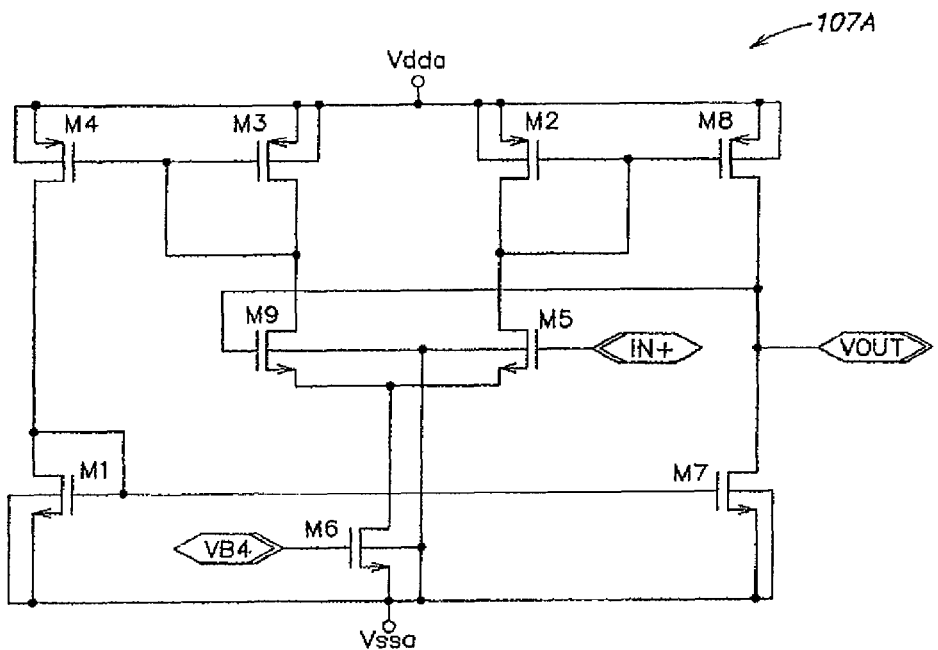
FIG. 9A illustrates a circuit diagram for an exemplary amplifier employed in the array column shown in FIG. 9.
Figure 9B:
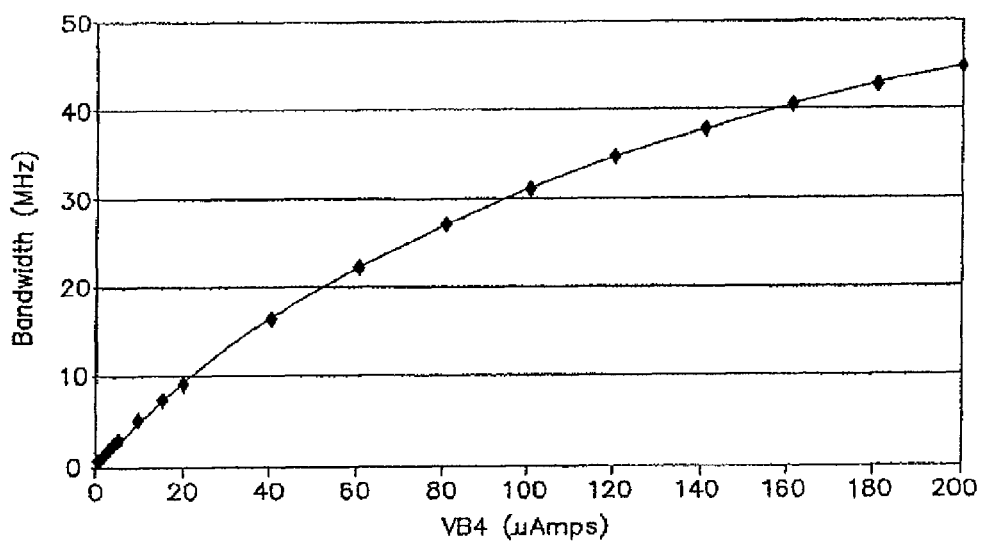
FIG. 9B is a graph of amplifier bias vs. bandwidth, according to one inventive embodiment of the present disclosure.

FIG. 9A illustrates an exemplary circuit diagram for one of the amplifiers 107A of the bias/readout circuitry 110*j* (the amplifier 107B is implemented identically), and FIG. 9B is a graph of amplifier bias vs. bandwidth for the amplifiers 107A and 107B. As shown in FIG. 9A, the amplifier 107A employs an arrangement of multiple current mirrors based on nine MOSFETs (M1 through M9) and is configured as a unity gain buffer, in which the amplifier's inputs and outputs are labeled for generality as IN+ and VOUT, respectively. The bias voltage VB4 (representing a corresponding bias current) controls the transimpedance of the amplifier and serves as a bandwidth control (i.e., increased bandwidth with increased current). With reference again to FIG. 9, due to the sample and hold capacitor $C_{sh}$, the output of the amplifier 107A essentially drives a filter when the sample and hold switch is closed. Accordingly, to achieve appreciably high data rates, the bias voltage VB4 may be adjusted to provide higher bias currents and increased amplifier bandwidth. From FIG. 9B, it may be observed that in some exemplary implementations, amplifier bandwidths of at least 40 MHz and significantly greater may be realized. In some implementations, amplifier bandwidths as high as 100 MHz may be appropriate to facilitate high data acquisition rates and relatively lower pixel sample or "dwell" times (e.g., on the order of 10 to 20 microseconds).

In another aspect of the embodiment shown in FIG. 9, unlike the pixel design of Milgrew et al. shown in FIG. 3, the pixels $105_1$ through $105_n$ do not include any transmission gates or other devices that require both n-channel and p-channel FET components; in particular, the pixels $105_1$ through $105_n$ of this embodiment include only FET devices of a same type (i.e., only n-channel or only p-channel). For purposes of illustration, the pixels $105_1$ and $105_n$ illustrated in FIG. 9 are shown as comprising only p-channel components, i.e., two p-channel MOSFETs Q2 and Q3 and a p-channel ISFET 150. By not employing a transmission gate to couple the source of the ISFET to the bias/readout circuitry 110*j*, some dynamic range for the ISFET output signal (i.e., the ISFET source voltage $V_S$) may be sacrificed. However, Applicants have recognized and appreciated that by potentially foregoing some output signal dynamic range (and thereby potentially limiting measurement range for a given static and/or dynamic chemical property, such as pH or concentration changes of other ion species), the requirement of different type FET devices (both n-channel and p-channel) in each pixel may be eliminated and the pixel component count reduced. As discussed further below in connection with FIGS. 10-12A, this significantly facilitates pixel size reduction. Thus, in one aspect, there is a beneficial tradeoff between reduced dynamic range and smaller pixel size.

In yet another aspect of the embodiment shown in FIG. 9, unlike the pixel design of Milgrew et al., the ISFET 150 of each pixel $105_1$ through $105_n$ does not have its body connection tied to its source (i.e., there is no electrical conductor coupling the body connection and source of the ISFET such that they are forced to be at the same electric potential during operation). Rather, the body connections of all ISFETs of the array are tied to each other and to a body bias voltage $V_{BODY}$. While not shown explicitly in FIG. 9, the body connections for the MOSFETs Q2 and Q3 likewise are not tied to their respective sources, but rather to the body bias voltage $V_{BODY}$. In one exemplary implementation based on pixels having all p-channel components, the body bias voltage $V_{BODY}$ is coupled to the highest voltage potential available to the array (e.g., VDDA), as discussed further below in connection with FIG. 17.

By not tying the body connection of each ISFET to its source, the possibility of some non-zero source-to-body voltage $V_{SB}$ may give rise to the "body effect," as discussed above in connection with FIG. 1, which affects the threshold voltage $V_{TH}$ of the ISFET according to a nonlinear relationship (and thus, according to Eqs. (3), (4) and (5) may affect detection and/or measurement of analyte activity giving rise to surface potential changes at the analyte/passivation layer interface). However, Applicants have recognized and appreciated that by focusing on a reduced ISFET output signal dynamic range, any body effect that may arise in the ISFET from a non-zero source-to-body voltage may be relatively minimal. Thus, any measurement nonlinearity that may result over the reduced dynamic range may be ignored as insignificant or taken into consideration and compensated (e.g., via array calibration and data processing techniques, as discussed further below in connection with FIG. 17). Applicants have also recognized and appreciated that by not tying each ISFET source to its body connection, all of the FETs constituting the pixel may share a common body connection, thereby further facilitating pixel size reduction, as discussed further below in connection with FIGS. 10-12A. Accordingly, in another aspect, there is a beneficial tradeoff between reduced linearity and smaller pixel size.

Figure 10:
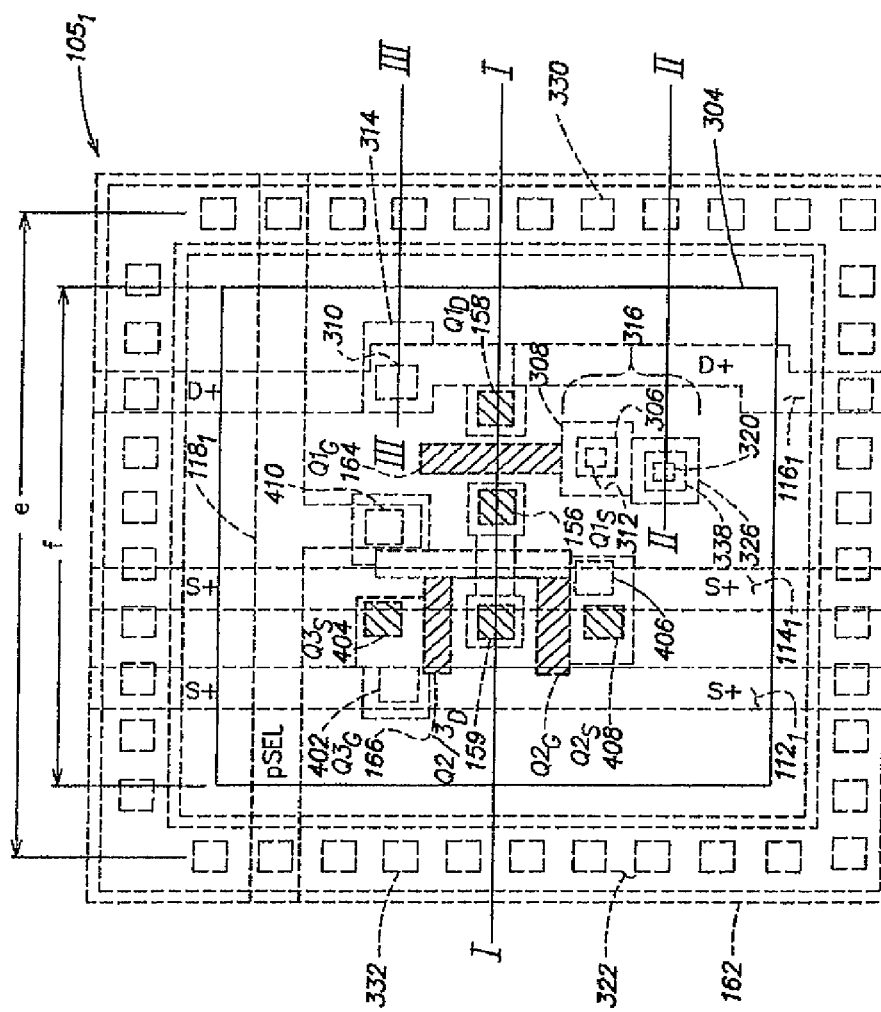
FIG. 10 illustrates a top view of a chip layout design for a pixel of the column of an chemFET array shown in FIG. 9, according to one inventive embodiment of the present disclosure.
Figures 1, 11A:
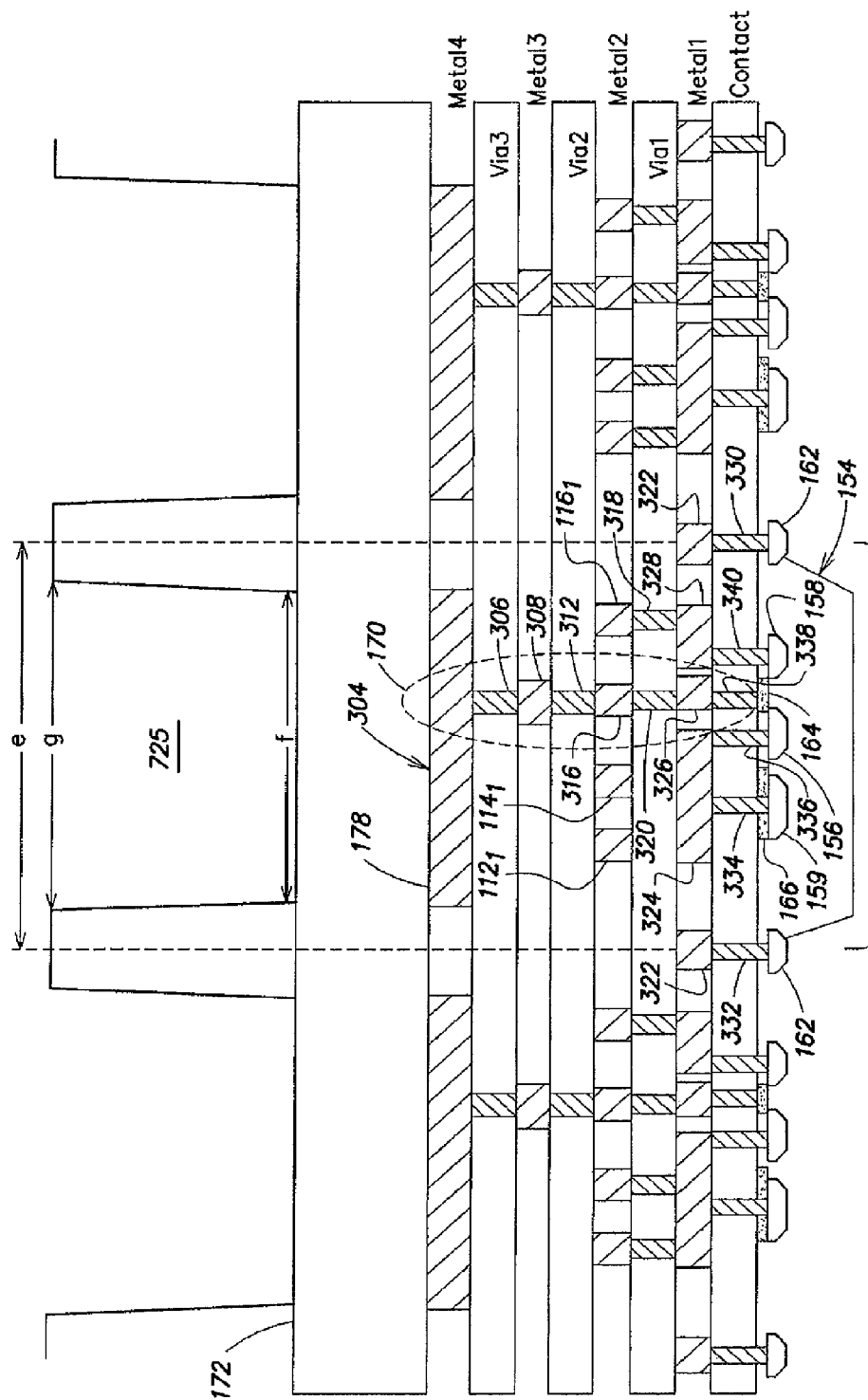
FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication according to one inventive embodiment of the present disclosure.
Figure 11E:
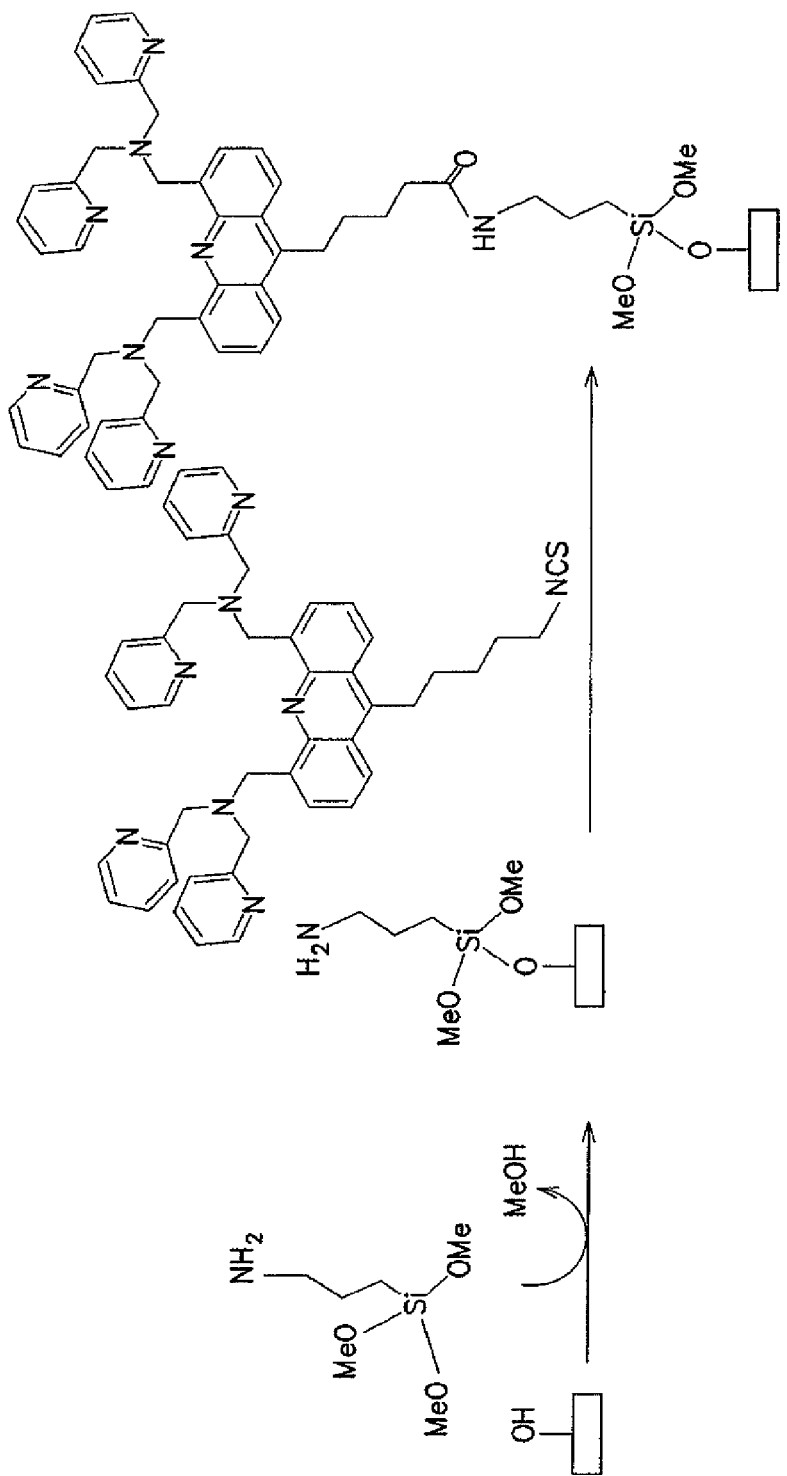
FIG. 11E is a schematic of attachment of compound 7 from FIG. 11B(3) to a metal oxide surface.
Figure 12A:
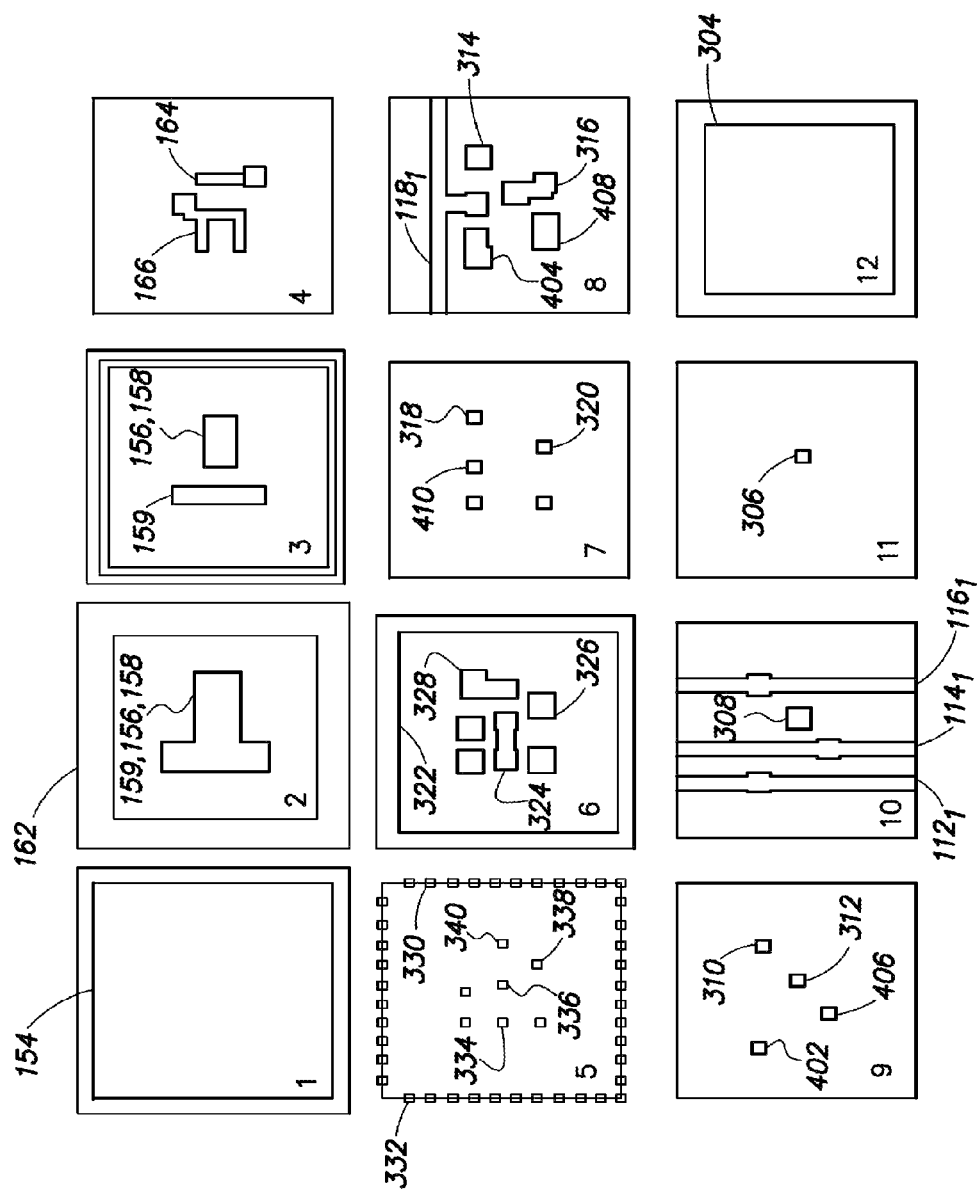

FIG. 10 illustrates a top view of a chip layout design for the pixel $105_1$ shown in FIG. 9, according to one inventive embodiment of the present disclosure. FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication, and FIGS. 12A1 through 12A12 provide top views of each of the fabrication layers shown in FIG. 11A (the respective images of FIGS. 12A1 through 12A12 are superimposed one on top of another to create the pixel chip layout design shown in FIG. 10). In one exemplary implementation, the pixel design illustrated in FIGS. 10-12A may be realized using a standard 4-metal, 2-poly, 0.35 micrometer CMOS process to provide a geometrically square pixel having a dimension "e" as shown in FIG. 10 of approximately 9 micrometers, and a dimension "f" corresponding to the ISFET sensitive area of approximately 7 micrometers.

In the top view of FIG. 10, the ISFET 150 (labeled as Q1 in FIG. 10) generally occupies the right center portion of the pixel illustration, and the respective locations of the gate, source and drain of the ISFET are indicated as $Q1_G$, $Q1_S$ and $Q1_D$. The MOSFETs Q2 and Q3 generally occupy the left center portion of the pixel illustration; the gate and source of the MOSFET Q2 are indicated as $Q2_G$ and $Q2_S$, and the gate and source of the MOSFET Q3 are indicated as $Q3_G$ and $Q3_S$. In one aspect of the layout shown in FIG. 10, the MOSFETs Q2 and Q3 share a drain, indicated as $Q2/3_D$. In another aspect, it may be observed generally from the top view of FIG. 10 that the ISFET is formed such that its channel lies along a first axis of the pixel (e.g., parallel to the line I-I), while the MOSFETs Q2 and Q3 are formed such that their channels lie along a second axis perpendicular to the first axis. FIG. 10 also shows the four lines required to operate the pixel, namely, the line $112_1$ coupled to the source of Q3, the line $114_1$ coupled to the source of Q2, the line $116_1$ coupled to the drain of the ISFET, and the row select line $118_1$ coupled to the gates of Q2 and Q3. With reference to FIG. 9, it may be appreciated that all pixels in a given column share the lines 112, 114 and 116 (e.g., running vertically across the pixel in FIG. 10), and that all pixels in a given row share the line 118 (e.g., running horizontally across the pixel in FIG. 10); thus, based on the pixel design of FIG. 9 and the layout shown in FIG. 10, only four metal lines need to traverse each pixel.

With reference now to the cross-sectional view of FIG. 11A, highly doped p-type regions 156 and 158 (lying along the line I-I in FIG. 10) in n-well 154 constitute the source (S) and drain (D) of the ISFET, between which lies a region 160 of the n-well in which the ISFETs p-channel is formed below the ISFETs polysilicon gate 164 and a gate oxide 165. According to one aspect of the inventive embodiment shown in FIGS. 10 and 11, all of the FET components of the pixel $105_1$ are fabricated as p-channel FETs in the single n-type well 154 formed in a p-type semiconductor substrate 152. This is possible because, unlike the design of Milgrew et al., 1) there is no requirement for a transmission gate in the pixel; and 2) the ISFETs source is not tied to the n-well's body connection. More specifically, highly doped n-type regions 162 provide a body connection (B) to the n-well 154 and, as shown in FIG. 10, the body connection B is coupled to a metal conductor 322 around the perimeter of the pixel $105_1$. However, the body connection is not directly electrically coupled to the source region 156 of the ISFET (i.e., there is no electrical conductor coupling the body connection and source such that they are forced to be at the same electric potential during operation), nor is the body connection directly electrically coupled to the gate, source or drain of any component in the pixel. Thus, the other p-channel FET components of the pixel, namely Q2 and Q3, may be fabricated in the same n-well 154.

In the composite cross-sectional view of FIG. 11A, a highly doped p-type region 159 is also visible (lying along the line I-I in FIG. 10), corresponding to the shared drain (D) of the MOSFETs Q2 and Q3. For purposes of illustration, a polysilicon gate 166 of the MOSFET Q3 also is visible in FIG. 11A, although this gate does not lie along the line I-I in FIG. 10, but rather "behind the plane" of the cross-section along the line I-I. However, for simplicity, the respective sources of the MOSFETs Q2 and Q3 shown in FIG. 10, as well as the gate of Q2, are not visible in FIG. 11A, as they lie along the same axis (i.e., perpendicular to the plane of the figure) as the shared drain (if shown in FIG. 11A, these elements would unduly complicate the composite cross-sectional view of FIG. 11A).

Above the substrate, gate oxide, and polysilicon layers shown in FIG. 11A, a number of additional layers are provided to establish electrical connections to the various pixel components, including alternating metal layers and oxide layers through which conductive vias are formed. Pursuant to the example of a 4-Metal CMOS process, these layers are labeled in FIG. 11A as "Contact," "Metal1," "Via1," "Metal2," "Via2," "Metal3," "Via3," and "Metal4." (Note that more or fewer metal layers may be employed.) To facilitate an understanding particularly of the ISFET electrical connections, the composite cross-sectional view of FIG. 11A shows additional elements of the pixel fabrication on the right side of the top view of FIG. 10 between the lines II-II and III-III. With respect to the ISFET electrical connections, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs "floating gate" structure 170, in a manner similar to that discussed above in connection with a conventional ISFET design shown in FIG. 1. An electrical connection to the ISFETs drain is provided by the conductors 340, 328, 318, 314 and 310 coupled to the line $116_1$. The ISFETs source is coupled to the shared drain of the MOSFETs Q2 and Q3 via the conductors 334 and 336 and the conductor 324 (which lies along the line I-I in FIG. 10). The body connections 162 to the n-well 154 are electrically coupled to a metal conductor 322 around the perimeter of the pixel on the "Metal1" layer via the conductors 330 and 332.'

As indicated above, FIGS. 12A1 through 12A12 provide top views of each of the fabrication layers shown in FIG. 11A (the respective images of FIGS. 12A1 through 12A12 are superimposed one on top of another to create the pixel chip layout design shown in FIG. 10). In FIG. 12A, the correspondence between the lettered top views of respective layers and the cross-sectional view of FIG. 11A is as follows: A) n-type well 154; B) Implant; C) Diffusion; D) polysilicon gates 164 (ISFET) and 166 (MOSFETs Q2 and Q3); E) contacts; F) Metal1; G) Via1; H) Metal2; I) Via2; J) Metal3; K) Via3; L) Metal4 (top electrode contacting ISFET gate). The various reference numerals indicated in FIGS. 12A1 through 12A12 correspond to the identical features that are present in the composite cross-sectional view of FIG. 11A.

Applicants have recognized and appreciated that, at least in some applications, pixel capacitance may be a salient parameter for some type of analyte measurements. Accordingly, in another embodiment related to pixel layout and design, various via and metal layers may be reconfigured so as to at least partially mitigate the potential for parasitic capacitances to arise during pixel operation. For example, in one such embodiment, pixels are designed such that there is a greater vertical distance between the signal lines $112_1$, $114_1$, $116_1$ and $118_1$, and the topmost metal layer 304 constituting the floating gate structure 170.

In the embodiment described immediately above, with reference again to FIG. 11A, it may be readily observed that the topmost metal layer 304 is formed in the Metal4 layer (also see FIG. 12A12), and the signal lines $112_1$, $114_1$, and $116_1$ are formed in the Metal3 layer (also see FIG. 12A10). Also, while not visible in the view of FIG. 11A, it may be observed from FIG. 12A8 that the signal line $118_1$ is formed in the Metal2 layer. As one or more of these signals may be grounded from time to time during array operation, a parasitic capacitance may arise between any one or more of these signal lines and metal layer 304. By increasing a distance between these signal lines and the metal layer 304, such parasitic capacitance may be reduced.

Figure 10A:
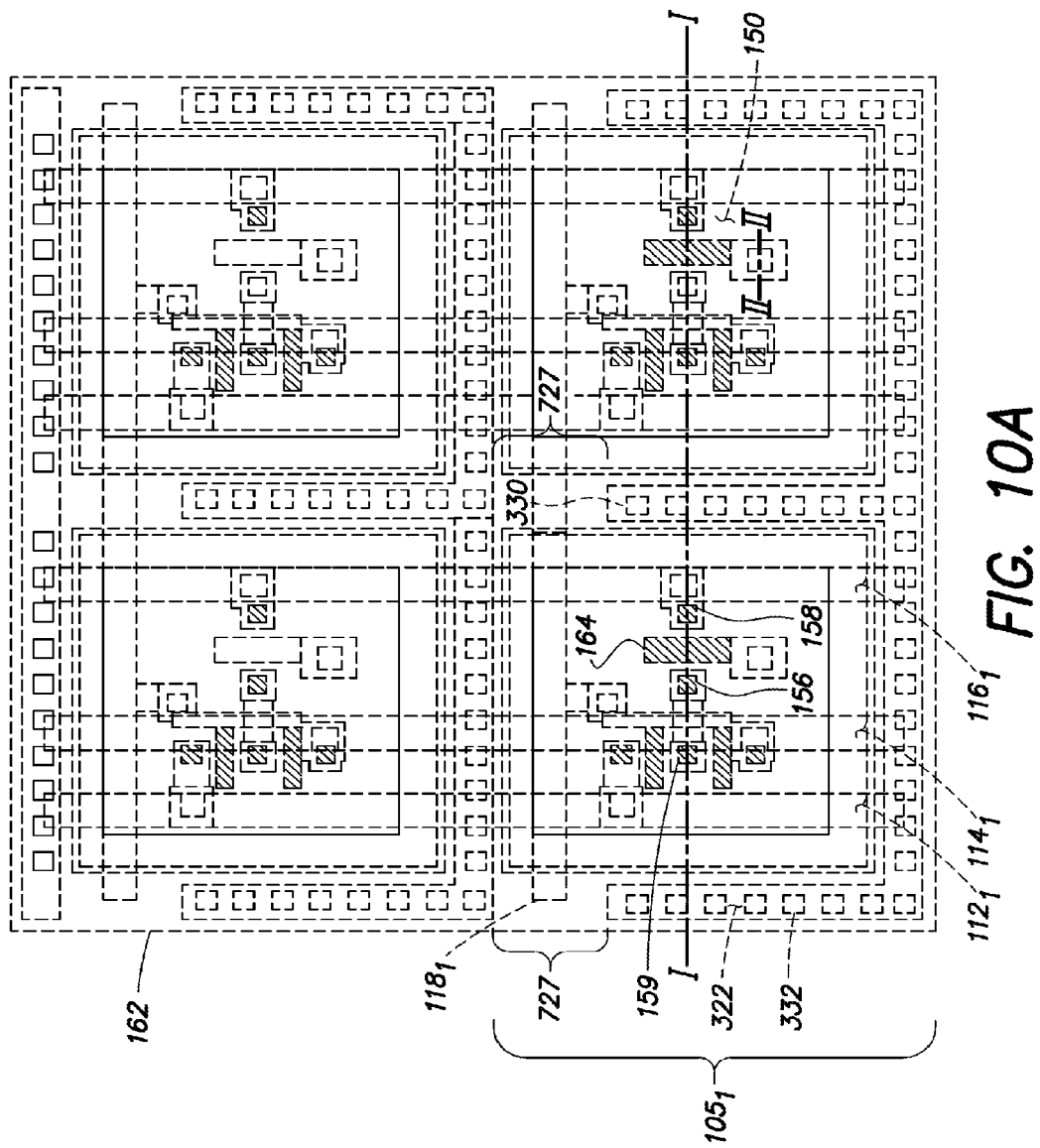
FIG. 10A illustrates a top view of a chip layout design for a cluster of four neighboring pixels of an chemFET array shown in FIG. 9, according to another inventive embodiment of the present disclosure.
Figure 12B:
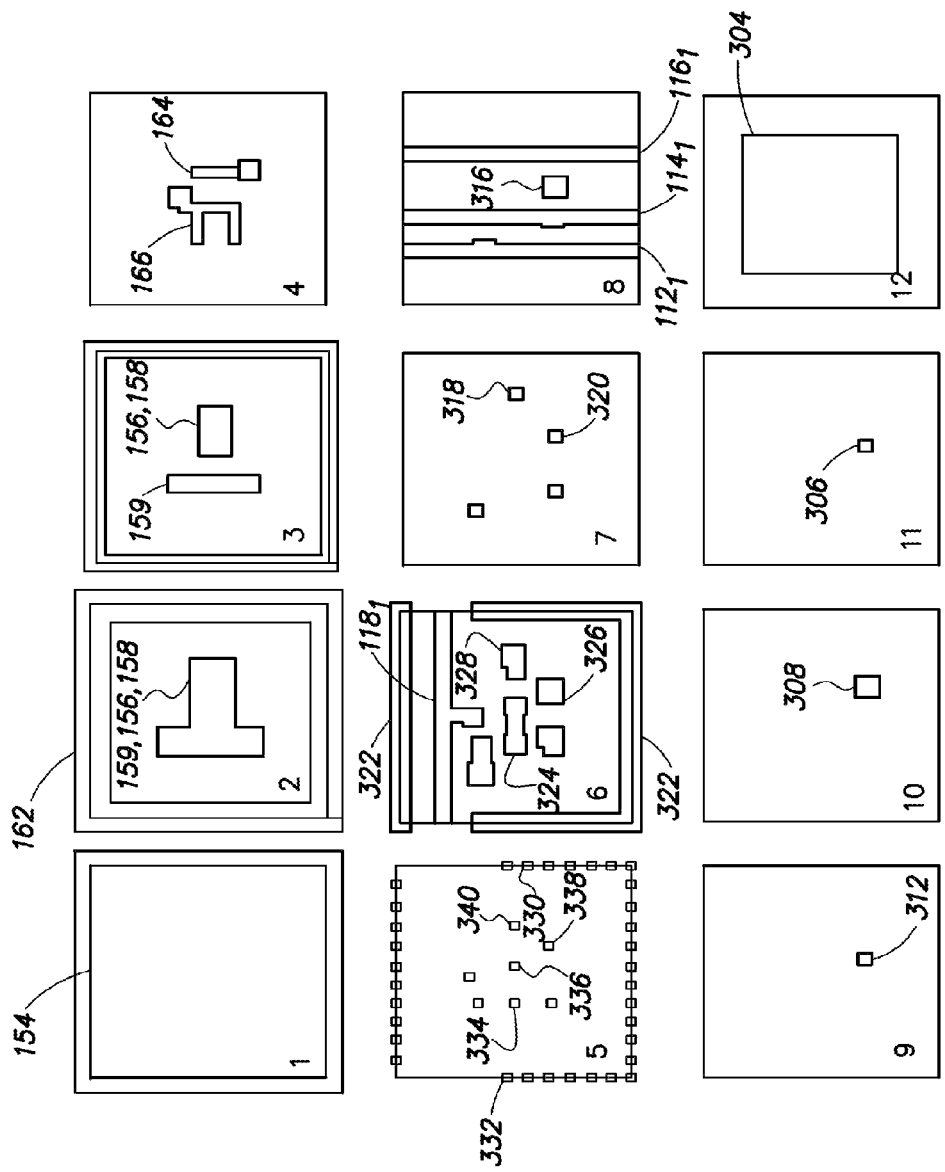

To this end, in another embodiment some via and metal layers are reconfigured such that the signal lines $112_1$, $114_1$, $116_1$ and $118_1$ are implemented in the Metal1 and Metal2 layers, and the Metal3 layer is used only as a jumper between the Metal2 layer component of the floating gate structure 170 and the topmost metal layer 304, thereby ensuring a greater distance between the signal lines and the metal layer 304. FIG. 10A illustrates a top view of a such a chip layout design for a cluster of four neighboring pixels of an chemFET array shown in FIG. 9, with one particular pixel $105_1$ identified and labeled. FIG. 11A-1 shows a composite cross-sectional view of neighboring pixels, along the line I-I of the pixel $105_1$ shown in FIG. 10A, including additional elements between the lines II-II, illustrating a layer-by-layer view of the pixel fabrication, and FIGS. 12B1 through 12B12 provide top views of each of the fabrication layers shown in FIG. 11A-1 (the respective images of FIGS. 12B1 through 12B12 are superimposed one on top of another to create the pixel chip layout design shown in FIG. 10A).

In FIG. 10A, it may be observed that the pixel top view layout is generally similar to that shown in FIG. 10. For example, in the top view, the ISFET 150 generally occupies the right center portion of each pixel, and the MOSFETs Q2 and Q3 generally occupy the left center portion of the pixel illustration. Many of the component labels included in FIG. 10 are omitted from FIG. 10A for clarity, although the ISFET polysilicon gate 164 is indicated in the pixel $105_1$ for orientation. FIG. 10A also shows the four lines ($112_1$, $114_1$, $116_1$ and $118_1$) required to operate the pixel. One noteworthy difference between FIG. 10 and FIG. 10A relates to the metal conductor 322 (located on the Metal1 layer) which provides an electrical connection to the body region 162; namely, in FIG. 10, the conductor 322 surrounds a perimeter of the pixel, whereas in FIG. 10A, the conductor 322 does not completely surround a perimeter of the pixel but includes discontinuities 727. These discontinuities 727 permit the line $118_1$ to also be fabricated on the Metal1 layer and traverse the pixel to connect to neighboring pixels of a row.

With reference now to the cross-sectional view of FIG. 11A-1, three adjacent pixels are shown in cross-section, with the center pixel corresponding to the pixel $105_1$ in FIG. 10A for purposes of discussion. As in the embodiment of FIG. 11A, all of the FET components of the pixel $105_1$ are fabricated as p-channel FETs in the single n-type well 154. Additionally, as in FIG. 11A, in the composite cross-sectional view of FIG. 11A-1 the highly doped p-type region 159 is also visible (lying along the line I-I in FIG. 10A), corresponding to the shared drain (D) of the MOSFETs Q2 and Q3. For purposes of illustration, the polysilicon gate 166 of the MOSFET Q3 also is visible in FIG. 11A-1, although this gate does not lie along the line I-I in FIG. 10A, but rather "behind the plane" of the cross-section along the line I-I. However, for simplicity, the respective sources of the MOSFETs Q2 and Q3 shown in FIG. 10A, as well as the gate of Q2, are not visible in FIG. 11A-1, as they lie along the same axis (i.e., perpendicular to the plane of the figure) as the shared drain. Furthermore, to facilitate an understanding of the ISFET floating gate electrical connections, the composite cross-sectional view of FIG. 11A-1 shows additional elements of the pixel fabrication between the lines II-II of FIG. 10A.

More specifically, as in the embodiment of FIG. 11A, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs floating gate structure 170. However, unlike the embodiment of FIG. 11A, an electrical connection to the ISFETs drain is provided by the conductors 340, 328, and 318, coupled to the line $116_1$ which is formed in the Metal2 layer rather than the Metal3 layer. Additionally, the lines $112_1$ and $114_1$ also are shown in FIG. 11A-1 as formed in the Metal2 layer rather than the Metal3 layer. The configuration of these lines, as well as the line $118_1$, may be further appreciated from the respective images of FIGS. 12B1 through 12B12 (in which the correspondence between the lettered top views of respective layers and the cross-sectional view of FIG. 11A-1 is the same as that described in connection with FIGS. 12A1-12A12); in particular, it may be observed in FIG. 12B6 that the line $118_1$, together with the metal conductor 322, is formed in the Metal1 layer, and it may be observed that the lines $112_1$, $114_1$ and $116_1$ are formed in the Metal2 layer, leaving only the jumper 308 of the floating gate structure 170 in the Metal3 layer shown in FIG. 12B10.

Accordingly, by consolidating the signal lines $112_1$, $114_1$, $116_1$ and $118_1$ to the Metal1 and Metal2 layers and thereby increasing the distance between these signal lines and the topmost layer 304 of the floating gate structure 170 in the Metal4 layer, parasitic capacitances in the ISFET may be at least partially mitigated. It should be appreciated that this general concept (e.g., including one or more intervening metal layers between signal lines and topmost layer of the floating gate structure) may be implemented in other fabrication processes involving greater numbers of metal layers. For example, distance between pixel signal lines and the topmost metal layer may be increased by adding additional metal layers (more than four total metal layers) in which only jumpers to the topmost metal layer are formed in the additional metal layers. In particular, a six-metal-layer fabrication process may be employed, in which the signal lines are fabricated using the Metal1 and Metal2 layers, the topmost metal layer of the floating gate structure is formed in the Metal6 layer, and jumpers to the topmost metal layer are formed in the Metal3, Metal4 and Metal5 layers, respectively (with associated vias between the metal layers). In another exemplary implementation based on a six-metal-layer fabrication process, the general pixel configuration shown in FIGS. 10, 11A, and 12A1-12A12 may be employed (signal lines on Metal2 and Metal3 layers), in which the topmost metal layer is formed in the Metal6 layer and jumpers are formed in the Metal4 and Metal5 layers, respectively.

In yet another aspect relating to reduced capacitance, a dimension "f" of the topmost metal layer 304 (and thus the ISFET sensitive area 178) may be reduced so as to reduce cross-capacitance between neighboring pixels. As may be observed in FIG. 11A-1 (and as discussed further below in connection with other embodiments directed to well fabrication above an ISFET array), the well 725 may be fabricated so as to have a tapered shape, such that a dimension "g" at the top of the well is smaller than the pixel pitch "e" but yet larger than a dimension "f" at the bottom of the well. Based on such tapering, the topmost metal layer 304 also may be designed with the dimension "f" rather than the dimension "g" so as to provide for additional space between the top metal layers of neighboring pixels. In some illustrative non-limiting implementations, for pixels having a dimension "e" on the order of 9 micrometers the dimension "f" may be on the order of 6 micrometers (as opposed to 7 micrometers, as discussed above), and for pixels having a dimension "c" on the order of 5 micrometers the dimension "f" may be on the order of 3.5 micrometers.

Thus, the pixel chip layout designs respectively shown in FIGS. 10, 11A, and 12A1 through 12A12, and FIGS. 10A, 11A-1, and 12B1 through 12B12, illustrate that according to various embodiments FET devices of a same type may be employed for all components of a pixel, and that all components may be implemented in a single well. This dramatically reduces the area required for the pixel, thereby facilitating increased pixel density in a given area.

In one exemplary implementation, the gate oxide 165 for the ISFET may be fabricated to have a thickness on the order of approximately 75 Angstroms, giving rise to a gate oxide capacitance per unit area $C_{ox}$ of 4.5 fF/μm². Additionally, the polysilicon gate 164 may be fabricated with dimensions corresponding to a channel width W of 1.2 μm and a channel length L of from 0.35 to 0.6 μm (i.e., W/L ranging from approximately 2 to 3.5), and the doping of the region 160 may be selected such that the carrier mobility for the p-channel is 190 cm²/V·s (i.e., 1.9 E10 μm²/V·s). From Eq. (2) above, this results in an ISFET transconductance parameter β on the order of approximately 170 to 300 μA/V². In other aspects of this exemplary implementation, the analog supply voltage VDDA is 3.3 Volts, and VB1 and VB2 are biased so as to provide a constant ISFET drain current $I_{Dj}$ on the order of 5 μA (in some implementations, VB1 and VB2 may be adjusted to provide drain currents from approximately 1 μA to 20 μA). Additionally, the MOSFET Q6 (see bias/readout circuitry 110j in FIG. 9) is sized to have a channel width to length ratio (e.g., W/L of approximately 50) such that the voltage across Q6, given $I_{Dj}$ of 5 μA, is 800 mV (i.e., $V_{DSj}$=800 mV). From Eq. (3), based on these exemplary parameters, this provides for pixel output voltages $V_{Sj}$ over a range of approximately 0.5 to 2.5 Volts for ISFET threshold voltage changes over a range of approximately 0 to 2 Volts.

With respect to the analyte-sensitive passivation layer 172 shown in FIG. 11A, in exemplary CMOS implementations the passivation layer may be significantly sensitive to the concentration of various ion species, including hydrogen, and may include silicon nitride ($Si_3N_4$) and/or silicon oxynitride ($Si_2N_2O$). In conventional CMOS processes, a passivation layer may be formed by one or more successive depositions of these materials, and is employed generally to treat or coat devices so as to protect against contamination and increase electrical stability. The material properties of silicon nitride and silicon oxynitride are such that a passivation layer comprising these materials provides scratch protection and serves as a significant barrier to the diffusion of water and sodium, which can cause device metallization to corrode and/or device operation to become unstable. A passivation layer including silicon nitride and/or silicon oxynitride also provides ion-sensitivity in ISFET devices, in that the passivation layer contains surface groups that may donate or accept protons from an analyte solution with which they are in contact, thereby altering the surface potential and the device threshold voltage $V_{TH}$, as discussed above in connection with FIGS. 1 and 2A.

For CMOS processes involving aluminum as the metal (which has a melting point of approximately 650 degrees Celsius), a silicon nitride and/or silicon oxynitride passivation layer generally is formed via plasma-enhanced chemical vapor deposition (PECVD), in which a glow discharge at 250-350 degrees Celsius ionizes the constituent gases that form silicon nitride or silicon oxynitride, creating active species that react at the wafer surface to form a laminate of the respective materials. In one exemplary process, a passivation layer having a thickness on the order of approximately 1.0 to 1.5 μm may be formed by an initial deposition of a thin layer of silicon oxynitride (on the order of 0.2 to 0.4 μm) followed by a slighting thicker deposition of silicon oxynitride (on the order of 0.5 μm) and a final deposition of silicon nitride (on the order of 0.5 μm). Because of the low deposition temperature involved in the PECVD process, the aluminum metallization is not adversely affected.

However, Applicants have recognized and appreciated that while a low-temperature PECVD process provides adequate passivation for conventional CMOS devices, the low-temperature process results in a generally low-density and somewhat porous passivation layer, which in some cases may adversely affect ISFET threshold voltage stability. In particular, during ISFET device operation, a low-density porous passivation layer over time may absorb and become saturated with ions from the solution, which may in turn cause an undesirable time-varying drift in the ISFETs threshold voltage $V_{TH}$, making accurate measurements challenging.

In view of the foregoing, in one embodiment a CMOS process that uses tungsten metal instead of aluminum may be employed to fabricate ISFET arrays according to the present disclosure. The high melting temperature of Tungsten (above 3400 degrees Celsius) permits the use of a higher temperature low pressure chemical vapor deposition (LPCVD) process (e.g., approximately 700 to 800 degrees Celsius) for a silicon nitride or silicon oxynitride passivation layer. The LPCVD process typically results in significantly more dense and less porous films for the passivation layer, thereby mitigating the potentially adverse effects of ion absorption from the analyte solution leading to ISFET threshold voltage drift.

In yet another embodiment in which an aluminum-based CMOS process is employed to fabricate ISFET arrays according to the present disclosure, the passivation layer 172 shown in FIG. 11A may comprise additional depositions and/or materials beyond those typically employed in a conventional CMOS process. For example, the passivation layer 172 may include initial low-temperature plasma-assisted depositions (PECVD) of silicon nitride and/or silicon oxynitride as discussed above; for purposes of the present discussion, these conventional depositions are illustrated in FIG. 11A as a first portion 172A of the passivation layer 172. In one embodiment, following the first portion 172A, one or more additional passivation materials are disposed to form at least a second portion 172B to increase density and reduce porosity of (and absorption by) the overall passivation layer 172. While one additional portion 172B is shown primarily for purposes of illustration in FIG. 11A, it should be appreciated that the disclosure is not limited in this respect, as the overall passivation layer 172 may comprise two or more constituent portions, in which each portion may comprise one or more layers/depositions of same or different materials, and respective portions may be configured similarly or differently.

Examples of materials suitable for the second portion 172B (or other additional portions) of the passivation layer 172 include, but are not limited to, silicon nitride, silicon oxynitride, aluminum oxide ($Al_2O_3$), tantalum oxide ($Ta_3O_5$), tin oxide ($SnO_2$) and silicon dioxide ($SiO_2$). In one aspect, the second portion 172B (or other additional portions) may be deposited via a variety of relatively low-temperature processes including, but not limited to, RF sputtering, DC magnetron sputtering, thermal or e-beam evaporation, and ion-assisted depositions. In another aspect, a pre-sputtering etch process may be employed, prior to deposition of the second portion 172B, to remove any native oxide residing on the first portion 172A (alternatively, a reducing environment, such as an elevated temperature hydrogen environment, may be employed to remove native oxide residing on the first portion 172A). In yet another aspect, a thickness of the second portion 172B may be on the order of approximately 0.04 μm to 0.06 μm (400 to 600 Angstroms) and a thickness of the first portion may be on the order of 1.0 to 1.5 μm, as discussed above. In some exemplary implementations, the first portion 172A may include multiple layers of silicon oxynitride and silicon nitride having a combined thickness of 1.0 to 1.5 μm, and the second portion 172B may include a single layer of either aluminum oxide or tantalum oxide having a thickness of approximately 400 to 600 Angstroms. Again, it should be appreciated that the foregoing exemplary thicknesses are provided primarily for purposes of illustration, and that the disclosure is not limited in these respects.

It has been found according to the invention that hydrogen ion sensitive passivation layers are also sensitive to other analytes including but not limited to PPi and unincorporated nucleotide triphosphates. As an example, a silicon nitride passivation layer is able to detect changes in the concentration of PPi and nucleotide triphosphates. The ability to measure the concentration change of these analytes using the same chemFET greatly facilitates the ability to sequence a nucleic acid using a single array, thereby simplifying the sequencing method.

Thus it is to be understood that the chemFET arrays described herein may be used to detect and/or measure various analytes and, by doing so, may monitor a variety of reactions and/or interactions. It is also to be understood that the discussion herein relating to hydrogen ion detection (in the form of a pH change) is for the sake of convenience and brevity and that static or dynamic levels/concentrations of other analytes (including other ions) can be substituted for hydrogen in these descriptions. In particular, sufficiently fast concentration changes of any one or more of various ion species present in the analyte may be detected via the transient or dynamic response of a chemFET, as discussed above in connection with FIG. 2A. As also discussed above in connection with the Site-Dissociation (or Site-Binding) model for the analyte/passivation layer interface, it should be appreciated that various parameters relating to the equilibrium reactions at the analyte/passivation layer interface (e.g., rate constants for forward and backward equilibrium reactions, total number of proton donor/acceptor sites per unit area on the passivation layer surface, intrinsic buffering capacity, pH at point of zero charge) are material dependent properties and thus are affected by the choice of materials employed for the passivation layer.

The chemFETs, including ISFETs, described herein are capable of detecting any analyte that is itself capable of inducing a change in electric field when in contact with or otherwise sensed or detected by the chemFET surface. The analyte need not be charged in order to be detected by the sensor. For example, depending on the embodiment, the analyte may be positively charged (i.e., a cation), negatively charged (i.e., an anion), zwitterionic (i.e., capable of having two equal and opposite charges but being neutral overall), and polar yet neutral. This list is not intended as exhaustive as other analyte classes as well as species within each class will be readily contemplated by those of ordinary skill in the art based on the disclosure provided herein.

In the broadest sense of the invention, the passivation layer may or may not be coated and the analyte may or may not interact directly with the passivation layer. As an example, the passivation layer may be comprised of silicon nitride and the analyte may be something other than hydrogen ions. As a specific example, the passivation layer may be comprised of silicon nitride and the analyte may be PPi. In these instances, PPi is detected directly (i.e., in the absence of PPi receptors attached to the passivation layer either directly or indirectly).

If the analyte being detected is hydrogen (or alternatively hydroxide), then it is preferable to use weak buffers so that changes in either ionic species can be detected at the passivation layer. If the analyte being detected is something other than hydrogen (or hydroxide) but there is some possibility of a pH change in the solution during the reaction or detection step, then it is preferable to use a strong buffer so that changes in pH do not interfere with the detection of the analyte. A buffer is an ionic molecule (or a solution comprising an ionic molecule) that resists to varying extents changes in pH. Some buffers are able to neutralize acids or bases added to or generated in a solution, resulting in no effective pH change in the solution. It is to be understood that any buffer is suitable provided it has a pKa in the desired range. For some embodiments, a suitable buffer is one that functions in about the pH range of 6 to 9, and more preferably 6.5 to 8.5. In other embodiments, a suitable buffer is one that functions in about the pH range of 7-10, including 8.5-9.5.

The strength of a buffer is a relative term since it depends on the nature, strength and concentration of the acid or base added to or generated in the solution of interest. A weak buffer is a buffer that allows detection (and therefore is not able to otherwise control) pH changes of about at least +/−0.005, about at least +/−0.01, about at least +/−0.015, about at least +/−0.02, about at least +/−0.03, about at least +/−0.04, about at least +/−0.05, about at least +/−0.10, about at least +/−0.15, about at least +/−0.20, about at least +/−0.25, about at least +/−0.30, about at least +/−0.35, about at least +/−0.45, about at least +/−0.50, or more.

A strong buffer is a buffer that controls pH changes of about at least +/−0.005, about at least +/−0.01, about at least +/−0.015, about at least +/−0.02, about at least +/−0.03, about at least +/−0.04, about at least +/−0.05, about at least +/−0.10, about at least +/−0.15, about at least +/−0.20, about at least +/−0.25, about at least +/−0.30, about at least +/−0.35, about at least +/−0.45, about at least +/−0.50, or more.

Buffer strength can be varied by varying the concentration of the buffer species itself. Thus low concentration buffers can be low strength buffers. Examples include those having less than 1 mM (e.g., 50-100 μM) buffer species. A non-limiting example of a weak buffer suitable for the sequencing reactions described herein wherein pH change is the readout is 0.1 mM Tris or Tricine. Examples of suitable weak buffers are provided in the Examples and are also known in the art. Higher concentration buffers can be stronger buffers. Examples include those having 1-25 mM buffer species. A non-limiting example of a strong buffer suitable for the sequencing reactions described herein wherein PPi and/or nucleotide triphosphates are read directly is 1, 5 or 25 mM (or more) Tris or Tricine. One of ordinary skill in the art will be able to determine the optimal buffer for use in the reactions and detection methods encompassed by the invention.

In some embodiments, the passivation layer and/or the layers and/or molecules coated thereon dictate the analyte specificity of the array readout.

Detection of hydrogen ions (in the form of pH), and other analytes as determined by the invention, can be carried out using a passivation layer made of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$), and the like.

The passivation layer can also detect other ion species directly including but not limited to calcium, potassium, sodium, iodide, magnesium, chloride, lithium, lead, silver, cadmium, nitrate, phosphate, dihydrogen phosphate, and the like.

In some embodiments, the passivation layer is coated with a receptor for the analyte of interest. Preferably, the receptor binds selectively to the analyte of interest or in some instances to a class of agents to which the analyte belongs. As used herein, a receptor that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor must also have an absolute binding affinity that is sufficiently high to efficiently bind the analyte of interest (i.e., it must have a sufficient sensitivity). Receptors having binding affinities in the picomolar to micromolar range are suitable. Preferably such interactions are reversible.

The receptor may be of any nature (e.g., chemical, nucleic acid, peptide, lipid, combinations thereof and the like). In such embodiments, the analyte too may be of any nature provided there exists a receptor that binds to it selectively and in some instances specifically. It is to be understood however that the invention further contemplates detection of analytes in the absence of a receptor. An example of this is the detection of PPi and Pi by the passivation layer in the absence of PPi or Pi receptors.

In one aspect, the invention contemplates receptors that are ionophores. As used herein, an ionophore is a molecule that binds selectively to an ionic species, whether anion or cation. In the context of the invention, the ionophore is the receptor and the ion to which it binds is the analyte. Ionophores of the invention include art-recognized carrier ionophores (i.e., small lipid-soluble molecules that bind to a particular ion) derived from microorganisms. Various ionophores are commercially available from sources such as Calbiochem.

Detection of some ions can be accomplished through the use of the passivation layer itself or through the use of receptors coated onto the passivation layer. For example, potassium can be detected selectively using polysiloxane, valinomycin, or salinomycin; sodium can be detected selectively using monensin, nystatin, or SQI-Pr; calcium can be detected selectively using ionomycin, calcimycine (A23187), or CA 1001 (ETH 1001).

Receptors able to bind more than one ion can also be used in some instances. For example, beauvericin can be used to detect calcium and/or barium ions, nigericin can be used to detect potassium, hydrogen and/or lead ions, and gramicidin can be used to detect hydrogen, sodium and/or potassium ions. One of ordinary skill in the art will recognize that these compounds can be used in applications in which single ion specificity is not required or in which it is unlikely (or impossible) that other ions which the compounds bind will be present or generated. Similarly, receptors that bind multiple species of a particular genus may also be useful in some embodiments including those in which only one species within the genus will be present or in which the method does not require distinction between species.

In other embodiments, including but not limited to nucleic acid sequencing applications, receptors that bind selectively to PPi can be used. Examples of PPi receptors include those compounds shown in FIG. 11B(1)-(3) (compounds 1-10). Compound 1 is described in Angew Chem Int Ed 2004 43:4777-4780 and US 2005/0119497 A1 and is referred to as p-naphthyl-bis[(bis(2-pyridylmethyl)amino)methyl]phenol. Compound 2 is described in J Am Chem Soc 2003 125:7752-7753 and US 2005/0119497 A1 and is referred to as p-(p-nitrophenylazo)-bis[(bis(2-pyridylmethyl-1)amino)methyl] phenol (or its dinuclear Zn complex). Synthesis schemes for compounds 1 and 2 are shown provided in US 2005/0119497 A1. Compound 3 is described in by Lee et al. Organic Letters 2007 9(2):243-246, and Sensors and Actuators B 1995 29:324-327. Compound 4 is described in Angew Chem Int Ed 2002 41(20):3811-3814. Compound 5 is described in WO 2007/002204 and is referred to therein as bis-$Zn^{2+}$-dipicolylamine ($Zn^{2+}$-DPA). Compound 6 is illustrated bound to PPi. (McDonough et al. Chem. Commun. 2006 2971-2973.) Exemplary syntheses for compounds 7, 8 and 9 are shown in FIGS. 11C(1)-(3) respectively. Attachment of compound 7 to a metal oxide surface is shown in FIG. 11E.

As another example, receptors for neurotoxins are described in Simonian Electroanalysis 2004, 16: 1896-1906.

Receptors may be attached to the passivation layer covalently or non-covalently. Covalent attachment of a receptor to the passivation layer may be direct or indirect (e.g., through a linker). FIGS. 11D(1) and (2) illustrate the use of silanol chemistry to covalently bind receptors to the passivation layer. Receptors may be immobilized on the passivation layer using for example aliphatic primary amines (bottom left panel) or aryl isothiocyanates (bottom right panel). In these and other embodiments, the passivation layer which itself may be comprised of silicon nitride, aluminum oxide, silicon oxide, tantalum pentoxide, or the like, is bonded to a silanation layer via its reactive surface groups. For greater detail on silanol chemistry for covalent attachment to the FET surface, reference can be made to at least the following publications: for silicon nitride, see Sensors and Actuators B 1995 29:324-327, Jpn J Appl Phys 1999 38:3912-3917 and Langmuir 2005 21:395-402; for silicon oxide, see Protein Sci 1995 4:2532-2544 and Am Biotechnol Lab 2002 20(7):16-18; and for aluminum oxide, see Colloids and Surfaces 1992 63:1-9, Sensors and Actuators B 2003 89:40-47, and Bioconjugate Chem 1997 8:424-433. The receptor is then conjugated to the silanation layer reactive groups. This latter binding can occur directly or indirectly through the use of a bifunctional linker, as illustrated in FIGS. 11D(1) and (2).

A bifunctional linker is a compound having at least two reactive groups to which two entities may be bound. In some instances, the reactive groups are located at opposite ends of the linker. In some embodiments, the bifunctional linker is a universal bifunctional linker such as that shown in FIGS. 11D(1) and (2). A universal linker is a linker that can be used to link a variety of entities. It should be understood that the chemistries shown in FIGS. 11D(1) and (2) are meant to be illustrative and not limiting.

The bifunctional linker may be a homo-bifunctional linker or a hetero-bifunctional linker, depending upon the nature of the molecules to be conjugated. Homo-bifunctional linkers have two identical reactive groups. Hetero-bifunctional linkers are have two different reactive groups. Various types of commercially available linkers are reactive with one or more of the following groups: primary amines, secondary amines, sulphydryls, carboxyls, carbonyls and carbohydrates. Examples of amine-specific linkers are bis(sulfosuccinimidyl)suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine.

Heterobifunctional linkers that react with amines and sulphydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio]propionyl hydrazide.

Alternatively, receptors may be non-covalently coated onto the passivation layer. Non-covalent deposition of the receptor onto the passivation layer may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acid (e.g., peptides, proteins (native or denatured), and the like, or mimics, derivatives, or combinations thereof), lipids, polysaccharides, and functionalized block copolymers. The receptor may be adsorbed onto and/or entrapped within the polymer matrix. The nature of the polymer will depend on the nature of the receptor being used and/or analyte being detected.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth) acrylic acid, polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

Another issue that relates to ISFET threshold voltage stability and/or predictability involves trapped charge that may accumulate (especially) on metal layers of CMOS-fabricated devices as a result of various processing activities during or following array fabrication (e.g., back-end-of-line processing such as plasma metal etching, wafer cleaning, dicing, packaging, handling, etc.). In particular, with reference to FIG. 11A, trapped charge may in some instances accumulate on one or more of the various conductors 304, 306, 308, 312, 316, 320, 326, 338, and 164 constituting the ISFETs floating gate structure 170. This phenomenon also is referred to in the relevant literature as the "antenna effect."

One opportunity for trapped charge to accumulate includes plasma etching of the topmost metal layer 304. Applicants have recognized and appreciated that other opportunities for charge to accumulate on one or more conductors of the floating gate structure or other portions of the FETs includes wafer dicing, during which the abrasive process of a dicing saw cutting through a wafer generates static electricity, and/or various post-processing wafer handling/packaging steps, such as die-to-package wire bonding, where in some cases automated machinery that handles/transports wafers may be sources of electrostatic discharge (ESD) to conductors of the floating gate structure. If there is no connection to the silicon substrate (or other semi-conductor substrate) to provide an electrical path to bleed off such charge accumulation, charge may build up to the point of causing undesirable changes or damage to the gate oxide 165 (e.g., charge injection into the oxide, or low-level oxide breakdown to the underlying substrate). Trapped charge in the gate oxide or at the gate oxide-semiconductor interface in turn can cause undesirable and/or unpredictable variations in ISFET operation and performance, such as fluctuations in threshold voltage.

In view of the foregoing, other inventive embodiments of the present disclosure are directed to methods and apparatus for improving ISFET performance by reducing trapped charge or mitigating the antenna effect. In one embodiment, trapped charge may be reduced after a sensor array has been fabricated, while in other embodiments the fabrication process itself may be modified to reduce trapped charge that could be induced by some conventional process steps. In yet other embodiments, both "during fabrication" and "post fabrication" techniques may be employed in combination to reduce trapped charge and thereby improve ISFET performance.

With respect to alterations to the fabrication process itself to reduce trapped charge, in one embodiment the thickness of the gate oxide 165 shown in FIG. 11A may be particularly selected so as to facilitate bleeding of accumulated charge to the substrate; in particular, a thinner gate oxide may allow a sufficient amount of built-up charge to pass through the gate oxide to the substrate below without becoming trapped. In another embodiment based on this concept, a pixel may be designed to include an additional "sacrificial" device, i.e., another transistor having a thinner gate oxide than the gate oxide 165 of the ISFET. The floating gate structure of the ISFET may then be coupled to the gate of the sacrificial device such that it serves as a "charge bleed-off transistor." Of course, it should be appreciated that some trade-offs for including such a sacrificial device include an increase in pixel size and complexity.

In another embodiment, the topmost metal layer 304 of the ISFETs floating gate structure 170 shown in FIG. 11A may be capped with a dielectric prior to plasma etching to mitigate trapped charge. As discussed above, charge accumulated on the floating gate structure may in some cases be coupled from the plasma being used for metal etching. Typically, a photoresist is applied over the metal to be etched and then patterned based on the desired geometry for the underlying metal. In one exemplary implementation, a capping dielectric layer (e.g., an oxide) may be deposited over the metal to be etched, prior to the application of the photoresist, to provide an additional barrier on the metal surface against charge from the plasma etching process. In one aspect, the capping dielectric layer may remain behind and form a portion of the passivation layer 172.

In yet another embodiment, the metal etch process for the topmost metal layer 304 may be modified to include wet chemistry or ion-beam milling rather than plasma etching. For example, the metal layer 304 could be etched using an aqueous chemistry selective to the underlying dielectric (e.g., see website for Transene relating to aluminum, which is hereby incorporated herein by reference). Another alternative approach employs ion-milling rather than plasma etching for the metal layer 304. Ion-milling is commonly used to etch materials that cannot be readily removed using conventional plasma or wet chemistries. The ion-milling process does not employ an oscillating electric field as does a plasma, so that charge build-up does not occur in the metal layer(s). Yet another metal etch alternative involves optimizing the plasma conditions so as to reduce the etch rate (i.e. less power density).

In yet another embodiment, architecture changes may be made to the metal layer to facilitate complete electrical isolation during definition of the floating gate. In one aspect, designing the metal stack-up so that the large area ISFET floating gate is not connected to anything during its final definition may require a subsequent metal layer serving as a "jumper" to realize the electrical connection to the floating gate of the transistor. This "jumper" connection scheme prevents charge flow from the large floating gate to the transistor. This method may be implemented as follows (M=metal layer): i) M1 contacting Poly gate electrode; ii) M2 contacting M1; iii) M3 defines floating gate and separately connects to M2 with isolated island; iv) M4 jumper, having very small area being etched over the isolated islands and connections to floating gate M3, connects the M3 floating gate to the M1/M2/M3 stack connected to the Poly gate immediately over the transistor active area; and v) M3 to M4 interlayer dielectric is removed only over the floating gate so as to expose the bare M3 floating gate. In the method outlined immediately above, step v) need not be done, as the ISFET architecture according to some embodiments discussed above leaves the M4 passivation in place over the M4 floating gate. In one aspect, removal may nonetheless improve ISFET performance in other ways (i.e. sensitivity). In any case, the final sensitive passivation layer may be a thin sputter-deposited ion-sensitive metal-oxide layer. It should be appreciated that the over-layer jumpered architecture discussed above may be implemented in the standard CMOS fabrication flow to allow any of the first three metal layers to be used as the floating gates (i.e. M1, M2 or M3).

With respect to post-fabrication processes to reduce trapped charge, in one embodiment a "forming gas anneal" may be employed as a post-fabrication process to mitigate potentially adverse effects of trapped charge. In a forming gas anneal, CMOS-fabricated ISFET devices are heated in a hydrogen and nitrogen gas mixture. The hydrogen gas in the mixture diffuses into the gate oxide 165 and neutralizes certain forms of trapped charges. In one aspect, the forming gas anneal need not necessarily remove all gate oxide damage that may result from trapped charges; rather, in some cases, a partial neutralization of some trapped charge is sufficient to significantly improve ISFET performance. In exemplary annealing processes according to the present disclosure, ISFETs may be heated for approximately 30 to 60 minutes at approximately 400 to 425 degrees Celsius in a hydrogen/nitrogen mixture that includes 10% to 15% hydrogen. In one particular implementation, annealing at 425 degrees Celsius at 30 minutes in a hydrogen/nitrogen mixture that includes 10% hydrogen is observed to be particularly effective at improving ISFET performance. For aluminum CMOS processes, the temperature of the anneal should be kept at or below 450 degrees Celsius to avoid damaging the aluminum metallurgy. In another aspect of an annealing process according to the present disclosure, the forming gas anneal is performed after wafers of fabricated ISFET arrays are diced, so as to ensure that damage due to trapped charge induced by the dicing process itself, and/or other pre-dicing processing steps (e.g., plasma etching of metals) may be effectively ameliorated. In yet another aspect, the forming gas anneal may be performed after die-to-package wirebonding to similarly ameliorate damage due to trapped charge. At this point in the assembly process, a diced array chip is typically in a heat and chemical resistant ceramic package, and low-tolerance wirebonding procedures as well as heat-resistant die-to-package adhesives may be employed to withstand the annealing procedure. Thus, in one exemplary embodiment, the invention encompasses a method for manufacturing an array of FETs, each having or coupled to a floating gate having a trapped charge of zero or substantially zero comprising: fabricating a plurality of FETs in a common semiconductor substrate, each of a plurality of which is coupled to a floating gate; applying a forming gas anneal to the semiconductor prior to a dicing step; dicing the semiconductor; and applying a forming gas anneal to the semiconductor after the dicing step. Preferably, the semiconductor substrate comprises at least 100,000 FETs. Preferably, the plurality of FETs are chemFETs. The method may further comprise depositing a passivation layer on the semiconductor, depositing a polymeric, glass, ion-reactively etchable or photodefineable material layer on the passivation layer and etching the polymeric, glass ion-reactively etchable or photodefineable material to form an array of reaction chambers in the glass layer.

In yet other processes for mitigating potentially adverse effects of trapped charge according to embodiments of the present disclosure, a variety of "electrostatic discharge (ESD)-sensitive protocols" may be adopted during any of a variety of wafer post-fabrication handling/packaging steps. For example, in one exemplary process, anti-static dicing tape may be employed to hold wafer substrates in place (e.g., during the dicing process). Also, although high-resistivity (e.g., 10 MΩ) deionized water conventionally is employed in connection with cooling of dicing saws, according to one embodiment of the present disclosure less resistive/more conductive water may be employed for this purpose to facilitate charge conduction via the water; for example, deionized water may be treated with carbon dioxide to lower resistivity and improve conduction of charge arising from the dicing process. Furthermore, conductive and grounded die-ejection tools may be used during various wafer dicing/handling/packaging steps, again to provide effective conduction paths for charge generated during any of these steps, and thereby reduce opportunities for charge to accumulate on one or more conductors of the floating gate structure of respective ISFETs of an array.

In yet another embodiment involving a post-fabrication process to reduce trapped charge, the gate oxide region of an ISFET may be irradiated with UV radiation. With reference again to FIG. 11A, in one exemplary implementation based on this embodiment, an optional hole or window 302 is included during fabrication of an ISFET array in the top metal layer 304 of each pixel of the array, proximate to the ISFET floating gate structure. This window is intended to allow UV radiation, when generated, to enter the ISFETs gate region; in particular, the various layers of the pixel $105_1$, as shown in FIGS. 11 and 12A1-12A12, are configured such that UV radiation entering the window 302 may impinge in an essentially unobstructed manner upon the area proximate to the polysilicon gate 164 and the gate oxide 165.

To facilitate a UV irradiation process to reduce trapped charge, Applicants have recognized and appreciated that materials other than silicon nitride and silicon oxynitride generally need to be employed in the passivation layer 172 shown in FIG. 11A, as silicon nitride and silicon oxynitride significantly absorb UV radiation. In view of the foregoing, these materials need to be substituted with others that are appreciably transparent to UV radiation, examples of which include, but are not limited to, phososilicate glass (PSG) and boron-doped phososilicate glass (BPSG). PSG and BPSG, however, are not impervious to hydrogen and hydroxyl ions; accordingly, to be employed in a passivation layer of an ISFET designed for pH sensitivity, PSG and BPSG may be used together with an ion-impervious material that is also significantly transparent to UV radiation, such as aluminum oxide ($Al_2O_3$), to form the passivation layer. For example, with reference again to FIG. 11A, PSG or BPSG may be employed as a substitute for silicon nitride or silicon oxynitride in the first portion 172A of the passivation layer 172, and a thin layer (e.g., 400 to 600 Angstroms) of aluminum oxide may be employed in the second portion 172B of the passivation layer 172 (e.g., the aluminum oxide may be deposited using a post-CMOS lift-off lithography process).

In another aspect of an embodiment involving UV irradiation, each ISFET of a sensor array must be appropriately biased during a UV irradiation process to facilitate reduction of trapped charge. In particular, high energy photons from the UV irradiation, impinging upon the bulk silicon region 160 in which the ISFET conducting channel is formed, create electron-hole pairs which facilitate neutralization of trapped charge in the gate oxide as current flows through the ISFETs conducting channel. To this end, an array controller, discussed further below in connection with FIG. 17, generates appropriate signals for biasing the ISFETs of the array during a UV irradiation process. In particular, with reference again to FIG. 9, each of the signals $\overline{RowSel_1}$ through $\overline{RowSel_n}$ is generated so as to enable/select (i.e., turn on) all rows of the sensor array at the same time and thereby couple all of the ISFETs of the array to respective controllable current sources $106_j$ in each column. With all pixels of each column simultaneously selected, the current from the current source $106_j$ of a given column is shared by all pixels of the column. The column amplifiers 107A and 107B are disabled by removing the bias voltage VB4, and at the same time the output of the amplifier 107B, connected to the drain of each ISFET in a given column, is grounded via a switch responsive to a control signal "UV." Also, the common body voltage $V_{BODY}$ for all ISFETs of the array is coupled to electrical ground (i.e., $V_{BODY}$=0 Volts) (as discussed above, during normal operation of the array, the body bias voltage $V_{BODY}$ is coupled to the highest voltage potential available to the array, e.g., VDDA). In one exemplary procedure, the bias voltage VB1 for all of the controllable current sources $106_j$ is set such that each pixel's ISFET conducts approximately 1 µA of current. With the ISFET array thusly biased, the array then is irradiated with a sufficient dose of UV radiation (e.g., from an EPROM eraser generating approximately 20 milliWatts/cm$^2$ of radiation at a distance of approximately one inch from the array for approximately 1 hour). After irradiation, the array may be allowed to rest and stabilize over several hours before use for measurements of chemical properties such as ion concentration.

Utilizing at least one of the above-described techniques for reducing trapped charge, we have been able to fabricate FETs floating gates having a trapped charge of zero or substantially zero. Thus, in some embodiments, an aspect of the invention encompasses a floating gate having a surface area of about 4 µm$^2$ to about 50 µm$^2$ having baseline threshold voltage and preferably a trapped charge of zero or substantially zero. Preferably the FETs are chemFETs. The trapped charge should be kept to a level that does not cause appreciable variations from FET to FET across the array, as that would limit the dynamic range of the devices, consistency of measurements, and otherwise adversely affect performance.

Figure 13:
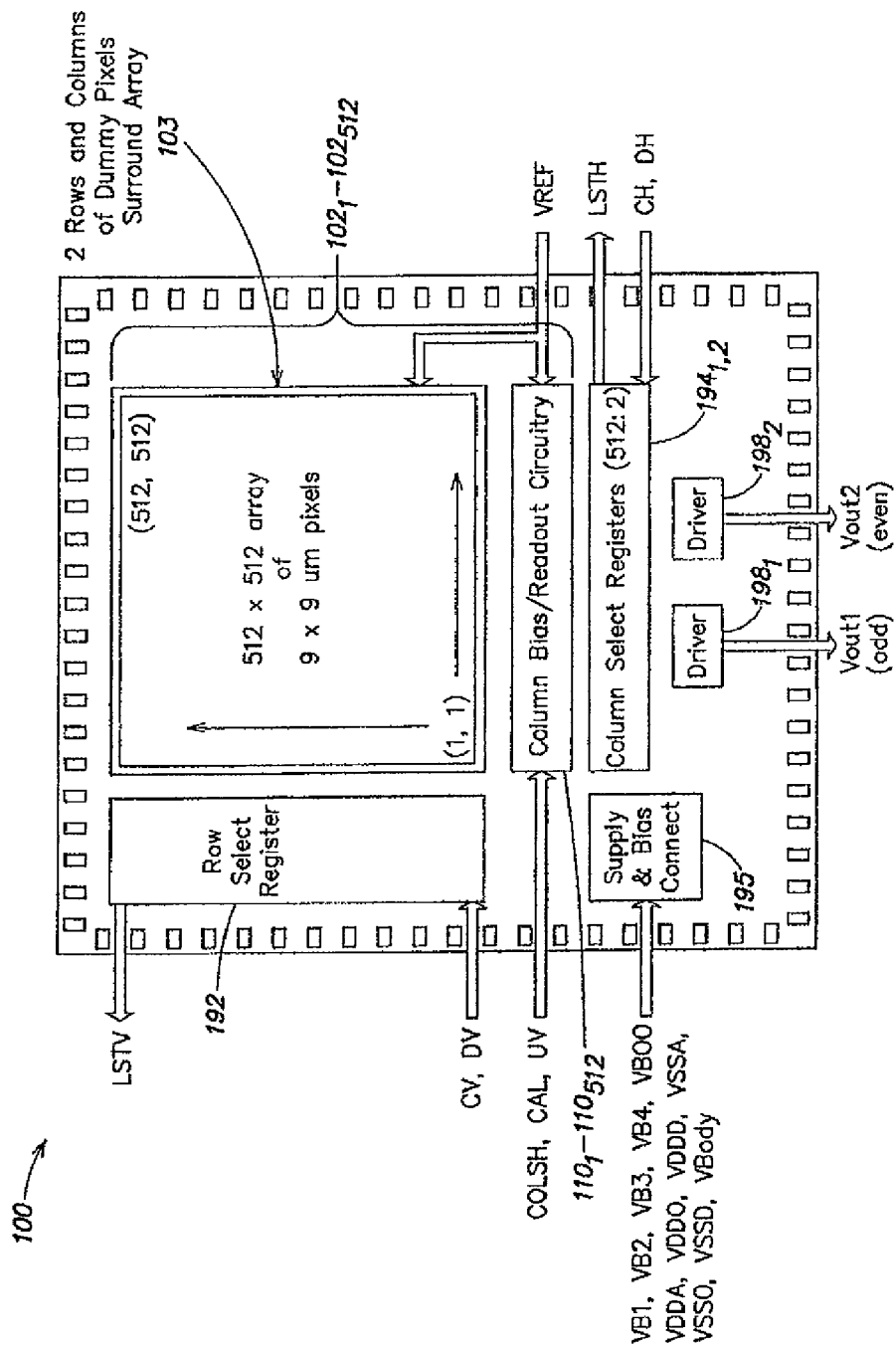
FIG. 13 illustrates a block diagram of an exemplary CMOS IC chip implementation of an chemFET sensor array similar to that shown in FIG. 8, based on the column and pixel designs shown in FIGS. 9-12A, according to one inventive embodiment of the present disclosure.

FIG. 13 illustrates a block diagram of an exemplary CMOS IC chip implementation of an ISFET sensor array 100 based on the column and pixel designs discussed above in connection with FIGS. 9-12A, according to one embodiment of the present disclosure. In one aspect of this embodiment, the array 100 includes 512 columns $102_1$ through $102_{512}$ with corresponding column bias/readout circuitry $110_1$ through $110_{512}$ (one for each column, as shown in FIG. 9), wherein each column includes 512 geometrically square pixels $105_1$ through $105_{512}$, each having a size of approximately 9 micrometers by 9 micrometers (i.e., the array is 512 columns by 512 rows). In another aspect, the entire array (including pixels together with associated row and column select circuitry and column bias/readout circuitry) may be fabricated on a semiconductor die as an application specific integrated circuit (ASIC) having dimensions of approximately 7 millimeters by 7 millimeters. While an array of 512 by 512 pixels is shown in the embodiment of FIG. 13, it should be appreciated that arrays may be implemented with different numbers of rows and columns and different pixel sizes according to other embodiments, as discussed further below in connection with FIGS. 19-23.

Also, as discussed above, it should be appreciated that arrays according to various embodiments of the present invention may be fabricated according to conventional CMOS fabrications techniques, as well as modified CMOS fabrication techniques (e.g., to facilitate realization of various functional aspects of the chemFET arrays discussed herein, such as additional deposition of passivation materials, process steps to mitigate trapped charge, etc.) and other semiconductor fabrication techniques beyond those conventionally employed in CMOS fabrication. Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one aspect of the array 100 shown in FIG. 13, the first and last two columns $102_1$, $102_2$, $102_{511}$ and $102_{512}$, as well as the first two pixels $105_1$ and $105_2$ and the last two pixels $105_{511}$ and $105_{512}$ of each of the columns $102_3$ through $102_{510}$ (e.g., two rows and columns of pixels around a perimeter of the array) may be configured as "reference" or "dummy" pixels 103. With reference to FIG. 11A, for the dummy pixels of an array, the topmost metal layer 304 of each dummy pixel's ISFET (coupled ultimately to the ISFETs polysilicon gate 164) is tied to the same metal layer of other dummy pixels and is made accessible as a terminal of the chip, which in turn may be coupled to a reference voltage VREF. As discussed above in connection with FIG. 9, the reference voltage VREF also may be applied to the bias/readout circuitry of respective columns of the array. In some exemplary implementations discussed further below, preliminary test/evaluation data may be acquired from the array based on applying the reference voltage VREF and selecting and reading out dummy pixels, and/or reading out columns based on the direct application of VREF to respective column buffers (e.g., via the CAL signal), to facilitate offset determination (e.g., pixel-to-pixel and column-to-column variances) and array calibration.

In yet another implementation of an array similar to that shown in FIG. 13, rather than reserving the first and last two columns of 512 columns and the first and last two pixels of each column of 512 pixels as reference pixels, the array may be fabricated to include an additional two rows/columns of reference pixels surrounding a perimeter of a 512 by 512 region of active pixels, such that the total size of the array in terms of actual pixels is 516 by 516 pixels. As arrays of various sizes and configurations are contemplated by the present disclosure, it should be appreciated that the foregoing concept may be applied to any of the other array embodiments discussed herein. For purposes of the discussion immediately below regarding the exemplary array 100 shown in FIG. 13, a total pixel count for the array of 512 by 512 pixels is considered.

In FIG. 13, various power supply and bias voltages required for array operation (as discussed above in connection with FIG. 9) are provided to the array via electrical connections (e.g., pins, metal pads) and labeled for simplicity in block 195 as "supply and bias connections." The array 100 of FIG. 13 also includes a row select shift register 192, two sets of column select shift registers $194_{1,2}$ and two output drivers $198_1$ and $198_2$ to provide two parallel array output signals, Vout1 and Vout2, representing sensor measurements (i.e., collections of individual output signals generated by respective ISFETs of the array). The various power supply and bias voltages, control signals for the row and column shift registers, and control signals for the column bias/readout circuitry shown in FIG. 13 are provided by an array controller, as discussed further below in connection with FIG. 17, which also reads the array output signals Vout1 and Vout2 (and other optional status/diagnostic signals) from the array 100. In another aspect of the array embodiment shown in FIG. 13, configuring the array such that multiple regions (e.g., multiple columns) of the array may be read at the same time via multiple parallel array output signals (e.g., Vout1 and Vout2) facilitates increased data acquisition rates, as discussed further below in connection with FIGS. 17 and 18. While FIG. 13 illustrates an array having two column select registers and parallel array output signals Vout1 and Vout2 to acquire data simultaneously from two columns at a time, it should be appreciated that, in other embodiments, arrays according to the present disclosure may be configured to have only one measurement signal output, or more than two measurement signal outputs; in particular, as discussed further below in connection with FIGS. 19-23, more dense arrays according to other inventive embodiments may be configured to have four our more parallel measurement signal outputs and simultaneously enable different regions of the array to provide data via the four or more outputs.

Figure 14:
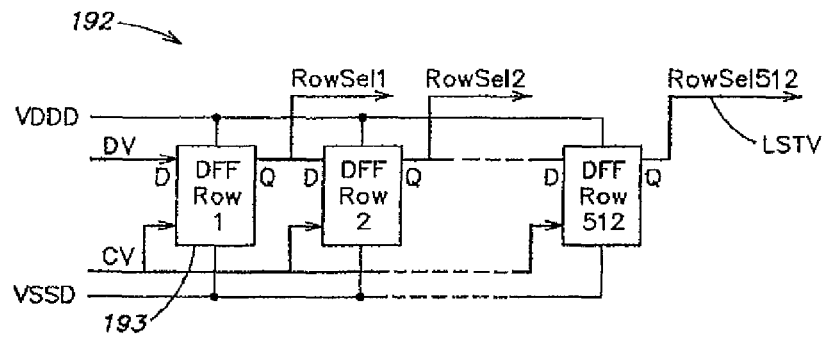
FIG. 14 illustrates a row select shift register of the array shown in FIG. 13, according to one inventive embodiment of the present disclosure.
Figure 15:
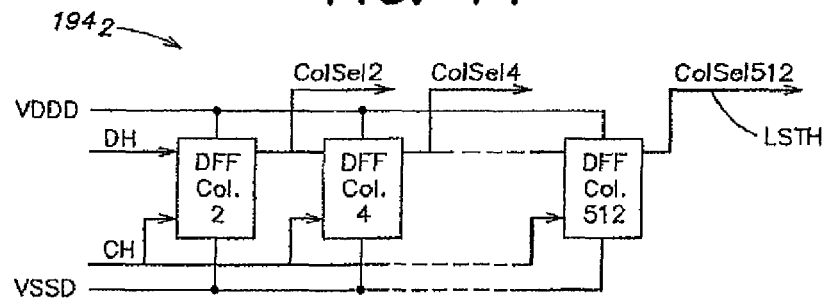
FIG. 15 illustrates one of two column select shift registers of the array shown in FIG. 13, according to one inventive embodiment of the present disclosure.
Figure 16:
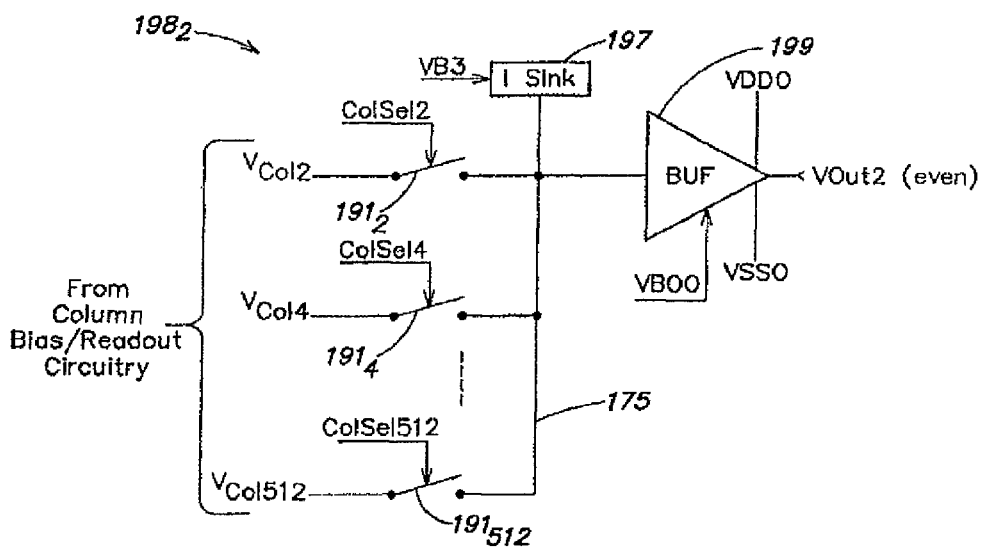
FIG. 16 illustrates one of two output drivers of the array shown in FIG. 13, according to one inventive embodiment of the present disclosure.

FIG. 14 illustrates the row select shift register 192, FIG. 15 illustrates one of the column select shift registers $194_2$ and FIG. 16 illustrates one of the output drivers $198_2$ of the array 100 shown in FIG. 13, according to one exemplary implementation. As shown in FIGS. 14 and 15, the row and column select shift registers are implemented as a series of D-type flip-flops coupled to a digital circuitry positive supply voltage VDDD and a digital supply ground VSSD. In the row and column shift registers, a data signal is applied to a D-input of first flip-flop in each series and a clock signal is applied simultaneously to a clock input of all of the flip-flops in the series. For each flip-flop, a "Q" output reproduces the state of the D-input upon a transition (e.g., falling edge) of the clock signal. With reference to FIG. 14, the row select shift register 192 includes 512 D-type flip-flops, in which a first flip-flop 193 receives a vertical data signal DV and all flip-flops receive a vertical clock signal CV. A "Q" output of the first flip-flop 193 provides the first row select signal $RowSel_1$ and is coupled to the D-input of the next flip-flop in the series. The Q outputs of successive flip-flops are coupled to the D-inputs of the next flip-flop in the series and provide the row select signals $RowSel_2$ through $RowSel_{512}$ with successive falling edge transitions of the vertical clock signal CV, as discussed further below in connection with FIG. 18. The last row select signal $RowSel_{512}$ also may be taken as an optional output of the array 100 as the signal LSTV (Last STage Vertical), which provides an indication (e.g., for diagnostic purposes) that the last row of the array has been selected. While not shown explicitly in FIG. 14, each of the row select signals $RowSel_1$ through $RowSel_{512}$ is applied to a corresponding inverter, the output of which is used to enable a given pixel in each column (as illustrated in FIG. 9 by the signals $\overline{RowSel_1}$ through $\overline{RowSel_n}$).

Regarding the column select shift registers $194_1$ and $194_2$, these are implemented in a manner similar to that of the row select shift registers, with each column select shift register comprising 256 series-connected flip-flops and responsible for enabling readout from either the odd columns of the array or the even columns of the array. For example, FIG. 15 illustrates the column select shift register $194_2$, which is configured to enable readout from all of the even numbered columns of the array in succession via the column select signals $ColSel_2$, $ColSel_4$, ... $ColSel_{512}$, whereas another column select shift register $194_1$ is configured to enable readout from all of the odd numbered columns of the array in succession (via column select signals $ColSel_1$, $ColSel_3$, ... $ColSel_{511}$). Both column select shift registers are controlled simultaneously by the horizontal data signal DH and the horizontal clock signal CH to provide the respective column select signals, as discussed further below in connection with FIG. 18. As shown in FIG. 15, the last column select signal $ColSel_{512}$ also may be taken as an optional output of the array 100 as the signal LSTH (Last STage Horizontal), which provides an indication (e.g., for diagnostic purposes) that the last column of the array has been selected.

With reference again for the moment to FIG. 7, Applicants have recognized and appreciated that an implementation for array row and column selection based on shift registers, as discussed above in connection with FIGS. 13-15, is a significant improvement to the row and column decoder approach employed in various prior art ISFET array designs, including the design of Milgrew et al. shown in FIG. 7. In particular, regarding the row decoder 92 and the column decoder 94 shown in FIG. 7, the complexity of implementing these components in an integrated circuit array design increases dramatically as the size of the array is increased, as additional inputs to both decoders are required. For example, an array having 512 rows and columns as discussed above in connection with FIG. 13 would require nine inputs ($2^9$=512) per row and column decoder if such a scheme were employed for row and column selection; similarly, arrays having 7400 rows and 7400 columns, as discussed below in connection with other embodiments, would require 13 inputs ($2^{13}$=8192) per row and column decoder. In contrast, the row and column select shift registers shown in FIGS. 14 and 15 require no additional input signals as array size is increased, but rather additional D-type flip-flops (which are routinely implemented in a CMOS process). Thus, the shift register implementations shown in FIGS. 14 and 15 provide an easily scalable solution to array row and column selection.

In the embodiment of FIG. 13, the "odd" column select shift register $194_1$ provides odd column select signals to an "odd" output driver $198_1$ and the even column select shift register $194_2$ provides even column select signals to an "even" output driver $198_2$. Both output drivers are configured similarly, and an example of the even output driver $198_2$ is shown in FIG. 16. In particular, FIG. 16 shows that respective even column output signals $V_{COL2}$, $V_{COL4}$, ... $V_{COL512}$ (refer to FIG. 9 for the generic column signal output $V_{COLj}$) are applied to corresponding switches $191_2$, $191_4$, ... $191_{512}$, responsive to the even column select signals $ColSel_2$, $ColSel_4$, ... $ColSel_{512}$ provided by the column select register $194_2$, to successively couple the even column output signals to the input of a buffer amplifier 199 (BUF) via a bus 175. In FIG. 16, the buffer amplifier 199 receives power from an output buffer positive supply voltage VDDO and an output buffer supply ground VSSO, and is responsive to an output buffer bias voltage VBO0 to set a corresponding bias current for the buffer output. Given the high impedance input of the buffer amplifier 199, a current sink 197 responsive to a bias voltage VB3 is coupled to the bus 175 to provide an appropriate drive current (e.g., on the order of approximately 100 µA) for the output of the column output buffer (see the buffer amplifier 111j of FIG. 9) of a selected column. The buffer amplifier 199 provides the output signal Vout2 based on the selected even column of the array; at the same time, with reference to FIG. 13, a corresponding buffer amplifier of the "odd" output driver $198_1$ provides the output signal Vout1 based on a selected odd column of the array.

In one exemplary implementation, the switches of both the even and odd output drivers $198_1$ and $198_2$ (e.g., the switches $191_2$, $191_4$, ... $191_{512}$ shown in FIG. 16) may be implemented as CMOS-pair transmission gates (including an n-channel MOSFET and a p-channel MOSFET; see FIG. 4), and inverters may be employed so that each column select signal and its complement may be applied to a given transmission gate switch 191 to enable switching. Each switch 191 has a series resistance when enabled or "on" to couple a corresponding column output signal to the bus 175; likewise, each switch adds a capacitance to the bus 175 when the switch is off. A larger switch reduces series resistance and allows a higher drive current for the bus 175, which generally allows the bus 175 to settle more quickly; on the other hand, a larger switch increases capacitance of the bus 175 when the switch is off, which in turn increases the settling time of the bus 175. Hence, there is a trade-off between switch series resistance and capacitance in connection with switch size.

The ability of the bus 175 to settle quickly following enabling of successive switches in turn facilitates rapid data acquisition from the array. To this end, in some embodiments the switches 191 of the output drivers $198_1$ and $198_2$ are particularly configured to significantly reduce the settling time of the bus 175. Both the n-channel and the p-channel MOSFETs of a given switch add to the capacitance of the bus 175; however, n-channel MOSFETs generally have better frequency response and current drive capabilities than their p-channel counterparts. In view of the foregoing, Applicants have recognized and appreciated that some of the superior characteristics of n-channel MOSFETs may be exploited to improve settling time of the bus 175 by implementing "asymmetric" switches in which respective sizes for the n-channel MOSFET and p-channel MOSFET of a given switch are different.

For example, in one embodiment, with reference to FIG. 16, the current sink 197 may be configured such that the bus 175 is normally "pulled down" when all switches $191_2$, $191_4$, ... $191_{512}$ are open or off (not conducting). Given a somewhat limited expected signal dynamic range for the column output signals based on ISFET measurements, when a given switch is enabled or on (conducting), in many instances most of the conduction is done by the n-channel MOSFET of the CMOS-pair constituting the switch. Accordingly, in one aspect of this embodiment, the n-channel MOSFET and the p-channel MOSFET of each switch 191 are sized differently; namely, in one exemplary implementation, the n-channel MOSFET is sized to be significantly larger than the p-channel MOSFET. More specifically, considering equally-sized n-channel and p-channel MOSFETs as a point of reference, in one implementation the n-channel MOSFET may be increased to be about 2 to 2.5 times larger, and the p-channel MOSFET may be decreased in size to be about 8 to 10 times smaller, such that the n-channel MOSFET is approximately 20 times larger than the p-channel MOSFET. Due to the significant decrease in size of the p-channel MOSFET and the relatively modest increase in size of the n-channel MOSFET, the overall capacitance of the switch in the off state is notably reduced, and there is a corresponding notable reduction in capacitance for the bus 175; at the same time, due to the larger n-channel MOSFET, there is a significant increase in current drive capability, frequency response and transconductance of the switch, which in turn results in a significant reduction in settling time of the bus 175.

While the example above describes asymmetric switches 191 for the output drivers $198_1$ and $198_2$ in which the n-channel MOSFET is larger than the p-channel MOSFET, it should be appreciated that in another embodiment, the converse may be implemented, namely, asymmetric switches in which the p-channel MOSFET is larger than the n-channel MOSFET. In one aspect of this embodiment, with reference again to FIG. 16, the current sink 197 may alternatively serve as a source of current to appropriately drive the output of the column output buffer (see the buffer amplifier 111j of FIG. 9) of a selected column, and be configured such that the bus 175 is normally "pulled up" when all switches $191_2$, $191_4$, ... $191_{512}$ are open or off (not conducting). In this situation, most of the switch conduction may be accomplished by the p-channel MOSFET of the CMOS-pair constituting the switch. Benefits of reduced switch capacitance (and hence reduced bus capacitance) may be realized in this embodiment, although the overall beneficial effect of reduced settling time for the bus 175 may be somewhat less than that described previously above, due to the lower frequency response of p-channel MOSFETs as compared to n-channel MOSFETs. Nevertheless, asymmetric switches based on larger p-channel MOSFETs may still facilitate a notable reduction in bus settling time, and may also provide for circuit implementations in which the column output buffer amplifier (111$j$ of FIG. 9) may be a body-tied source follower with appreciably increased gain.

In yet another embodiment directed to facilitating rapid settling of the bus 175 shown in FIG. 16, it may be appreciated that fewer switches 191 coupled to the bus 175 results in a smaller bus capacitance. With this in mind, and with reference again to FIG. 13, in yet another embodiment, more than two output drivers $198_1$ and $198_2$ may be employed in the ISFET array 100 such that each output driver handles a smaller number of columns of the array. For example, rather than having all even columns handled by one driver and all odd columns handled by another driver, the array may include four column select registers $194_{1,2,3,4}$ and four corresponding output drivers $198_{1,2,3,4}$ such that each output driver handles one-fourth of the total columns of the array, rather than one-half of the columns. In such an implementation, each output driver would accordingly have half the number of switches 191 as compared with the embodiment discussed above in connection with FIG. 16, and the bus 175 of each output driver would have a corresponding lower capacitance, thereby improving bus settling time. While four output drivers are discussed for purposes of illustration in this example, it should be appreciated that the present disclosure is not limited in this respect, and virtually any number of output drivers greater than two may be employed to improve bus settling time in the scenario described above. Other array embodiments in which more than two output drivers are employed to facilitate rapid data acquisition from the array are discussed in greater detail below (e.g., in connection with FIGS. 19-23).

For purposes of illustration, the bus 175 may have a capacitance in the range of approximately 5 pF to 20 pF in any of the embodiments discussed immediately above (e.g. symmetric switches, asymmetric switches, greater numbers of output drivers, etc.). Of course, it should be appreciated that the capacitance of the bus 175 is not limited to these exemplary values, and that other capacitance values are possible in different implementations of an array according to the present disclosure.

In one aspect of the array design discussed above in connection with FIGS. 13-16, separate analog supply voltage connections (for VDDA, VSSA), digital supply voltage connections (for VDDD, VSSD) and output buffer supply voltage connections (for VDDO, VSSO) are provided on the array to facilitate noise isolation and reduce signal cross-talk amongst various array components, thereby increasing the signal-to-noise ratio (SNR) of the output signals Vout1 and Vout2. In one exemplary implementation, the positive supply voltages VDDA, VDDD and VDDO each may be approximately 3.3 Volts. In another aspect, these voltages respectively may be provided "off chip" by one or more programmable voltage sources, as discussed further below in connection with FIG. 17.

Figure 17:
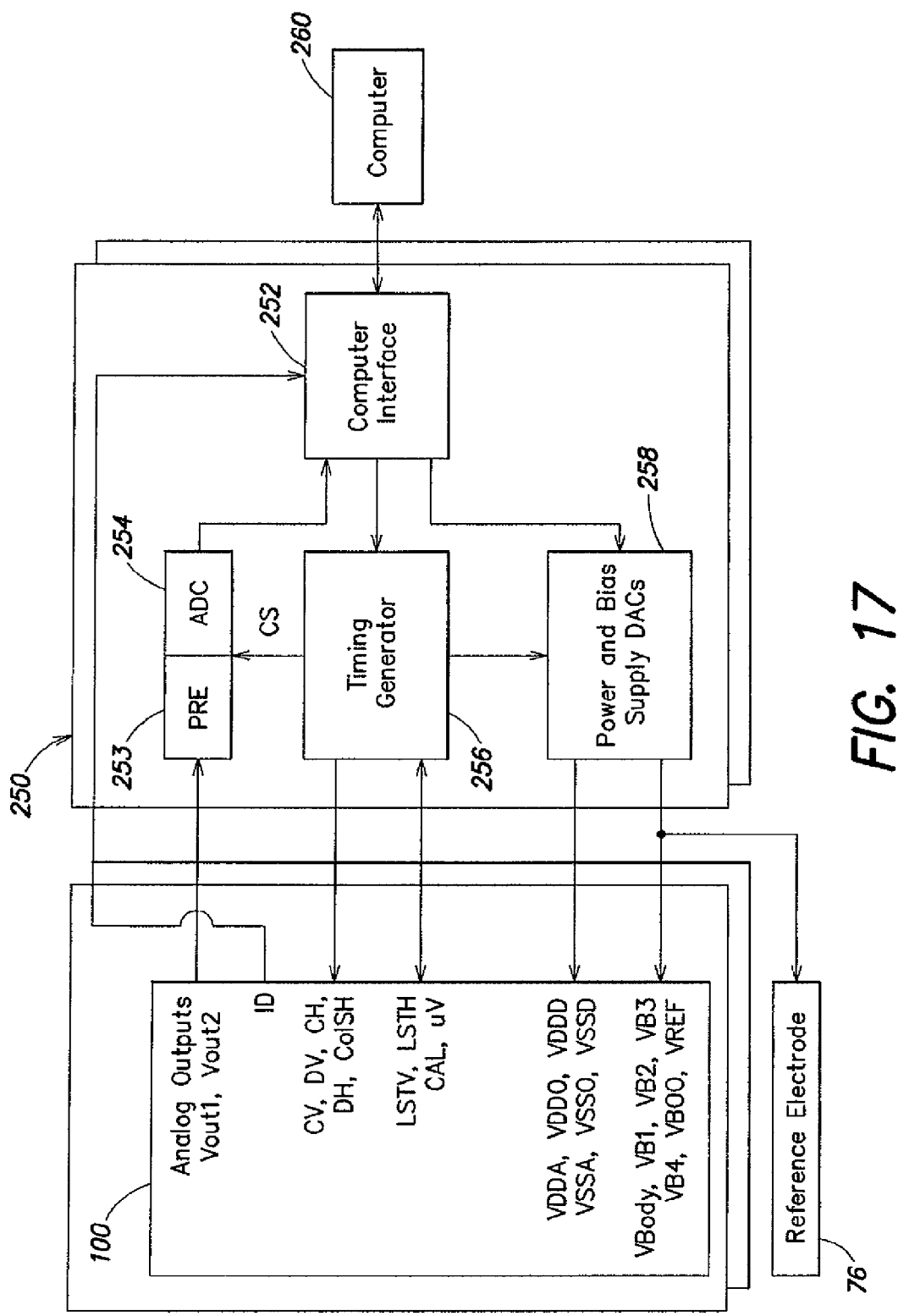
FIG. 17 illustrates a block diagram of the chemFET sensor array of FIG. 13 coupled to an array controller, according to one inventive embodiment of the present disclosure.

FIG. 17 illustrates a block diagram of the sensor array 100 of FIG. 13 coupled to an array controller 250, according to one inventive embodiment of the present disclosure. In various exemplary implementations, the array controller 250 may be fabricated as a "stand alone" controller, or as one or more computer compatible "cards" forming part of a computer 260, as discussed above in connection with FIG. 8. In one aspect, the functions of the array controller 250 may be controlled by the computer 260 through an interface block 252 (e.g., serial interface, via USB port or PCI bus, Ethernet connection, etc.), as shown in FIG. 17. In one embodiment, all or a portion of the array controller 250 is fabricated as one or more printed circuit boards, and the array 100 is configured to plug into one of the printed circuit boards, similar to a conventional IC chip (e.g., the array 100 is configured as an ASIC that plugs into a chip socket, such as a zero-insertion-force or "ZIF" socket, of a printed circuit board). In one aspect of such an embodiment, an array 100 configured as an ASIC may include one or more pins/terminal connections dedicated to providing an identification code, indicated as "ID" in FIG. 17, that may be accessed/read by the array controller 250 and/or passed on to the computer 260. Such an identification code may represent various attributes of the array 100 (e.g., size, number of pixels, number of output signals, various operating parameters such as supply and/or bias voltages, etc.) and may be processed to determine corresponding operating modes, parameters and or signals provided by the array controller 250 to ensure appropriate operation with any of a number of different types of arrays 100. In one exemplary implementation, an array 100 configured as an ASIC may be provided with three pins dedicated to an identification code, and during the manufacturing process the ASIC may be encoded to provide one of three possible voltage states at each of these three pins (i.e., a tri-state pin coding scheme) to be read by the array controller 250, thereby providing for 27 unique array identification codes. In another aspect of this embodiment, all or portions of the array controller 250 may be implemented as a field programmable gate array (FPGA) configured to perform various array controller functions described in further detail below.

Generally, the array controller 250 provides various supply voltages and bias voltages to the array 100, as well as various signals relating to row and column selection, sampling of pixel outputs and data acquisition. In particular, the array controller 250 reads one or more analog output signals (e.g., Vout1 and Vout2) including multiplexed respective pixel voltage signals from the array 100 and then digitizes these respective pixel signals to provide measurement data to the computer 260, which in turn may store and/or process the data. In some implementations, the array controller 250 also may be configured to perform or facilitate various array calibration and diagnostic functions, and an optional array UV irradiation treatment as discussed above in connection with FIG. 11A.

As illustrated in FIG. 17, the array controller 250 generally provides to the array 100 the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts. In another implementation, the supply voltages VDDA, VDDD and VDDO may be as low as approximately 1.8 Volts. As discussed above, in one aspect each of these power supply voltages is provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VB1, VB2, VB3, VB4, VBO0, $V_{BODY}$) and the reference voltage VREF used for array diagnostics and calibration.

In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control (e.g., via software execution) may facilitate adjustment of one or more of the supply voltages (e.g., switching between 3.3 Volts and 1.8 Volts depending on chip type as represented by an identification code), and or adjustment of one or more of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As also shown in FIG. 17, the reference electrode 76 which is typically employed in connection with an analyte solution to be measured by the array 100 (as discussed above in connection with FIG. 1), may be coupled to the power supply 258 to provide a reference potential for the pixel output voltages. For example, in one implementation the reference electrode 76 may be coupled to a supply ground (e.g., the analog ground VSSA) to provide a reference for the pixel output voltages based on Eq. (3) above. In other exemplary implementations, the reference electrode voltage may be set by placing a solution/sample of interest having a known pH level in proximity to the sensor array 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 17 may include one or more preamplifiers 253 to further buffer one or more output signals (e.g., Vout1 and Vout2) from the sensor array and provide selectable gain. In one aspect, the array controller 250 may include one preamplifier for each output signal (e.g., two preamplifiers for two analog output signals). In other aspects, the preamplifiers may be configured to accept input voltages from 0.0 to 1.8 Volts or 0.0 to 3.3 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). With respect to noise reduction and increasing signal-to-noise ratio, in one implementation in which the array 100 is configured as an ASIC placed in a chip socket of a printed circuit board containing all or a portion of the array controller 250, filtering capacitors may be employed in proximity to the chip socket (e.g., the underside of a ZIF socket) to facilitate noise reduction. In yet another aspect, the preamplifiers may have a programmable/computer selectable offset for input and/or output voltage signals to set a nominal level for either to a desired range.

The array controller 250 of FIG. 17 also comprises one or more analog-to-digital converters 254 (ADCs) to convert the sensor array output signals Vout1 and Vout2 to digital outputs (e.g., 10-bit or 12-bit) so as to provide data to the computer 260. In one aspect, one ADC may be employed for each analog output of the sensor array, and each ADC may be coupled to the output of a corresponding preamplifier (if preamplifiers are employed in a given implementation). In another aspect, the ADC(s) may have a computer-selectable input range (e.g., 50 mV, 200 mV, 500 mV, 1V) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater).

In the embodiment of FIG. 17, ADC acquisition timing and array row and column selection may be controlled by a timing generator 256. In particular, the timing generator provides the digital vertical data and clock signals (DV, CV) to control row selection, the digital horizontal data and clock signals (DH, CH) to control column selection, and the column sample and hold signal COL SH to sample respective pixel voltages for an enabled row, as discussed above in connection with FIG. 9. The timing generator 256 also provides a sampling clock signal CS to the ADC(s) 254 so as to appropriately sample and digitize consecutive pixel values in the data stream of a given array analog output signal (e.g., Vout1 and Vout2), as discussed further below in connection with FIG. 18. In some implementations, the timing generator 256 may be implemented by a microprocessor executing code and configured as a multi-channel digital pattern generator to provide appropriately timed control signals. In one exemplary implementation, the timing generator 256 may be implemented as a field-programmable gate array (FPGA).

Figure 18:
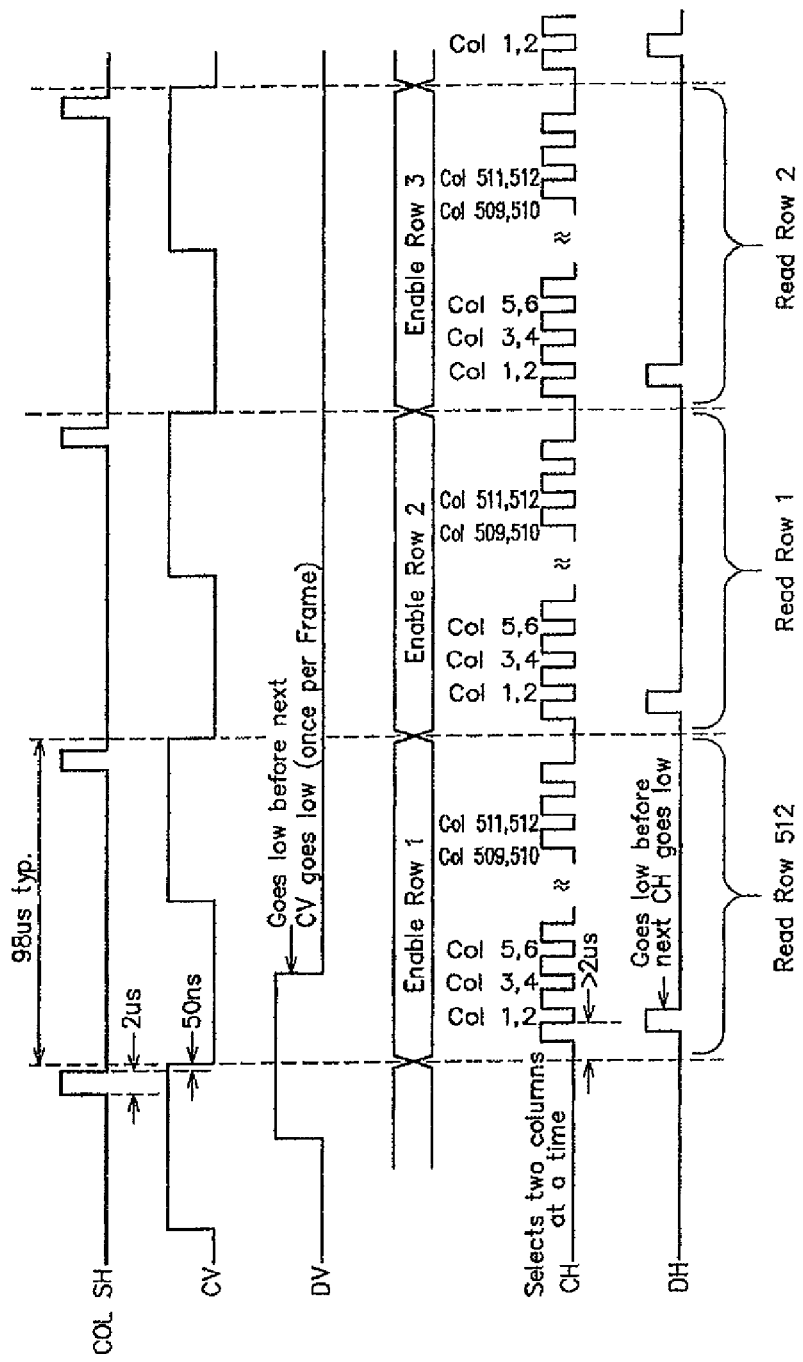
FIG. 18 illustrates an exemplary timing diagram for various signals provided by the array controller of FIG. 17, according to one inventive embodiment of the present disclosure.

FIG. 18 illustrates an exemplary timing diagram for various array control signals, as provided by the timing generator 256, to acquire pixel data from the sensor array 100. For purposes of the following discussion, a "frame" is defined as a data set that includes a value (e.g., pixel output signal or voltage $V_S$) for each pixel in the array, and a "frame rate" is defined as the rate at which successive frames may be acquired from the array. Thus, the frame rate corresponds essentially to a "pixel sampling rate" for each pixel of the array, as data from any given pixel is obtained at the frame rate.

In the example of FIG. 18, an exemplary frame rate of 20 frames/sec is chosen to illustrate operation of the array (i.e., row and column selection and signal acquisition); however, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array ASIC and reagent preparation for a subsequent experiment.

For example, with respect to the method for detecting nucleotide incorporation, discussed above, in which one or more ion pulses are generated in the output signal of a given ISFET pixel of the array during a nucleic acid synthesis or sequencing reaction in a reaction well above the ISFET, appropriate frame rates may be chosen to sufficiently sample the ISFET's output signal so as to effectively detect the presence of one or more pulses and the time interval between pulses. In some exemplary implementations, one or more ion pulses may be generated having a full-width at half-maximum (FWHM) on the order of approximately 1 second to approximately 2.5 seconds, and time intervals between successive pulse peaks (if multiple pulses are generated) on the order of approximately 1 to 20 seconds, depending on the number of nucleotide incorporation events. Given these exemplary values, a frame rate (or pixel sampling rate) of 20 Hz is sufficient to reliably resolve the one or more pulses in a given pixel's output signal. Again, the pulse characteristics and frame rate given in this example are provided primarily for purposes of illustration, and different pulse characteristics and frame rates may be involved in other implementations.

In one implementation, the array controller 250 controls the array 100 to enable rows successively, one at a time. For example, with reference again for the moment to FIG. 9, a first row of pixels is enabled via the row select signal $\overline{RowSel_1}$. The enabled pixels are allowed to settle for some time period, after which the COL SH signal is asserted briefly to close the sample/hold switch in each column and store on the column's sample/hold capacitor $C_{sh}$ the voltage value output by the first pixel in the column. This voltage is then available as the column output voltage $V_{COLj}$ applied to one of the two (odd and even column) array output drivers $198_1$ and $198_2$ (e.g., see FIG. 16). The COL SH signal is then de-asserted, thereby opening the sample/hold switches in each column and decoupling the column output buffer 111j from the column amplifiers 107A and 107B. Shortly thereafter, the second row of pixels is enabled via the row select signal $\overline{RowSel_2}$. During the time period in which the second row of pixels is allowed to settle, the column select signals are generated two at a time (one odd and one even; odd column select signals are applied in succession to the odd output driver, even column select signals are applied in succession to the even output driver) to read the column output voltages associated with the first row. Thus, while a given row in the array is enabled and settling, the previous row is being read out, two columns at a time. By staggering row selection and sampling/readout (e.g., via different vertical and horizontal clock signals and column sample/hold), and by reading multiple columns at a time for a given row, a frame of data may be acquired from the array in a significantly streamlined manner.

FIG. 18 illustrates the timing details of the foregoing process for an exemplary frame rate of 20 frames/sec. Given this frame rate and 512 rows in the array, each row must be read out in approximately 98 microseconds, as indicated by the vertical delineations in FIG. 18. Accordingly, the vertical clock signal CV has a period of 98 microseconds (i.e., a clock frequency of over 10 kHz), with a new row being enabled on a trailing edge (negative transition) of the CV signal. The left side of FIG. 18 reflects the beginning of a new frame cycle, at which point the vertical data signal DV is asserted before a first trailing edge of the CV signal and de-asserted before the next trailing edge of the CV signal (for data acquisition from successive frames, the vertical data signal is reasserted again only after row 512 is enabled). Also, immediately before each trailing edge of the CV signal (i.e., new row enabled), the COL SH signal is asserted for 2 microseconds, leaving approximately 50 nanoseconds before the trailing edge of the CV signal.

In FIG. 18, the first occurrence of the COL SH signal is actually sampling the pixel values of row 512 of the array. Thus, upon the first trailing edge of the CV signal, the first row is enabled and allowed to settle (for approximately 96 microseconds) until the second occurrence of the COL SH signal. During this settling time for the first row, the pixel values of row 512 are read out via the column select signals. Because two column select signals are generated simultaneously to read 512 columns, the horizontal clock signal CH must generate 256 cycles within this period, each trailing edge of the CH signal generating one odd and one even column select signal. As shown in FIG. 18, the first trailing edge of the CH signal in a given row is timed to occur two microseconds after the selection of the row (after deactivation of the COL SH signal) to allow for settling of the voltage values stored on the sample/hold capacitors $C_{sh}$ and provided by the column output buffers. It should be appreciated however that, in other implementations (e.g., as discussed below in connection with FIG. 18A), the time period between the first trailing edge of the CH signal and a trailing edge (i.e., deactivation) of the COL SH signal may be significantly less than two microseconds, and in some cases as small as just over 50 nanoseconds. Also for each row, the horizontal data signal DH is asserted before the first trailing edge of the CH signal and de-asserted before the next trailing edge of the CH signal. The last two columns (e.g., 511 and 512) are selected before the occurrence of the COL SH signal which, as discussed above, occurs approximately two microseconds before the next row is enabled. Thus, 512 columns are read, two at a time, within a time period of approximately 94 microseconds (i.e., 98 microseconds per row, minus two microseconds at the beginning and end of each row). This results in a data rate for each of the array output signals Vout1 and Vout2 of approximately 2.7 MHz.

Figure 18A:
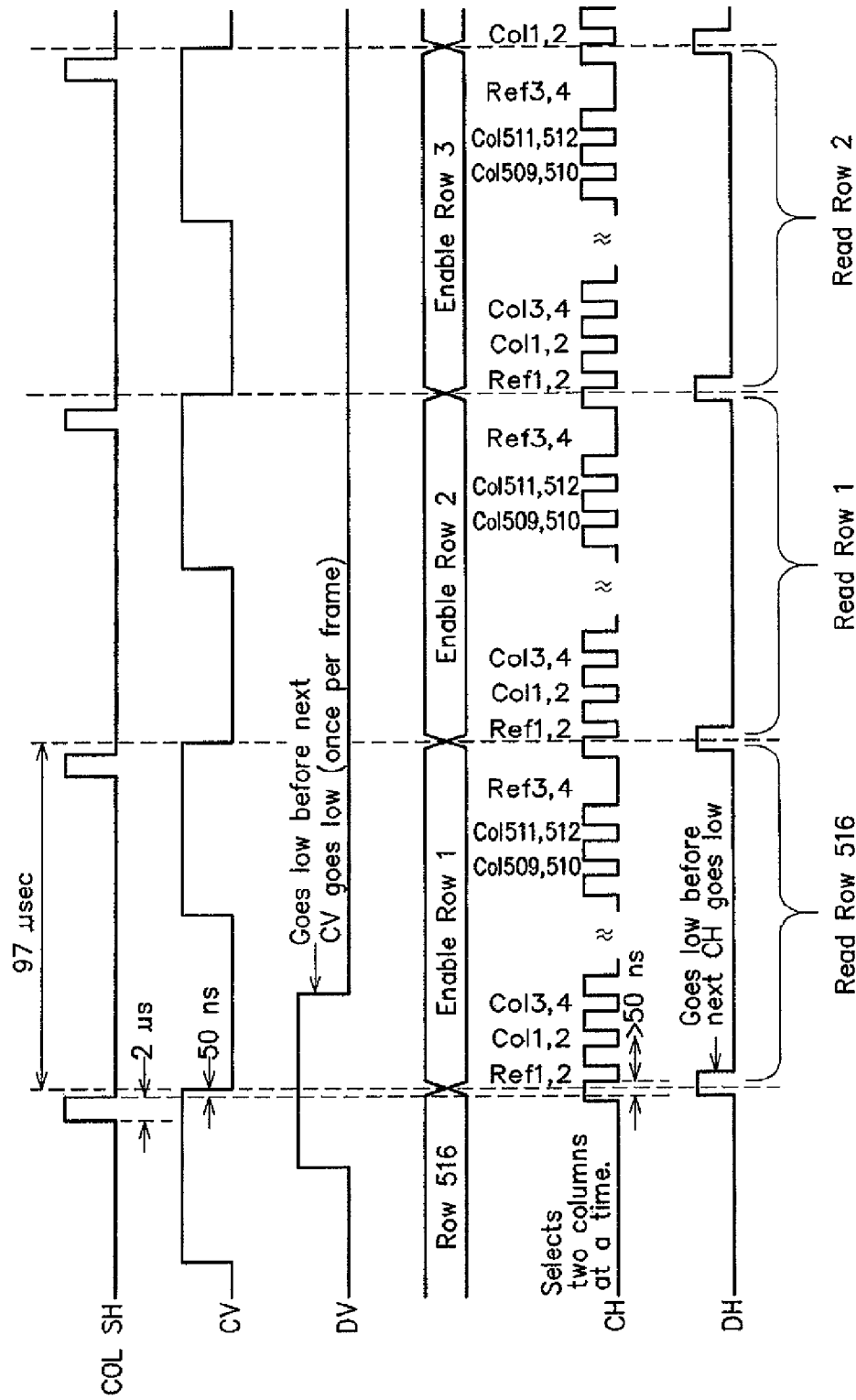
FIG. 18A illustrates another exemplary timing diagram for various signals provided by the array controller of FIG. 17, according to one inventive embodiment of the present disclosure.

FIG. 18A illustrates another timing diagram of a data acquisition process from an array 100 that is slightly modified from the timing diagram of FIG. 18. As discussed above in connection with FIG. 13, in some implementations an array similar to that shown in FIG. 13 may be configured to include a region of 512 by 512 "active" pixels that are surrounded by a perimeter of reference pixels (i.e., the first and last two rows and columns of the array), resulting in an array having a total pixel count of 516 by 516 pixels. Accordingly, given the exemplary frame rate of 20 frames/sec and 516 rows in the array, each row must be read out in approximately 97 microseconds, as indicated by the vertical delineations in FIG. 18A. Accordingly, the vertical clock signal CV has a slightly smaller period of 97 microseconds. Because two column select signals are generated simultaneously to read 516 columns, the horizontal clock signal CH must generate 258 cycles within this period, as opposed to the 256 cycles referenced in connection with FIG. 18. Accordingly, in one aspect illustrated in FIG. 18A, the first trailing edge of the CH signal in a given row is timed to occur just over 50 nanoseconds from the trailing edge (i.e., deactivation) of the COL SH signal, so as to "squeeze" additional horizontal clock cycles into a slightly smaller period of the vertical clock signal CV. As in FIG. 18, the horizontal data signal DH is asserted before the first trailing edge of the CH signal, and as such also occurs slightly earlier in the timing diagram of FIG. 18A as compared to FIG. 18. The last two columns (i.e., columns 515 and 516, labeled as "Ref3,4 in FIG. 18A) are selected before the occurrence of the COL SH signal which, as discussed above, occurs approximately two microseconds before the next row is enabled. Thus, 516 columns are read, two at a time, within a time period of approximately 95 microseconds (i.e., 97 microseconds per row, minus two microseconds at the end of each row and negligible time at the beginning of each row). This results in essentially the same data rate for each of the array output signals Vout1 and Vout2 provided by the timing diagram of FIG. 18, namely, approximately 2.7 MHz.

As discussed above in connection with FIG. 17, the timing generator 256 also generates the sampling clock signal CS to the ADC(s) 254 so as to appropriately sample and digitize consecutive pixel values in the data stream of a given array output signal. In one aspect, the sampling clock signal CS provides for sampling a given pixel value in the data stream at least once. Although the sampling clock signal CS is not shown in the timing diagrams of FIGS. 18 and 18A, it may be appreciated that in exemplary implementations the signal CS may essentially track the timing of the horizontal clock signal CH; in particular, the sampling clock signal CS may be coordinated with the horizontal clock signal CH so as to cause the ADC(s) to sample a pixel value immediately prior to a next pixel value in the data stream being enabled by CH, thereby allowing for as much signal settling time as possible prior to sampling a given pixel value. For example, the ADC(s) may be configured to sample an input pixel value upon a positive transition of CS, and respective positive transitions of CS may be timed by the timing generator 256 to occur immediately prior to, or in some cases essentially coincident with, respective negative transitions of CH, so as to sample a given pixel just prior to the next pixel in the data stream being enabled. In another exemplary implementation, the ADC(s) 254 may be controlled by the timing generator 256 via the sampling clock signal CS to sample the output signals Vout1 and Vout2 at a significantly higher rate to provide multiple digitized samples for each pixel measurement, which may then be averaged (e.g., the ADC data acquisition rate may be approximately 100 MHz to sample the 2.7 MHz array output signals, thereby providing as many as approximately 35-40 samples per pixel measurement).

Figure 18B:
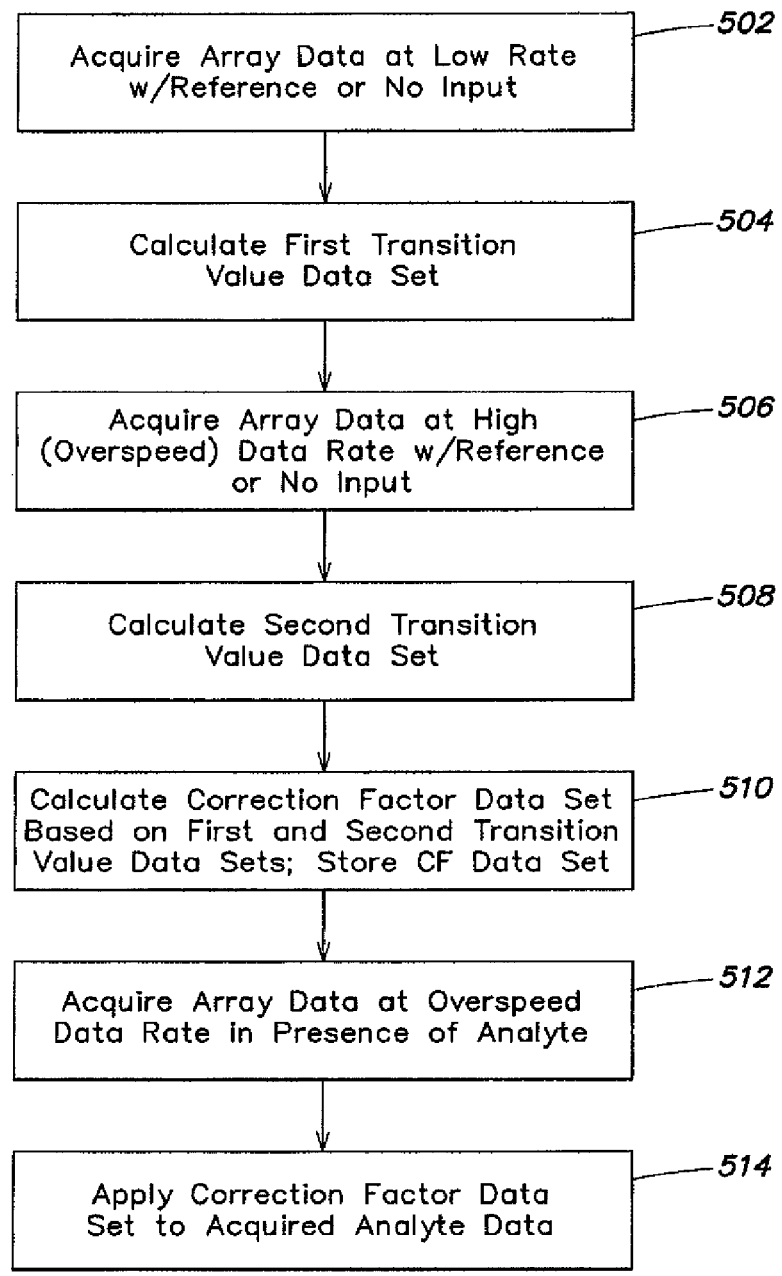
FIG. 18B shows a flow chart illustrating an exemplary method for processing and correction of array data acquired at high acquisition rates, according to one inventive embodiment of the present disclosure.

In one embodiment, once pixel values are sampled and digitized by the ADC(s) 254, the computer 260 may be programmed to process pixel data obtained from the array 100 and the array controller 250 so as to facilitate high data acquisition rates that in some cases may exceed a sufficient settling time for pixel voltages represented in a given array output signal. A flow chart illustrating an exemplary method according to one embodiment of the present invention that may be implemented by the computer 260 for processing and correction of array data acquired at high acquisition rates is illustrated in FIG. 18B. In various aspects of this embodiment, the computer 260 is programmed to first characterize a sufficient settling time for pixel voltages in a given array output signal, as well as array response at appreciably high operating frequencies, using a reference or "dry" input to the array (e.g., no analyte present). This characterization forms the basis for deriving correction factors that are subsequently applied to data obtained from the array at the high operating frequencies and in the presence of an analyte to be measured.

Figure 18C:
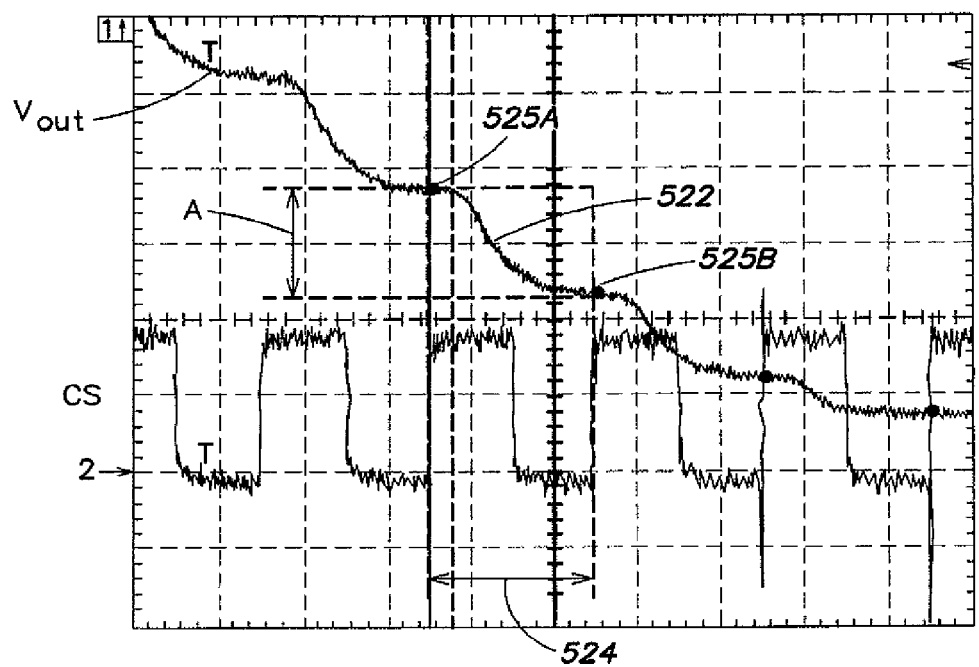
FIGS. 18C and 18D illustrate exemplary pixel voltages showing pixel-to-pixel transitions in a given array output signal, according to one embodiment of the present disclosure.
Figure 18D:
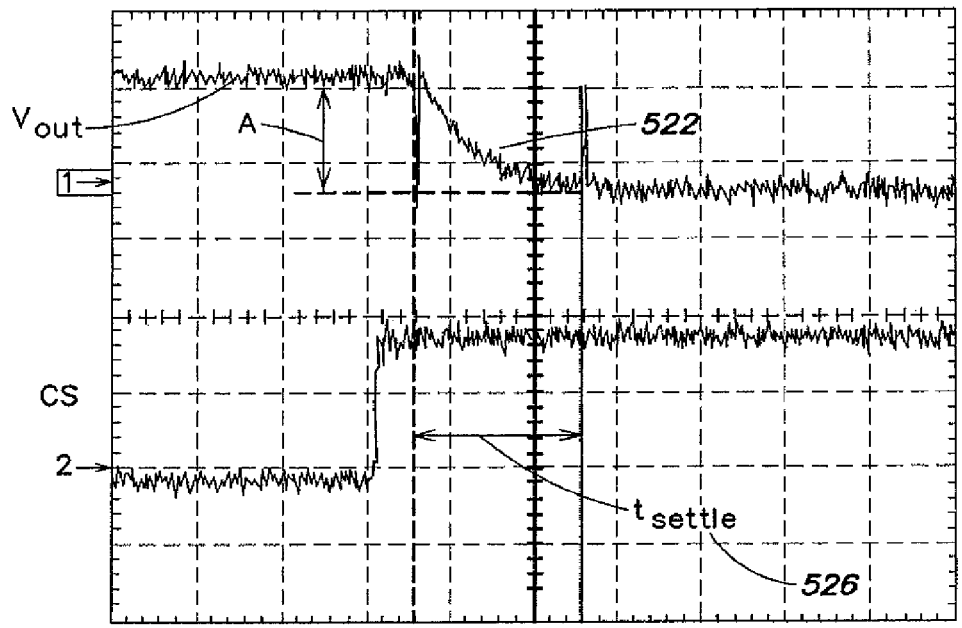

Regarding pixel settling time, with reference again to FIG. 16, as discussed above a given array output signal (e.g., Vout2 in FIG. 16) includes a series of pixel voltage values resulting from the sequential operation of the column select switches 191 to apply respective column voltages $V_{COLj}$ via the bus 175 to the buffer amplifier 199 (the respective column voltages $V_{COLj}$ in turn represent buffered versions of ISFET source voltages $V_{Sj}$). In some implementations, it is observed that voltage changes $\Delta V_{PIX}$ in the array output signal between two consecutive pixel reads is characterized as an exponential process given by $$\Delta V_{PIX}(t) = A(1 - e^{-t/k}), \quad (PP)$$

where A is the difference ($V_{COLj} - V_{COLj-1}$) between two pixel voltage values and k is a time constant associated with a capacitance of the bus 175. FIGS. 18C and 18D illustrate exemplary pixel voltages in a given array output signal Vout (e.g., one of Vout1 and Vout2) showing pixel-to-pixel transitions in the output signal as a function of time, plotted against exemplary sampling clock signals CS. In FIG. 18C, the sampling clock signal CS has a period 524, and an ADC controlled by CS samples a pixel voltage upon a positive transition of CS (as discussed above, in one implementation CS and CH have essentially a same period). FIG. 18C indicates two samples 525A and 525B, between which an exponential voltage transition 522 corresponding to $\Delta V_{PIX}(t)$, between a voltage difference A, may be readily observed.

For purposes of the present discussion, pixel "settling time" $t_{settle}$ is defined as the time t at which $\Delta V_{PIX}(t)$ attains a value that differs from it's final value by an amount that is equal to the peak noise level of the array output signal. If the peak noise level of the array output signal is denoted as $n_p$, then the voltage at the settling time $t_{settle}$ is given by $\Delta V_{PIX}(t_{settle}) = A[1 - (n_p/A)]$. Substituting in Eq. (PP) and solving for $t_{settle}$ yields $$t_{settle} = -k \ln\left(\frac{n_p}{A}\right). \quad (QQ)$$

FIG. 18D conceptually illustrates a pixel settling time $t_{settle}$ (reference numeral 526) for a single voltage transition 522 between two pixel voltages having a difference A, using a sampling clock signal CS having a sufficiently long period so as to allow for full settling. To provide some exemplary parameters for purposes of illustration, in one implementation a maximum value for A, representing a maximum range for pixel voltage transitions (e.g., consecutive pixels at minimum and maximum values), is on the order of approximately 250 mV. Additionally, a peak noise level $n_p$ of the array output signal is taken as approximately 100 μV, and the time constant k is taken as 5 nanoseconds. These values provide an exemplary settling time $t_{settle}$ of approximately 40 nanoseconds. If a maximum data rate of an array output signal is taken as the inverse of the settling time $t_{settle}$, a settling time of 40 nanoseconds corresponds to maximum data rate of 25 MHz. In other implementations, A may be on the order of 20 mV and the time constant k may be on the order of 15 nanoseconds, resulting in a settling time $t_{settle}$ of approximately 80 nanoseconds and a maximum data rate of 12.5 MHz. The values of k indicated above generally correspond to capacitances for the bus 175 in a range of approximately 5 pF to 20 pF. It should be appreciated that the foregoing values are provided primarily for purposes of illustration, and that various embodiments of the present invention are not limited to these exemplary values; in particular, arrays according to various embodiment of the present invention may have different pixel settling times $t_{settle}$ (e.g., in some cases less than 40 nanoseconds).

As indicated above, in one embodiment pixel data may be acquired from the array at data rates that exceed those dictated by the pixel settling time. FIG. 18B illustrates a flow chart for such a method according to one inventive embodiment of the present disclosure. In the method of FIG. 18B, sufficiently slow clock frequencies initially are chosen for the signals CV, CH and CS such that the resulting data rate per array output signal is equal to or lower than the reciprocal of the pixel settling time $t_{settle}$ to allow for fully settled pixel voltage values from pixel to pixel in a given output signal. With these clock frequencies, as indicated in block 502 of FIG. 18B, settled pixel voltage values are then acquired for the entire array in the absence of an analyte (or in the presence of a reference analyte) to provide a first "dry" or reference data image for the array. In block 504 of FIG. 18B, for each pixel voltage constituting the first data image, a transition value between the pixel's final voltage and the final voltage of the immediately preceding pixel in the corresponding output signal data stream (i.e., the voltage difference A) is collected and stored. The collection of these transition values for all pixels of the array provides a first transition value data set.

Subsequently, in block 506 of FIG. 18B, the clock frequencies for the signals CV, CH and CS are increased such that the resulting data rate per array output signal exceeds a rate at which pixel voltage values are fully settled (i.e., a data rate higher than the reciprocal of the settling time $t_{settle}$). For purposes of the present discussion, the data rate per array output signal resulting from the selection of such increased clock frequencies for the signals CV, CH and CS is referred to as an "overspeed data rate." Using the clock frequencies corresponding to the overspeed data rate, pixel voltage values are again obtained for the entire array in the absence of an analyte (or in the presence of the same reference analyte) to provide a second "dry" or reference data image for the array. In block 508 of FIG. 18B, a second transition value data set based on the second data image obtained at the overspeed data rate is calculated and stored, as described above for the first data image.

In block 510 of FIG. 18B, a correction factor for each pixel of the array is calculated based on the values stored in the first and second transition value data sets. For example, a correction factor for each pixel may be calculated as a ratio of its transition value from the first transition value data set and its corresponding transition value from the second transition value data set (e.g., the transition value from the first data set may be divided by the transition value from the second data set, or vice versa) to provide a correction factor data set which is then stored. As noted in blocks 512 and 514 of FIG. 18B, this correction factor data set may then be employed to process pixel data obtained from the array operated at clock frequencies corresponding to the overspeed data rate, in the presence of an actual analyte to be measured; in particular, data obtained from the array at the overspeed data rate in the presence of an analyte may be multiplied or divided as appropriate by the correction factor data set (e.g., each pixel multiplied or divided by a corresponding correction factor) to obtain corrected data representative of the desired analyte property to be measured (e.g., ion concentration). It should be appreciated that once the correction factor data set is calculated and stored, it may be used repeatedly to correct multiple frames of data acquired from the array at the overspeed data rate.

In addition to controlling the sensor array and ADCs, the timing generator 256 may be configured to facilitate various array calibration and diagnostic functions, as well as an optional UV irradiation treatment. To this end, the timing generator may utilize the signal LSTV indicating the selection of the last row of the array and the signal LSTH to indicate the selection of the last column of the array. The timing generator 256 also may be responsible for generating the CAL signal which applies the reference voltage VREF to the column buffer amplifiers, and generating the UV signal which grounds the drains of all ISFETs in the array during a UV irradiation process (see FIG. 9). The timing generator also may provide some control function over the power supply 258 during various calibration and diagnostic functions, or UV irradiation, to appropriately control supply or bias voltages; for example, during UV irradiation, the timing generator may control the power supply to couple the body voltage $V_{BODY}$ to ground while the UV signal is activated to ground the ISFET drains. With respect to array calibration and diagnostics, as well as UV irradiation, in some implementations the timing generator may receive specialized programs from the computer 260 to provide appropriate control signals. In one aspect, the computer 260 may use various data obtained from reference and/or dummy pixels of the array, as well as column information based on the application of the CAL signal and the reference voltage VREF, to determine various calibration parameters associated with a given array and/or generate specialized programs for calibration and diagnostic functions.

With respect to the computer interface 252 of the array controller 250, in one exemplary implementation the interface is configured to facilitate a data rate of approximately 200 MB/sec to the computer 260, and may include local storage of up to 400 MB or greater. The computer 260 is configured to accept data at a rate of 200 MB/sec, and process the data so as to reconstruct an image of the pixels (e.g., which may be displayed in false-color on a monitor). For example, the computer may be configured to execute a general-purpose program with routines written in C++ or Visual Basic to manipulate the data and display is as desired.

The systems described herein, when used for sequencing, typically involve a chemFET array supporting reaction chambers, the chemFETs being coupled to an interface capable of executing logic that converts the signals from the chemFETs into sequencing information.

In some embodiments, the invention encompasses logic (preferably computer executable logic) for polymer sequencing, comprising logic for determining ion pulses associated with an ionic interaction with a PPi or a dNTP or both. Typically, the logic converts characteristic(s) of the ion pulses into polymer sequencing information.

In some embodiments, the invention encompasses logic (preferably computer executable logic) comprising logic for determining a sequence of a nucleic acid template based on time between ion pulses or a characteristic of a single ion pulse. The logic may optionally further comprise logic for determining spatial location of the ion pulse on an array of chemFETs.

In some embodiments, the invention encompasses logic (preferably computer executable logic) comprising logic for determining a sequence of a nucleic acid template based on a duration of time it takes for a particular dNTP to be utilized in a sequencing reaction. Typically, the logic receives signal from one or more chemFETs. Preferably, the sequence is displayed in substantially real time.

In some embodiments, the invention encompasses logic (preferably computer executable logic) for processing ion pulses from an array of chemFETs to determine the sequence of a polymer of interest. The logic may optionally further comprise logic for file management, file storage, and visualization. The logic may also optionally further comprise logic for converting the ion pulses into nucleotide sequences. Preferably, the sequence is displayed in substantially real time.

The sequencing information obtained from the system may be delivered to a handheld computing device, such as a personal digital assistant. Thus, in one embodiment, the invention encompasses logic for displaying a complete genome of an organism on a handheld computing device. The invention also encompasses logic adapted for sending data from a chemFET array to a handheld computing device. Any of such logic may be computer-implemented.

Having discussed several aspects of an exemplary ISFET array and an array controller according to the present disclosure, FIGS. 19-23 illustrate block diagrams of alternative CMOS IC chip implementations of ISFET sensor arrays having greater numbers of pixels, according to yet other inventive embodiments. In one aspect, each of the ISFET arrays discussed further below in connection with FIGS. 19-23 may be controlled by an array controller similar to that shown in FIG. 17, in some cases with minor modifications to accommodate higher numbers of pixels (e.g., additional preamplifiers 253 and analog-to-digital converters 254).

Figure 19:
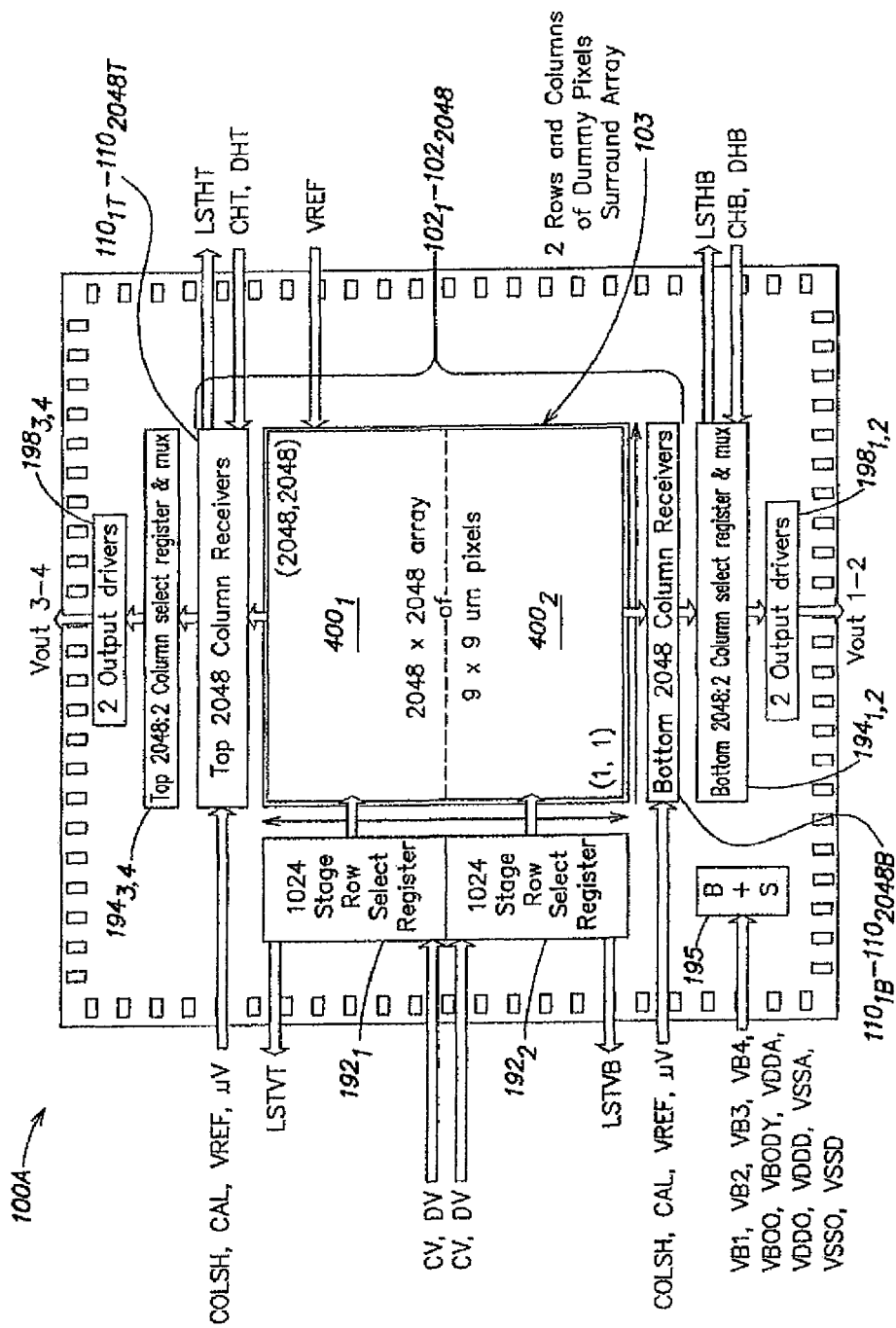
FIGS. 19-20 illustrate block diagrams of alternative CMOS IC chip implementations of chemFET sensor arrays, according to other inventive embodiments of the present disclosure.

FIG. 19 illustrates a block diagram of an ISFET sensor array 100A based on the column and pixel designs discussed above in connection with FIGS. 9-12A and a 0.35 micrometer CMOS fabrication process, according to one inventive embodiment. The array 100A includes 2048 columns $102_1$ through $102_{2048}$, wherein each column includes 2048 geometrically square pixels $105_1$ through $105_{2048}$, each having a size of approximately 9 micrometers by 9 micrometers. Thus, the array includes over four million pixels (>4 Mega-pixels) and, in one exemplary implementation, the complete array (ISFET pixels and associated circuitry) may be fabricated as an integrated circuit chip having dimensions of approximately 20.5 millimeters by 20.5 millimeters.

In one aspect of the embodiment shown in FIG. 19, the array 100A may be configured, at least in part, as multiple groups of pixels that may be respectively controlled. For example, each column of pixels may be divided into top and bottom halves, and the collection of pixels in respective top halves of columns form a first group $400_1$ of rows (e.g., a top group, rows 1-1024) and the collection of pixels in respective bottom halves of columns form a second group $400_2$ of rows (e.g., a bottom group, rows 1025-2048). In turn, each of the first and second (e.g., top and bottom) groups of rows is associated with corresponding row select registers, column bias/readout circuitry, column select registers, and output drivers. In this manner, pixel selection and data acquisition from each of the first and second groups of rows $400_1$ and $400_2$ is substantially similar to pixel selection and data acquisition from the entire array 100 shown in FIG. 13; stated differently, in one aspect, the array 100A of FIG. 19 substantially comprises two simultaneously controlled "sub-arrays" of different pixel groups to provide for significantly streamlined data acquisition from higher numbers of pixels.

In particular, FIG. 19 shows that row selection of the first group $400_1$ of rows may be controlled by a first row select register $192_1$, and row selection of the second group $400_2$ of rows may be controlled by a second row select register $192_2$. In one aspect, each of the row select registers $192_1$ and $192_2$ may be configured as discussed above in connection with FIG. 14 to receive vertical clock (CV) and vertical data (DV) signals and generate row select signals in response; for example the first row select register $192_1$ may generate the signals $\overline{\text{RowSel}_1}$ through $\overline{\text{RowSel}_{1024}}$ and the second row select register $192_2$ may generate the signals $\overline{\text{RowSel}_{1025}}$ through $\overline{\text{RowSel}_{2048}}$. In another aspect, both row select registers $192_1$ and $192_2$ may simultaneously receive common vertical clock and data signals, such that two rows of the array are enabled at any given time, one from the top group and another from the bottom group.

For each of the first and second groups of rows, the array 100A of FIG. 19 further comprises column bias/readout circuitry $110_{1T}$-$110_{2048T}$ (for the first row group $400_1$) and $110_{1B}$-$110_{2048B}$ (for the second row group $400_2$), such that each column includes two instances of the bias/readout circuitry $110j$ shown in FIG. 9. The array 100A also comprises two column select registers $192_{1,2}$ (odd and even) and two output drivers $198_{1,2}$ (odd and even) for the second row group $400_2$, and two column select registers $192_{3,4}$ (odd and even) and two output drivers $198_{3,4}$ (odd and even) for the first row group $400_1$ (i.e., a total of four column select registers and four output drivers). The column select registers receive horizontal clock signals (CHT and CHB for the first row group and second row group, respectively) and horizontal data signals (DHT and DHB for the first row group and second row group, respectively) to control odd and even column selection. In one implementation, the CHT and CHB signals may be provided as common signals, and the DHT and DHB may be provided as common signals, to simultaneously read out four columns at a time from the array (i.e., one odd and one even column from each row group); in particular, as discussed above in connection with FIGS. 13-18, two columns may be simultaneously read for each enabled row and the corresponding pixel voltages provided as two output signals. Thus, via the enablement of two rows at any given time, and reading of two columns per row at any given time, the array 100A may provide four simultaneous output signals Vout1, Vout2, Vout3 and Vout4.

In one exemplary implementation of the array 100A of FIG. 19, in which complete data frames (all pixels from both the first and second row groups $400_1$ and $400_2$) are acquired at a frame rate of 20 frames/sec, 1024 pairs of rows are successively enabled for periods of approximately 49 microseconds each. For each enabled row, 1024 pixels are read out by each column select register/output driver during approximately 45 microseconds (allowing 2 microseconds at the beginning and end of each row, as discussed above in connection with FIG. 18). Thus, in this example, each of the array output signals Vout1, Vout2, Vout3 and Vout4 has a data rate of approximately 23 MHz. Again, it should be appreciated that in other implementations, data may be acquired from the array 100A of FIG. 19 at frame rates other than 20 frames/sec (e.g., 50-100 frames/sec).

Like the array 100 of FIG. 13, in yet other aspects the array 100A of FIG. 19 may include multiple rows and columns of dummy or reference pixels 103 around a perimeter of the array to facilitate preliminary test/evaluation data, offset determination an/or array calibration. Additionally, various power supply and bias voltages required for array operation (as discussed above in connection with FIG. 9) are provided to the array 100A in block 195, in a manner similar to that discussed above in connection with FIG. 13.

Figure 20:
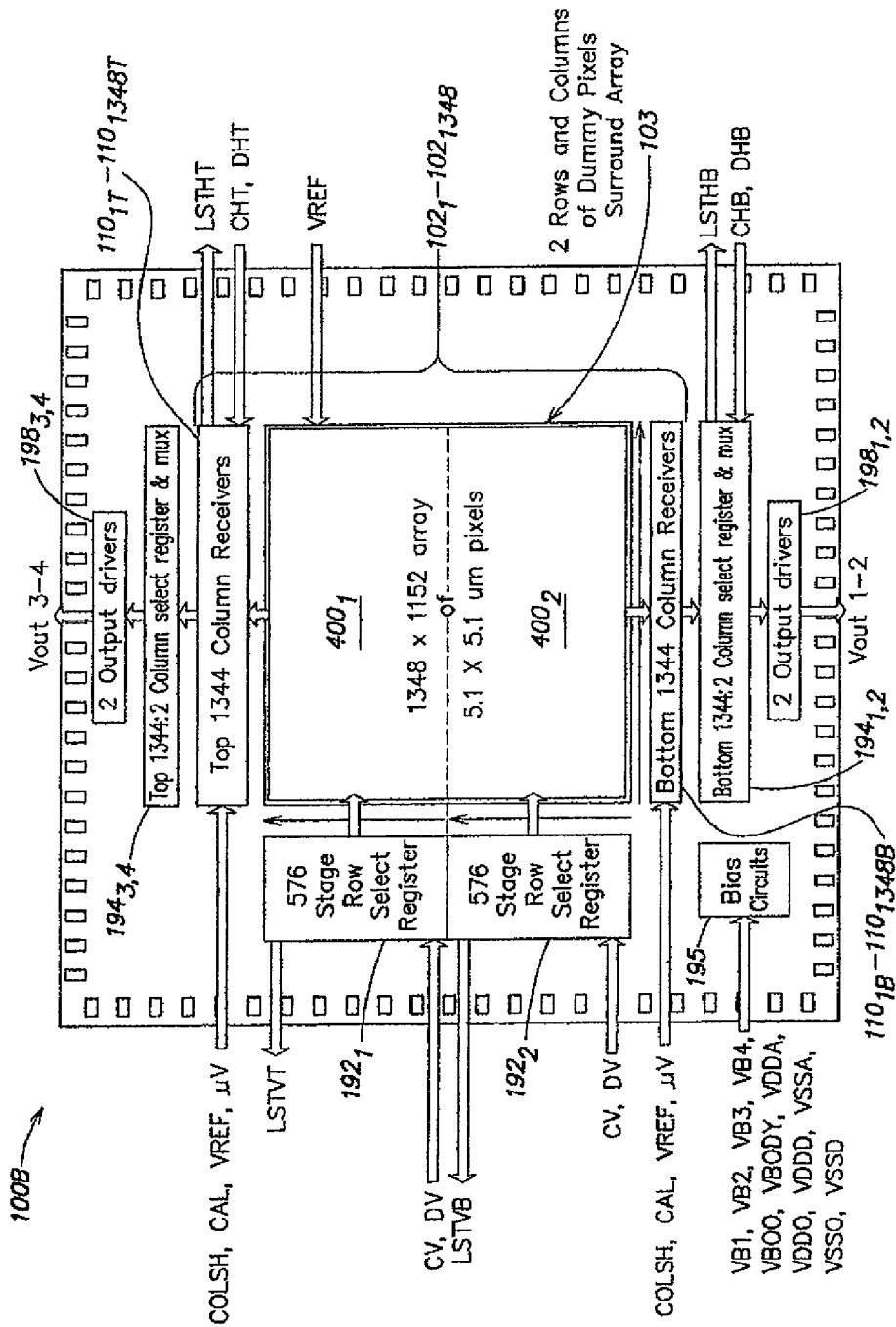

FIG. 20 illustrates a block diagram of an ISFET sensor array 100B based on a 0.35 micrometer CMOS fabrication process and having a configuration substantially similar to the array 100A discussed above in FIG. 19, according to yet another inventive embodiment. While the array 100B also is based generally on the column and pixel designs discussed above in connection with FIGS. 9-12A, the pixel size/pitch in the array 100B is smaller than that of the pixel shown in FIG. 10. In particular, with reference again to FIGS. 10 and 11, the dimension "e" shown in FIG. 10 is substantially reduced in the embodiment of FIG. 20, without affecting the integrity of the active pixel components disposed in the central region of the pixel, from approximately 9 micrometers to approximately 5 micrometers; similarly, the dimension "f" shown in FIG. 10 is reduced from approximately 7 micrometers to approximately 4 micrometers. Stated differently, some of the peripheral area of the pixel surrounding the active components is substantially reduced with respect to the dimensions given in connection with FIG. 10, without disturbing the top-view and cross-sectional layout and design of the pixel's active components as shown in FIGS. 10 and 11. A top view of such a pixel 105A is shown in FIG. 20A, in which the dimension "e" is 5.1 micrometers and the dimension "f" is 4.1 micrometers. In one aspect of this pixel design, to facilitate size reduction, fewer body connections B are included in the pixel 105A (e.g., one at each corner of the pixel) as compared to the pixel shown in FIG. 10, which includes several body connections B around the entire perimeter of the pixel.

As noted in FIG. 20, the array 100B includes 1348 columns $102_1$ through $102_{1348}$, wherein each column includes 1152 geometrically square pixels $105A_1$ through $105A_{1152}$, each having a size of approximately 5 micrometers by 5 micrometers. Thus, the array includes over 1.5 million pixels (>1.5 Mega-pixels) and, in one exemplary implementation, the complete array (ISFET pixels and associated circuitry) may be fabricated as an integrated circuit chip having dimensions of approximately 9 millimeters by 9 millimeters. Like the array 100A of FIG. 19, in one aspect the array 100B of FIG. 20 is divided into two groups of rows $400_1$ and $400_2$, as discussed above in connection with FIG. 19. In one exemplary implementation, complete data frames (all pixels from both the first and second row groups $400_1$ and $400_2$) are acquired at a frame rate of 50 frames/sec, thereby requiring 576 pairs of rows to be successively enabled for periods of approximately 35 microseconds each. For each enabled row, 674 pixels are read out by each column select register/output driver during approximately 31 microseconds (allowing 2 microseconds at the beginning and end of each row, as discussed above in connection with FIG. 18). Thus, in this example, each of the array output signals Vout1, Vout2, Vout3 and Vout4 has a data rate of approximately 22 MHz. Again, it should be appreciated that in other implementations, data may be acquired from the array 100B of FIG. 20 at frame rates other than 50 frames/sec.

Figure 21:
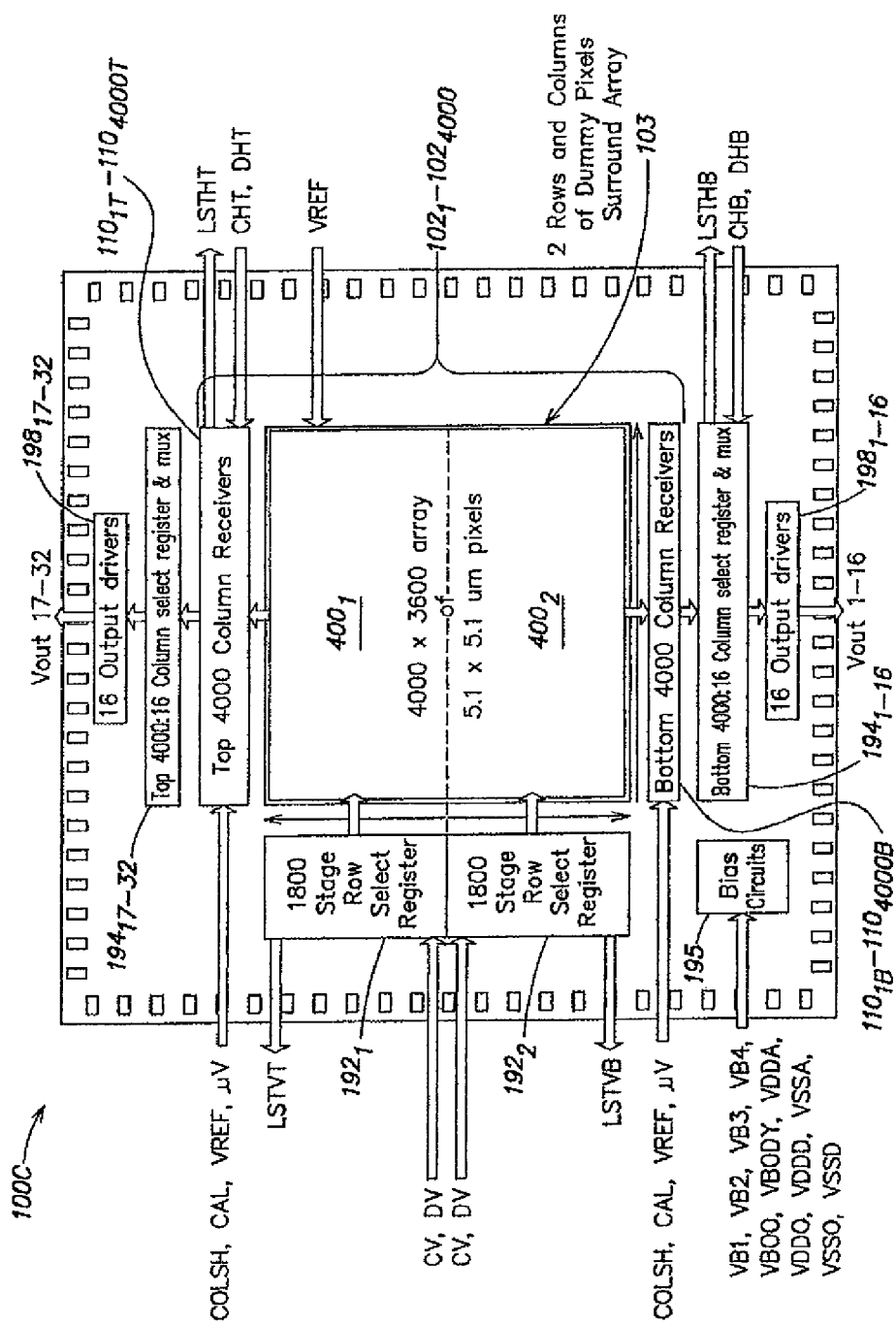
FIGS. 21-23 illustrate block diagrams of additional alternative CMOS IC chip implementations of chemFET sensor arrays, according to other inventive embodiments of the present disclosure.

FIG. 21 illustrates a block diagram of an ISFET sensor array 1000 based on a 0.35 micrometer CMOS fabrication process and incorporating the smaller pixel size discussed above in connection with FIGS. 20 and 20A (5.1 micrometer square pixels), according to yet another embodiment. As noted in FIG. 21, the array 100C includes 4000 columns $102_1$ through $102_{4000}$, wherein each column includes 3600 geometrically square pixels $105A_1$ through $105A_{3600}$, each having a size of approximately 5 micrometers by 5 micrometers. Thus, the array includes over 14 million pixels (>14 Mega-pixels) and, in one exemplary implementation, the complete array (ISFET pixels and associated circuitry) may be fabricated as an integrated circuit chip having dimensions of approximately 22 millimeters by 22 millimeters. Like the arrays 100A and 100B of FIGS. 19 and 20, in one aspect the array 100C of FIG. 21 is divided into two groups of rows $400_1$ and $400_2$. However, unlike the arrays 100A and 100B, for each row group the array 100C includes sixteen column select registers and sixteen output drivers to simultaneously read sixteen pixels at a time in an enabled row, such that thirty-two output signals Vout1-Vout32 may be provided from the array 100C. In one exemplary implementation, complete data frames (all pixels from both the first and second row groups $400_1$ and $400_2$) may be acquired at a frame rate of 50 frames/sec, thereby requiring 1800 pairs of rows to be successively enabled for periods of approximately 11 microseconds each. For each enabled row, 250 pixels (4000/16) are read out by each column select register/output driver during approximately 7 microseconds (allowing 2 microseconds at the beginning and end of each row). Thus, in this example, each of the array output signals Vout1-Vout32 has a data rate of approximately 35 MHz. As with the previous embodiments, it should be appreciated that in other implementations, data may be acquired from the array 100C at frame rates other than 50 frames/sec.

Figure 22:
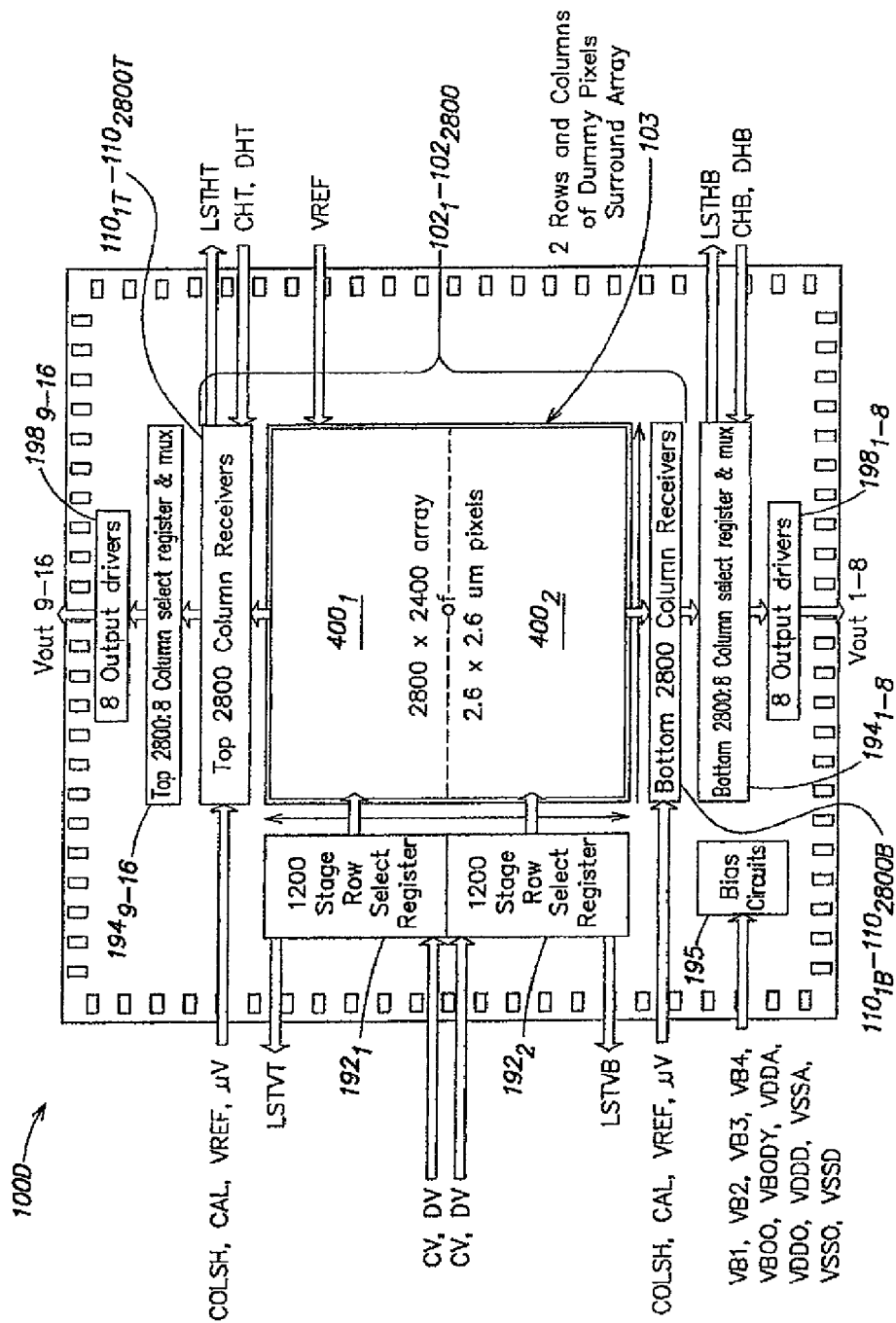
Figure 23:
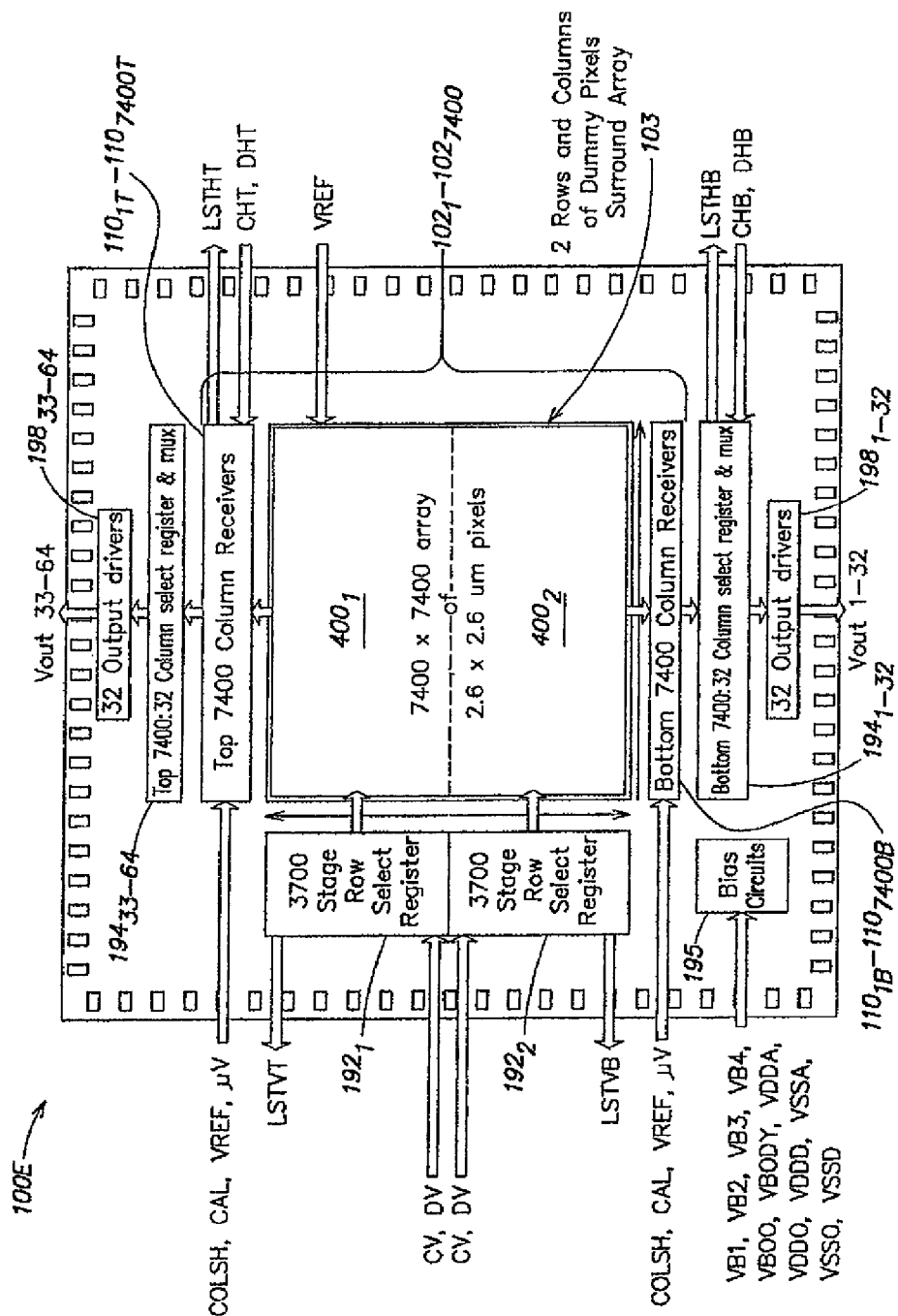

While the exemplary arrays discussed above in connection with FIGS. 13-21 are based on a 0.35 micrometer conventional CMOS fabrication process, it should be appreciated that arrays according to the present disclosure are not limited in this respect, as CMOS fabrication processes having feature sizes of less than 0.35 micrometers may be employed (e.g., 0.18 micrometer CMOS processing techniques) to fabricate such arrays. Accordingly, ISFET sensor arrays with a pixel size/pitch significantly below 5 micrometers may be fabricated, providing for significantly denser ISFET arrays. For example, FIGS. 22 and 23 illustrate respective block diagrams of ISFET sensor arrays 100D and 100E according to yet other embodiments based on a 0.18 micrometer CMOS fabrication process, in which a pixel size of 2.6 micrometers is achieved. The pixel design itself is based substantially on the pixel 105A shown in FIG. 20A, albeit on a smaller scale due to the 0.18 micrometer CMOS process.

The array 100D of FIG. 22 includes 2800 columns $102_1$ through $102_{2800}$, wherein each column includes 2400 geometrically square pixels each having a size of approximately 2.6 micrometers by 2.6 micrometers. Thus, the array includes over 6.5 million pixels (>6.5 Mega-pixels) and, in one exemplary implementation, the complete array (ISFET pixels and associated circuitry) may be fabricated as an integrated circuit chip having dimensions of approximately 9 millimeters by 9 millimeters. Like the arrays 100A, 100B and 100C of FIGS. 19-21, in one aspect the array 100D of FIG. 22 is divided into two groups of rows $400_1$ and $400_2$. However, unlike the arrays 100A, 100B, and 100C, for each row group the array 100D includes eight column select registers and eight output drivers to simultaneously read eight pixels at a time in an enabled row, such that sixteen output signals Vout1-Vout16 may be provided from the array 100D. In one exemplary implementation, complete data frames (all pixels from both the first and second row groups $400_1$ and $400_2$) may be acquired at a frame rate of 50 frames/sec, thereby requiring 1200 pairs of rows to be successively enabled for periods of approximately 16-17 microseconds each. For each enabled row, 350 pixels (2800/8) are read out by each column select register/output driver during approximately 14 microseconds (allowing 1 to 2 microseconds at the beginning and end of each row). Thus, in this example, each of the array output signals Vout1-Vout16 has a data rate of approximately 25 MHz. As with the previous embodiments, it should be appreciated that in other implementations, data may be acquired from the array 100D at frame rates other than 50 frames/sec.

The array 100E of FIG. 23 includes 7400 columns $102_1$ through $102_{7400}$, wherein each column includes 7400 geometrically square pixels each having a size of approximately 2.6 micrometers by 2.6 micrometers. Thus, the array includes over 54 million pixels (>54 Mega-pixels) and, in one exemplary implementation, the complete array (ISFET pixels and associated circuitry) may be fabricated as an integrated circuit chip having dimensions of approximately 21 millimeters by 21 millimeters. Like the arrays 100A-100D of FIGS. 19-22, in one aspect the array 100E of FIG. 23 is divided into two groups of rows $400_1$ and $400_2$. However, unlike the arrays 100A-100D, for each row group the array 100E includes thirty-two column select registers and thirty-two output drivers to simultaneously read thirty-two pixels at a time in an enabled row, such that sixty-four output signals Vout1-Vout64 may be provided from the array 100E. In one exemplary implementation, complete data frames (all pixels from both the first and second row groups $400_1$ and $400_2$) may be acquired at a frame rate of 100 frames/sec, thereby requiring 3700 pairs of rows to be successively enabled for periods of approximately 3 microseconds each. For each enabled row, 230 pixels (7400/32) are read out by each column select register/output driver during approximately 700 nanoseconds. Thus, in this example, each of the array output signals Vout1-Vout64 has a data rate of approximately 328 MHz. As with the previous embodiments, it should be appreciated that in other implementations, data may be acquired from the array 100D at frame rates other than 100 frames/sec.

Thus, in various examples of ISFET arrays based on the inventive concepts disclosed herein, an array pitch of approximately nine (9) micrometers (e.g., a sensor surface area of less than ten micrometers by ten micrometers) allows an ISFET array including over 256,000 pixels (i.e., a 512 by 512 array), together with associated row and column select and bias/readout electronics, to be fabricated on a 7 millimeter by 7 millimeter semiconductor die, and a similar sensor array including over four million pixels (i.e., a 2048 by 2048 array, over 4 Mega-pixels) to be fabricated on a 21 millimeter by 21 millimeter die. In other examples, an array pitch of approximately 5 micrometers allows an ISFET array including approximately 1.55 Mega-pixels (i.e., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pixel size/pitch significantly below 5 micrometers may be fabricated (e.g., array pitch of 2.6 micrometers or pixel/sensor area of less than 8 or 9 micrometers$^2$), providing for significantly dense ISFET arrays.

In the embodiments of ISFET arrays discussed above, array pixels employ a p-channel ISFET, as discussed above in connection with FIG. 9. It should be appreciated, however, that ISFET arrays according to the present disclosure are not limited in this respect, and that in other embodiments pixel designs for ISFET arrays may be based on an n-channel ISFET. In particular, any of the arrays discussed above in connection with FIGS. 13 and 19-23 may be implemented with pixels based on n-channel ISFETs.

Figure 24:
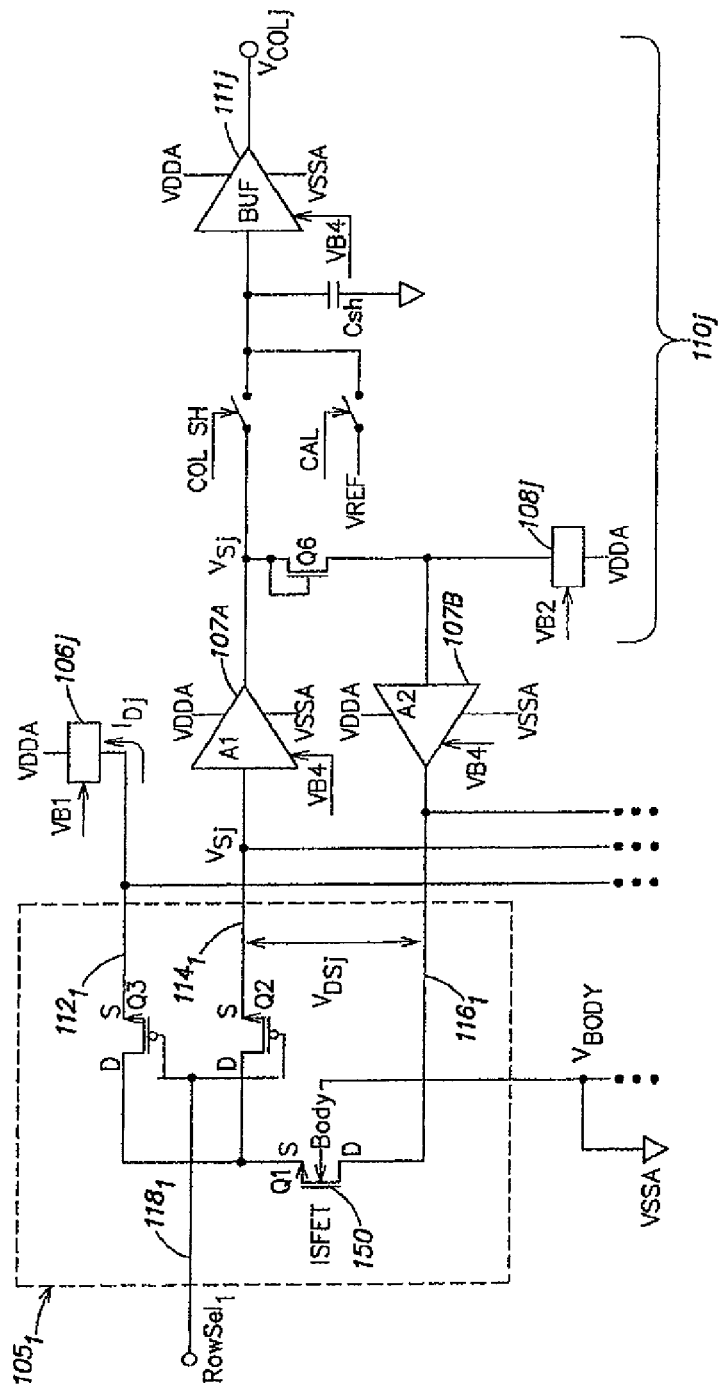
FIG. 24 illustrates the pixel design of FIG. 9 implemented with an n-channel chemFET and accompanying n-channel MOSFETs, according to another inventive embodiment of the present disclosure.

For example, FIG. 24 illustrates the pixel design of FIG. 9 implemented with an n-channel ISFET and accompanying n-channel MOSFETs, according to another inventive embodiment of the present disclosure. More specifically, FIG. 24 illustrates one exemplary pixel $105_1$ of an array column (i.e., the first pixel of the column), together with column bias/readout circuitry $110j$, in which the ISFET 150 (Q1) is an n-channel ISFET. Like the pixel design of FIG. 9, the pixel design of FIG. 24 includes only three components, namely, the ISFET 150 and two n-channel MOSFET switches Q2 and Q3, responsive to one of n row select signals (RowSel$_1$ through RowSel$_n$, logic high active). No transmission gates are required in the pixel of FIG. 24, and all devices of the pixel are of a "same type," i.e., re-channel devices. Also like the pixel design of FIG. 9, only four signal lines per pixel, namely the lines $112_1$, $114_1$, $116_1$ and $118_1$, are required to operate the three components of the pixel $105_1$ shown in FIG. 24. In other respects, the pixel designs of FIG. 9 and FIG. 24 are similar, in that they are both configured with a constant drain current $I_{Dj}$ and a constant drain-to-source voltage $V_{DSj}$ to obtain an output signal $V_{Sj}$ from an enabled pixel.

One of the primary differences between the n-channel ISFET pixel design of FIG. 24 and the p-channel ISFET design of FIG. 9 is the opposite direction of current flow through the pixel. To this end, in FIG. 24, the element $106_j$ is a controllable current sink coupled to the analog circuitry supply voltage ground VSSA, and the element $108_j$ of the bias/readout circuitry $110j$ is a controllable current source coupled to the analog positive supply voltage VDDA. Additionally, the body connection of the ISFET 150 is not tied to its source, but rather to the body connections of other ISFETs of the array, which in turn is coupled to the analog ground VSSA, as indicated in FIG. 24.

Figure 25:
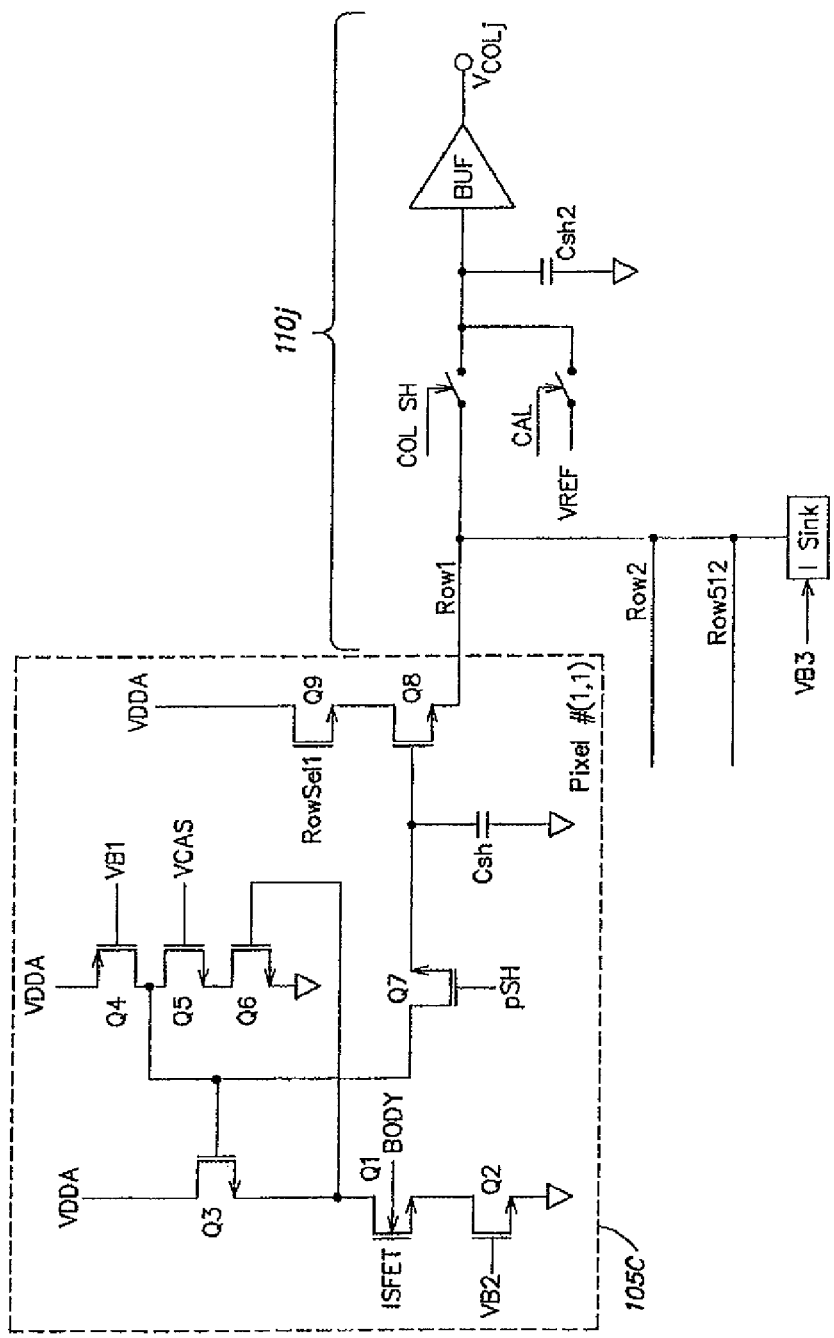
FIGS. 25-27 illustrate alternative pixel designs and associated column circuitry for chemFET arrays according to other inventive embodiments of the present disclosure.
Figure 26:
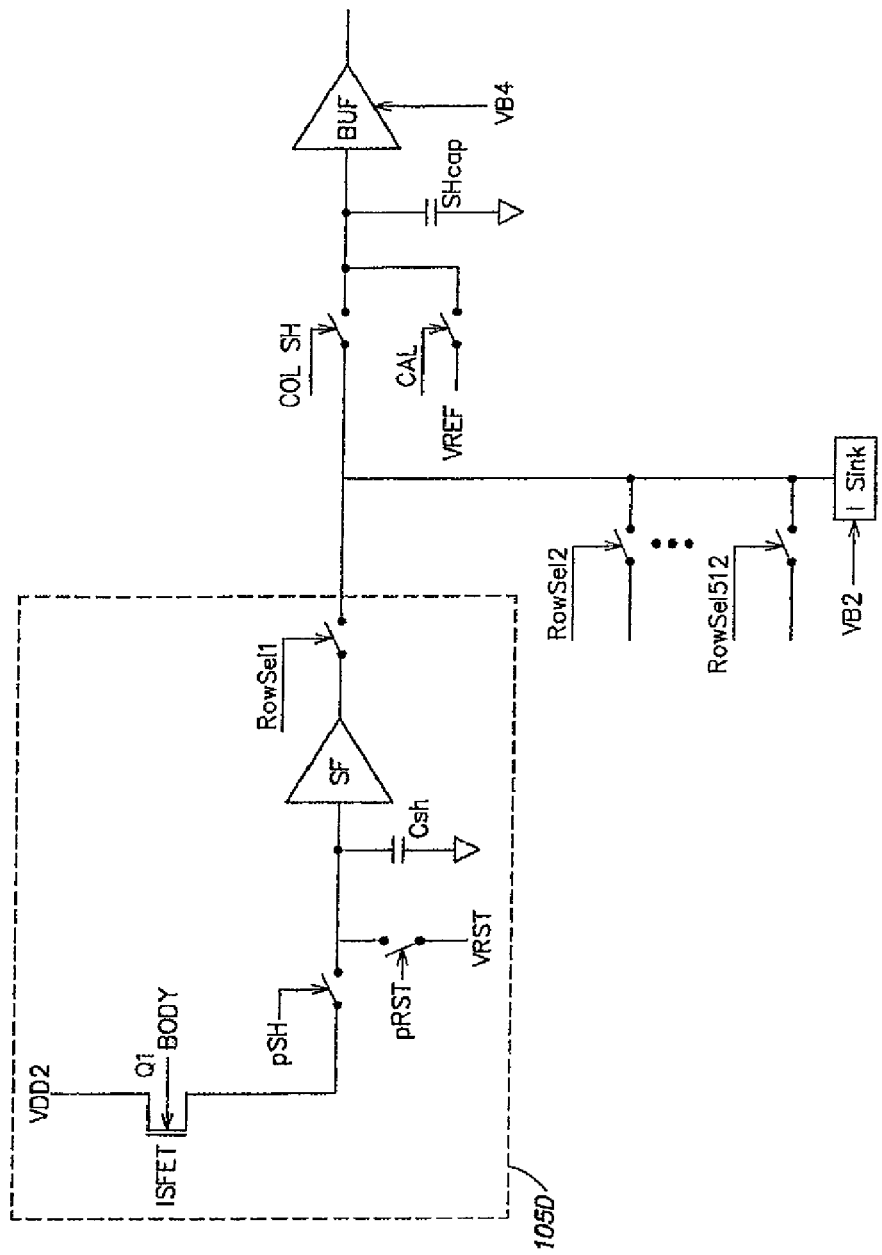
Figure 27:
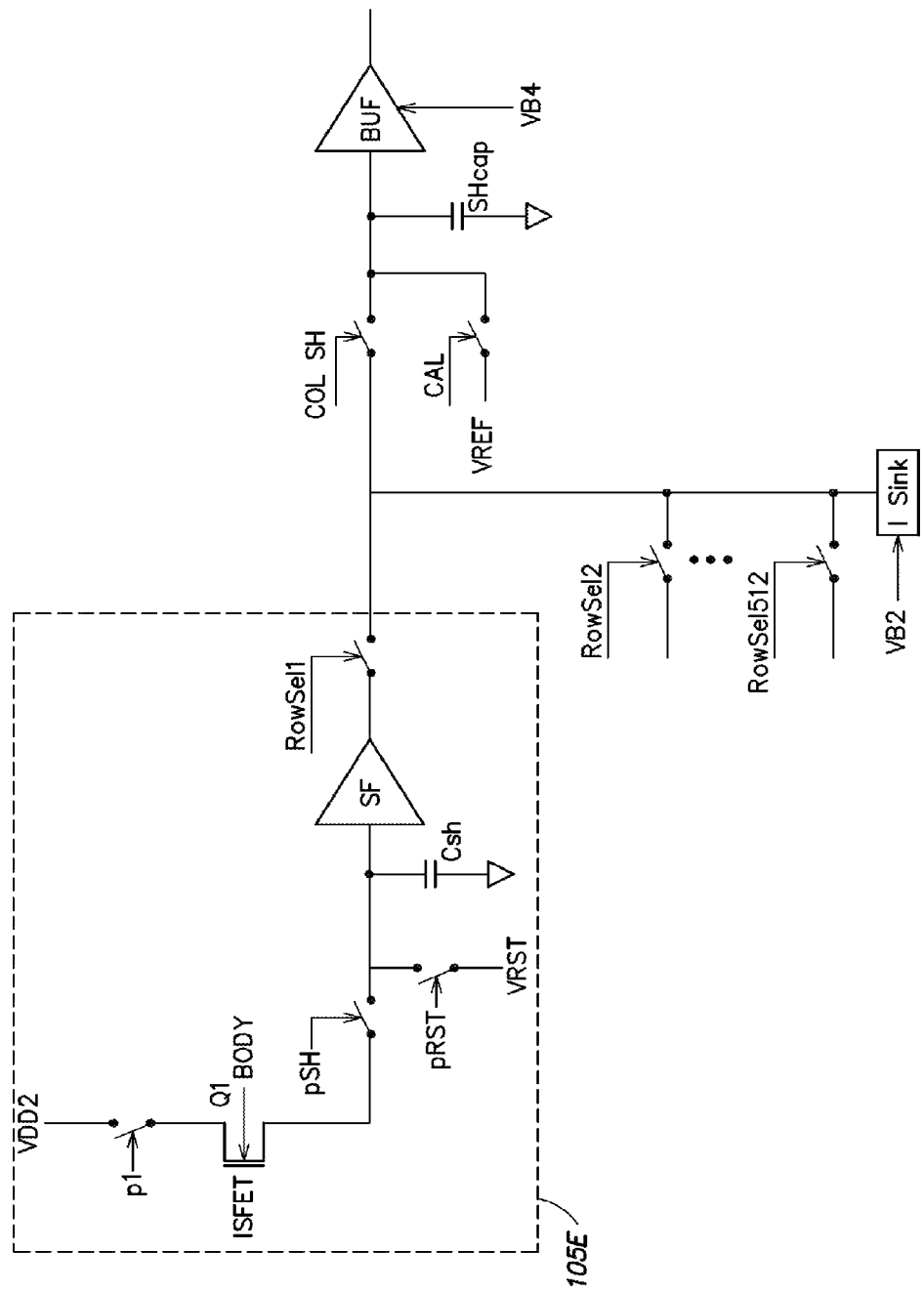

In addition to the pixel designs shown in FIGS. 9 and 24 (based on a constant ISFET drain current and constant ISFET drain-source voltage), alternative pixel designs are contemplated for ISFET arrays, based on both p-channel ISFETs and n-channel ISFETs, according to yet other inventive embodiments of the present disclosure, as illustrated in FIGS. 25-27. As discussed below, some alternative pixel designs may require additional and/or modified signals from the array controller 250 to facilitate data acquisition. In particular, a common feature of the pixel designs shown in FIGS. 25-27 includes a sample and hold capacitor within each pixel itself, in addition to a sample and hold capacitor for each column of the array. While the alternative pixel designs of FIGS. 25-27 generally include a greater number of components than the pixel designs of FIGS. 9 and 24, the feature of a pixel sample and hold capacitor enables "snapshot" types of arrays, in which all pixels of an array may be enabled simultaneously to sample a complete frame and acquire signals representing measurements of one or more analytes in proximity to respective ISFETs of the array. In some applications, this may provide for higher data acquisition speeds and/or improved signal sensitivity (e.g., higher signal-to-noise ratio).

FIG. 25 illustrates one such alternative design for a single pixel 105C and associated column circuitry $110j$. The pixel 105C employs an n-channel ISFET and is based generally on the premise of providing a constant voltage across the ISFET Q1 based on a feedback amplifier (Q4, Q5 and Q6). In particular, transistor Q4 constitutes the feedback amplifier load, and the amplifier current is set by the bias voltage VB1 (provided by the array controller). Transistor Q5 is a common gate amplifier and transistor Q6 is a common source amplifier. Again, the purpose of feedback amplifier is to hold the voltage across the ISFET Q1 constant by adjusting the current supplied by transistor Q3. Transistor Q2 limits the maximum current the ISFET Q1 can draw (e.g., so as to prevent damage from overheating a very large array of pixels). This maximum current is set by the bias voltage VB2 (also provided by the array controller). In one aspect of the pixel design shown in FIG. 25, power to the pixel 105C may be turned off by setting the bias voltage VB2 to 0 Volts and the bias voltage VB1 to 3.3 Volts. In this manner, the power supplied to large arrays of such pixels may be modulated (turned on for a short time period and then off by the array controller) to obtain ion concentration measurements while at the same time reducing overall power consumption of the array. Modulating power to the pixels also reduces heat dissipation of the array and potential heating of the analyte solution, thereby also reducing any potentially deleterious effects from sample heating.

In FIG. 25, the output of the feedback amplifier (the gate of transistor Q3) is sampled by MOS switch Q7 and stored on a pixel sample and hold capacitor Csh within the pixel itself. The switch Q7 is controlled by a pixel sample and hold signal pSII (provided to the array chip by the array controller), which is applied simultaneously to all pixels of the array so as to simultaneously store the readings of all the pixels on their respective sample and hold capacitors. In this manner, arrays based on the pixel design of FIG. 25 may be considered as "snapshot" arrays, in that a full frame of data is sampled at any given time, rather than sampling successive rows of the array. After each pixel value is stored on the corresponding pixel sample and hold capacitor Csh, each pixel 105C (ISFET and feedback amplifier) is free to acquire another pH reading or it can by turned off to conserve power.

In FIG. 25, the pixel values stored on all of the pixel sample and hold capacitors Csh are applied to the column circuitry 110j one row at a time through source follower Q8, which is enabled via the transistor Q9 in response to a row select signal (e.g., RowSel1). In particular, after a row is selected and has settled out, the values stored in the pixel sample and hold capacitors are then in turn stored on the column sample and hold capacitors Csh2, as enabled by the column sample and hold signal COL SH, and provided as the column output signal $V_{COLj}$.

FIG. 26 illustrates another alternative design for a single pixel 105D and associated column circuitry 110j, according to one embodiment of the present disclosure. In this embodiment, the ISFET is shown as a p-channel device. At the start of a data acquisition cycle, CMOS switches controlled by the signals pSH (pixel sample/hold) and pRST (pixel reset) are closed (these signals are supplied by the array controller). This pulls the source of ISFET (Q1) to the voltage VRST. Subsequently, the switch controlled by the signal pRST is opened, and the source of ISFET Q1 pulls the pixel sample and hold capacitor Csh to a threshold below the level set by pH. The switch controlled by the signal pSH is then opened, and the pixel output value is coupled, via operation of a switch responsive to the row select signal RowSel1, to the column circuitry 110j to provide the column output signal $V_{COLj}$. Like the pixel design in the embodiment illustrated in FIG. 25, arrays based on the pixel 105D are "snapshot" type arrays in that all pixels of the array may be operated simultaneously. In one aspect, this design allows a long simultaneous integration time on all pixels followed by a high-speed read out of an entire frame of data.

FIG. 27 illustrates yet another alternative design for a single pixel 105E and associated column circuitry 110j, according to one embodiment of the present disclosure. In this embodiment, again the ISFET is shown as a p-channel device. At the start of a data acquisition cycle, the switches operated by the control signals p1 and pRST are briefly closed. This clears the value stored on the sampling capacitor Csh and allows a charge to be stored on ISFET (Q1). Subsequently, the switch controlled by the signal pSH is closed, allowing the charge stored on the ISFET Q1 to be stored on the pixel sample and hold capacitor Csh. The switch controlled by the signal pSH is then opened, and the pixel output value is coupled, via operation of a switch responsive to the row select signal RowSel1, to the column circuitry 110j to provide the column output signal $V_{COLj}$. Gain may be provided in the pixel 105E via the ratio of the ISFET capacitance to the Csh cap, i.e., gain=$C_{Q1}/C_{sh}$, or by enabling the pixel multiple times (i.e., taking multiple samples of the analyte measurement) and accumulating the ISFET output on the pixel sample and hold capacitor Csh without resetting the capacitor (i.e., gain is a function of the number of accumulations). Like the embodiments of FIGS. 25 and 26, arrays based on the pixel 105D are "snapshot" type arrays in that all pixels of the array may be operated simultaneously.

Figure 28A:
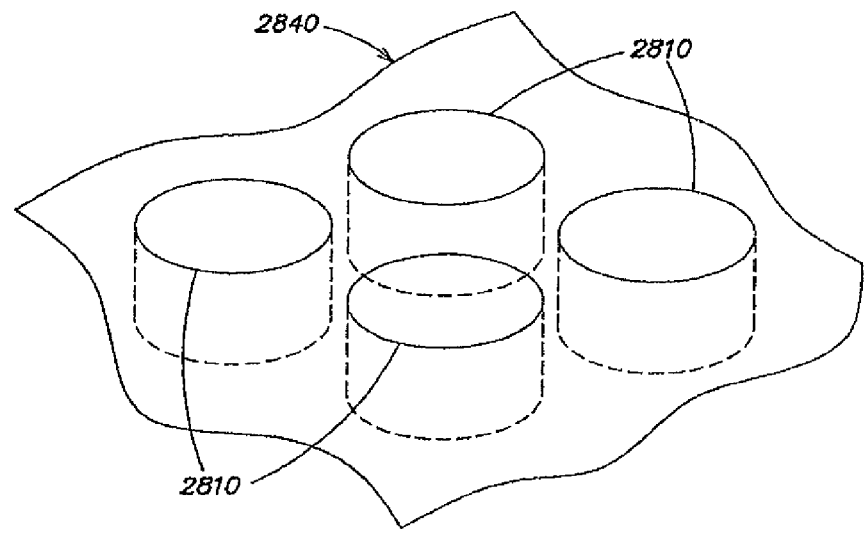
FIGS. 28A and 28B are isometric illustrations of portions of microwell arrays as employed herein, showing round wells and rectangular wells, to assist three-dimensional visualization of the array structures.
Figure 28B:
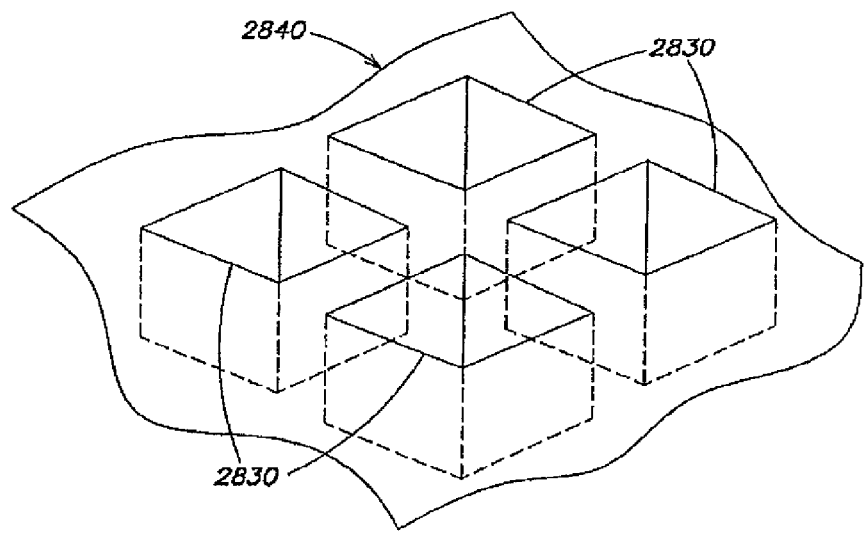

Turning from the sensor discussion, we will now be addressing the combining of the ISFET array with a microwell array and the attendant fluidics. As most of the drawings of the microwell array structure are presented only in cross-section or showing that array as only a block in a simplified diagram, FIGS. 28A and 28B are provided to assist the reader in beginning to visualize the resulting apparatus in three-dimensions. FIG. 28A shows a group of round cylindrical wells 2810 arranged in an array, while FIG. 28B shows a group of rectangular cylindrical wells 2830 arranged in an array. It will be seen that the wells are separated (isolated) from each other by the material 2840 forming the well walls. While it is certainly possible to fabricate wells of other cross sections, in some embodiments it may not be advantageous to do so. Such an array of microwells sits over the above-discussed ISFET array, with one or more ISFETs per well. In the subsequent drawings, when the microwell array is identified, one may picture one of these arrays.

Fluidic System: Apparatus and Method for Use with High Density Electronic Sensor Arrays For many uses, to complete a system for sensing chemical reactions or chemical agents using the above-explained high density electronic arrays, techniques and apparatus are required for delivery to the array elements (called "pixels") fluids containing chemical or biochemical components for sensing. In this section, exemplary techniques and methods will be illustrated, which are useful for such purposes, with desirable characteristics.

As high speed operation of the system may be desired, it is preferred that the fluid delivery system, insofar as possible, not limit the speed of operation of the overall system.

Accordingly, needs exist not only for high-speed, high-density arrays of ISFETs or other elements sensitive to ion concentrations or other chemical attributes, or changes in chemical attributes, but also for related mechanisms and techniques for supplying to the array elements the samples to be evaluated, in sufficiently small reaction volumes as to substantially advance the speed and quality of detection of the variable to be sensed.

There are two and sometimes three components or subsystems, and related methods, involved in delivery of the subject chemical samples to the array elements: (1) macrofluidic system of reagent and wash fluid supplies and appropriate valving and ancillary apparatus, (2) a flow cell and (3) in many applications, a microwell array. Each of these subsystems will be discussed, though in reverse order.

Microwell Array

As discussed elsewhere, for many uses, such as in DNA sequencing, it is desirable to provide over the array of semiconductor sensors a corresponding array of microwells, each microwell being small enough preferably to receive only one DNA-loaded bead, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

The systems described herein can include an array of microfluidic reaction chambers integrated with a semiconductor comprising an array of chemFETs. In some embodiments, the invention encompasses such an array. The reaction chambers may, for example, be formed in a glass, dielectric, photodefineable or etchable material. The glass material may be silicon dioxide.

Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns.

The above-described array can also be provided in a kit for sequencing. Thus, in some embodiments, the invention encompasses a kit comprising an array of microfluidic reaction chambers integrated with an array of chemFETs, and one or more amplification reagents.

In some embodiments, the invention encompasses a sequencing apparatus comprising a dielectric layer overlying a chemFET, the dielectric layer having a recess laterally centered atop the chemFET. Preferably, the dielectric layer is formed of silicon dioxide.

Microwell Array Fabrication

Microwell fabrication may be accomplished in a number of ways. The actual details of fabrication may require some experimentation and vary with the processing capabilities that are available.

In general, fabrication of a high density array of microwells involves photo-lithographically patterning the well array configuration on a layer or layers of material such as photoresist (organic or inorganic), a dielectric, using an etching process. The patterning may be done with the material on the sensor array or it may be done separately and then transferred onto the sensor array chip, of some combination of the two. However, techniques other than photolithography are not to be excluded if they provide acceptable results.

Figure 29:
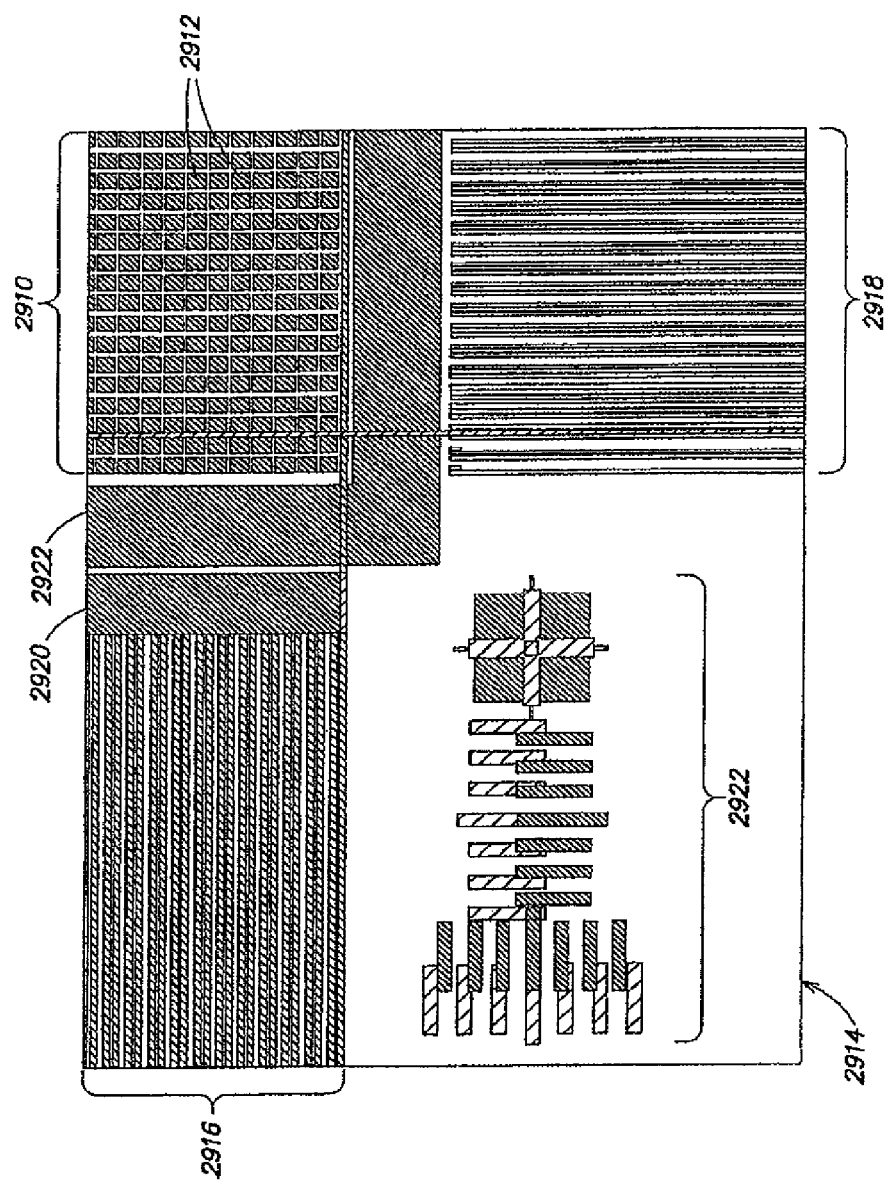
FIG. 29 is a diagrammatic depiction of a top view of one corner (i.e., the lower left corner) of the layout of a chip showing an array of individual ISFET sensors on a CMOS die.

One example of a method for forming a microwell array is now discussed, starting with reference to FIG. 29. That figure diagrammatically depicts a top view of one corner (i.e., the lower left corner) of the layout of a chip showing an array 2910 of the individual ISFET sensors 2912 on the CMOS die 2914. Signal lines 2916 and 2918 are used for addressing the array and reading its output. Block 2920 represents some of the electronics for the array, as discussed above, and layer 2922 represents a portion of a wall which becomes part of a microfluidics structure, the flow cell, as more fully explained below; the flow cell is that structure which provides a fluid flow over the microwell array or over the sensor surface directly, if there is no microwell structure. On the surface of the die, a pattern such as pattern 2922 at the bottom left of FIG. 29 may be formed during the semiconductor processing to form the ISFETs and associated circuitry, for use as alignment marks for locating the wells over the sensor pixels when the dielectric has covered the die's surface.

After the semiconductor structures, as shown, are formed, the microwell structure is applied to the die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 4-12 μm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter. Based on signal-to-noise considerations, there is a relationship between dimensions and the required data sampling rates to achieve a desired level of performance. Thus there are a number of factors that will go into selecting optimum parameters for a given application.) Alternatively, multiple layers of different photoresists may be applied or another form of dielectric material may be deposited. Various types of chemical vapor deposition may also be used to build up a layer of materials suitable for microwell formation therein.

Once the photoresist layer (the singular form "layer" is used to encompass multiple layers in the aggregate, as well) is in place, the individual wells (typically mapped to have either one or four ISFET sensors per well) may be generated by placing a mask (e.g., of chromium) over the resist-coated die and exposing the resist to cross-linking (typically UV) radiation. All resist exposed to the radiation (i.e., where the mask does not block the radiation) becomes cross-linked and as a result will form a permanent plastic layer bonded to the surface of the chip (die). Unreacted resist (i.e., resist in areas which are not exposed, due to the mask blocking the light from reaching the resist and preventing cross-linking) is removed by washing the chip in a suitable solvent (i.e., developer) such as propyleneglycolmethylethylacetate (PGMEA) or other appropriate solvent. The resultant structure defines the walls of the microwell array.

Figure 30:
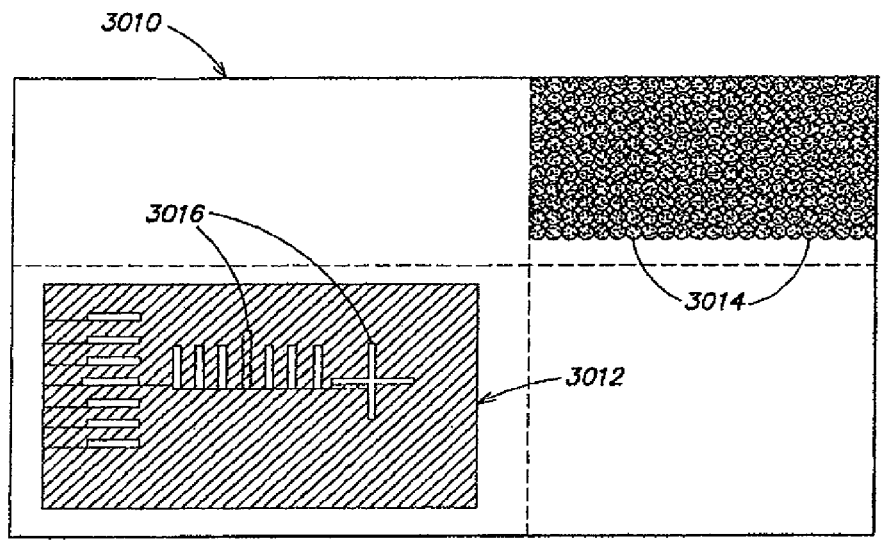
FIG. 30 is an illustration of an example of a layout for a portion of a (typically chromium) mask for a one-sensor-per-well embodiment of the above-described sensor array, corresponding to the portion of the die shown in FIG. 29.

FIG. 30 shows an example of a layout for a portion of a chromium mask 3010 for a one-sensor-per-well embodiment, corresponding to the portion of the die shown in FIG. 29. The grayed areas 3012, 3014 are those that block the UV radiation. The alignment marks in the white portions 3016 on the bottom left quadrant of FIG. 30, within gray area 3012, are used to align the layout of the wells with the ISFET sensors on the chip surface. The array of circles 3014 in the upper right quadrant of the mask block radiation from reaching the well areas, to leave unreacted resist which can be dissolved in forming the wells.

Figure 31:
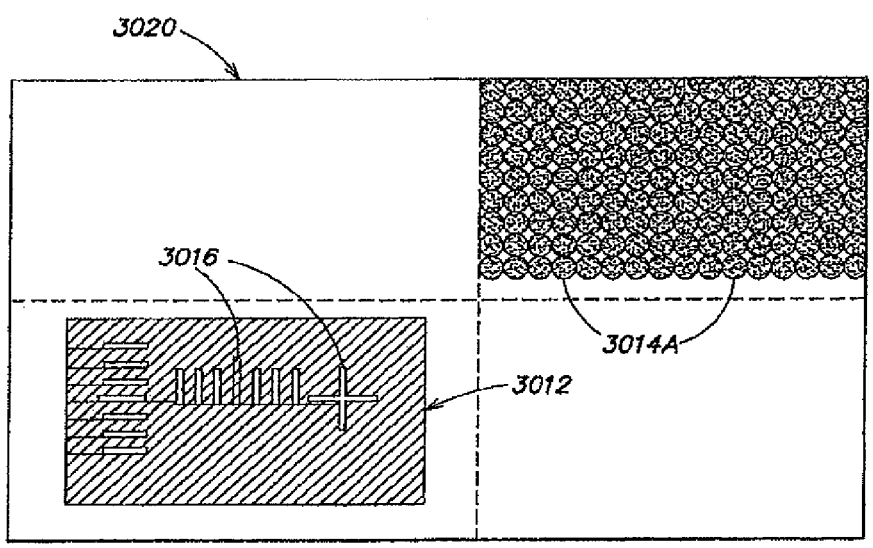
FIG. 31 is a corresponding layout for a mask for a 4-sensors-per-well embodiment.

FIG. 31 shows a corresponding layout for the mask 3020 for a 4-sensors-per-well embodiment. Note that the alignment pattern 3016 is still used and that the individual well-masking circles 3014A in the array 2910 now have twice the diameter as the wells 3014 in FIG. 30, for accommodating four sensors per well instead of one sensor-per-well.

Figure 32:
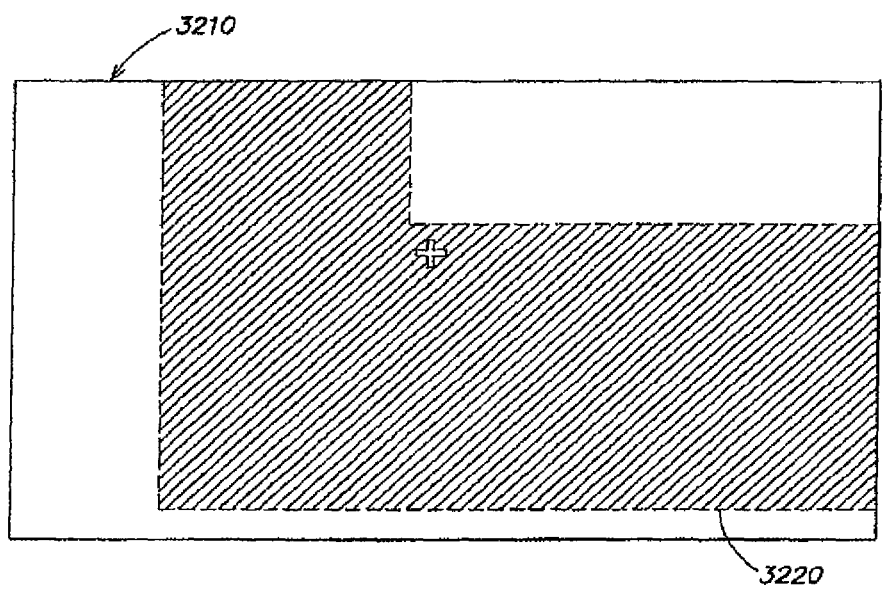
FIG. 32 is an illustration of a second mask used to mask an area which surrounds the array, to build a collar or wall (or basin, using that term in the geological sense) of resist which surrounds the active array of sensors on a substrate, as shown in FIG. 33A.
Figure 33:
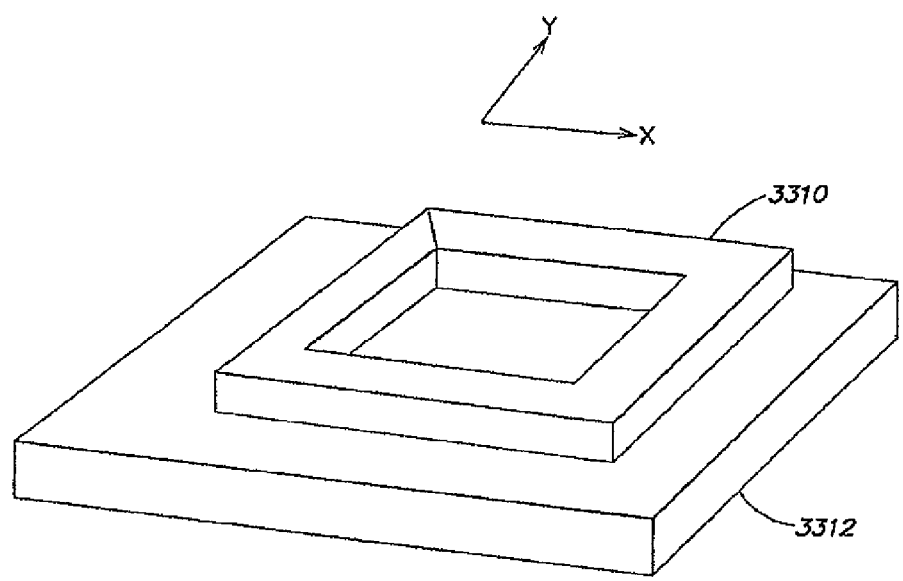
FIG. 33 is an illustration of the resulting basin.

After exposure of the die/resist to the UV radiation, a second layer of resist may be coated on the surface of the chip. This layer of resist may be relatively thick, such as about 400-450 μm thick, typically. A second mask 3210 (FIG. 32), which also may be of chromium, is used to mask an area 3220 which surrounds the array, to build a collar or wall (or basin, using that term in the geological sense) 3310 of resist which surrounds the active array of sensors on substrate 3312, as shown in FIG. 33. In the particular example being described, the collar is 150 μm wider than the sensor array, on each side of the array, in the x direction, and 9 μm wider on each side than the sensor array, in the y direction. Alignment marks on mask 3210 (most not shown) are matched up with the alignment marks on the first layer and the CMOS chip itself.

Other photolithographic approaches may be used for formation of the microwell array, of course, the foregoing being only one example.

For example, contact lithography of various resolutions and with various etchants and developers may be employed. Both organic and inorganic materials may be used for the layer(s) in which the microwells are formed. The layer(s) may be etched on a chip having a dielectric layer over the pixel structures in the sensor array, such as a passivation layer, or the layer(s) may be formed separately and then applied over the sensor array. The specific choice or processes will depend on factors such as array size, well size, the fabrication facility that is available, acceptable costs, and the like.

Among the various organic materials which may be used in some embodiments to form the microwell layer(s) are the above-mentioned SU-8 type of negative-acting photoresist, a conventional positive-acting photoresist and a positive-acting photodefineable polyimide. Each has its virtues and its drawbacks, well known to those familiar with the photolithographic art.

Naturally, in a production environment, modifications will be appropriate.

Contact lithography has its limitations and it may not be the production method of choice to produce the highest densities of wells—i.e., it may impose a higher than desired minimum pitch limit in the lateral directions. Other techniques, such as a deep UV step-and-repeat process, are capable of providing higher resolution lithography and can be used to produce small pitches and possibly smaller well diameters. Of course, for different desired specifications (e.g., numbers of sensors and wells per chip), different techniques may prove optimal. And pragmatic factors, such as the fabrication processes available to a manufacturer, may motivate the use of a specific fabrication method. While novel methods are discussed, various aspects of the invention are limited to use of these novel methods.

Preferably the CMOS wafer with the ISFET array will be planarized after the final metallization process. A chemical mechanical dielectric planarization prior to the silicon nitride passivation is suitable. This will allow subsequent lithographic steps to be done on very flat surfaces which are free of back-end CMOS topography.

By utilizing deep-UV step-and-repeat lithography systems, it is possible to resolve small features with superior resolution, registration, and repeatability. However, the high resolution and large numerical aperture (NA) of these systems precludes their having a large depth of focus. As such, it may be necessary, when using such a fabrication system, to use thinner photodefinable spin-on layers (i.e., resists on the order of 1-2 μm rather than the thicker layers used in contact lithography) to pattern transfer and then etch microwell features to underlying layer or layers. High resolution lithography can then be used to pattern the microwell features and conventional $SiO_2$ etch chemistries can be used—one each for the bondpad areas and then the microwell areas—having selective etch stops; the etch stops then can be on aluminum bondpads and silicon nitride passivation (or the like), respectively. Alternatively, other suitable substitute pattern transfer and etch processes can be employed to render microwells of inorganic materials.

Another approach is to form the microwell structure in an organic material. For example, a dual-resist "soft-mask" process may be employed, whereby a thin high-resolution deep-UV resist is used on top of a thicker organic material (e.g., cured polyimide or opposite-acting resist). The top resist layer is patterned. The pattern can be transferred using an oxygen plasma reactive ion etch process. This process sequence is sometimes referred to as the "portable conformable mask" (PCM) technique. Sec B. J. Lin et al., "Practicing the Novolac deep-UV portable conformable masking technique", Journal of Vacuum Science and Technology 19, No. 4, 1313-1319 (1981); and A. Cooper et al, "Optimization of a photosensitive spin-on dielectric process for copper inductor coil and interconnect protection in RF SoC devices."

Alternatively a "drill-focusing" technique may be employed, whereby several sequential step-and-repeat exposures are done at different focal depths to compensate for the limited depth of focus (DOF) of high-resolution steppers when patterning thick resist layers. This technique depends on the stepper NA and DOF as well as the contrast properties of the resist material.

Figure 33A:
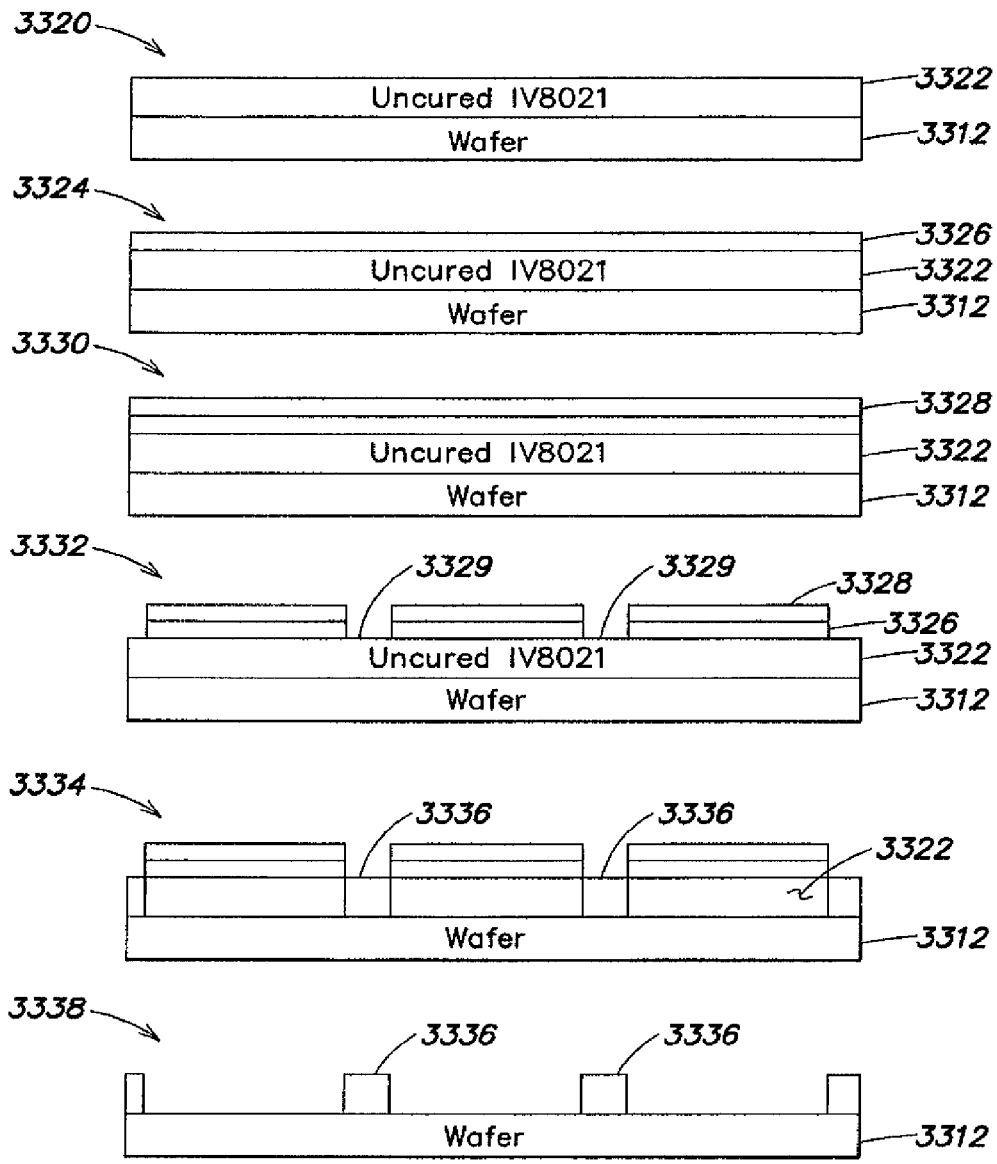
FIG. 33A is an illustration of a three-layer PCM process for making the microwell array.

Another PCM technique may be adapted to these purposes, such as that shown in U.S. patent application publication no. 2006/0073422 by Edwards et al. This is a three-layer PCM process and it is illustrated in FIG. 33A. As shown there, basically six major steps are required to produce the microwell array and the result is quite similar to what contact lithography would yield.

In a first step, 3320, a layer of high contrast negative-acting photoresist such as type Shipley InterVia Photodielectric Material 8021 (IV8021) 3322 is spun on the surface of a wafer, which we shall assume to be the wafer providing the substrate 3312 of FIG. 33 (in which the sensor array is fabricated), and a soft bake operation is performed. Next, in step 3324, a blocking anti-reflective coating (BARC) layer 3326, is applied and soft baked. On top of this structure, a thin resist layer 3328 is spun on and soft baked, step 3330, the thin layer of resist being suitable for fine feature definition. The resist layer 3328 is then patterned, exposed and developed, and the BARC in the exposed regions 3329, not protected any longer by the resist 3328, is removed, Step 3332. This opens up regions 3329 down to the uncured IV8021 layer. The BARC layer can now act like a conformal contact mask A blanket exposure with a flooding exposure tool, Step 3334, cross-links the exposed IV8021, which is now shown as distinct from the uncured IV8021 at 3322. One or more developer steps 3338 are then performed, removing everything but the cross-linked IV8021 in regions 3336. Regions 3336 now constitute the walls of the microwells.

Although as shown above, the wells bottom out (i.e. terminate) on the top passivation layer of the ISFETs, it is believed that an improvement in ISFET sensor performance (i.e. such as signal-to-noise ratio) can be obtained if the active bead(s) is(are) kept slightly elevated from the ISFET passivation layer. One way to do so is to place a spacer "hump" within the boundary of the pixel microwell. An example of how this could be rendered would be not etching away a portion of the layer-or-layers used to form the microwell structure (i.e. two lithographic steps to form the microwells—one to etch part way done, the other to pattern the bump and finish the etch to bottom out), by depositing and lithographically defining and etching a separate layer to form the "bump", by using a permanent photo-definable material for the bump once the microwells are complete, or by forming the bump prior to forming the microwell. The bump feature is shown as 3350 in FIG. 33B. An alternative (or additional) non-integrated approach is to load the wells with a layer or two of very small packing beads before loading the DNA-bearing beads.

Figure 33B:
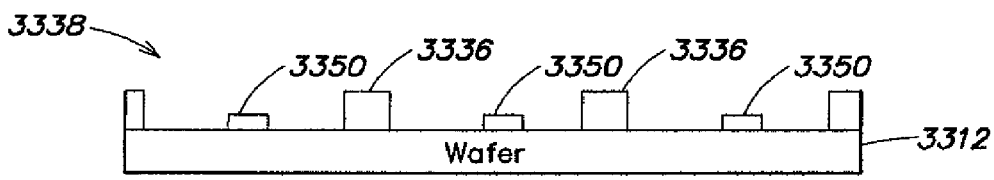
FIG. 33B is a diagrammatic cross-section of a microwell with a "bump" feature etched into the bottom.
Figures 1, 33B:
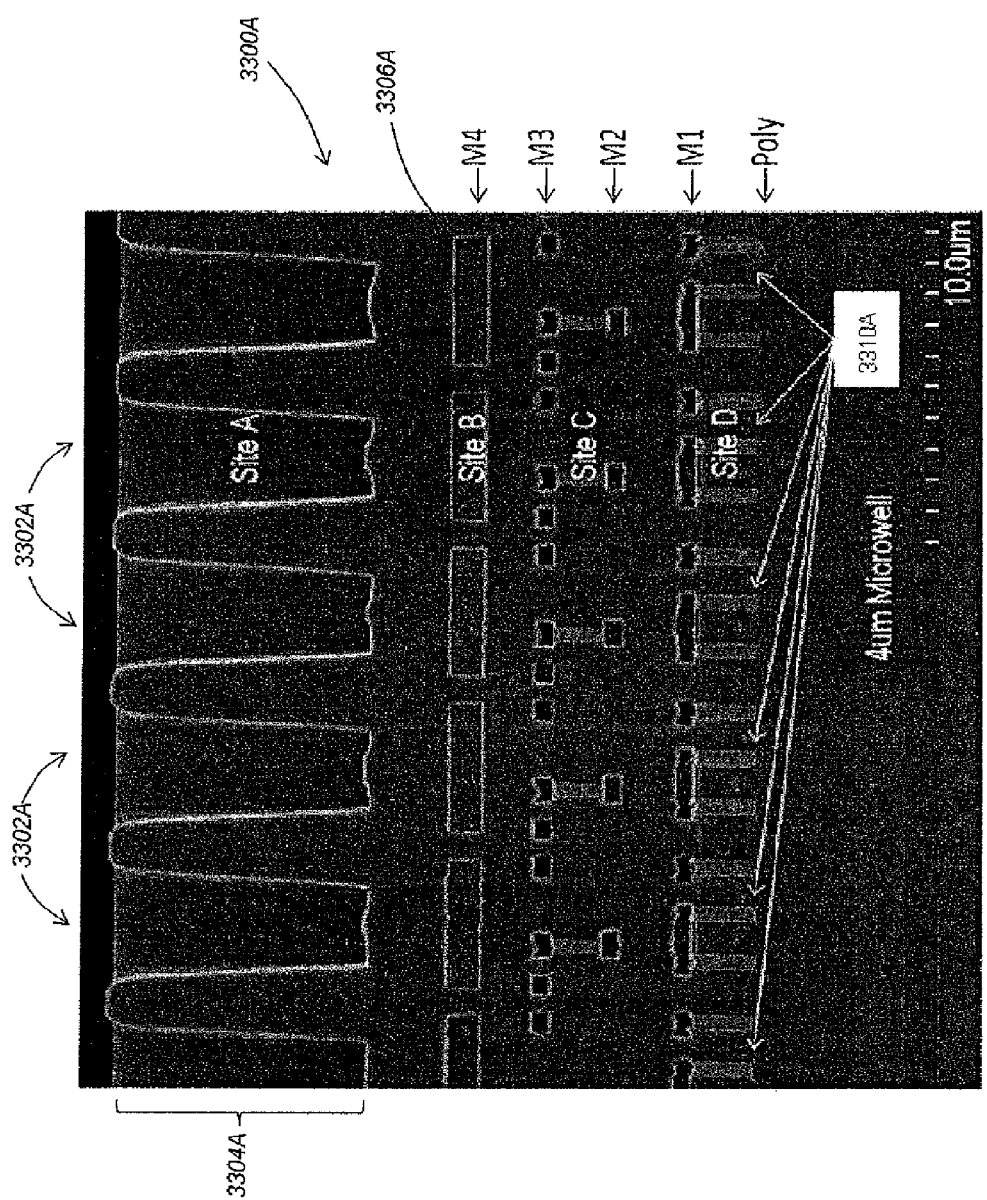
Figures 2, 33B:
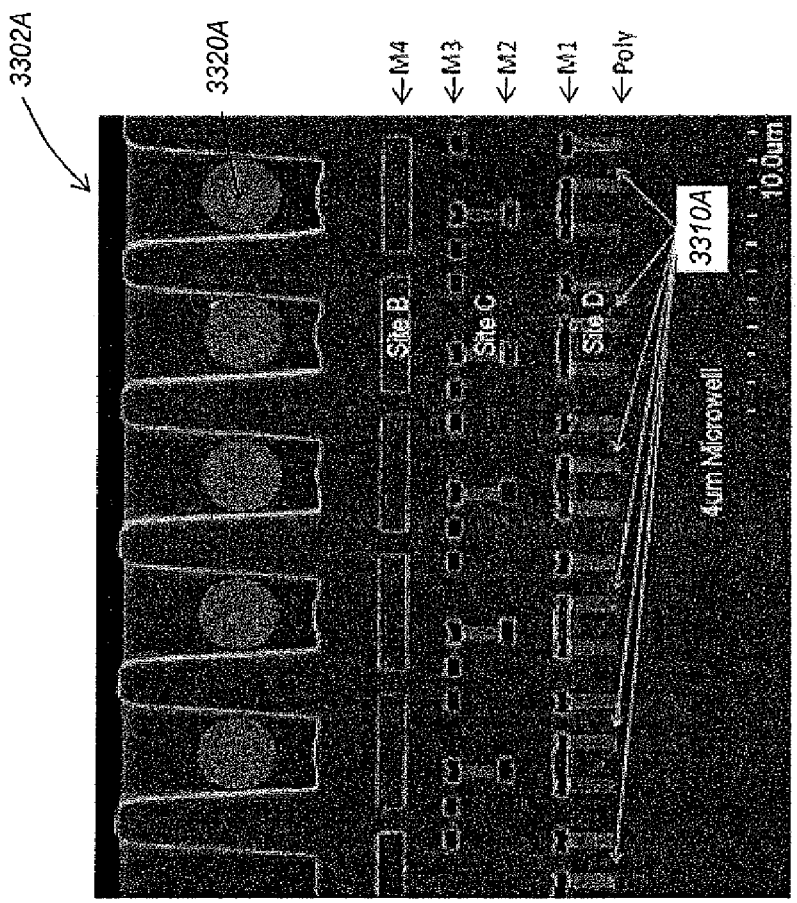
Figures 3, 33B:
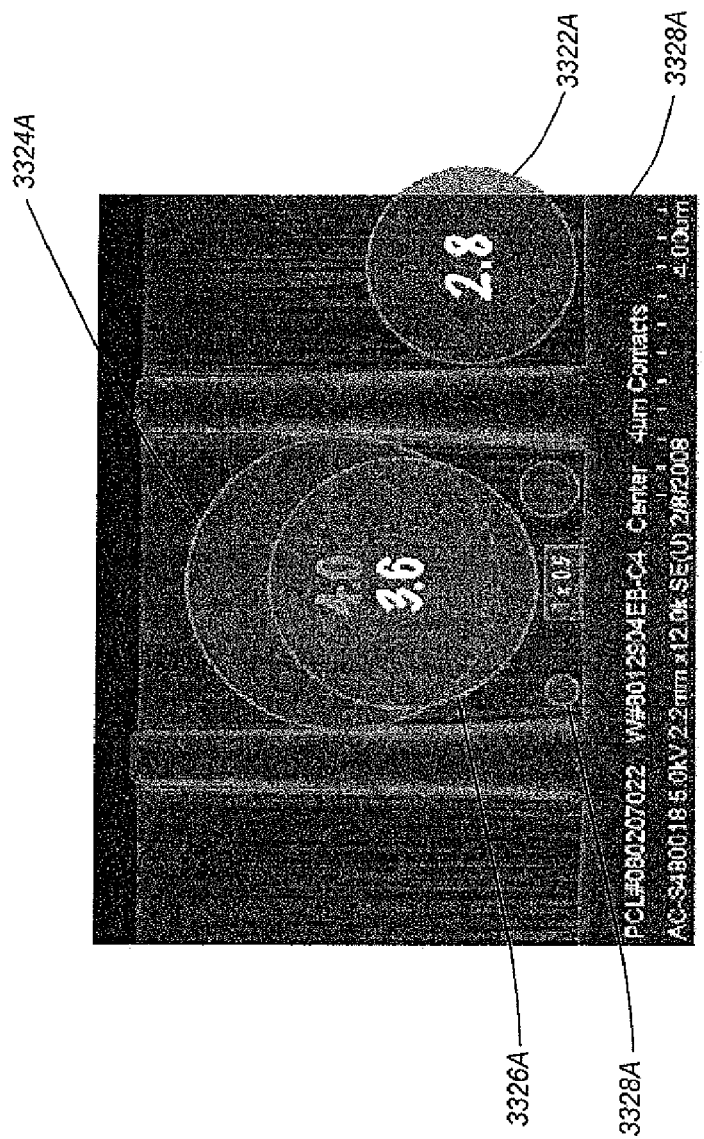

Using a 6 μm (micron) thick layer of tetra-methyl-orthosilicate (TEOS) as a $SiO_2$-like layer for microwell formation, FIG. 33B-1 shows a scanning electron microscope (SEM) image of a cross-section of a portion 3300A of an array architecture as taught herein. Microwells 3302A are formed in the TEOS layer 3304A. The wells extend about 4 μm into the 6 μm thick layer. Typically, the etched well bottoms on an etch-stop material which may be, for example, an oxide, an organic material or other suitable material known in semiconductor processing for etch-stopping use. A thin layer of etch stop material may be formed on top of a thicker layer of polyimide or other suitable dielectric, such that there is about 2 μm of etch stop+polyimide between the well bottom and the Metal4 (M4) layer of the chip in which the extended gate electrode 3308A is formed for each underlying ISFET in the array. As labeled on the side, the CMOS metallization layers M3, M2 and M1, which form lower level interconnects and structures, are shown, with the ISFET channels being formed in the areas indicated by arrows 3310A.

In the orthogonal cross-sectional view (i.e., looking down from the top), the wells may be formed in either round or square shape. Round wells may improve head capture and may obviate the need for packing beads at the bottom or top of the wells.

Figure 2:
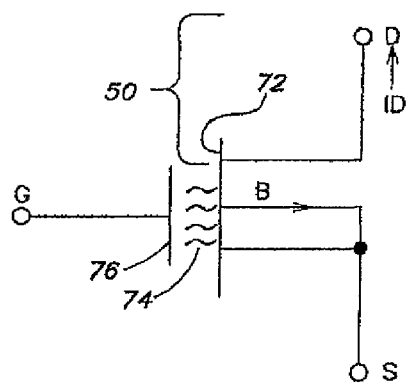
FIG. 2 illustrates an electric circuit representation of the p-channel ISFET shown in FIG. 1.
Figure 2A:
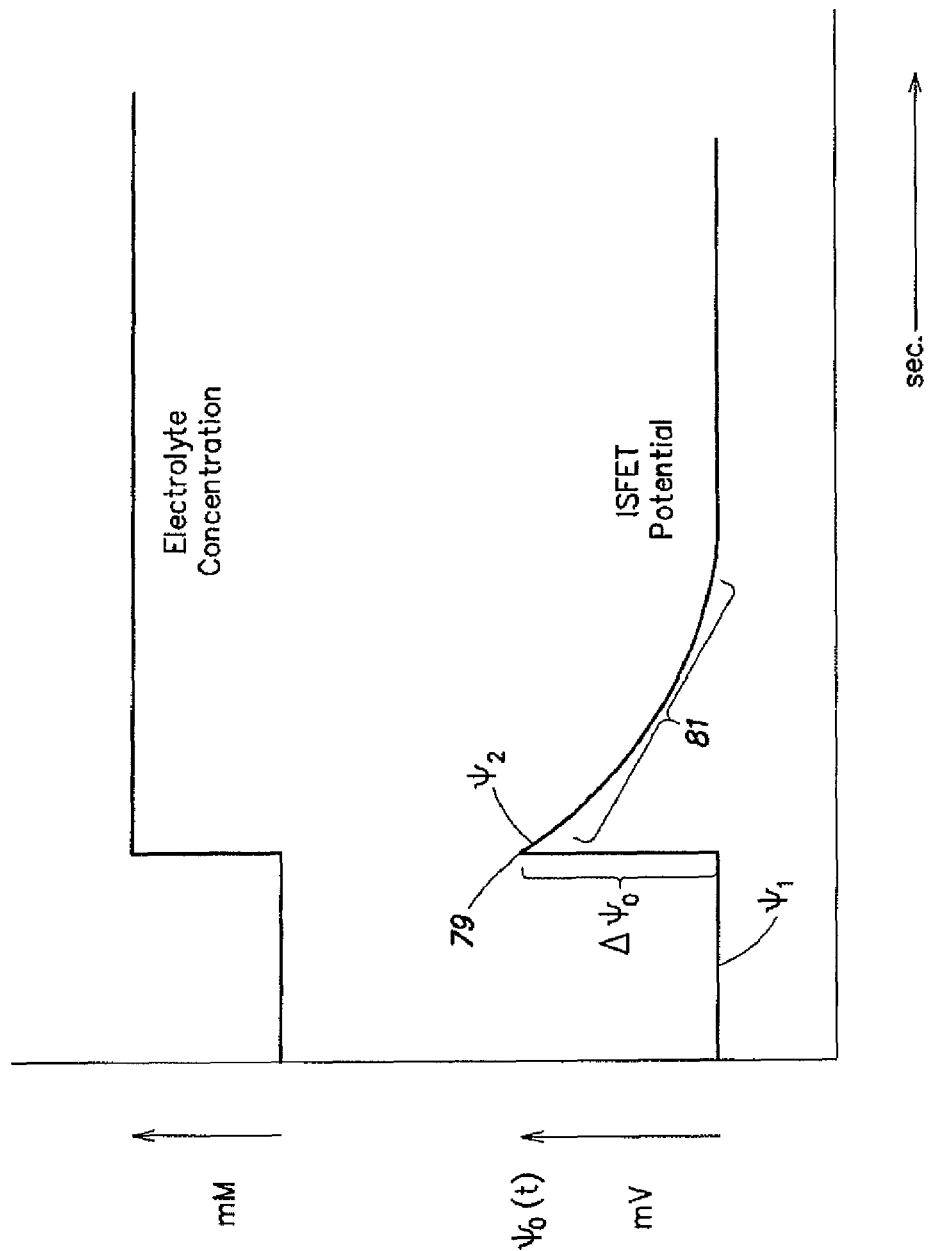
FIG. 2A illustrates an exemplary ISFET transient response to a step-change in ion concentration of an analyte.

The tapered slopes to the sides of the microwells also may be used to advantage. Referring to FIG. 33B-2, if the beads 3320A have a diameter larger than the bottom span across the wells, but small enough to fit into the mouths of the wells, the beads will be spaced off the bottom of the wells due to the geometric constraints. For example, FIG. 33B-2 illustrates the example of microwells that are square in cross-section as viewed from the top, 4 um on a side, with 3.8 um diameter beads 3320A loaded. Experimentally and with some calculation, one may determine suitable bead size and well dimension combinations. FIG. 33B-3 shows a portion of one 4 um well loaded with a 2.8 um diameter bead 3322A, which obviously is relatively small and falls all the way to the bottom of the well; a 4.0 um diameter bead 3324A which is stopped from reaching the bottom by the sidewall taper of the well; and an intermediate-sized bead 3326A of 3.6 um diameter which is spaced from the well bottom by packing beads 3328A. Clearly, bead size has to be carefully matched to the microwell etch taper.

Thus, microwells can be fabricated by any high aspect ratio photo-definable or etchable thin-film process, that can provide requisite thickness (e.g., about 4-10 um). Among the materials believed to be suitable are photosensitive polymers, deposited silicon dioxide, non-photosensitive polymer which can be etched using, for example, plasma etching processes, etc. In the silicon dioxide family, TEOS and silane nitrous oxide (SILOX) appear suitable. The final structures are similar but the various materials present differing surface compositions that may cause the target biology or chemistry to react differently.

When the microwell layer is formed, it may be necessary to provide an etch stop layer so that the etching process does not proceed further than desired. For example, there may be an underlying layer to be preserved, such as a low-K dielectric. The etch stop material should be selected according to the application. SiC and SiN materials may be suitable, but that is not meant to indicate that other materials may not be employed, instead. These etch-stop materials can also serve to enhance the surface chemistry which drives the ISFET sensor sensitivity, by choosing the etch-stop material to have an appropriate point of zero charge (PZC). Various metal oxides may be suitable addition to silicon dioxide and silicon nitride.

The PZCs for various metal oxides may be found in various texts, such as "Metal Oxides—Chemistry and Applications" by J. Fierro. We have learned that $Ta_2O_5$ may be preferred as an etch stop over $Al_2O_3$ because the PZC of $Al_2O_3$ is right at the pH being used (i.e., about 8.8) and, hence, right at the point of zero charge. In addition $Ta_2O_5$ has a higher sensitivity to pH (i.e., mV/pH), another important factor in the sensor performance. Optimizing these parameters may require judicious selection of passivation surface materials.

Using thin metal oxide materials for this purpose (i.e., as an etch stop layer) is difficult due to the fact of their being so thinly deposited (typically 200-500 Å). A post-microwell fabrication metal oxide deposition technique may allow placement of appropriate PZC metal oxide films at the bottom of the high aspect ratio microwells.

Electron-beam depositions of (a) reactively sputtered tantalum oxide, (b) non-reactive stoichiometric tantalum oxide, (c) tungsten oxide, or (d) Vanadium oxide may prove to have superior "down-in-well" coverage due to the superior directionality of the deposition process.

The array may typically comprise 100 microfluidic wells (i.e., it has a minimum of 100 microfluidic wells although it may have more), each of which is coupled to one or more chemFET sensors. Preferably, the wells are formed in at least one of a glass (e.g., $SiO_2$), a polymeric material, a photodefinable material or a reactively ion etchable thin film material. Preferably, the wells have a width to height ratio less than about 1:1. Preferably the sensor is a field effect transistor, and more preferably a chemFET. The chemFET may optionally be coupled to a PPi receptor. Preferably, each of the chemFETs occupies an area of the array that is $10^2$ microns or less.

In some embodiments, the invention encompasses a sequencing device comprising a semiconductor wafer device coupled to a dielectric layer such as a glass (e.g., $SiO_2$), polymeric, photodefinable or reactive ion etchable material in which reaction chambers are formed. Typically, the glass, dielectric, polymeric, photodefinable or reactive ion etchable material is integrated with the semiconductor wafer layer. In some instances, the glass, polymeric, photodefinable or reactive ion etchable layer is non-crystalline. In some instances, the glass may be $SiO_2$. The device can optionally further comprise a fluid delivery module of a suitable material such as a polymeric material, preferably an injection moldable material. More preferably, the polymeric layer is polycarbonate.

In some embodiments, the invention encompasses a method for manufacturing a sequencing device comprising: using photolithography, generating wells in a glass, dielectric, photodefinable or reactively ion etchable material on top of an array of transistors.

Mounting the Flow Cell (Fluidic Interface) to the Sensor Chip

The process of using the assembly of an array of sensors on a chip combined with an array of microwells to sequence the DNA in a sample is referred to as an "experiment." Executing an experiment requires loading the wells with the DNA-bound beads and the flowing of several different fluid solutions (i.e., reagents and washes) across the wells. A fluid delivery system (e.g., valves, conduits, pressure source(s), etc.) coupled with a fluidic interface is needed which flows the various solutions across the wells in a controlled even flow with acceptably small dead volumes and small cross contamination between sequential solutions. Ideally, the fluidic interface to the chip (sometimes referred to as a "flow cell") would cause the fluid to reach all microwells at the same time. To maximize array speed, it is necessary that the array outputs be available at as close to the same time as possible. The ideal clearly is not possible, but it is desirable to minimize the differentials, or skews, of the arrival times of an introduced fluid, at the various wells, in order to maximize the overall speed of acquisition of all the signals from the array.

Flow cell designs of many configurations are possible; thus the system and methods presented herein are not dependent on use of a specific flow cell configuration. It is desirable, though, that a suitable flow cell substantially conform to the following set of objectives:

- have connections suitable for interconnecting with a fluidics delivery system—e.g., via appropriately-sized tubing;
- have appropriate head space above wells;
- minimize dead volumes encountered by fluids;
- minimize small spaces in contact with liquid but not quickly swept clean by flow of a wash fluid through the flow cell (to minimize cross contamination);
- be configured to achieve uniform transit time of the flow over the array;
- generate or propagate minimal bubbles in the flow over the wells;
- be adaptable to placement of a removable reference electrode inside or as close to the flow chamber as possible;
- facilitate easy loading of beads;
- be manufacturable at acceptable cost; and
- be easily assembled and attached to the chip package.

Satisfaction of these criteria so far as possible will contribute to system performance positively. For example, minimization of bubbles is important so that signals from the array truly indicate the reaction in a well rather than being spurious noise.

Each of several example designs will be discussed, meeting these criteria in differing ways and degrees. In each instance, one typically may choose to implement the design in one of two ways: either by attaching the flow cell to a frame and gluing the frame (or otherwise attaching it) to the chip or by integrating the frame into the flow cell structure and attaching this unified assembly to the chip. Further, designs may be categorized by the way the reference electrode is integrated into the arrangement. Depending on the design, the reference electrode may be integrated into the flow cell (e.g., form part of the ceiling of the flow chamber) or be in the flow path (typically to the outlet or downstream side of the flow path, after the sensor array).

A first example of a suitable experiment apparatus 3410 incorporating such a fluidic interface is shown in FIGS. 34-37, the manufacture and construction of which will be discussed in greater detail below.

The apparatus comprises a semiconductor chip 3412 (indicated generally, though hidden) on or in which the arrays of wells and sensors are formed, and a fluidics assembly 3414 on top of the chip and delivering the sample to the chip for reading. The fluidics assembly includes a portion 3416 for introducing fluid containing the sample, a portion 3418 for allowing the fluid to be piped out, and a flow chamber portion 3420 for allowing the fluid to flow from inlet to outlet and along the way interact with the material in the wells. Those three portions are unified by an interface comprising a glass slide 3422 (e.g., Erie Microarray Cat #C22-5128-M20 from Erie Scientific Company, Portsmouth, N.H., cut in thirds, each to be of size about 25 mm×25 mm).

Mounted on the top face of the glass slide are two fittings, 3424 and 3426, such as nanoport fittings Part #N-333 from Upchurch Scientific of Oak Harbor, Wash. One port (e.g., 3424) serves as an inlet delivering liquids from the pumping/valving system described below but not shown here. The second port (e.g., 3426) is the outlet which pipes the liquids to waste. Each port connects to a conduit 3428, 3432 such as flexible tubing of appropriate inner diameter. The nanoports are mounted such that the tubing can penetrate corresponding holes in the glass slide. The tube apertures should be flush with the bottom surface of the slide.

On the bottom of the glass slide, flow chamber 3420 may comprise various structures for promoting a substantially laminar flow across the microwell array. For example, a series of microfluidic channels fanning out from the inlet pipe to the edge of the flow chamber may be patterned by contact lithography using positive photoresists such as SU-8 photoresist from MicroChem. Corp. of Newton, Mass. Other structures will be discussed below.

The chip 3412 will in turn be mounted to a carrier 3430, for packaging and connection to connector pins 3432.

Figure 36:
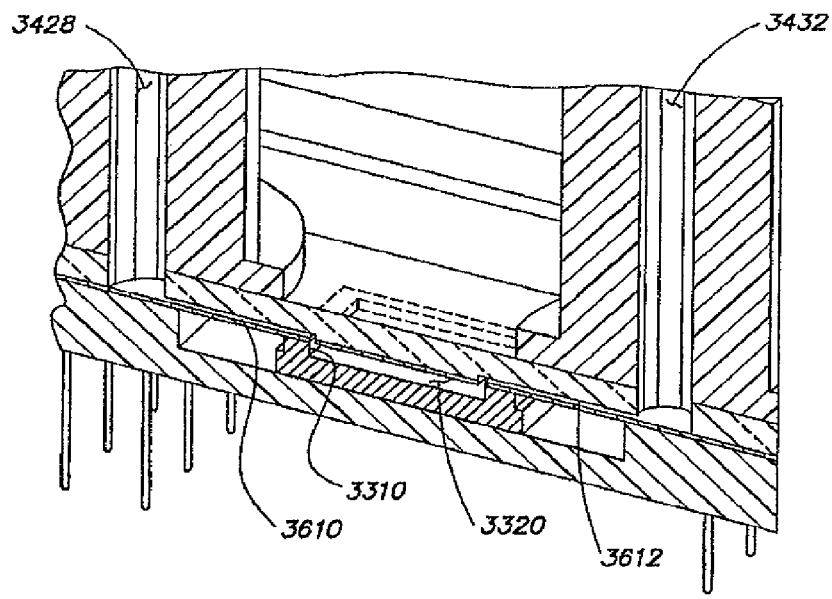
Figure 37:
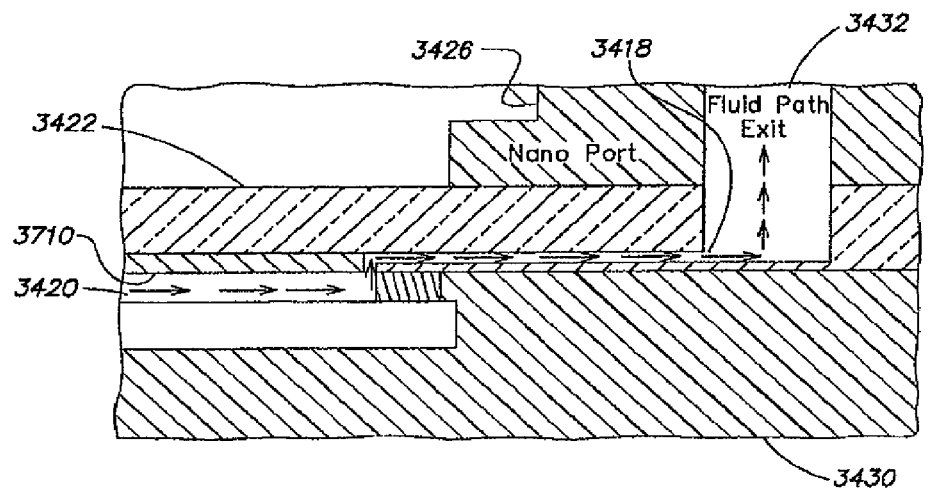
Figure 38:
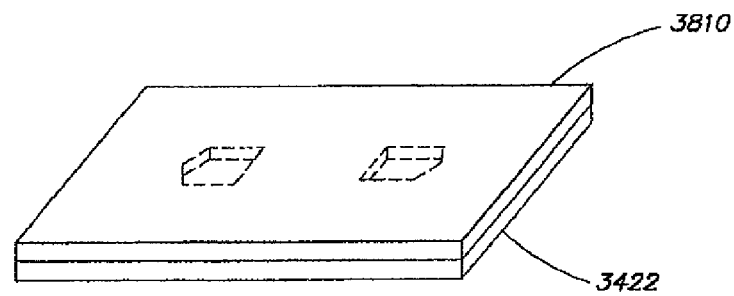
FIG. 38 is a diagrammatic illustration of a substrate with an etched photoresist layer beginning the formation of an example flow cell of a certain configuration.

For ease of description, to discuss fabrication starting with FIG. 38 we shall now consider the glass slide 3422 to be turned upside down relative to the orientation it has in FIGS. 34-37.

Figure 39:
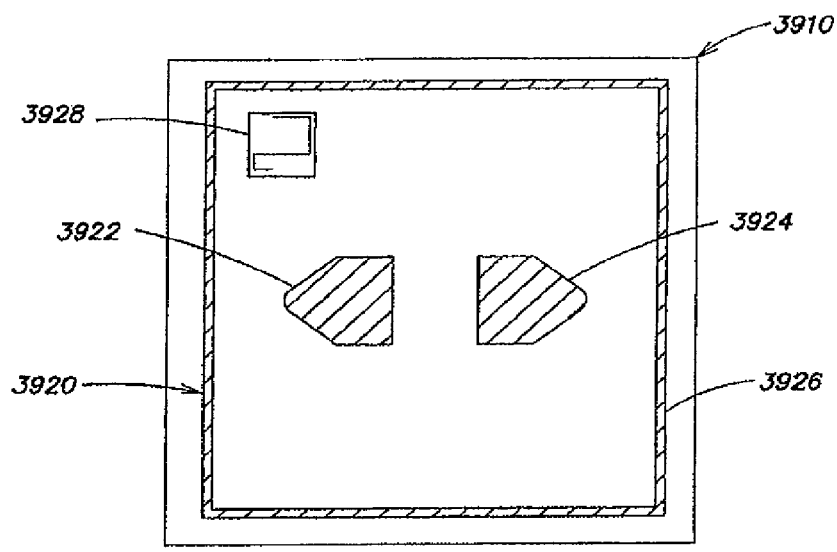
FIGS. 39-41 are diagrams of masks suitable for producing a first configuration of flow cell consistent with FIG. 38.

A layer of photoresist 3810 is applied to the "top" of the slide (which will become the "bottom" side when the slide and its additional layers is turned over and mounted to the sensor assembly of ISFET array with microwell array on it). Layer 3810 may be about 150 μm thick in this example, and it will form the primary fluid carrying layer from the end of the tubing in the nanoports to the edge of the sensor array chip. Layer 3810 is patterned using a mask such as the mask 3910 of FIG. 39 ("patterned" meaning that a radiation source is used to expose the resist through the mask and then the non-plasticized resist is removed). The mask 3910 has radiation-transparent regions which are shown as white and radiation-blocking regions 3920, which are shown in shading. The radiation-blocking regions are at 3922-3928. The region 3926 will form a channel around the sensor assembly; it is formed about 0.5 mm inside the outer boundary of the mask 3920, to avoid the edge bead that is typical. The regions 3922 and 3924 will block radiation so that corresponding portions of the resist are removed to form voids shaped as shown. Each of regions 3922, 3924 has a rounded end dimensioned to receive an end of a corresponding one of the tubes 3428, 3432 passing through a corresponding nanoport 3424, 3426. From the rounded end, the regions 3922, 3924 fan out in the direction of the sensor array to allow the liquid to spread so that the flow across the array will be substantially laminar. The region 3928 is simply an alignment pattern and may be any suitable alignment pattern or be replaced by a suitable substitute alignment mechanism. Dashed lines on FIG. 38 have been provided to illustrate the formation of the voids 3822 and 3824 under mask regions 3922 and 3924.

Figure 40:
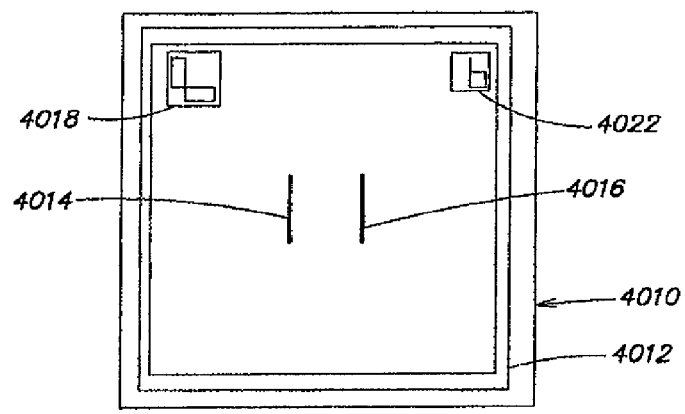

A second layer of photoresist is formed quite separately, not on the resist 3810 or slide 3422. Preferably it is formed on a flat, flexible surface (not shown), to create a peel-off, patterned plastic layer. As shown in FIG. 40, this second layer of photoresist may be formed using a mask such as mask 4010, which will leave on the flexible substrate, after patterning, the border under region 4012, two slits under regions 4014, 4016, whose use will be discussed below, and alignment marks produced by patterned regions 4018 and 4022. The second layer of photoresist is then applied to the first layer of photoresist using one alignment mark or set of alignment marks, let's say produced by pattern 4018, for alignment of these layers. Then the second layer is peeled from its flexible substrate and the latter is removed.

The other alignment mark or set of marks produced by pattern 4022 is used for alignment with a subsequent layer to be discussed.

The second layer is preferably about 150 μm deep and it will cover the fluid-carrying channel with the exception of a slit about 150 μm long at each respective edge of the sensor array chip, under slit-forming regions 4014 and 4016.

Figure 41:
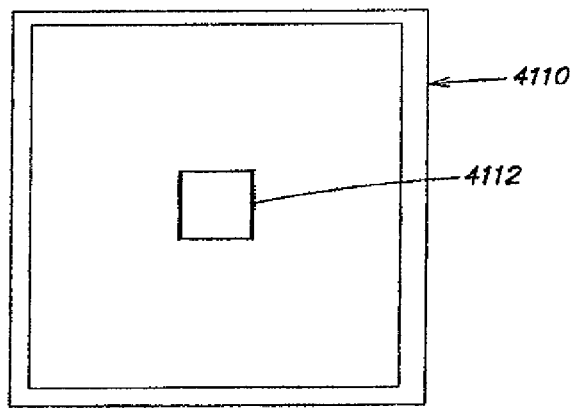

Once the second layer of photoresist is disposed on the first layer, a third patterned layer of photoresist is formed over the second layer, using a mask such as mask 4110, shown in FIG. 41. The third layer provides a baffle member under region 4112 which is as wide as the collar 3310 on the sensor chip array (see FIG. 33) but about 300 μm narrower to allow overlap with the fluid-carrying channel of the first layer. The third layer may be about 150 μm thick and will penetrate the chip collar 3310, toward the floor of the basin formed thereby, by 150 μm. This configuration will leave a headspace of about 300 μm above the wells on the sensor array chip. The liquids are flowed across the wells along the entire width of the sensor array through the 150 μm slits under 4014, 4016.

Figure 34:
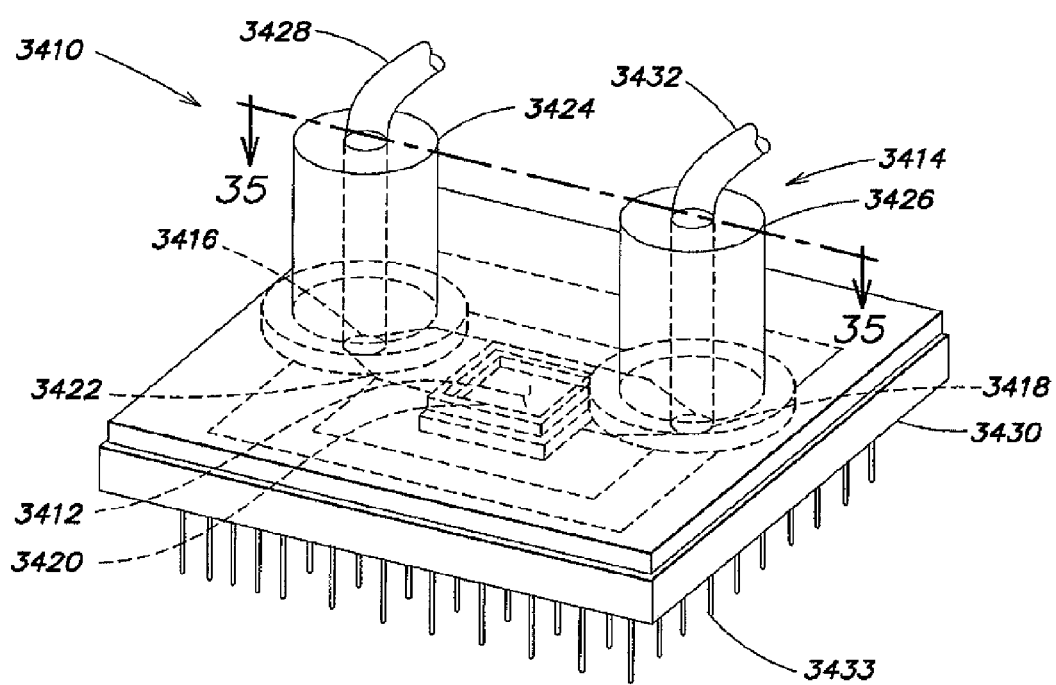
Figure 35:
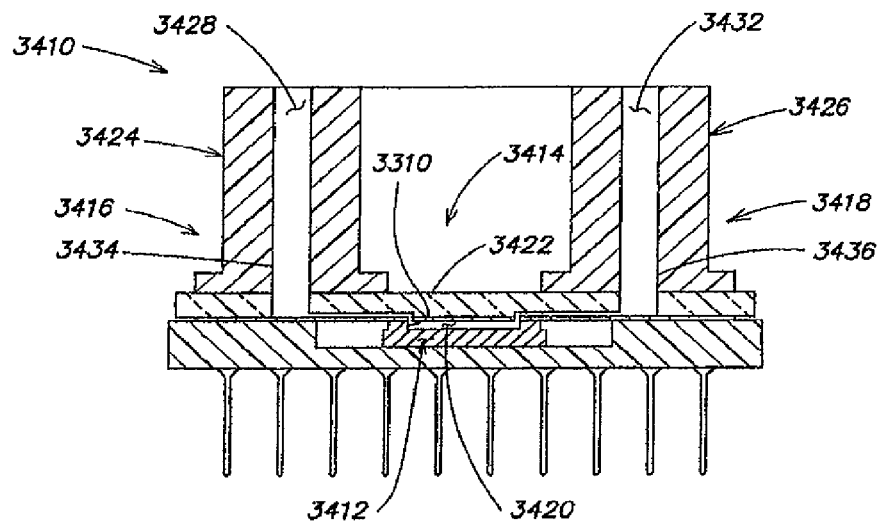

FIG. 36 shows a partial sectional view, in perspective, of the above-described example embodiment of a microfluidics and sensor assembly, also depicted in FIGS. 34 and 35, enlarged to make more visible the fluid flow path. (A further enlarged schematic of half of the flow path is shown in FIG. 37.) Here, it will be seen that fluid enters via the inlet pipe 3428 in inlet port 3424. At the bottom of pipe 3428, the fluid flows through the flow expansion chamber 3610 formed by mask area 3922, that the fluid flows over the collar 3310 and then down into the bottom 3320 of the basin, and across the die 3412 with its microwell array. After passing over the array, the fluid then takes a vertical turn at the far wall of the collar 3310 and flows over the top of the collar to and across the flow concentration chamber 3612 formed by mask area 3924, exiting via outlet pipe 3432 in outlet port 3426. Part of this flow, from the middle of the array to the outlet, may be seen also in the enlarged diagrammatic illustration of FIG. 37, wherein the arrows indicate the flow of the fluid.

The fluidics assembly may be secured to the sensor array chip assembly by applying an adhesive to parts of mating surfaces of those two assemblies, and pressing them together, in alignment.

Though not illustrated in FIGS. 34-36, the reference electrode may be understood to be a metallization 3710, as shown in FIG. 37, at the ceiling of the flow chamber.

Another way to introduce the reference electrode is shown in FIG. 42. There, a hole 4210 is provided in the ceiling of the flow chamber and a grommet 4212 (e.g., of silicone) is fitted into that hole, providing a central passage or bore through which a reference electrode 4220 may be inserted. Baffles or other microfeatures (not shown in FIG. 42 but discussed below in connection with FIG. 42A) may be patterned into the flow channel to promote laminar flow over the microwell array.

Achieving a uniform flow front and eliminating problematic flow path areas is desirable for a number of reasons. One reason is that very fast transition of fluid interfaces within the system's flow cell is desired for many applications, particularly gene sequencing. In other words, an incoming fluid must completely displace the previous fluid in a short period of time. Uneven fluid velocities and diffusion within the flow cell, as well as problematic flow paths, can compete with this requirement. Simple flow through a conduit of rectangular cross section can exhibit considerable disparity of fluid velocity from regions near the center of the flow volume to those adjacent the sidewalls, one sidewall being the top surface of the microwell layer and the fluid in the wells. Such disparity leads to spatially and temporally large concentration gradients between the two traveling fluids. Further, bubbles are likely to be trapped or created in stagnant areas like sharp corners interior the flow cell. (The surface energy (hydrophilic vs. hydrophobic) can significantly affect bubble retention. Avoidance of surface contamination during processing and use of a surface treatment to create a more hydrophilic surface should be considered if the as-molded surface is too hydrophobic.) Of course, the physical arrangement of the flow chamber is probably the factor which most influences the degree of uniformity achievable for the flow front.

Figure 42B:
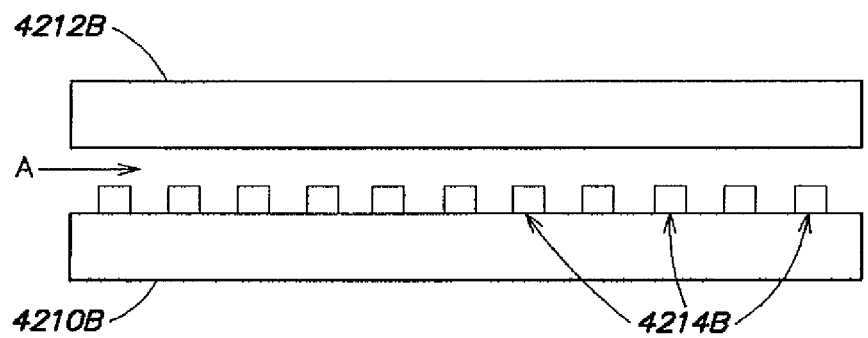
FIGS. 42B-42F are diagrammatic illustrations of examples of flow cell structures for unifying fluid flow.
Figure 42C:
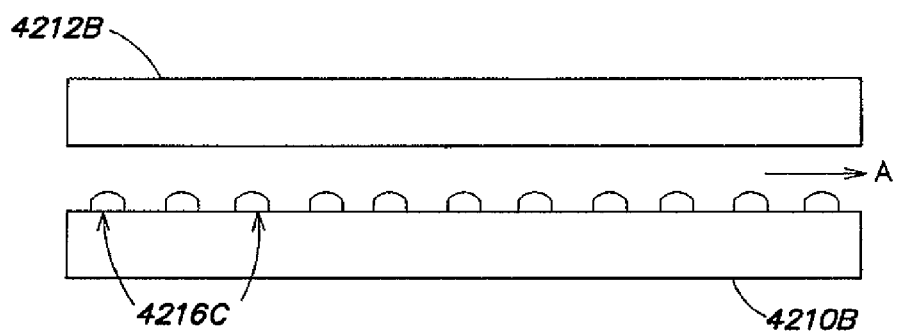
Figure 42D:
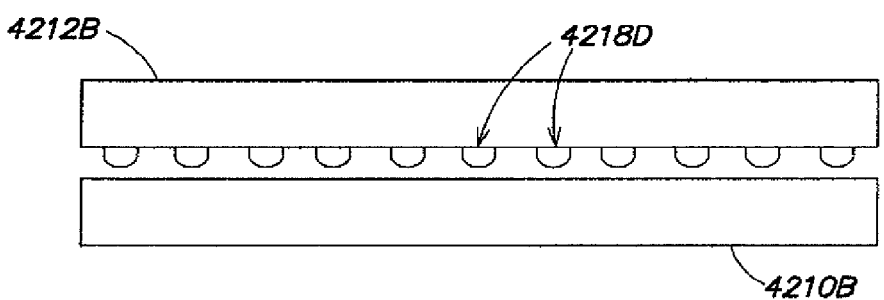
Figure 42A:
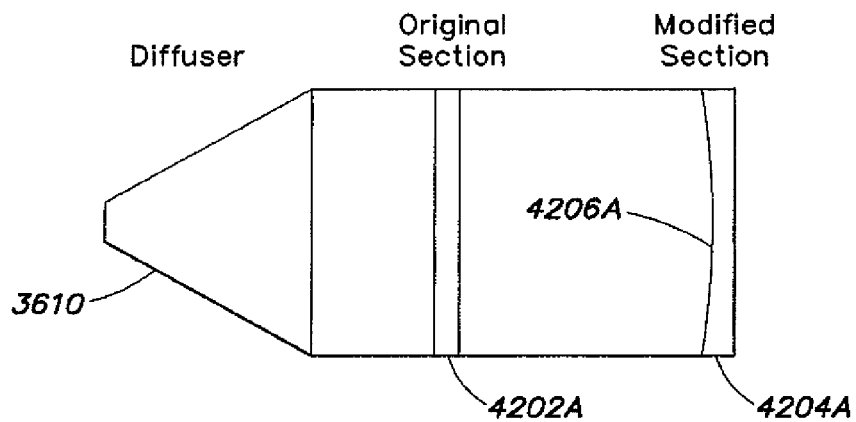
FIG. 42A is an illustration of a possible cross-sectional configuration of a non-rectangular flow chamber antechamber (diffuser section) for use to promote laminar flow into a flow cell as used in the arrangements shown herein.
Figure 42E:
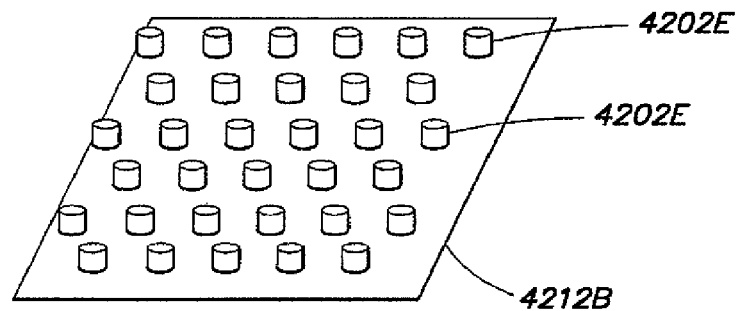

One approach is to configure the flow cross section of the flow chamber to achieve flow rates that vary across the array width so that the transit times are uniform across the array. For example, the cross section of the diffuser (i.e., flow expansion chamber) section 3416, 3610 may be made as shown at 4204A in FIG. 42A, instead of simply being rectangular, as at 4204A. That is, it may have a curved (e.g., concave) wall. The non-flat wall 4206A of the diffuser can be the top or the bottom. Another approach is to configure the effective path lengths into the array so that the total path lengths from entrance to exit over the array are essentially the same. This may be achieved, for example, by placing flow-disrupting features such as cylinders or other structures oriented normal to the flow direction, in the path of the flow. If the flow chamber has as a floor the top of the microwell array and as a ceiling an opposing wall, these flow-disrupting structures may be provided either on the top of the microwell layer or on (or in) the ceiling wall. The structures must project sufficiently into the flow to have the desired effect, but even small flow disturbances can have significant impact. Turning to FIGS. 42B-42F, there are shown diagrammatically some examples of such structures. In FIG. 42B, on the surface of microwell layer 4210B there are formed a series of cylindrical flow disruptors 4214B extending vertically toward the flow chamber ceiling wall 4212B, and serving to disturb laminar flow for the fluid moving in the direction of arrow A. FIG. 42C depicts a similar arrangement except that the flow disruptors 4216C have rounded tops and appear more like bumps, perhaps hemispheres or cylinders with spherical tops. By contrast, in FIG. 42D, the flow disruptors 4218D protrude, or depend, from the ceiling wall 4212B of the flow chamber. Only one column of flow disruptors is shown but it will be appreciated that a plurality of more or less parallel columns typically would be required. For example, FIG. 42E shows several columns 4202E of such flow disruptors (projecting outwardly from ceiling wall 4212B (though the orientation is upside down relative to FIGS. 42B-42D). The spacing between the disruptors and their heights may be selected to influence the distance over which the flow profile becomes parabolic, so that transit time equilibrates.

Figure 42F:
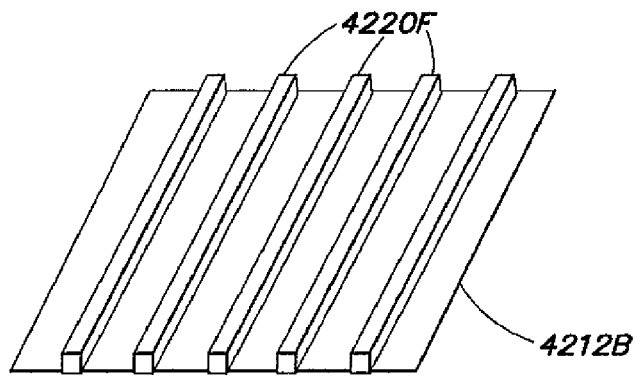

Another configuration, shown in FIGS. 42F and 42F1, involves the use of solid, beam-like projections or baffles 4220F as disruptors. This concept may be used to form a ceiling member for the flow chamber. Such an arrangement encourages more even fluid flow and significantly reduces fluid displacement times as compared with a simple rectangular cross-section without disruptor structure. Further, instead of fluid entry to the array occurring along one edge, fluid may be introduced at one corner 4242F, through a small port, and may exit from the opposite corner, 4244F, via a port in fluid communication with that corner area. The series of parallel baffles 4220F separates the flow volume between input and outlet corners into a series of channels. The lowest fluid resistant path is along the edge of the chip, perpendicular to the baffles. As incoming liquid fills this channel, the fluid is then directed between the baffles to the opposite side of the chip. The channel depth between each baffle pair preferably is graded across the chip, such that the flow is encouraged to travel toward the exit port through the farthest channel, thereby evening the flow front between the baffles. The baffles extend downwardly nearly to the chip (i.e., microwell layer) surface, but because they are quite thin, fluid can diffuse under them quickly and expose the associated area of the array assembly.

Figure 7:
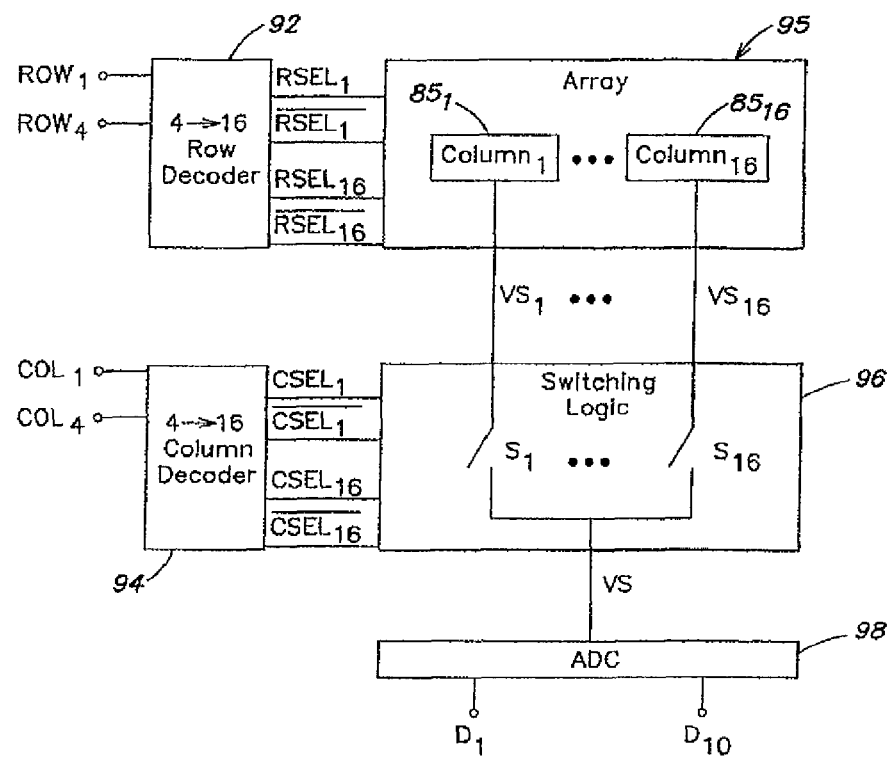
FIG. 7 illustrates an example of a complete two-dimensional ISFET pixel array based on the column design of FIG. 3, together with accompanying row and column decoder circuitry and measurement readout circuitry.

FIGS. 42F2-42F8 illustrate an example of a single-piece, injection-molded (preferably of polycarbonate) flow cell member 42F200 which may be used to provide baffles 4220F, a ceiling to the flow chamber, fluid inlet and outlet ports and even the reference electrode. FIG. 42F7 shows an enlarged view of the baffles on the bottom of member 42F200 and the baffles are shown as part of the underside of member 42F200 in FIG. 42F6. As it is difficult to form rectangular features in small dimensions by injection molding, the particular instance of these baffles, shown as 4220F', are triangular in cross section.

Figure 4:
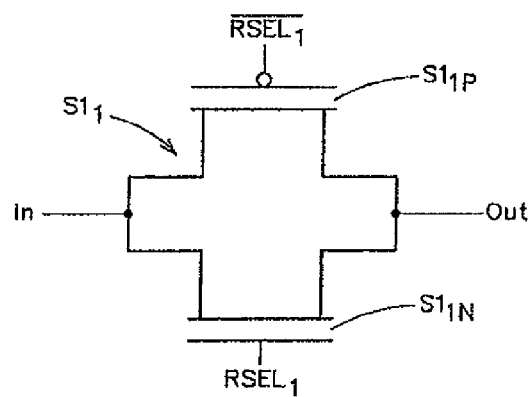
FIG. 4 illustrates a transmission gate including a p-channel MOSFET and an re-channel MOSFET that is employed in each pixel of the array column shown in FIG. 3.

In FIG. 42F2, there is a top, isometric view of member 42F200 mounted onto a sensor array package 42F300, with a seal 42F202 formed between them and contact pins 42F204 depending from the sensor array chip package. FIGS. 42F3 and 42F4 show sections, respectively, through section lines H-H and I-I of FIG. 42F5, permitting one to see in relationship the sensor array chip 42F250, the baffles 4220F' and fluid flow paths via inlet 42F260 and outlet 42F270 ports.

By applying a metallization to bottom 42F280 of member 42F200, the reference electrode may be formed.

Various other locations and approaches may be used for introducing fluid flow into the flow chamber, as well. In addition to embodiments in which fluid may be introduced across the width of an edge of the chip assembly 42F1, as in FIGS. 57-58, for example, or fluid may be introduced at one corner of the chip assembly, as in FIG. 42F1. Fluid also may be introduced, for example, as in FIGS. 42G and 42H, where fluid is flowed through an inlet conduit 4252G to be discharged adjacent and toward the center of the chip, as at 4254G, and flowed radially outwardly from the introduction point.

Figure 42G:
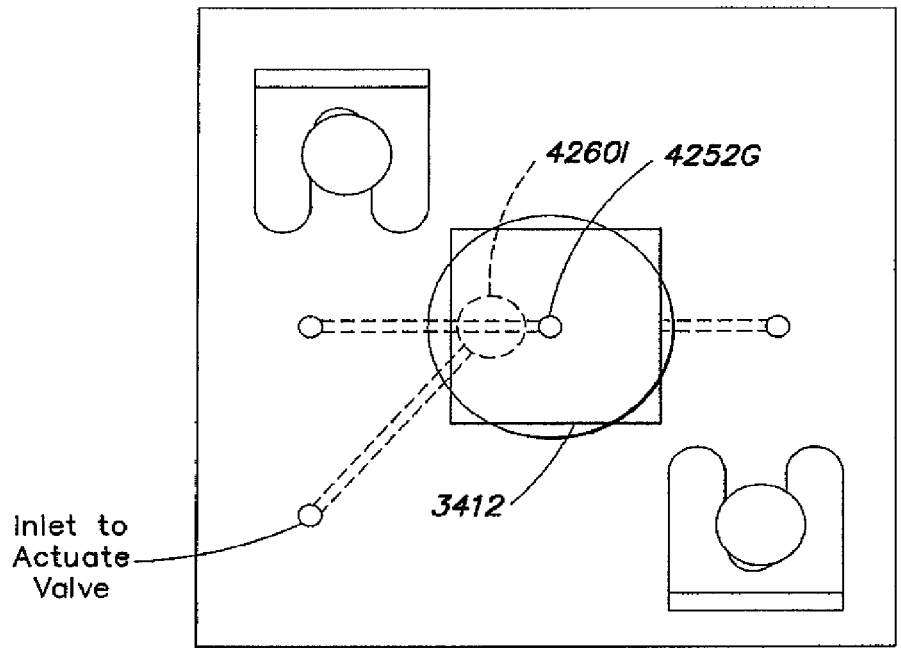
FIGS. 42G and 42H are diagrammatic illustrations of alternative embodiments of flow cells in which fluid flow is introduced to the middle of the chip assembly.
Figure 42H:
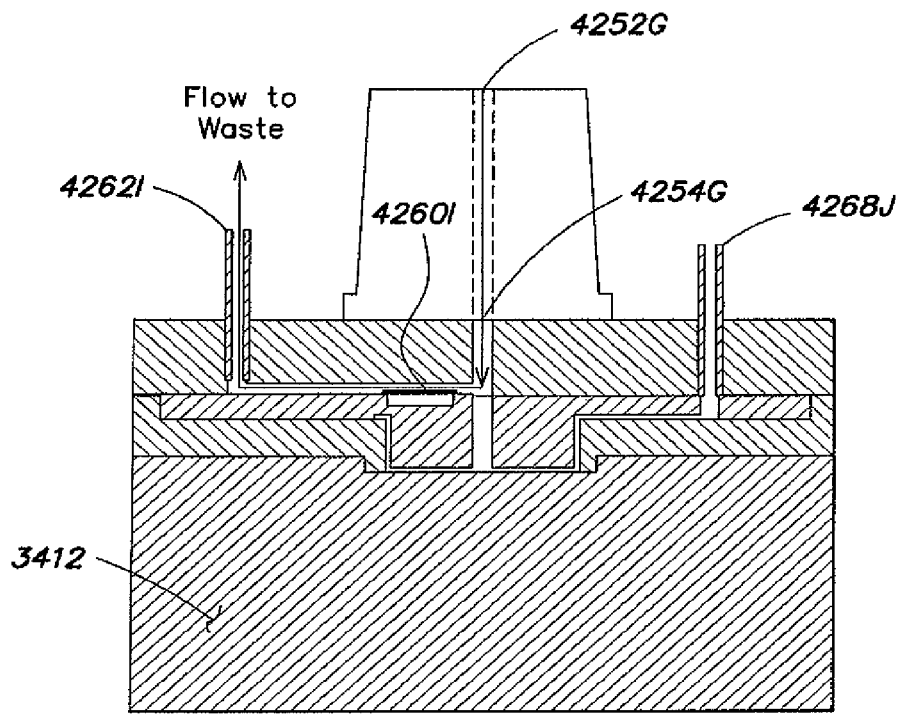
Figure 42I:
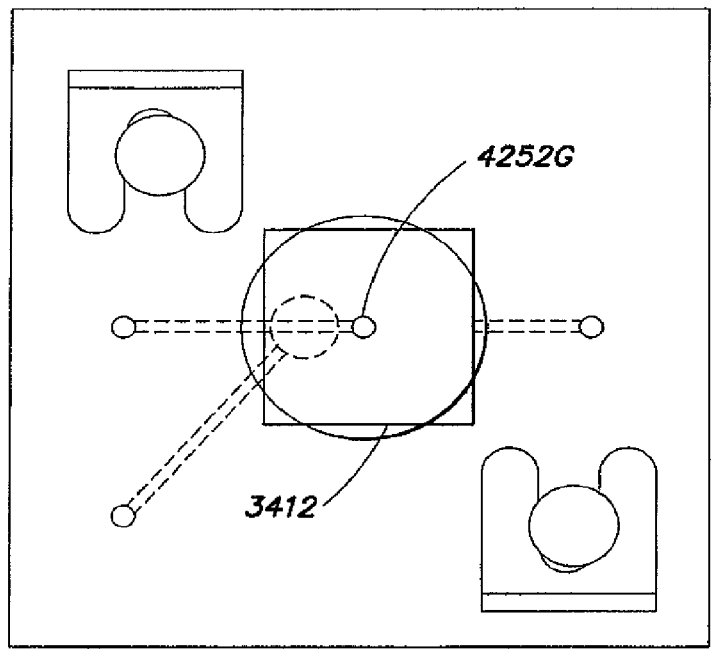
FIGS. 42I and 42J are cross-sectional illustrations of the type of flow cell embodiments shown in FIGS. 42G and 42H, mounted on a chip assembly.
Figure 42J:
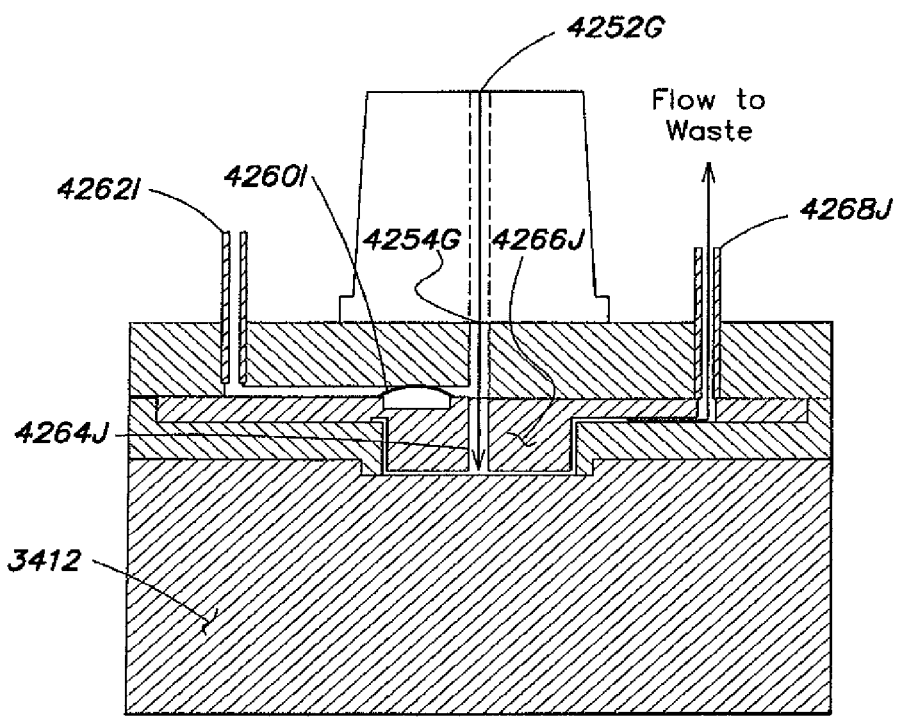

FIGS. 42I and 42J in conjunction with FIGS. 42G and 42H depict in cross-section an example of such a structure and its operation. In contrast with earlier examples, this embodiment contains an additional element, a diaphragm valve, 4260I. Initially, as shown in FIG. 42H, the valve 4260I is open, providing a path via conduit 4262I to a waste reservoir (not shown). The open valve provides a low impedance flow to the waste reservoir or outlet. Air pressure is then applied to the diaphragm valve, as in FIG. 42J, closing the low impedance path and causing the fluid flow to continue downwardly through central bore 4264J in member 4266J which forms the ceiling of the flow chamber, and across the chip (sensor) assembly. The flow is collected by the channels at the edges of the sensor, as described above, and exits to the waste output via conduit 4268J.

Figure 42K:
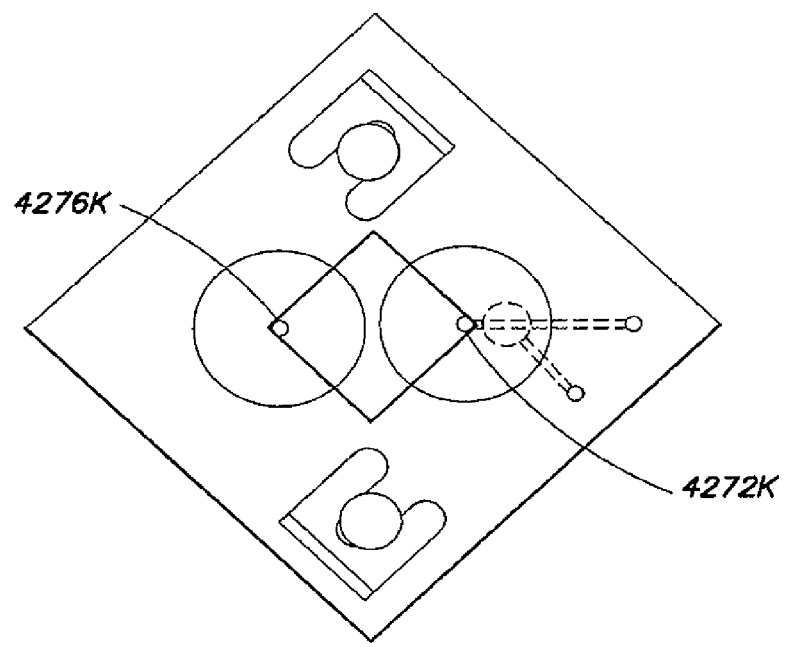
FIGS. 42K and 42L are diagrammatic illustrations of flow cells in which the fluid is introduced at a corner of the chip assembly.
Figure 42L:
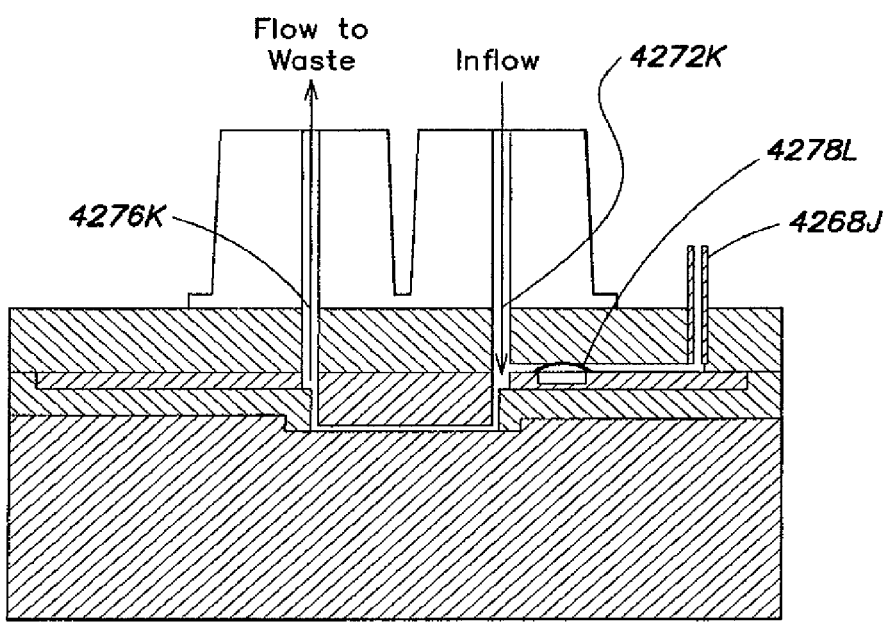
Figure 42M:
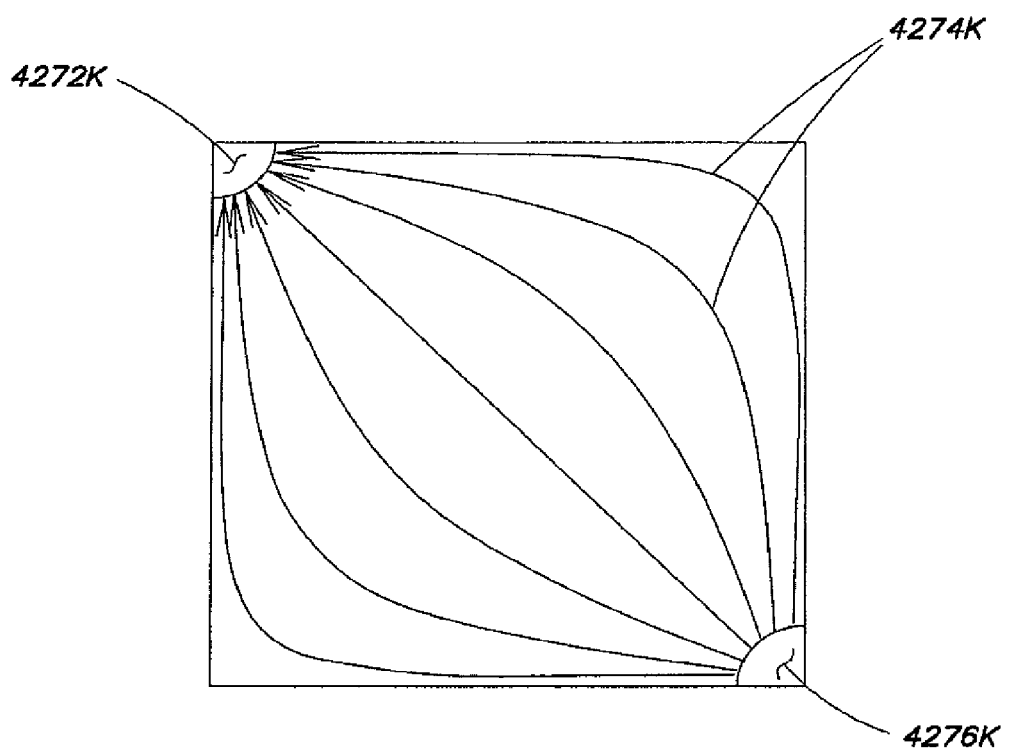
FIG. 42M is a diagrammatic illustration of fluid flow from one corner of an array on a chip assembly to an opposite corner, in apparatus such as that depicted in FIGS. 42K and 42L.

A variation on this idea is depicted in FIGS. 42K-42M, which show fluid being introduced not at the center of the chip assembly, but at one corner, 4272K, instead. It flows across the chip 3412 as symbolically indicated by lines 4274K and is removed at the diagonally opposing corner, 4276K. The advantage of this concept is that it all but eliminates any stagnation points. It also has the advantage that the sensor array can be positioned vertically so that the flow is introduced at the bottom and removed at the top to aid in the clearance of bubbles. This type of embodiment, by the way, may be considered as one quadrant of the embodiments with the flow introduced in the center of the array. An example of an implementation with a valve 4278L closed and shunting flow to the waste outlet or reservoir is shown in FIG. 42L. The main difference with respect to the embodiment of FIGS. 42I and 42J is that the fluid flow is introduced at a corner of the array rather than at its center.

In all cases, attention should be given to assuring a thorough washing of the entire flow chamber, along with the microwells, between reagent cycles. Flow disturbances may exacerbate the challenge of fully cleaning out the flow chamber.

Flow disturbances may also induce or multiply bubbles in the fluid. A bubble may prevent the fluid from reaching a microwell, or delay its introduction to the microwell, introducing error into the microwell reading or making the output from that microwell useless in the processing of outputs from the array. Thus, care should be taken in selecting configurations and dimensions for the flow disruptor elements to manage these potential adverse factors. For example, a tradeoff may be made between the heights of the disruptor elements and the velocity profile change that is desired.

Figure 43:
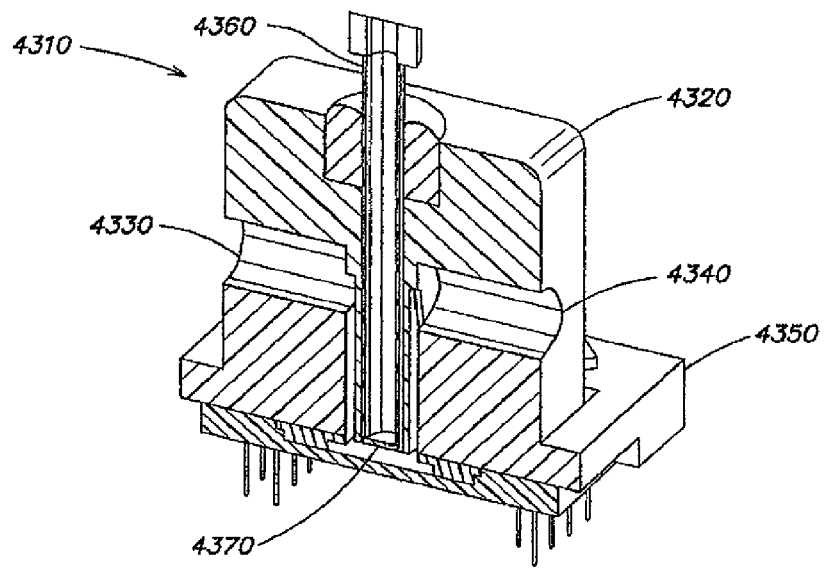
Figure 44:
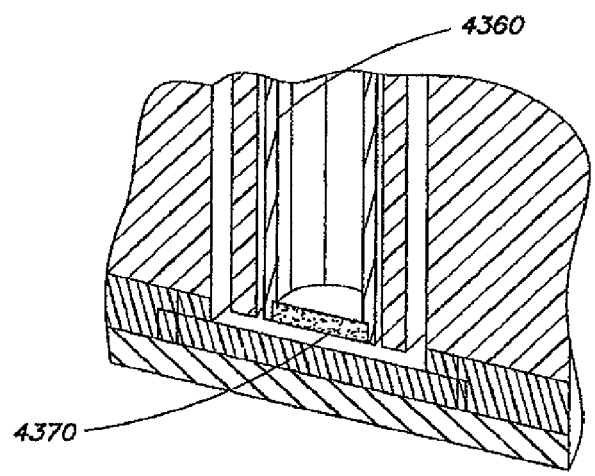

FIGS. 43-44 show another alternative flow cell design, 4310. This design relies on the molding of a single plastic piece or member 4320 to be attached to the chip to complete the flow cell. The connection to the fluidic system is made via threaded connections tapped into appropriate holes in the plastic piece at 4330 and 4340. Or, if the member 4320 is made of a material such as polydimethylsiloxane (PDMS), the connections may be made by simply inserting the tubing into an appropriately sized hole in the member 4320. A vertical cross section of this design is shown in FIGS. 43-44. This design may use an overhanging plastic collar 4350 (which may be a solid wall as shown or a series of depending, spaced apart legs forming a downwardly extending fence-like wall) to enclose the chip package and align the plastic piece with the chip package, or other suitable structure, and thereby to alignment the chip frame with the flow cell forming member 4320. Liquid is directed into the flow cell via one of apertures 4330, 4340, thence downwardly towards the flow chamber.

In the illustrated embodiment, the reference electrode is introduced to the top of the flow chamber via a bore 4325 in the member 4320. The placement of the removable reference electrode is facilitated by a silicone sleeve 4360 and an epoxy stop ring 4370 (see the blow-up of FIG. 44). The silicone sleeve provides a tight seal and the epoxy stop ring prevent the electrode from being inserted too far into the flow cell. Of course, other mechanisms may be employed for the same purposes, and it may not be necessary to employ structure to stop the electrode. And if a material such as PDMS is used for member 4320, the material itself may form a watertight seal when the electrode is inserted, obviating need for the silicone sleeve.

Figure 45:
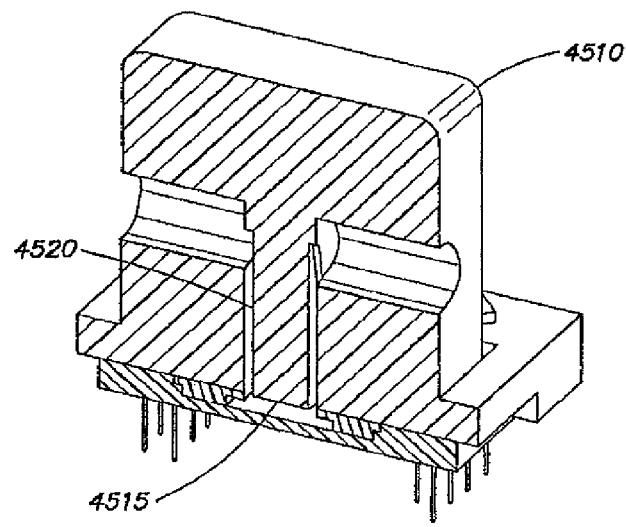
Figure 46:
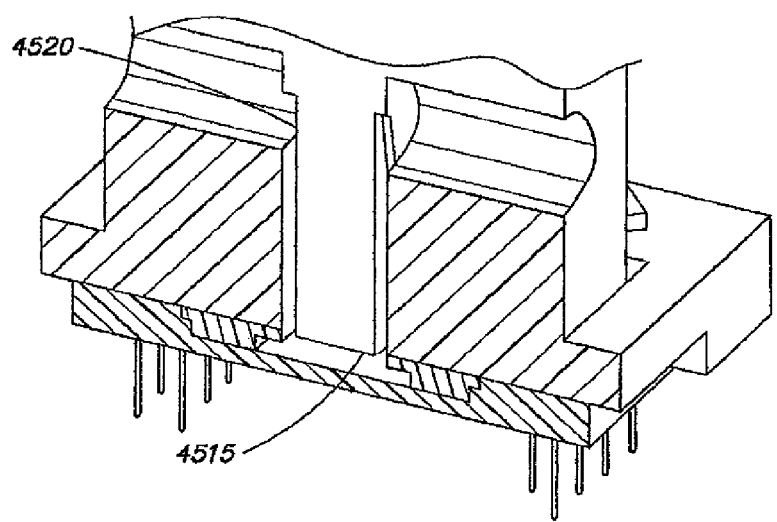

FIGS. 45 and 46 show a similar arrangement except that member 4510 lacks a bore for receiving a reference electrode. Instead, the reference electrode 4515 is formed on or affixed to the bottom of central portion 4520 and forms at least part of the flow chamber ceiling. For example, a metallization layer may be applied onto the bottom of central portion 4520 before member 4510 is mounted onto the chip package.

Figure 47:
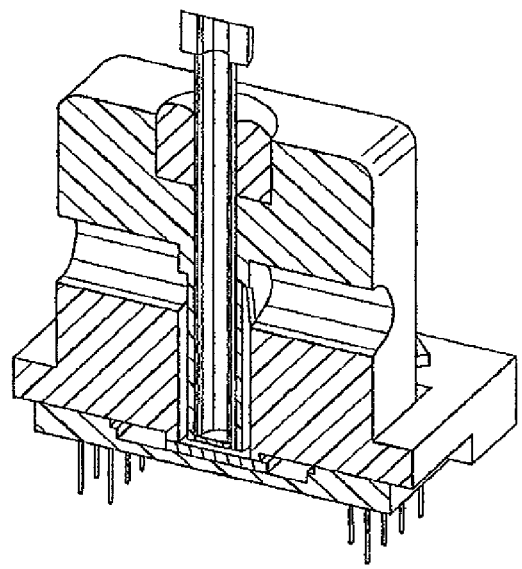
Figure 48:
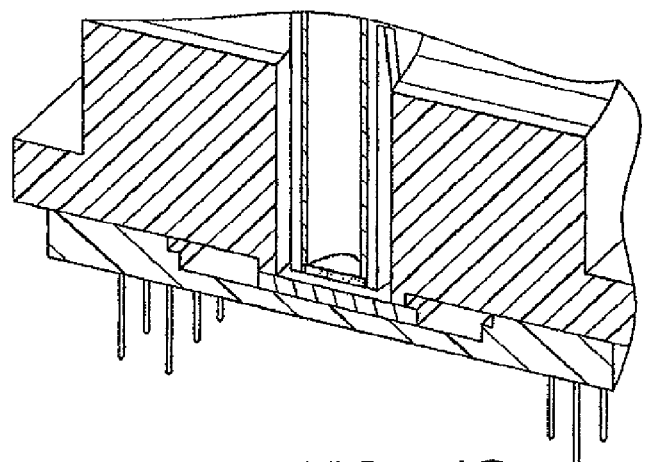
Figure 49:
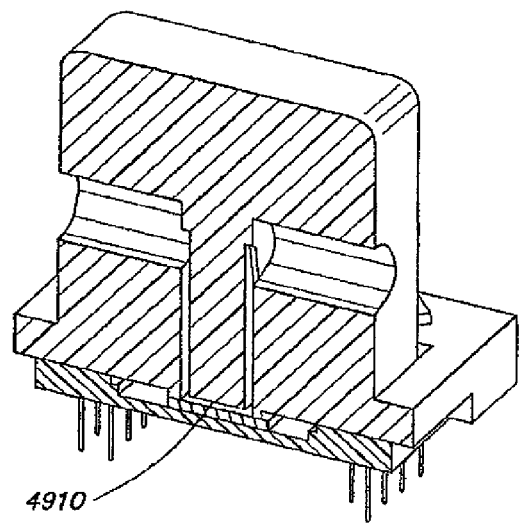
Figure 50:
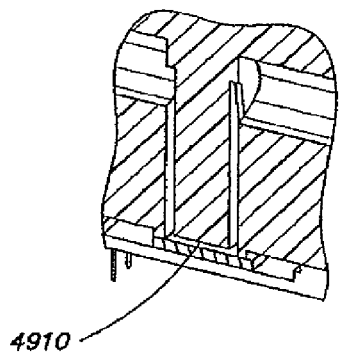

FIGS. 47-48 show another example, which is a variant of the embodiment shown in FIGS. 43-44, but wherein the frame is manufactured as part of the flow cell rather attaching a flow port structure to a frame previously attached to the chip surface. In designs of this type, assembly is somewhat more delicate since the wirebonds to the chip are not protected by the epoxy encapsulating the chip. The success of this design is dependent on the accurate placement and secure gluing of the integrated "frame" to the surface of the chip. A counterpart embodiment to that of FIGS. 45-46, with the reference electrode 4910 on the ceiling of the flow chamber, and with the frame manufactured as part of the flow cell, is shown in FIGS. 49-50.

Figure 51:
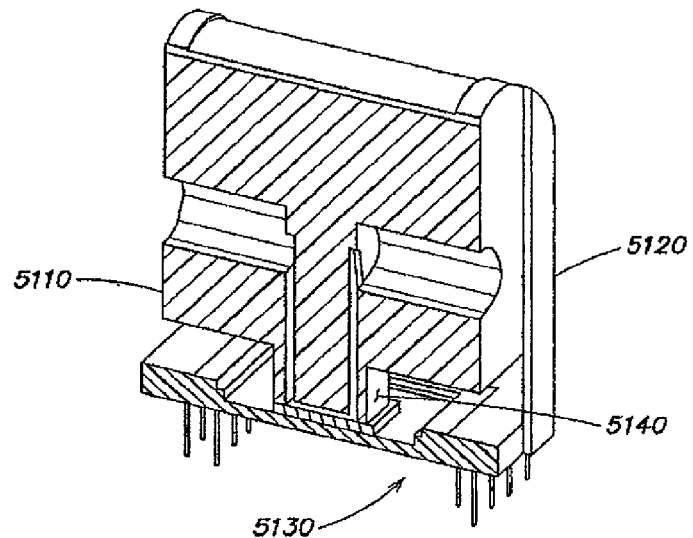
Figure 52:
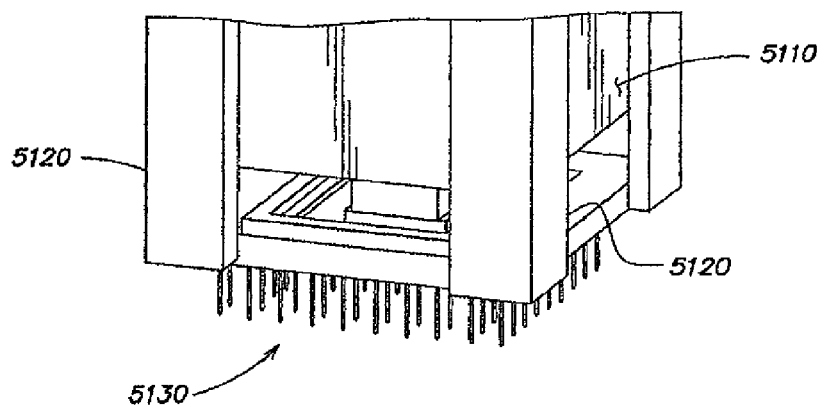

Yet another alternative for a fluidics assembly, as shown in FIGS. 51-52, has a fluidics member 5110 raised by about 5.5 mm on stand-offs 5120 from the top of the chip package 5130. This allows for an operator to visually inspect the quality of the bonding between plastic piece 5140 and chip surface and reinforce the bonding externally if necessary.

Figure 53:
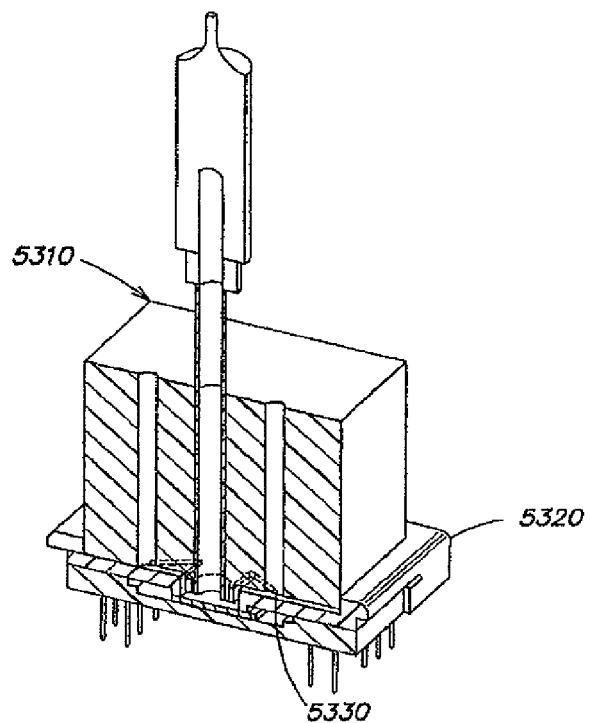
Figure 54:
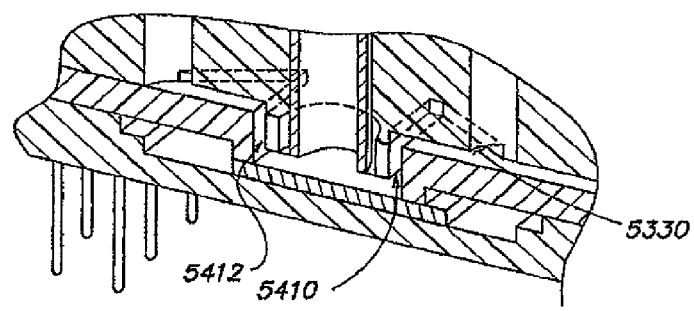

Some of the foregoing alternative embodiments also may be implemented in a hybrid plastic/PDMS configuration. For example, as shown in FIGS. 53-54, a plastic part 5310 may make up the frame and flow chamber, resting on a PDMS "base" portion 5320. The plastic part 5310 may also provides a region 5330 to the array, for expansion of the fluid flow from the inlet port; and the PDMS part may then include communicating slits 5410, 5412 through which liquids are passed from the PDMS part to and from the flow chamber below.

The fluidic structure may also be made from glass as discussed above, such as photo-definable (PD) glass. Such a glass may have an enhanced etch rate in hydrofluoric acid once selectively exposed to UV light and features may thereby be micromachined on the top-side and back-side, which when glued together can form a three-dimensional low aspect ratio fluidic cell.

Figure 55:
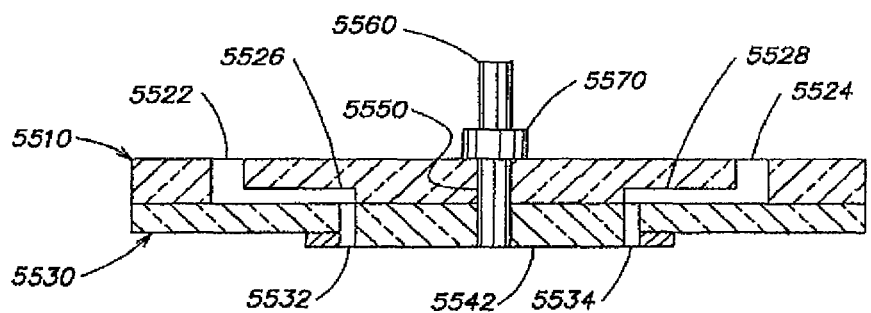
FIGS. 55 and 56 are schematic, cross-sectional views of two-layer glass (or plastic) arrangements for manufacturing fluidic apparatus for mounting onto a chip for use as taught herein.

An example is shown in FIG. 55. A first glass layer or sheet 5510 has been patterned and etched to create nanoport fluidic holes 5522 and 5524 on the top-side and fluid expansion channels 5526 and 5528 on the back-side. A second glass layer or sheet 5530 has been patterned and etched to provide downward fluid input/output channels 5532 and 5534, of about 300 μm height (the thickness of the layer). The bottom surface of layer 5530 is thinned to the outside of channels 5532 and 5534, to allow the layer 5530 to rest on the chip frame and protrusion area 5542 to be at an appropriate height to form the top of the flow channel. Two glass layers, or wafers, and four lithography steps required. Both wafers should be aligned and bonded (e.g., with an appropriate glue, not shown) such that the downward fluid input/output ports are aligned properly with the fluid expansion channels. Alignment targets may be etched into the glass to facilitate the alignment process.

Nanoports may be secured over the nanoport fluidic holes to facilitate connection of input and output tubing.

A central bore 5550 may be etched through the glass layers for receiving a reference electrode, 5560. The electrode may be secured and sealed in place with a silicone collar 5570 or like structure; or the electrode may be equipped integrally with a suitable washer for effecting the same purpose.

Figure 56:
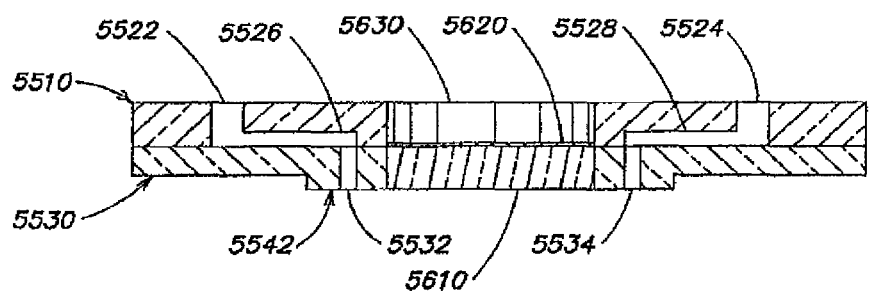

By using glass materials for the two-layer fluidic cell, the reference electrode may also be a conductive layer or pattern deposited on the bottom surface of the second glass layer (not shown). Or, as shown in FIG. 56, the protrusion region may be etched to form a permeable glass membrane 5610 on the top of which is coated a silver (or other material) thin-film 5620 to form an integrated reference electrode. A hole 5630 may be etched into the upper layer for accessing the electrode and if that hole is large enough, it can also serve as a reservoir for a silver chloride solution. Electrical connection to the thin-film silver electrode may be made in any suitable way, such as by using a clip-on pushpin connector or alternatively wirebonded to the ceramic ISFET package.

Another alternative is to integrate the reference electrode to the sequencing chip/flow cell by using a metalized surface on the ceiling of the flow chamber—i.e., on the underside of the member forming the ceiling of the fluidic cell. An electrical connection to the metalized surface may be made in any of a variety of ways, including, but not limited to, by means of applying a conductive epoxy to the ceramic package seal ring that, in turn, may be electrically connected through a via in the ceramic substrate to a spare pin at the bottom of the chip package. Doing this would allow system-level control of the reference potential in the fluid cell by means of inputs through the chip socket mount to the chip's control electronics.

By contrast, an externally inserted electrode requires extra fluid tubing to the inlet port, which requires additional fluid flow between cycles.

Ceramic pin grid array (PGA) packaging may be used for the ISFET array, allowing customized electrical connections between various surfaces on the front face with pins on the back.

The flow cell can be thought of as a "lid" to the ISFET chip and its PGA. The flow cell, as stated elsewhere, may be fabricated of many different materials. Injection molded polycarbonate appears to be quite suitable. A conductive metal (e.g., gold) may be deposited using an adhesion layer (e.g., chrome) to the underside of the glow cell roof (the ceiling of the flow chamber). Appropriate low-temperature thin-film deposition techniques preferably are employed in the deposition of the metal reference electrode due to the materials (e.g., polycarbonate) and large step coverage topography at the bottom-side of the fluidic cell (i.e., the frame surround of ISFET array). One possible approach would be to use electron-beam evaporation in a planetary system.

The active electrode area is confined to the central flow chamber inside the frame surround of the ISFET array, as that is the only metalized surface that would be in contact with the ionic fluid during sequencing.

Once assembly is complete—conductive epoxy (e.g., Epo-Tek H20E or similar) may be dispensed on the seal ring with the flow cell aligned, placed, pressed and cured—the ISFET flow cell is ready for operation with the reference potential being applied to the assigned pin of the package.

The resulting fluidic system connections to the ISFET device thus incorporate shortened input and output fluidic lines, which is desirable.

Figure 57:
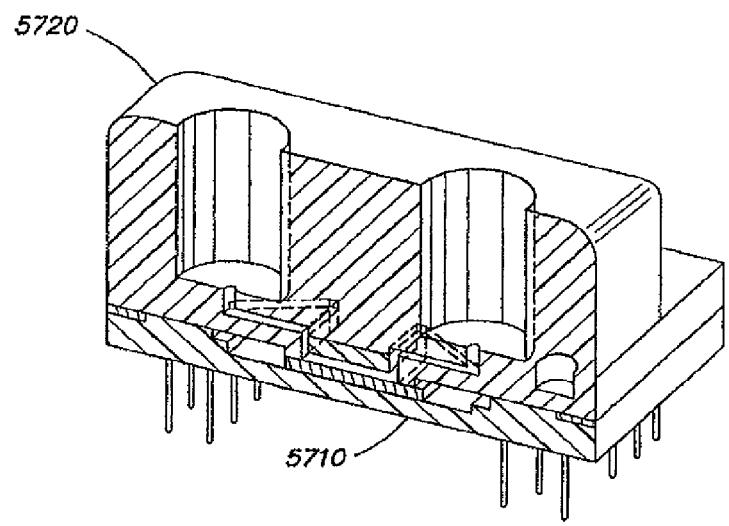
FIGS. 57 and 58 are schematic embodiments of a fluidic assembly.
Figure 58:
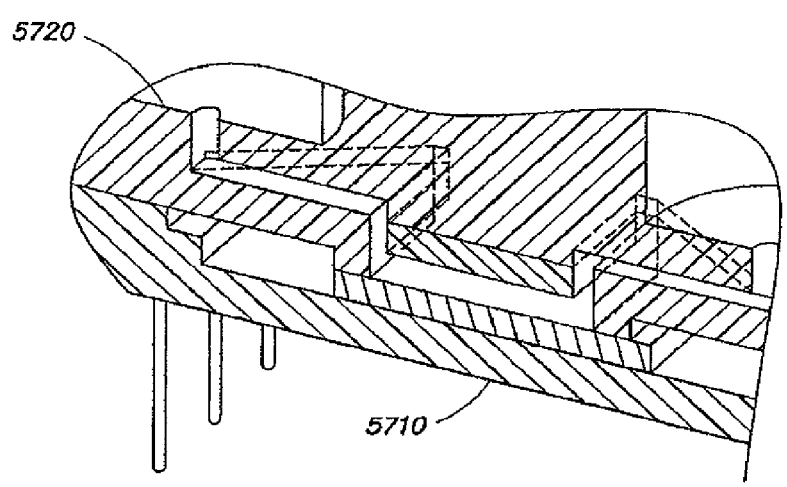

Still another example embodiment for a fluidic assembly is shown in FIGS. 57-58. This design is limited to a plastic piece 5710 which incorporates the frame and is attached directly to the chip surface, and to a second piece 5720 which is used to connect tubing from the fluidic system and similarly to the PDMS piece discussed above, distributes the liquids from the small bore tube to a wide flat slit. The two pieces are glued together and multiple (e.g., three) alignment markers (not shown) may be used to precisely align the two pieces during the gluing process. A hole may be provided in the bottom plate and the hole used to fill the cavity with an epoxy (for example) to protect the wirebonds to the chip and to fill in any potential gaps in the frame/chip contact. In the illustrated example, the reference electrode is external to the flow cell (downstream in the exhaust stream, through the outlet port—see below), though other configurations of reference electrode may, of course, be used.

Figure 59A:
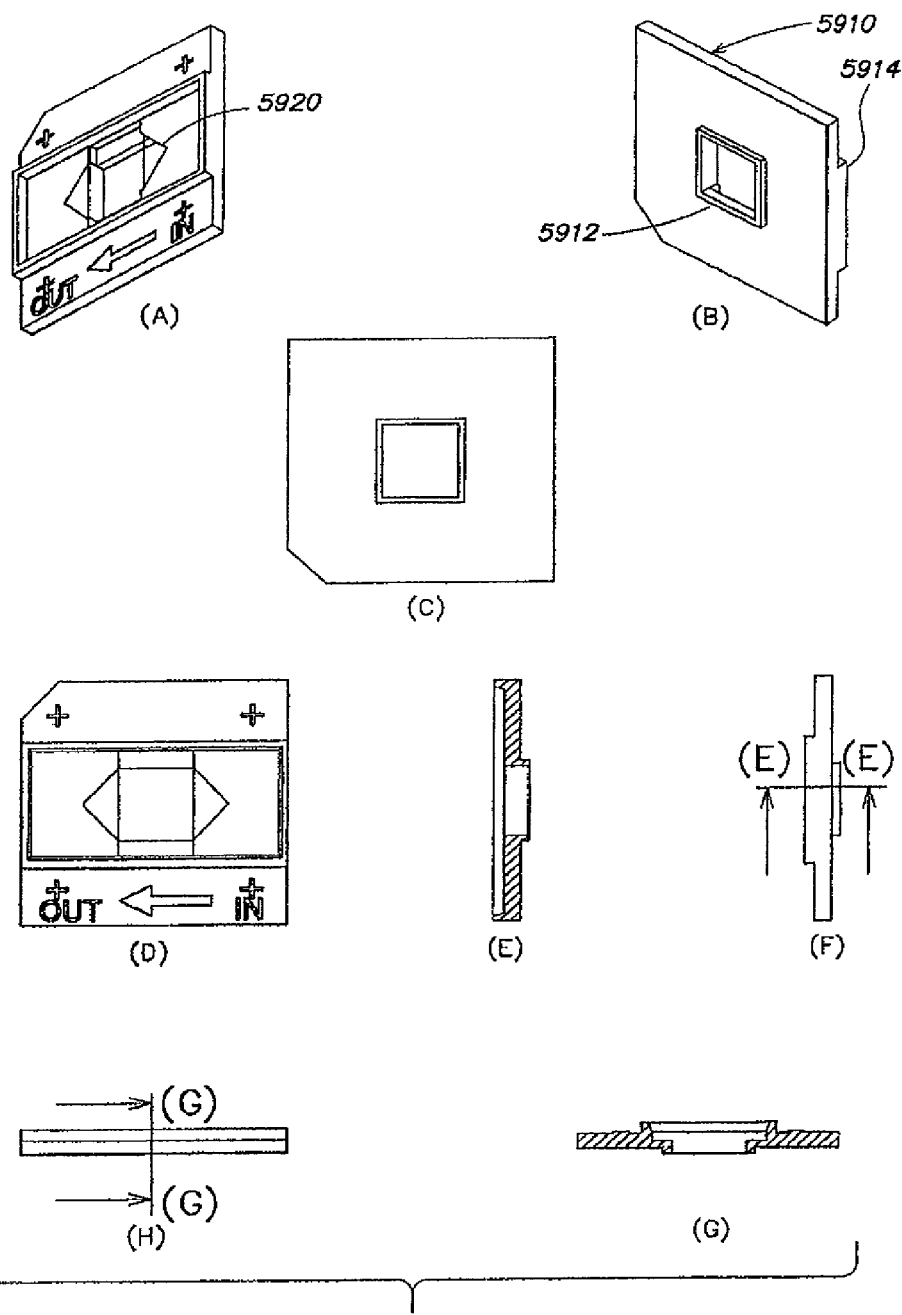
Figure 59B:
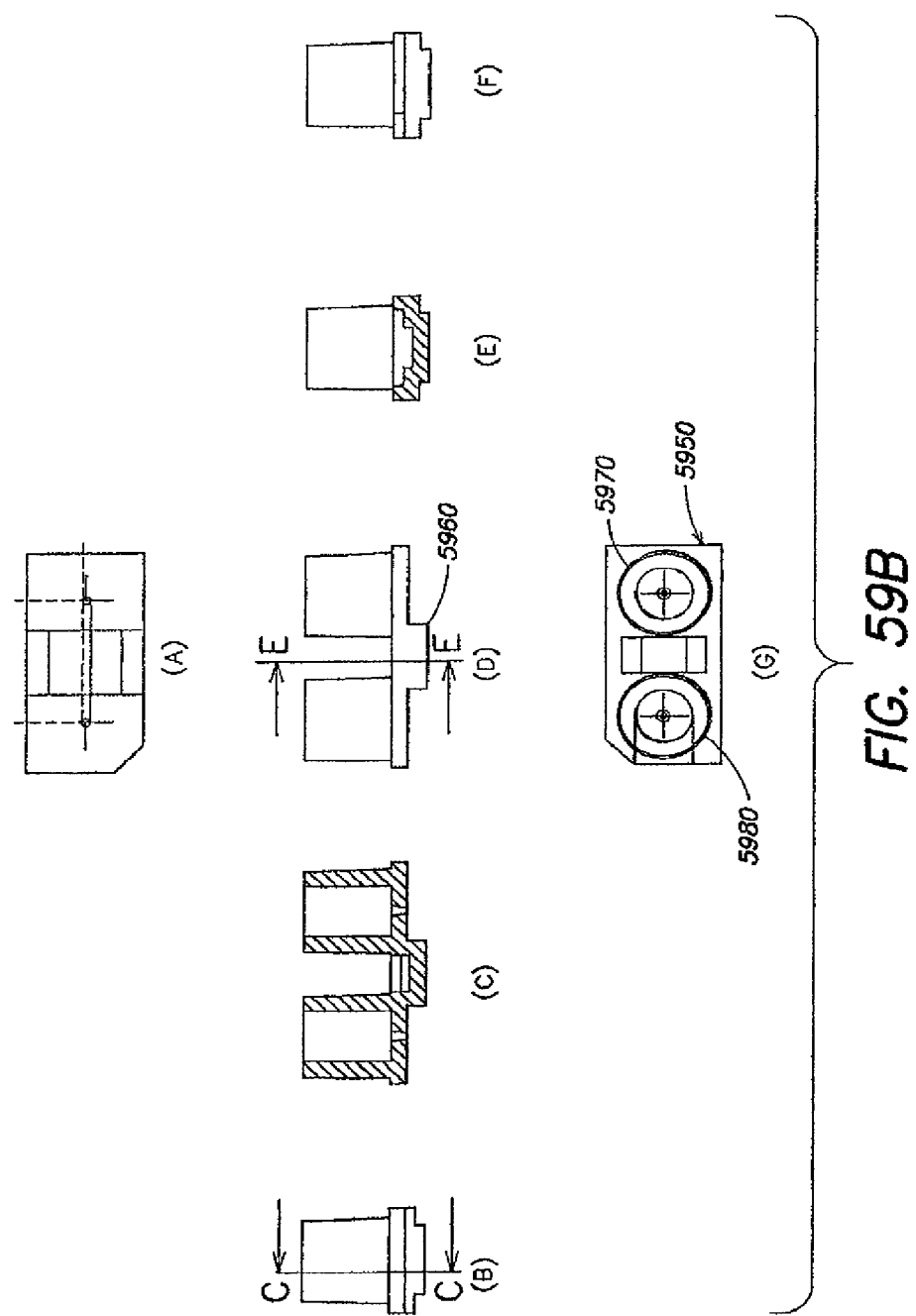
Figure 60:
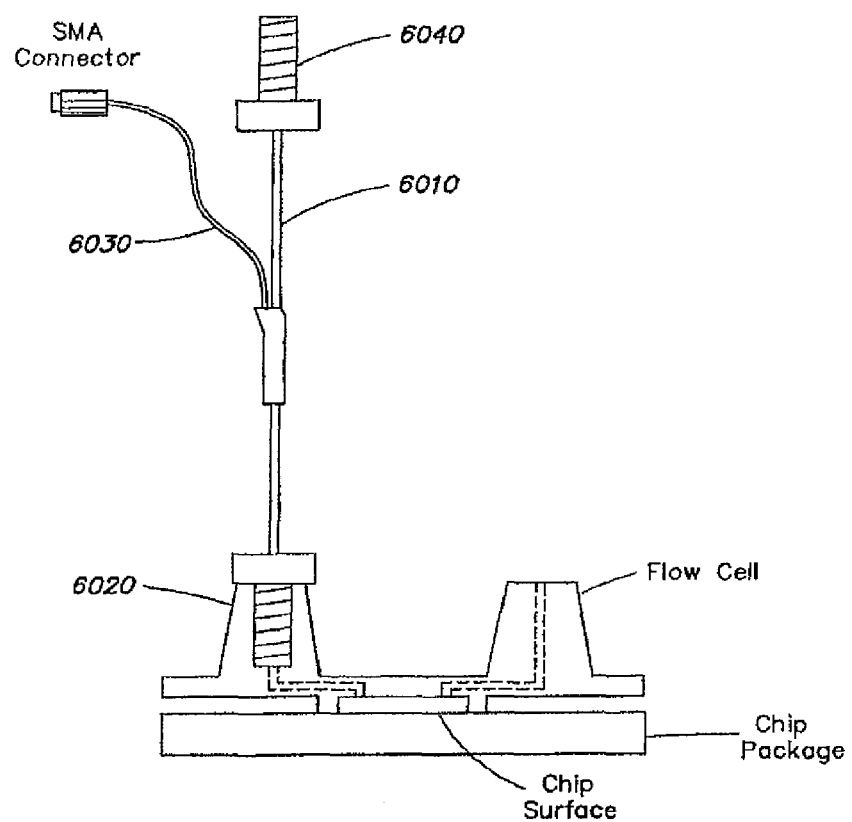
FIG. 60 is a schematic illustration, in cross-section, for introducing a stainless steel capillary tube as an electrode, into a downstream port of a flow cell such as the flow cells of FIGS. 59A-59C, or other flow cells.

Still further examples of flow cell structures are shown in FIGS. 59-60. FIG. 59A comprises eight views (A-H) of an injection molded bottom layer, or plate, 5910, for a flow cell fluidics interface, while FIG. 59B comprises seven views (A-G) of a mating, injection molded top plate, or layer, 5950. The bottom of plate 5910 has a downwardly depending rim 5912 configured and arranged to enclose the sensor chip and an upwardly extending rim 5914 for mating with the top plate 5610 along its outer edge. To form two fluid chambers (an inlet chamber and an outlet chamber) between them. A stepped, downwardly depending portion 5960 of top plate 5950, separates the input chamber from the output chamber. An inlet tube 5970 and an outlet tube 5980 are integrally molded with the rest of top plate 5950. From inlet tube 5970, which empties at the small end of the inlet chamber formed by a depression 5920 in the top of plate 5910, to the outlet edge of inlet chamber fans out to direct fluid across the whole array.

Whether glass or plastic or other material is used to form the flow cell, it may be desirable, especially with larger arrays, to include in the inlet chamber of the flow cell, between the inlet conduit and the front edge of the array, not just a gradually expanding (fanning out) space, but also some structure to facilitate the flow across the array being suitably laminar. Using the bottom layer 5990 of an injection molded flow cell as an example, one example type of structure for this purpose, shown in FIG. 59C, is a tree structure 5992 of channels from the inlet location of the flow cell to the front edge of the microwell array or sensor array, which should be understood to be under the outlet side of the structure, at 5994.

The above-described systems for sequencing typically utilize a laminar fluid flow system to sequence a biological polymer. In part, the fluid flow system preferably includes a flow chamber formed by the sensor chip and a single piece, injection molded member comprising inlet and outlet ports and mountable over the chip to establish the flow chamber. The surface of such member interior to the chamber is preferably formed to facilitate a desired expedient fluid flow, as described herein.

In some embodiments, the invention encompasses an apparatus for detection of ion pulses comprising a laminar fluid flow system. Preferably, the apparatus is used for sequencing a plurality of nucleic acid templates, wherein the nucleic acid templates are optionally deposited on an array.

The apparatus typically includes a fluidics assembly comprising a member comprising one or more apertures for non-mechanically directing a fluid to flow to an array of at least 100K, 500K, or 1M microfluidic reaction chambers such that the fluid reaches all of the microfluidic reaction chambers at the same time or substantially the same time. Typically, the fluid flow is parallel to the sensor surface. Typically, the assembly has a Reynolds number of less than 1000, 500, 200, 100, 50, 20, or 10. Preferably, the member further comprises a first aperture for directing fluid towards the sensor array and a second aperture for directing fluid away from the sensor array.

In some embodiments, the invention encompasses a method for directing a fluid to a sensor array comprising: providing a fluidics assembly comprising an aperture fluidly coupling a fluid source to the sensor array; and non-mechanically directing a fluid to the sensor array. By "non-mechanically" it is meant that the fluid is moved under pressure from a gaseous pressure source, as opposed to a mechanical pump.

In some embodiments, the invention encompasses an array of wells, each of which is coupled to a lid having an inlet port and an outlet port and a fluid delivery system for delivering and removing fluid from said inlet and outlet ports non-mechanically.

In some embodiments, the invention encompasses a method for sequencing a biological polymer utilizing the above-described apparatus, comprising: directing a fluid comprising a monomer to an array of reaction chambers wherein the fluid has a fluid flow Reynolds number of at most 2000, 1000, 200, 100, 50, or 20. The method may optionally further comprise detecting an ion pulse from each said reaction chamber. The ion pulse is typically detected by ion diffusion to the sensor surface. There are various other ways of providing a fluidics assembly for delivering an appropriate fluid flow across the microwell and sensor array assembly, and the forgoing examples are thus not intended to be exhaustive.

Reference Electrode

Commercial flow-type fluidic electrodes, such as silver chloride proton-permeable electrodes, may be inserted in series in a fluidic line and are generally designed to provide a stable electrical potential along the fluidic line for various electrochemical purposes. In the above-discussed system, however, such a potential must be maintained at the fluidic volume in contact with the microwell ISFET chip. With conventional silver chloride electrodes, it has been found difficult, due to an electrically long fluidic path between the chip surface and the electrode (through small channels in the flow cell), to achieve a stable potential. This led to reception of noise in the chip's electronics. Additionally, the large volume within the flow cavity of the electrode tended to trap and accumulate gas bubbles that degraded the electrical connection to the fluid. With reference to FIG. 60, a solution to this problem has been found in the use of a stainless steel capillary tube electrode 6010, directly connected to the chip's flow cell outlet port 6020 and connected to a voltage source (not shown) through a shielded cable 6030. The metal capillary tube 6010 has a small inner diameter (e.g., on the order of 0.01") that does not trap gas to any appreciable degree and effectively transports fluid and gas like other microfluidic tubing. Also, because the capillary tube can be directly inserted into the flow cell port 6020, it close to the chip surface, reducing possible electrical losses through the fluid. The large inner surface area of the capillary tube (typically about 2" long) may also contribute to its high performance. The stainless steel construction is highly chemically resistant, and should not be subject to electrochemical effects due to the very low electrical current use in the system (<1 μA fluidic fitting 6040 is attached to the end of the capillary that is not in the flow cell port, for connection to tubing to the fluid delivery and removal subsystem.

Fluidics System

A complete system for using the sensor array will include suitable fluid sources, valving and a controller for operating the valving to low reagents and washes over the microarray or sensor array, depending on the application. These elements are readily assembled from off-the-shelf components, with and the controller may readily be programmed to perform a desired experiment.

It should be understood that the readout at the chemFET may be current or voltage (and change thereof) and that any particular reference to either readout is intended for simplicity and not to the exclusion of the other readout. Therefore any reference in the following text to either current or voltage detection at the chemFET should be understood to contemplate and apply equally to the other readout as well. In important embodiments, the readout reflects a rapid, transient change in concentration of an analyte. The concentration of more than one analyte may be detected at different times. Such measurements are to be contrasted with prior art methods which focused on steady state concentration measurements.

Applications Generally

As already discussed, the apparatus and systems of the invention can be used to detect and/or monitor interactions between various entities. These interactions include biological and chemical reactions and may involve enzymatic reactions and/or non-enzymatic interactions such as but not limited to binding events. As an example, the invention contemplates monitoring enzymatic reactions in which substrates and/or reagents are consumed and/or reaction intermediates, byproducts and/or products are generated. An example of a reaction that can be monitored according to the invention is a nucleic acid synthesis method such as one that provides information regarding nucleic acid sequence. This reaction will be discussed in greater detail herein.

Sequencing Applications

In the context of a sequencing reaction, the apparatus and system provided herein is able to detect nucleotide incorporation based on changes in the chemFET current and/or voltage, as those latter parameters are interrelated. Current changes may be the result of one or more of the following events either singly or some combination thereof: generation of PPi, generation of Pi (e.g., in the presence of pyrophosphatase), generation of hydrogen (and concomitant changes in pH for example in the presence of low strength buffer), reduced concentration of unincorporated dNTP at the chemFET surface, delayed arrival of unincorporated dNTP at the chemFET surface, and the like. The methods described herein are able to detect changes in analyte concentration at the chemFET surface, and such changes may result from one or more of the afore-mentioned events. The invention contemplates the use of a chemFET such as an ISFET in the sequencing methods described herein, even if the readout is independent of (or insensitive to) pH. In other words, the invention contemplates the use of an ISFET for the detection of analytes such as PPi and unincorporated nucleotides. The methods provided herein in regards to sequencing can be contrasted to those in the literature including Pourmand et al. PNAS 2006

103(17):6466-6470. As discussed herein, the invention contemplates methods for determining the nucleotide sequence (i.e., the "sequence") of a nucleic acid. Such methods involve the synthesis of a new nucleic acid (primed by a pre-existing nucleic acid, as will be appreciated by those of ordinary skill), based on the sequence of a template nucleic acid. That is, the sequence of the newly synthesized nucleic acid is complimentary to the sequence of the template nucleic acid and therefore knowledge of sequence of the newly synthesized nucleic acid yields information about the sequence of the template nucleic acid. Knowledge of the sequence of the newly synthesized nucleic acid is derived by determining whether a known nucleotide has been incorporated into the newly synthesized nucleic acid and, if so, how many of such known nucleotides have been incorporated. Nucleotide incorporation can be monitored in a number of ways, including the production of products such as PPi, Pi and/or $H^+$.

The nucleic acid being sequenced is referred to herein as the target nucleic acid. Target nucleic acids include but are not limited to DNA such as but not limited to genomic DNA, mitochondrial DNA, cDNA and the like, and RNA such as but not limited to mRNA, miRNA, and the like. The nucleic acid may be from any source including naturally occurring sources or synthetic sources. The nucleic acids may be PCR products, cosmids, plasmids, naturally occurring or synthetic libraries, and the like. The invention is not intended to be limited in this regard. The methods provided herein can be used to sequence nucleic acids of any length.

Target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands nucleotides in length. In some embodiments, the fragments are 200-1000 base pairs in size, or 300-800 base pairs in size, about 200, about 300, about 400, about 500, about 600, about 700, about 800, about 900, or about 1000 base pairs in length, although they are not so limited. Nucleic acids may be fragmented by any means including but not limited to mechanical, enzymatic or chemical means. Examples include shearing, sonication, nebulization, endonuclease (e.g., DNase I) digestion, amplification such as PCR amplification, or any other technique known in the art to produce nucleic acid fragments, preferably of a desired length. As used herein, fragmentation also embraces the use of amplification to generate a population of smaller sized fragments of the target nucleic acid. That is, the target nucleic acids may be melted and then annealed to two (and preferably more) amplification primers and then amplified using for example a thermostable polymerase (such as Taq). An example is a massively parallel PCR-based amplification. Fragmentation can be followed by size selection techniques to enrich or isolate fragments of a particular length or size. Such techniques are also known in the art and include but are not limited to gel electrophoresis or SPRI.

Alternatively, target nucleic acids that are already of sufficient small size (or length) may be used. Such target nucleic acids include those derived from an exon enrichment process. Thus, rather than fragmenting (randomly or non-randomly) longer target nucleic acids, the targets may be nucleic acids that naturally exist or can be isolated in shorter, useable lengths such as mRNAs, cDNAs, exons, PCR products (as described above), and the like. See Albert et al. Nature Methods 2007 4(11):903-905 (microarray hybridization of exons and locus-specific regions), Porreca et al. Nature Methods 2007 4(11):931-936, and Okou et al. Nature Methods 2007 4(11):907-909 for methods of isolating and/or enriching sequences such as exons prior to sequencing.

In some embodiments, the size selected target nucleic acids are ligated to adaptor sequences on both the 5' and 3' ends. These adaptor sequences comprise sequences complementary to amplification primer sequences, to be used in amplifying the target nucleic acids. One adaptor sequence may also comprise a sequence complementary to the sequencing primer. The opposite adaptor sequence may comprise a moiety that facilitates binding of the nucleic acid to a solid support such as but not limited to a bead. An example of such a moiety is a biotin molecule (or a double biotin moiety, as described by Diehl et al. Nature Methods, 2006, 3(7):551-559) and such a labeled nucleic acid can therefore be bound to a solid support having avidin or streptavidin groups. Another moiety that can be used is the NHS-ester and amine affinity pair. It is to be understood that the invention is not limited in this regard and one of ordinary skill is able to substitute these affinity pairs with other binding pairs. The resulting nucleic acid is referred to herein as a template nucleic acid. The template nucleic acid comprises at least the target nucleic acid and usually comprises nucleotide sequences in addition to the target at both the 5' and 3' ends.

The solid support to which the template nucleic acids are bound is referred to herein as the "capture solid support". If the solid support is a bead, then such bead is referred to herein as a "capture bead". The beads can be made of any material including but not limited to cellulose, cellulose derivatives, gelatin, acrylic resins, glass, silica gels, polyvinyl pyrrolidine (PVP), co-polymers of vinyl and acrylamide, polystyrene, polystyrene cross-linked with divinylbenzene or the like (see, Merrifield Biochemistry 1964, 3, 1385-1390), polyacrylamides, latex gels, dextran, crosslinked dextrans (e.g., Sephadex™), rubber, silicon, plastics, nitrocellulose, natural sponges, metal, and agarose gel (Sepharose™). In one embodiment, the beads are streptavidin-coated beads. The bead diameter will depend on the density of the chemFET and microwell array used with larger arrays (and thus smaller sized wells) requiring smaller beads. Generally the bead size may be about 1-10 μM, and more preferably 2-6 μM. In some embodiments, the beads are about 5.91 μM while in other embodiments the beads are about 2.8 μM. In still other embodiments, the beads are about 1.5 μm, or about 1 μm in diameter. It is to be understood that the beads may or may not be perfectly spherical in shape. It is also to be understood that other beads may be used and other mechanisms for attaching the nucleic acid to the beads may be used. In some instances the capture beads (i.e., the beads on which the sequencing reaction occurs) are the same as the template preparation beads including the amplification beads.

Important aspects of the invention contemplate sequencing a plurality of different template nucleic acids simultaneously. This may be accomplished using the sensor arrays described herein. In one embodiment, the sensor arrays are overlayed (and/or integral with) an array of microwells (or reaction chambers or wells, as those terms are used interchangeably herein), with the proviso that there be at least one sensor per microwell. Present in a plurality of microwells is a population of identical copies of a template nucleic acid. There is no requirement that any two microwells carry identical template nucleic acids, although in some instances such templates may share overlapping sequence. Thus, each microwell comprises a plurality of identical copies of a template nucleic acid, and the templates between microwells may be different.

The microwells may vary in size between arrays. The microwell size may be described in terms of cross section.

The cross section may refer to a "slice" parallel to the depth (or height) of the well, or it may be a slice perpendicular to the depth (or height) of the well.

The size of these microwells may be described in terms of a width (or diameter) to height ratio. In some embodiments, this ratio is 1:1 to 1:1.5. The bead to well size (e.g., the bead diameter to well width, diameter, or height) is preferably in the range of 0.6-0.8. The microwells may be square in cross-section, but they are not so limited. The dimensions at the bottom of a microwell (i.e., in a cross section that is perpendicular to the depth of the well) may be 1.5 µm by 1.5 µm, or it may be 1.5 µm by 2 µm. Various diameters are shown in the Examples and include but are not limited to diameters at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µn, 3 µm, 2 µm, 1 µm or less. In some particular embodiments, the diameters may be at or about 44 µm, 32 µm, 8 µm, 4 µm, or 1.5 µm. Various heights are shown in the Examples and include but are not limited to heights at or about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9µm, 8 µm, 7 µm, 6 µm, 5 µm, 4 µm, 3 µm, 2 µm, 1 µm or less. In some particular embodiments, the heights may be at or about 55 µm, 48 µm, 32 µm, 12 µm, 8 µm, 6 µm, 4 µm, 2.25 µm, 1.5 µm, or less. Various embodiments of the invention contemplate the combination of any of these diameters with any of these heights. In still other embodiments, the reaction well dimensions may be (diameter in µm by height in µm) 44 by 55, 32 by 32, 32 by 48, 8 by 8, 8 by 12, 4 by 4, 4 by 6, 1.5 by 1.5, or 1.5 by 2.25.

The reaction well volume may range (between arrays, and preferably not within a single array) based on the well dimensions. This volume may be at or about 100 picoliter (pL), 90, 80, 70, 60, 50, 40, 30, 20, 10, or fewer pL. In important embodiments, the well volume is less than 1 pL, including equal to or less than 0.5 pL, equal to or less than 0.1 pL, equal to or less than 0.05 pL, equal to or less than 0.01 pL, equal to or less than 0.005 pL, or equal to or less than 0.001 pL. The volume may be 0.001 to 0.9 pL, 0.001 to 0.5 pL, 0.001 to 0.1 pL, 0.001 to 0.05 pL, or 0.005 to 0.05 pL. In particular embodiments, the well volume is 75 pL, 34 pL, 23 pL, 0.54 pL, 0.36 pL, 0.07 pL, 0.045 pL, 0.0024 pL, or 0.004 pL. The plurality of templates in each microwell may be introduced into the microwells (e.g., via a nucleic acid loaded bead), or it may be generated in the microwell itself. A plurality is defined herein as at least two, and in the context of template nucleic acids in a microwell or on a nucleic acid loaded bead includes tens, hundreds, thousands, ten thousands, hundred thousands, millions, or more copies of the template nucleic acid. The limit on the number of copies will depend on a number of variables including the number of binding sites for template nucleic acids (e.g., on the beads or on the walls of the microwells), the size of the beads, the length of the template nucleic acid, the extent of the amplification reaction used to generate the plurality, and the like. It is generally preferred to have as many copies of a given template per well in order to increase signal to noise ratio as much as possible. Amplification and conjugation of nucleic acids to solid supports such as beads may be accomplished in a number of ways, including but not limited to emulsion PCR (i.e., water in oil emulsion amplification) as described by Margulies et al. Nature 2005 437(15): 376-380 and accompanying supplemental materials. In some embodiments, the amplification is a representative amplification. A representative amplification is an amplification that does not alter the relative representation of any nucleic acid species. The wells generally also include sequencing primers, polymerases and other substrates or catalysts necessary for the synthesis reaction.

The degree of saturation of any capture (i.e., sequencing) bead with template nucleic acid to be sequenced may not be 100%. In some embodiments, a saturation level of 10%-100% exists. As used herein, the degree of saturation of a capture bead with a template refers to the proportion of sites on the head that are conjugated to template. In some instances this may be at least 5%, 10%, 15%, 20%, 25%, 30%, 35%, 40%, 45%, 50%, 55%, 60%, 65%, 70%, 75%, 80%, 85%, 90%, 95%, or it may be 100%.

It will be understood that the amount of sequencing primers and polymerases may be saturating, above saturating level, or in some instances below saturating levels. As used herein, a saturating level of a sequencing primer or a polymerase is a level at which every template nucleic acid is hybridized to a sequencing primer or bound by a polymerase, respectively. Thus the saturating amount is the number of polymerases or primers that is equal to the number of templates on a single bead. In some embodiments, the level is at greater than this, including at least 2 fold, 3 fold, 4 fold, 5 fold, 10 fold, or more over the level of the template nucleic acid. In other embodiments, the number of polymerases and/or primers may be 10%, 20%, 30%, 40%, 50%, 60%, 70%, 80%, 90%, or up to 100% of the number of templates on a single bead in a single well.

Thus, for example, before and/or while in the wells, the template nucleic acids are incubated with a sequencing primer that binds to its complementary sequence located on the 3' end of the template nucleic acid (i.e., either in the amplification primer sequence or in another adaptor sequence ligated to the 3' end of the target nucleic acid) and with a polymerase for a time and under conditions that promote hybridization of the primer to its complementary sequence and that promote binding of the polymerase to the template nucleic acid. The primer can be of virtually any sequence provided it is long enough to be unique. The hybridization conditions are such that the primer will hybridize to only its true complement on the 3' end of the template. Suitable conditions are disclosed in Margulies et al. Nature 2005 437(15): 376-380 and accompanying supplemental materials.

As described herein, the template nucleic acids may be engineered such that different templates have identical 5' ends and identical 3' ends. In some embodiments, however, the invention contemplates the use of a plurality of template populations, wherein each member of a given plurality shares the same 3' end but different template populations differ from each other based on their 3' end sequences. As an example, the invention contemplates in some instances sequencing nucleic acids from more than one subject or source. Nucleic acids from first source may have a first 3' sequence, nucleic acids from a second source may have a second 3' sequence, and so on, provided that the first and second 3' sequences are different. In this respect, the 3' end, which is typically a unique sequence, can be used as a barcode or identifier to label (or identify) the source of the particular nucleic acid in a given well. Reference can be made to Meyer et al. Nucleic Acids Research 2007 35(15):e97 for a discussion of labeling nucleic acid with barcodes followed by sequencing. In some instances, the sequencing primers (if used) may be hybridized (or annealed, as the terms are used interchangeably herein) to the templates prior to loading (or introducing) the beads to the wells or after such loading.

The 5' and 3' ends on every individual template however are preferably different in sequence. In particular, the templates share identical primer binding sequences. This facilitates the use of an identical primer across microwells and also ensures that a similar (or identical) degree of primer hybridization occurs across microwells. Once annealed to complementary primers such as sequencing primers, the templates are in a complex referred to herein as a template/primer hybrid. In this hybrid, one region of the template is double stranded (i.e., where it is bound to its complementary primer) and one region is single stranded. It is this single stranded region that acts as the template for the incorporation of nucleotides to the end of the primer and thus it is also this single stranded region which is ultimately sequenced according to the invention.

Data capture rates can vary and be for example anywhere from 10-100 frames per second and the choice of which rate to use will be dictated at least in part by the well size and the presence of packing beads or other diffusion limiting techniques. Smaller well sizes generally require faster data capture rates.

The systems described herein can be used for sequencing unlabeled biological polymers without optical detection.

In some embodiments, the invention encompasses a sequencing apparatus adapted for sequencing unlabeled biological polymers without optical detection and comprising an array of at least 100 reaction chambers.

Typically, each reaction chamber is capacitively coupled to a chemFET.

Preferably, each reaction chamber is no greater than about 0.39 pL in volume and about 49 $\mu m^2$ surface aperture, and more preferably has an aperture no greater than about 16 $\mu m^2$ and volume no greater than about 0.064 pL. Preferably, the array has at least 1,000, 10,000, 100,000, or 1,000,000 reaction chambers.

Typically, the reaction chambers comprise microfluidic wells.

In another embodiment, the invention encompasses a method for sequencing a biological polymer with the above-described apparatus comprising measuring time of incorporation of individual monomers into an elongating polymer.

Typically, the biological polymer is a nucleic acid template and the monomer is a nucleotide. Preferably, the nucleic acid template has 200-700 base pairs. Preferably, the nucleic acid template is amplified prior to determining the sequence.

The nucleic acid template used in this and other methods of the invention may be derived from a variety of sources by a variety of methods, all known to those of ordinary skill in the art. Templates may be derived from, but are not limited to, entire genomes of varying complexity, cDNA, mRNA or siRNA samples, or may represent entire populations, as in the various environmental and metabiome sequencing projects. Template nucleic acids may also be generated from specific subsets of nucleic acid populations including but not limited to PCR products, specific exons or regions of interest, or 16S or other diagnostic or identifying genomic regions.

Non-Sequencing Applications

It is to be understood that interactions between receptors and ligands or between two members of a binding pair or between components of a molecular complex can also be detected using the chemFET arrays. Examples of such interactions include hybridization of nucleic acids to each other, protein-nucleic acid binding, protein-protein binding, enzyme-substrate binding, enzyme-inhibitor binding, antigen-antibody binding, and the like. Any binding or hybridization event that causes a change of the semiconductor charge density at the chemFET interface and thus changes the current that flows from the source to the drain of the sensors described herein can be detected according to the invention.

The invention contemplates combining such nucleic acid arrays with the chemFET arrays and particularly the "large scale" chemFET arrays described herein. These arrays include those comprising $10^3$, $10^4$, $10^5$, $10^6$, $10^7$ or more sensors. These arrays also include those having center-to-center spacings between adjacent sensors in the range of 1-10 microns, as described herein. These arrays may also be characterized as having total surface areas of equal to or less than 441 $mm^2$ (e.g., 21 mm by 21 mm), or 81 $mm^2$ (e.g., 9 mm by 9 mm), or 49 $mm^2$ (e.g., 7 mm by 7 mm), for example.

The chemFET/nucleic acid array can be used in a variety of applications, some of which will not require the wells (or microwells or reaction chambers, as they are interchangeably referred to herein). Since analyses may still be carried out in flow, including in a "closed" system (i.e., where the flow of reagents and wash solutions and the like is automated), there will be one or more flow chambers situated above and in contact with the array. The use of multiple flow chambers allows multiple, preferably different, samples (including, for example, nucleic acid libraries) to be analyzed simultaneously. There may be 2, 3, 4, 5, 6, 7, 8, 9, 10 or more flow chambers. This configuration applies equally to other biological arrays including those discussed herein such as protein arrays, antibody arrays, enzyme arrays, chemical arrays, and the like.

Since the binding event between binding partners or between components of a complex is detected electronically via the underlying chemFET, such assays may be carried out without the need to manipulate (e.g., extrinsically label) the sample being assayed. This is advantageous since such manipulation invariably results in loss of sample and generally requires increased time and work up. In addition, the present method allows binding interactions to be studied in real time.

It is further to be understood that many of the terms including various nucleic acid embodiments, chemFET array embodiments, and reaction chambers embodiments, inter alia, described herein in the context of sequencing applications are equally applicable to the non-sequencing applications contemplated by the invention and described in greater detail below.

In these embodiments, the passivation layer (or possibly an intermediate layer coated onto the passivation layer) is functionalized with nucleic acids (e.g., DNA, RNA, miRNA, cDNA, and the like), antigens (which can be of any nature), proteins (e.g., enzymes, cofactors, antibodies, antibody fragments, and the like), and the like. Conjugation of these entities to the passivation layer can be direct or indirect (e.g., using bifunctional linkers that bind to both the passivation layer reactive group and the entity to be bound).

Development of the very large chemFET arrays and systems provides considerable advantages to a wide assortment of applications beyond the particular DNA sequencing process described above. Briefly, some of those applications will now be discussed, recognizing that in doing so, there may be some repetition over the discussion already presented.

The configurations of the chemFET arrays and the biological or chemical arrays are similar in each instance and the discussion of one combination array will apply to others described herein or otherwise known in the art.

In most or all of the applications noted below, the analyte may be presented in a liquid medium or under air or other gas flow.

Methods for attaching nucleic acids, proteins, molecules, and the like to solid supports, particularly in the context of an array, have been described in the art. See for example Lipshutz et al. Nat. Genet. (supplement) 1999 21:20-24; Li et al. *Proc. Natl. Acad. Sci.*, 2001, 98:31-36; Lockhart et al. Nat. Biotechnol. 1996 14:1675-1680; Wodicka et al. *Nat. Biotech-* nol. 1997 15: 1359-1367; Chen et al. Journal of Biomedical Optics 1997 2:364; Duggan et al. Nat Genet 1991 21(1 Suppl):10-4; Marton et al. Nat Med. 1998 4(11):1293-301; Kononen et al. Nat Med 1998 4(7):844-847; MacBeath et al., Science 2000 289(5485):1760-1763; Haab et al. Genome Biology 2001 2(2); Pollack et al. Nat Genet 1999 23(1):41-6; Wang D G et al. Science 1998 280(5366):1077-82; Fodor et al. Science 1991 251:767-773; Fodor et al. Nature 1993 364: 555-556; Pease et al. Proc. Natl. Acad. Sci. USA 1994 91:5022-5026; Fodor Science 1997 277:393-395; Southern et al. Genomics 1992 13: 1008-1017; Schena et al. Science 1995 270(5235):467-70; Shalon et al. Genome Res 1996 6(7):639-45; Jongsma Proteomics 2006, 6:2650-2655; Sakata, Biosensors and Bioelectronics 2007, 22: 1311-1316.

Oligonucleotide Microarrays

One such application involves the generation and interrogation of oligonucleotide arrays comprised of nucleic acids (e.g., DNA), single or double stranded, immobilized on the chemFET array.

As an example, reaction groups such as amine or thiol groups may be added to a nucleic acid at any nucleotide during synthesis to provide a point of attachment for a bifunctional linker. As another example, the nucleic acid may be synthesized by incorporating conjugation-competent reagents such as Uni-Link AminoModifier, 3'-DMT-C6-Amine-ON CPG, AminoModifier II, N-TFA-C6-Amino-Modifier, C6-ThiolModifier, C6-Disulfide Phosphoramidite and C6-Disulfide CPG (Clontech, Palo Alto, Calif.). Other methods for attaching nucleic acids are discussed below.

In one aspect of the invention, the chemFET arrays are provided in combination with nucleic acid arrays. Nucleic acids in the form of short nucleic acids (e.g., oligonucleotides) or longer nucleic acids (e.g., full length cDNAs) can be provided on chemFET surfaces of the arrays described herein. Nucleic acid arrays generally comprise a plurality of physically defined regions on a planar surface (e.g., "spots") each of which has conjugated to it one and more preferably more nucleic acids. The regions are aligned with the sensors in the sensor array such that there is one sensor for each region. The nucleic acids are usually single stranded. The nucleic acids conjugated to a given spot are usually identical. The nucleic acids conjugated to different spots may be different from each other or they may be identical.

Thus, the nucleic acid arrays may comprise a plurality of identical (and thus homogeneous) nucleic acids (e.g., where more than one chemFET surface (or spots), and optionally the entire chemFET array surface has conjugated to it identical nucleic acids). Thus, the identical nucleic acids may be uniformly distributed on a planar surface or they may be organized into discrete regions (or cells) on that surface. Alternatively, the nucleic acid arrays may comprise a plurality of different (and thus heterogeneous) nucleic acids.

The plurality of nucleic acids in a single region may vary depending on the length of the nucleic acid, the size of the region, and the method used to attach the nucleic acid thereto, and may be but is not limited to at least 10, 50, 100, 500, $10^3$, $10^4$ or more. The array itself may have any number of regions, including but not limited to at least 10, $10^2$, $10^3$, $10^4$, $10^5$, $10^6$, $10^7$, or more. In these and other embodiments, the regions (or cells) are aligned with the sensors in the sensor array such that there is one sensor for each region (or cell).

In the context of an oligonucleotide array, these nucleic acids may be on the order of less 100 nucleotides in length (including about 10, 20, 25, 30, 40, 50, 60, 70, 80, 90 or 100 nucleotides in length). If the arrays are used to detect certain genes (including mutations in such genes or expression levels of such genes), then the array may include a number of spots each of which contains oligonucleotides that span a defined and potentially different sequence of the gene. These spots are then located across the planar surface in order to exclude position related effects in the hybridization and readout means of the array.

The binding or hybridization of the sample nucleic acids and the immobilized nucleic acids is generally performed under stringent hybridization conditions as that term is understood in the art. (See for example Sambrook et al. "Maniatis".) Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. By way of example hybridization may be performed at 50% formamide and 4×SSC followed by washes of 2×SSC/formamide at 50° C. and with 1×SSC.

Nucleic acid arrays include those in which already formed nucleic acids such as cDNAs are deposited (or "spotted") on the array in a specific location. Nucleic acids can be spotted onto a surface by piezoelectrically deposition, UV cross-linking of nucleic acids to polymer layers such as but not limited to poly-L-lysine or polypyrrole, direct conjugation to silicon coated $SiO_2$ as described in published US patent application 2003/0186262, direct conjugation to a silanised chemFET surface (e.g., a surface treated with 3-aminopropyltriethoxysilane (APTES) as described by Uslu et al. Biosensors and Bioelectronics 2004, 19:1723-1731, for example.

Nucleic acid arrays also include those in which nucleic acids (such as oligonucleotides of known sequence) are synthesized directly on the array. Nucleic acids can be synthesized on arrays using art-recognized techniques such as but not limited to printing with fine-pointed pins onto glass slides, photolithography using pre-made masks, photolithography using dynamic micromirror devices (such as DLP mirrors), ink-jet printing, or electrochemistry on microelectrode arrays. Reference can also be made to Nuwaysir et al. 2002 "Gene expression analysis using oligonucleotide arrays produced by maskless photolithography." Genome Res 12: 1749-1755. Commercial sources of this latter type of array include Agilent, Affymetrix, and NimbleGen.

Thus the chemFET passivation layer may be coated with an intermediate layer of reactive molecules (and therefore reactive groups) to which the nucleic acids are bound and/or from which they are synthesized.

Any of the binding chemistries traditionally utilized to generate for example DNA arrays on substrates, such as glass, plastic, nylon, nitrocellulose and activated gels, may be used to immobilize nucleic acids on the chemFET array. Some of the more common chemistries are summarized in the review in Zammatteo, N. et al., "Comparison between different strategies of covalent attachment of DNA to glass surfaces to build DNA microarrays," Anal Biochem 280, 143-50 (2000), and detailed briefly herein.

DNA immobilization can entail non-covalent (e.g., ionic) or covalent binding chemistries. Ionic binding most commonly employs the interaction of negatively charged species, such as DNA, with a positively charged surface, such as glass slides coated with poly-lysine. See Schena et al. "Quantitative monitoring of gene expression patterns with a complementary DNA microarray," Science 270, 467-70 (1995). Hydrophobic interactions have also been used to attach nucleic acids to various surfaces. See Allemand, et al. "pH-dependent specific binding and combing of DNA," *Biophys J* 73, 2064-70 (1997).

Covalent binding can also be used through a variety of methods. For example, UV radiation can be used to cross-link nucleic acids (such as DNA) to amino group containing substances, for example by forming covalent bonds between positively charged amino groups on a functionalized surface and thymidine residues present along the length of the nucleic acid strand. In this way, the nucleic acid is attached to the solid support along its length, in a random or non-random manner. See Duggan et al. "Expression profiling using cDNA microarrays," *Nature Genetics* 21, 10-14 (1999).

Alternatively, nucleic acids (such as DNA) can be attached to the solid support by their 5' or 3' ends, particularly where such ends are carboxylated or phosphorylated. See Joos et al. "Covalent attachment of hybridizable oligonucleotides to glass supports," *Anal Biochem* 247, 96-101 (1997) and Joos et al. "Covalent attachment of hybridizable oligonucleotides to glass supports," *Anal Biochem* 247, 96-101 (1997). Nucleic acids (such as DNA) can be coupled on aminated supports, or the nucleic acids themselves may be aminated and then attached to carboxylated, phosphorylated, epoxide-modified, isothiocyanate-activated, or aldehyde-activated supports or surfaces such as glass surfaces. See Ghosh et al. "Covalent attachment of oligonucleotides to solid supports," *Nucl. Acids Res.* 15, 5353-5372 (1987), Lamture et al. "Direct detection of nucleic acid hybridization on the surface of a charge coupled device," *Nucleic Acids Res.* 22, 2121-5 (1994), Guo et al. "Direct fluorescence analysis of genetic polymorphisms by hybridization with oligonucleotide arrays on glass supports. *Nucleic Acids Res.* 22, 5456-5465 (1994), Schena et al., "Parallel human genome analysis: microarray-based expression monitoring of 1000 genes," *PNAS* 93, 10614-9 (1996).

Hetero-bifunctional cross-linkers have been used to bind thiol- or disulfide-modified oligonucleotides onto gold (Boncheva et al. "Design of Oligonucleotide Arrays at Interfaces," *Langmuir* 15, 4317-4320 (1999)), aminosilane- (Chrisey et al. "Covalent attachment of synthetic DNA to self-assembled monolayer films," *Nucl. Acids Res.* 24, 3031-3039 (1996)) or 3-mercaptopropylsilane-modified (Rogers et al. "Immobilization of oligonucleotides onto a glass support via disulfide bonds: A method for preparation of DNA microarrays," *Analytical Biochemistry* 266, 23-30 (1999)) glass surfaces.

Additionally, the use of dendrimeric linker molecules as a substrate for covalent attachment of Peptide Nucleic Acids (PNAs), PCR products or oligonucleotides, including oligodeoxynucleotides, to glass or polypropylene supports has been demonstrated (Beier et al. "Versatile derivatisation of solid support media for covalent bonding on DNA-microchips," *Nucleic Acids Res* 27, 1970-7 (1999)), as has direct synthesis of nucleic acids on support surfaces using photolithographic techniques (Pease et al. "Light-Generated Oligonucleotide Arrays for Rapid DNA Sequence Analysis," *PNAS* 91 (1994) 5022).

The invention contemplates the attachment, whether covalent or non-covalent, and whether direct or indirect, of chromosomal nucleic acids, shorter nucleic acids such as oligonucleotides (including oligodeoxyribonucleotides and oligoribonucleotides), nucleic acids such as DNA, RNA, PNA, LNA, or nucleic acids that comprise any combination and/or level of these various constituents, peptides, proteins including glycoproteins, carbohydrates, oligosaccharides, polysaccharides, and other molecule of interest, regardless of nature. Any of these can be applied to the surface of the chemFET arrays in any of the ways currently used for microarrays or in any other way as the invention is not limited with respect to these binding chemistries. Known approaches include mechanical spotting (for example pin-type spotters), piezo or print-head (i.e., ink jet, aka drop-on-demand) printing, in situ synthesis or application through attachment from a solution, such as limiting dilution or dipping.

In addition to the attachment of preformed nucleic acids to the chemFET arrays, the invention also contemplates synthesis of nucleic acids onto the chemFET array (i.e., in situ synthesis). Thus, the various methods of in situ nucleic acid synthesis, as reviewed by Guo et al. are also applicable to chemFET arrays. A non-comprehensive list of examples includes in situ synthesis via ink-jet printing delivery of phosphoramidites (Blanchard et al. "High-density oligonucleotide arrays," *Biosensors and Bioelecironics* 11, 687-690 (1996)), parallel synthesis directed by individually electronically addressable wells (Egeland et al. "Electrochemically directed synthesis of oligonucleotides for DNA microarray fabrication," *Nucleic Acids Res* 33, e125 (2005)), maskless photo-generated acid (PGA) controlled synthesis (LeProust et al. "Digital light-directed synthesis. A microarray platform that permits rapid reaction optimization on a combinatorial basis," *J Comb Chem* 2, 349-54 (2000); Gao et al. "A flexible light-directed DNA chip synthesis gated by deprotection using solution photogenerated acids," *Nucleic Acids Res* 29, 4744-50 (2001)), mask directed synthesis utilizing photolithography (PLPG) (Fodor et al. "Light-directed, spatially addressable parallel chemical synthesis," *Science* 251, 767-73 (1991)) and maskless PLPG parallel in situ synthesis (Singh-Gasson et al. "Maskless fabrication of light-directed oligonucleotide microarrays using a digital micromirror array," *Nat Biotechnol* 17, 974-8 (1999)).

Nucleic acid templates have been immobilized onto individual (i.e., single) chemFETs for various purposes. For example, amine-labeled oligonucleotides bound to a silanized $Si_3N_4$ surface of a single ISFET, and the change in electrical potential resulting from complementary DNA hybridization was used to detect specific single nucleotide polymorphisms (SNPs). Sakata et al. "Potentiometric Detection of Single Nucleotide Polymorphism by Using a Genetic Field-effect transistor," *Chembiochem* 6, 703-10 (2005). Silanized ISFETs have been proposed for monitoring the voltage signal associated with both the adsorption of PCR products to the ISFET surface as well as the secondary voltage signal resulting from hybridization of complementary strands. Uslu et al. "Labelfree fully electronic nucleic acid detection system based on a field-effect transistor device," *Biosens Bioelectron* 19, 1723-31 (2004). Single ISFETs have been reported to detect the pH change associated with polymerase-directed nucleotide incorporation in a replicating DNA strand, thus monitoring polymerase activity on immobilized DNA templates in real-time. Sakurai et al. "Real-time monitoring of DNA polymerase reactions by a micro ISFET pH sensor," *Anal Chem* 64, 1996-7 (1992).

To date, the throughput of such systems has been low, as demonstrated by DNA detection systems utilizing only 10 (Sakata et al. "Detection of DNA recognition events using multi-well field effect devices," *Biosens Bioelectron* 21, 827-32 (2005)) or 16 (Barbaro et al., "Fully electronic DNA hybridization detection by a standard CMOS biochip," *Sensors & Actuators: B. Chemical* 118, 41-46 (2006)) ISFETs. The invention provides significant advantages over these approaches by providing very large scale chemFET arrays that are able to interrogate hundreds, thousands, and even millions of samples concurrently and rapidly.

The arrays are contacted with a sample being tested. The sample may be a genomic DNA sample, a cDNA sample from a cell, a tissue or a mass (e.g., a tumor), a population of cells that are grown on the array, potentially in a two dimensional array that corresponds to the underlying sensor array, and the like. Such arrays are therefore useful for determining presence and/or level of a particular gene or of its expression, detecting mutations within particular genes (such as but not limited to deletions, additions, substitutions, including single nucleotide polymorphisms), and the like.

Besides SNP detection and polymerase activity assays, the ability to deposit large numbers of immobilized nucleic acids on to the surface of an ISFET array provides real-time, label-free quantification and analysis for a variety of biological, chemical and other applications, including but not limited to gene expression analysis, comparative genome hybridization (CGH), and array-based exon enrichment processes. Additionally, such arrays may be used to screen samples including but not limited to naturally occurring samples such as bodily fluids and/or tissues such as blood, urine, saliva, CSF, lavages, and the like, environmental samples such as water supply samples, air samples, and the like, for the presence or absence of a substance or in order to characterize such sample for example for its origin or identity based on nucleic acid content, protein content, or other analyte content. As an example, the arrays of the invention may be used to determine the presence or absence of pathogens such as viruses, bacteria, parasites, and the like based on genomic, proteomic, and/or other cellular or organismic element. The arrays may also be used to identify the presence or absence, and optionally characterize cancer cells or cells that are indicative of another condition or disorder, in a subject.

Analysis of samples for types and quantities miRNA and siRNA, whether or not in the presence of total RNA, would have considerable utility. Thus, the invention therefore contemplates ISFET arrays having immobilized thereon various capture reagents specific for one or more miRNA and/or siRNA species.

In still other embodiments, the invention contemplates immobilizing riboswitches. Riboswitches are transcripts that are able to sense metabolites. (Mironov et al. Sensing small molecules by nascent RNA: a mechanism to control transcription in bacteria. *Cell* 111, 747-756 (2002); and Winkler et al. Thiamine derivatives bind messenger RNAs directly to regulate bacterial gene expression. *Nature* 419, 952-956 (2002).) ISFET arrays having riboswitches immobilized thereto can then detect metabolites either in or ex situ.

Antibody, Aptamer and Protein Arrays

Protein arrays used in combination with the chemFET arrays of the invention are also contemplated. Protein arrays comprise proteins or peptides or other amino acid comprising biological moiety bound to a planar surface in an organized and predetermined manner. Such proteins include but are not limited to enzymes, antibodies and antibody fragments or antibody mimics (e.g., single chain antibodies).

In one embodiment, a protein array may comprise a plurality of different (and thus heterogeneous) proteins (or other amino acid containing biological moieties). Each protein, and preferably a plurality of proteins, is present in a predetermined region or "cell" of the array. The regions (or cells) are aligned with the sensors in the sensor array such that there is one sensor for each region (or cell). The plurality of proteins in a single region (or cell) may vary depending on the size of the protein and the size of the region (or cell) and may be but is not limited to at least 10, 50, 100, 500, $10^3$, $10^4$ or more. The array itself may have any number of cells, including but not limited to at least 10, $10^2$, $10^3$, $10^4$, $10^5$, $10^6$, $10^7$, or more. In one application, the array is exposed to a sample that is known to contain or is suspected of containing an analyte that binds to the protein. The analyte may be a substrate or an inhibitor if the protein is an enzyme. The analyte may be any molecule that binds to the protein including another protein, a nucleic acid, a chemical species (whether synthetic or naturally occurring), and the like.

It is to be understood that, like the nucleic acid arrays contemplated herein, the readout from the protein arrays will be a change in current through the chemFET and thus no additional step of labeling and/or label detection is required in these array methods.

In another embodiment, the protein array may comprise a plurality of identical (and thus homogeneous) proteins (or other amino acid containing biological moieties). The identical proteins may be uniformly distributed on a planar surface or they may be organized into discrete regions (or cells) on that surface. In these latter embodiments, the regions (or cells) are aligned with the sensors in the sensor array such that there is one sensor for each region (or cell).

The proteins may be synthesized off-chip, then purified and attached to the array. Proteins, like other moieties discussed herein such as nucleic acids, may be attached to the array via an avidin-biotin (including a streptavidin-biotin) interaction. As an example, avidin (or streptavidin) may be first bound to the array followed by biotinylated protein. It will be understood that a similar non-covalent scheme can be used for attaching other moieties including nucleic acids to the array.

Alternatively they can be synthesized on-chip, similarly to the nucleic acids discussed above. Synthesis of proteins using cell-free DNA expression or chemical synthesis is amenable to on-chip synthesis. Using cell-free DNA expression, proteins are attached to the solid support once synthesized. Alternatively, proteins may be chemically synthesized on the solid support using solid phase peptide synthesis. Selective deprotection is carried out through lithographic methods or by SPOT-synthesis. Reference can be made to at least MacBeath and Schreiber, Science, 2000, 289:1760-1763, or Jones et al. Nature, 2006, 439:168-174. Reference can also be made to U.S. Pat. No. 6,919,211 to Fodor et al.

Many of the chemistries used to immobilize nucleic acids to solid surfaces can similarly be employed to bind amino acid containing molecules such as peptides and proteins and fragments thereof (Zhu et al. "Protein arrays and microarrays," *Curr Opin Chem Biol* 5, 40-5 (2001); Schweitzer et al. "Measuring proteins on microarrays," *Curr Opin Biotechnol* 13, 14-9 (2002); Schweitzer et al. "Multiplexed protein profiling on microarrays by rolling-circle amplification," *Nat Biotechnol* 20, 359-65 (2002)) including but not limited to enzymes (Eppinger et al. "Enzyme microarrays: On-chip determination of inhibition constants based on affinity-label detection of enzymatic activity," *Angew Chem Int Ed Engl* 43, 3806-10 (2004); Funeriu et al. "Enzyme family-specific and activity-based screening of chemical libraries using enzyme microarrays," *Nat Biotechnol* 23, 622-7 (2005)) and antibodies (Schweitzer et al. "Immunoassays with rolling circle amplification: A versatile platform for ultrasensitve antigen detection," *Proc. Natl. Acad. Sci. USA* 97, 10113-10119 (2000)). These binding processes are summarized in a review by Gao et al. (Gao, X. et al., "High density peptide microarrays. In situ synthesis and applications," *Mol Divers* 8, 177-87 (2004), and have been applied to single individual ISFETs (Schasfoort et al. "Modulation of the ISFET response by an immunological reaction," *Sens. Actuators* 17, 531-535 (1989); Schasfoort et al. "Possibilities and limitations of direct detection of protein charges by means of an immunological field-effect transistor," *Analylica Chimica Acta* 238, 323-329 (1990); Besselink et al. "Modification of ISFETs with a monolayer of latex beads for specific detection of proteins," *Biosens Bioelectron* 18, 1109-14 (2003)).

The invention contemplates covalent and non-covalent (e.g., ionic) attachment of peptides and/or proteins or fragments thereof including antibody fragments to the ISFET array surface from an applied solution, direct printing of peptides or proteins, self-assembly of peptides or proteins on the array using for example oligonucleotide tags, immobilization of high affinity nucleic acid aptamers, and various methods of in situ peptide synthesis as ways of attaching peptides or proteins onto the chemFET surface. Such peptide or protein arrays provide a valuable tool for real-time detection of small molecule targets that interact with the immobilized proteins, antibody/antigen interaction, receptor/ligand, enzyme/inhibitor, enzyme/activator, transcription factor/nucleic acid target, receptor enzyme/inhibitor, and other processes or interactions known to the art.

Aptamers are nucleic acid molecules that bind to various molecular targets like small molecules, proteins, peptides, DNA, RNA, and the like with high affinity. Aptamers are easily chemically synthesized, are stable, and show less immunogenicity in humans compared to animal-derived antibodies. Aptamers can be immobilized to a chemFET array via standard coupling chemistry and have been shown to be successful sensors when coupled to individual ISFETs, as reviewed by Li et al. Recent advances of aptamer sensors. *Science in China Series B: Chemistry* 51, 193-204 (2008). Due to their low immunogenicity, aptamer FETs may be implanted into a subject and used to monitor physiological or biochemical processes and/or status in and of a subject, and thereby provides real-time readouts.

The invention further contemplates use of ISFET arrays to measure the number of protein molecules bound to all RNA in a transcriptome. In this process, RNA-protein interactions would be preserved during cell lysis and RNAs would be captured by specific oligonucleotides immobilized on the surface of an ISFET array. Enzyme-conjugated antibodies would then be introduced to bind to protein antigens following which nonspecific interactions would be washed away. Similarly, antibodies could be used against translational machinery such as the 80S, 48S, 43S and 40S subunits, or specifically against RNA binding proteins. Detection on the ISFET array could be accomplished through conjugating antibodies to enzymes that generate ionic products when presented with non-ionic substrates, for example converting NADPH to NADP$^+$, NADH to NAD$^+$, or any oxidase or reductase that generates a detectable change in the net electronic charge. An additional benefit of such a scheme is that antibodies could be combined for multiplexing, generating quantitative data on multiple proteins and protein/nucleic acid interactions.

The arrays of the invention can also be used to measure the kinetics of a reaction and/or compare the activities of enzymes. In this way, the array may be used to select from more efficient enzymes from for example a pool or library of enzymes. Typically, the reactions being monitored or measured are those that generate a change in charge that can be detected at the FET surface. Similarly, the arrays may be used to determine the effect of different reaction conditions on reaction kinetics. Depending on the embodiment and the reaction being monitored, the enzyme, its substrate (or an analog thereof capable of being acted upon by the enzyme and still be bound to the array), a co-factor, or another moiety required for readout of the reaction may be attached to the array. As an example, a sequencing reaction may be monitored using luciferase bound to the array while the polymerase and its template substrate are free in solution.

Nucleic Acid/Protein Interactions

A chemFET-based array may also be used to explore various protein/nucleic acid interactions. For example, RNA/protein binding may be investigated by lysing cells and capturing the RNA (with associated proteins) on oligonucleotides immobilized on the chemFET array. Enzyme-conjugated antibodies may then be bound to protein antigen and nonspecific interactions can be washed away. Specific antibodies may be employed against translational machinery and 80S, 40S, 43S, or 48S RNA regions. Antibodies may also be used against RNA binding proteins, or conjugated to enzymes that produce ionic products when presented with nonionic substrates (for example NADPH to NADP+, NADH to NAD+, and possibly $H_2O_2$ or Glutathione). These antibodies can be combined for multiplexing.

Chemical compound microarrays in combination with chemFET arrays are also envisioned. Chemical compound microarrays can be made by covalently immobilizing the compounds (e.g., organic compounds) on the solid surface with diverse linking techniques (may be referred to in the literature as "small molecule microarray"), by spotting and drying compounds (e.g., organic compounds) on the solid surface without immobilization (may be referred to in the literature as "micro arrayed compound screening (μARCS)"), or by spotting organic compounds in a homogenous solution without immobilization and drying effect (commercialized as DiscoveryDot™ technology by Reaction Biology Corporation).

Protein Sequencing

The amino acid sequence of proteins also may be determined using a chemFET array. For example, proteins may be denatured before or after capture on beads, or alternatively, proteins may be captured to the chemFET surface, preferably one protein per well and/or bead (presuming a one bead—one well ratio). These ratios can be achieved using limiting dilution or with nanotechnology. (See RainDance Technologies, etc.) Amino-acyl synthetases are sequentially introduced (by flow) into each well. Each amino-acyl synthetase will be specific for each naturally occurring amino acid. The amino-acyl synthetases will also be conjugated (covalently or non-covalently) to a moiety that can be detected by its ability to change ionic concentration and, optionally, to a protease that is capable of cleaving the immobilized protein one amino acid at a time. An example of a suitable moiety is hydrogen peroxidase which acts upon its substrate hydrogen peroxide to release ions. The synthetase will bind or not bind to the protein depending on whether the amino acid it specifically recognizes and binds to is present at the free end of the protein (whether C or N terminus). Excess (and unbound) synthetase is washed away and, in this example, hydrogen peroxide is added. An ion change resulting from the presence of hydrogen peroxidase is then detected. It will be appreciated that other enzyme and substrate systems may be used in place of hydrogen peroxidase and hydrogen peroxide. Enzymes may be preferred given the amplified signal that can be achieved. The last amino acid is then cleaved together with the bound amino-acyl synthetase using limited Edman degradation or by proximity based radical cleavage, and washed away. The process is repeated using the same sequential order of synthetases (i.e., each cycle will introduce each of the 20 synthetases into the wells). The last amino acid may be cleaved using a protease that is conjugated to the synthetase, as an example, in order to limit its activity and prevent unnecessary degradation of the protein. This method can quantitate the number of proteins, similar to SAGE.

Specific Chemical & Other Molecular Recognition Sites

Other applications for the chemFET arrays involve the use of molecular recognition sites, wherein molecules that specifically recognize particular target molecules are either indentified or designed and applied to the surface of the array. Previous work with chemFETs has demonstrated the ability of single individual ISFETs to recognize ions such as potassium (Brzozka et al. "Enhanced performance of potassium CHEMFETs by optimization of a polysiloxane membrane," *Sensors and Actuators B. Chemical* 18, 38-41 (1994)), hydrogen, calcium and sodium (Sibbald et al. "A miniature flow-through cell with a four-function ChemFET integrated circuit for simultaneous measurements of potassium, hydrogen, calcium and sodium ions," *Analytica chimica acta.* 159, 47-62 (1984)), heavy metals (Cobben et al. "Transduction of selective recognition of heavy metal ions by chemically modified field effect transistors (CHEMFETs)," *Journal of the American Chemical Society* 114, 10573-10582 (1992)). Such recognition elements may either be uniformly applied to the surface, or may be precisely applied to specific locations using any of the binding or in situ chemistries mentioned above, thereby producing an array of individual recognition elements across the surface of the ISFET array.

Additionally other surface modifications have been reported with single individual FETs that would be applicable to the chemFET arrays of the invention. These include the use of "catcher molecules" (Han et al. "Detection of DNA hybridization by a field-effect transistor with covalently attached catcher molecules," *Surface and Interface Analysis* 38, 176-181 (2006)), elongated tethers such as PEG, PEA or conductive molecules such as carbon nanotubes (Martel et al. "Single- and multi-wall carbon nanotube field-effect transistors," *Applied Physics Letters* 73, 2447-2449 (1998)) that serve to permit molecular detection via ISFET activity.

Non-Invasive Biological Monitoring

Tissue microarrays in combination with chemFET arrays are further contemplated by the invention. Tissue microarrays are discussed in greater detail in Battifora Lab Invest 1986, 55:244-248; Battifora and Mehta Lab Invest 1990, 63:722-724; and Kononen et al. Nat Med 1998, 4:844-847.

In yet another aspect, the invention contemplates analysis of cell cultures (e.g., two-dimensional cells cultures) (see for example Baumann et al. Sensors and Actuators B 55 1999 77:89), and tissue sections placed in contact with the chemFET array. As an example, a brain section may be placed in contact with the chemFET array of the invention and changes in the section may be detected either in the presence or absence of stimulation such as but not limited to neurotoxins and the like. Transduction of neural processes and/or stimulation can thereby be analyzed. In these embodiments, the chemFETs may operate by detecting calcium and/or potassium fluxes via the passivation layer itself or via receptors for these ions that are coated onto the passivation layer.

chemFET arrays may also be employed to monitor large numbers of cells simultaneously. In practice, cells and tissues are surrounded in a complex liquid medium containing many different ion species. The concentration of the various ions relates to the health, nutrition, and function of the cells. In order to better understand this relationship, planar ISFET arrays could be employed for the temporal and spatial analysis of a single cell or a large number of cells grown in vitro. Similar work has been shown using a simple 2×2 (Milgrew et al. "The development of scalable sensor arrays using standard CMOS technology," *Sensors and Actuators B: Chemical* 103, 37-42 (2004)) or 16×16 (Milgrew et al. "A large transistor-based sensor array chip for direct extracellular imaging," *Sensors and Actuators B: Chemical* 111-112, 347-353 (2005)) MOSFET arrays to monitor the solution pH in cell cultures. These previous attempts were unable to solve the trapped-charge issue, and/or to obtain functional arrays beyond the 16×16 size, and were similarly unable to get these arrays to operate quickly. The arrays of the invention facilitate higher pixel density, increased speed, greater sensitivity, and the ability to couple the array with specific molecular recognition as outlined above.

One contemplated application involves culture (with or without division) of cells such as brain cells, heart cells, or other tissues on the chemFET array surface and monitoring cellular responses of such cells either in the absence or presence of one or more chemical, biological, mechanical, or environmental stimuli. As an example, the cellular response may be ionic flux (pH), release or uptake of other ions such as $Na^+$, $K^+$, $Ca^{++}$, or $Mg^{++}$, or other electrochemical activity, any of which may be detected as a change in ion concentration at the chemFET surface.

Furthermore, by adopting the principle of electrical impedance tomography (Barber, C. C., Brown et al. "Imaging spatial distribution of resistivity using applied potential tomography." *Electronics Letters* 19, 933-935 (1983), and Chai et al. "Electrical impedance tomography for sensing with integrated microelectrodes on a CMOS microchip." *Sensors and Actuators B: Chemical* 127, 97-101 (2007)) and applying it to these measurements, a reconstruction algorithm can be used to detect and characterize off-plane ion concentration and flow from cells in situ. This would allow analysis of the biology in the depths of the tissue, beyond the conventional reach of the surface-based ISFET sensor array.

The maintenance of ionic disequilibria is a fundamental process directly affected by metabolic activity. One important measure of metabolism is cellular respiration, which involves both glycolysis and oxidative phosphorylation. These two properties have been implicated in a number of cellular activities (Table 2). In order to monitor cellular respiration, a planar array of pH-sensitive ISFETs can be complemented with integrated on-chip dissolved oxygen sensors. These would be based on conventional amperometric Clark cells using an electrochemical three-electrode cell system connected to a potentiostat (Amatore et al. "Analysis of individual biochemical events based on artificial synapses using ultramicroelectrodes: cellular oxidative burst." *Faraday Discussions* 116, 319-333 (2000)).

In general, a potentiostat circuit can be built directly into CMOS. The three electrodes are fabricated as a post-processing step by using electroless plating to deposit gold onto three standard aluminium bond pads (Chai et al. "Modification of a CMOS microelectrode array for a bioimpedance imaging system." *Sensors and Actuators B: Chemical* 111, 305-309 (2005)) and then the electrodes are formed by depositing silver or platinum directly on to the gold. Alternatively, if the cells are in an unbuffered medium, then a CMOS-based oxygen sensor can be implemented by taking advantage of the local pH change that occurs during the oxygen reduction reaction (Lehmann et al. "Simultaneous measurement of cellular respiration and acidification with a single CMOS ISFET." *Biosensors and Bioelectronics* 16, 195-203 (2001)). A working electrode can be fabricated around the gate of a pH-sensitive ISFET and would electrolyze dissolved oxygen. This results in a pH variation due to the generation of hydroxyl ions in close proximity to the gate. This variation is logarithmically proportional to oxygen content and can be measured by the ISFET.

TABLE 2

Dynamic cell types, activities, and energy requirements as supported by a combination of glycolysis and oxidative phosphorylation (Alberts et al. *Molecular Biology of the Cell*, 4th Edition, Garland Science, NY, USA (2002)).

| Cell | Main Cellular Activity | Metabolic Rate $O_2$ | Glycolysis |
|---|---|---|---|
| Heart | Contraction force, membrane potential changes | High | High |
| Skeletal Muscle | Membrane potential changes, contraction force | Low/High | High/Low |
| Liver | Catabolism, metabolism | Medium | High |
| Kidney | Ion and metabolite gradients | Medium | Medium |
| Bone | Extracellular matrix turnover | Medium | Medium |
| Neuron | Membrane potential changes, release of substances | Medium | High |

Furthermore, there is strong evidence to suggest that cells change their metabolism according to structure, topography, chemical properties, and condition of the extracellular matrix that they are suspended in, or to which they are attached (Boateng et al. "RGD and YIGSR synthetic peptides facilitate cellular adhesion identical to that of laminin and fibronectin but alter the physiology of neonatal cardiac myocytes." *American Journal of Physiology: Cell Physiology* 288, C30-C38 (2005), and McBeath et al. "Cell shape, cytoskeletal tension, and RhoA regulate stem cell lineage commitment." *Developmental Cell* 6, 483-495 (2004)). Understand the effects of culture conditions on cellular metabolism would be particularly important in the wider context of tissue engineering. To this end, ISFET arrays can be used with small polymer cell chips (cell constructs) to analyze single cells, cell lines, cell sheets, and multi-layered cell sheets. The cell constructs could be fabricated using embossing, micro-contact printing, and photolithography to offer a convenient platform for cells. To date, there are no cell culture systems available to measure cell metabolism relative to the effects of transition from monolayer to truly three-dimensional environments. However, by using a polymer chip that includes a recess filled with collagen gel incorporating cells, a three-dimensional culture can be analyzed with a planar ISFET array.

Invasive Biological Monitoring

In yet another aspect, the invention contemplates the use of chemFET arrays, functionalized as described herein or in another manner, for use in vivo. Such an array may be introduced into a subject (e.g., in the brain or other region that is subject to ion flux) and then analyzed for changes based on the status of the subject.

An chemFET array may be directly implanted into a test environment and used to monitor the presence and amount of specific molecules of interest. Some such applications include environmental testing for specific toxins and important elements, or direct implantation of the device into the body of a subject, providing a 3D image of the concentration of specific molecules within the tissue.

Electrically active cells display electrical activity because of ionic flows. Hence, in order to better understand tissue physiology in vivo, an ISFET array can be integrated onto a novel ion-discriminating tissue probe. The invention contemplates a generic platform technology that can be applied to analyses in at least three distinct areas: (i) the behavior of epithelia and the role of ions in wound healing, (ii) neural recording, and (iii) optical stimulation and recording. Each of these is discussed in greater detail below.

Epithelia form a barrier between the body and the external environment. Moreover, they provide a tight seal against the leakage of ions and their selective ion-pumping activity generates a large electrochemical gradient. The resultant bioelectrical fields, apparent in regions where the epithelial sheet is damaged, have been shown to stimulate and orient cell migration, optimizing closure (Zhao et al. "Electrical signals control wound healing through phosphatidylinositol-3-OH kinase-gamma and PTEN." *Nature* 442, 457-460 (2006)). There is a distinct difference between the fields generated by individual cells, cell-clusters, and sheets. Hence, an ISFET array probe can be used to analyze this transition by imaging the lateral and spatio-temporal ion dynamics and measuring potential generation during wound healing. Typically, cells with identified channelopathies can be used to analyze how genetic diseases change the ion dynamics and impact on wound healing. This would improve our understanding of the underlying mechanisms in health and disease, and also lead to new tissue repair strategies.

The parallel action of large numbers of neurons is fundamental to the operation of the nervous system and results in various characteristic macroscopic oscillations (for example, gamma rhythms) that are important to brain function. Techniques for simultaneously measuring the activity of many neurons are consequently of great interest and utility (Wise et al. "Wireless implantable microsystems: high-density electronic interfaces to the nervous system." *Proceedings of the IEEE* 92, 76-97 (2004)). The potential at any given point in nervous tissue is generated by many distinct ionic currents. For example, synaptic vesicle release involves $Ca^{2+}$ flux, synaptic inhibition of $Cl^-$ flux, and action potential generation by $Na^+/K^+$ flux. Previous work has defined these rhythms in terms of net macroscopic currents (e.g., local field potentials less than 100 Hz (Cunningham et al. "A role for fast rhythmic bursting neurons in cortical gamma oscillations in vitro." *PNAS* 101, 7152-7157 (2004)). Hence, an ISFET array probe can be used to probe cortical rhythmic states for the first time at the ionic level. This would identify the contribution of the major ionic species to the gamma, and other rhythms, and therefore increase our understanding of cortical function. In turn, this knowledge would contribute to research into therapeutic drugs and technologies for a wide range of neurological dysfunction.

Electronic stimulation of neurons has become increasingly important in recent years. Notable examples are in the field of cochlear prosthesis where electronically acquired data is used to stimulate the cochlear nerve of a patient to restore auditory function. Unfortunately, electrode-based implants fail to perform in large-scale arrays due to problems with electrolytic degradation, cellular dielectric shielding, and subsequent power consumption problems. Consequently, their use in retinal and cortical implants has been somewhat limited to date. (Humayun et al. "Visual perception in a blind subject with a chronic microelectronic retinal prosthesis." *Vision Research* 43, 2573-2581 (2003), and Normann et al. "A neural interface for a cortical vision prosthesis." *Vision Research* 39, 2577-2587 (1999).) Optical stimulation of functionalized neurons using engineered opsins could offer an alternative that is an energetically more favorable route forward. Furthermore, it would be possible to specifically target certain types of ion flow. For instance, channelrhodopsin-2 (Nagel et al. "Channelrhodopsin-2, a directly light-gated cation-selective membrane channel." *PNAS* 100, 13940-13945 (2003)) could be used to target $Na^+$ and $Ca^{2+}$ flow while halorhodopsin (Gradinaru et al. "Targeting and readout strategies for fast optical neural control in vitro and in vivo." *Journal of Neuroscience* 27, 14231-14238 (2007)) could be used to target Cl⁻ flow. Hence, integrating this technology with an ISFET sensor array can enable, for the first time, a route to feedback-controlled stimulation and function.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for sequencing a polypeptide, comprising:
    disposing a plurality of polypeptides into each of a plurality of reaction chambers, at least one reaction chamber of the plurality of reaction chambers coupled to at least one chemical-sensitive field effect transistor (chemFET) having a floating gate;
    sequentially introducing amino acyl synthetases into the at least one reaction chamber, the amino acyl synthetase operable to bind to a specific amino acid when present at a free end of the polypeptide;
    detecting the presence of an amino acyl synthetase bound to the free end of the polypeptide; and
    cleaving the amino acid from the free end of the polypeptide.

2. The method of claim 1, wherein detecting the presence of the amino acyl synthetase includes detecting a detection moiety conjugated to the amino acyl synthetase.

3. The method of claim 2, wherein the detection moiety includes an enzyme.

4. The method of claim 3, wherein the detecting the detection moiety includes measuring a change in the electrical properties of the chemFET in response to a reaction catalyzed by the enzyme.

5. The method of claim 1, wherein the plurality of polypeptides are bound to a bead, and at least one bead is disposed into each of the plurality of reaction chambers.

6. The method of claim 1, further comprising denaturing the polypeptide.

7. The method of claim 1, wherein cleaving further includes cleaving the amino acid using a protease conjugated to the amino acyl synthetase.

8. The method of claim 1, wherein cleaving further includes cleaving the amino acid using a limited Edmond degradation or a proximity based radical cleavage.

9. The method of claim 1, wherein the floating gate of the at least one chemFET is coupled to the at least one reaction chamber via a passivation layer sensitive to hydrogen ions.

10. A method for sequencing a polypeptide, comprising:
    disposing a plurality of polypeptides into at least one of a plurality of reaction chambers, at least one reaction chamber of the plurality of reaction chambers coupled to at least one chemical-sensitive field effect transistor (chemFET) having a floating gate;
    sequentially cleaving amino acids from an end of the polypeptide;
    sequentially detecting the identity of the amino acids by a change in an electrical property of the at least one chemFET having the floating gate.

11. The method of claim 10, wherein a center-to-center distance between adjacent reaction chambers is selected from a range of about 1 μm to about 10 μm.

12. The method of claim 10, wherein the plurality of reaction chambers includes at least $10^5$ reaction chambers.

13. The method of claim 10, wherein the floating gate of the at least one chemFET is coupled to the at least one reaction chamber via a passivation layer sensitive to hydrogen ions.

14. The method of claim 10, wherein the change in the electrical property is due to a change in threshold voltage of the at least one chemFET resulting from a change in ion concentration related to a chemical reaction catalyzed by a detection moiety.

15. The method of claim 10, wherein the detection moiety is conjugated to an amino acyl synthetase specific for the amino acid being detected.

16. The method of claim 15, wherein the detection moiety is a hydrogen peroxidase.

17. A method for sequencing a polypeptide, comprising:
    disposing a plurality of polypeptides into at least one of a plurality of reaction chambers, at least one reaction chamber of the plurality of reaction chambers coupled to at least one chemical-sensitive field effect transistor (chemFET) having a floating gate;
    sequentially cleaving amino acids from an end of the polypeptide;
    detecting a change in the level of a reaction product of a detection moiety conjugated to an amino acyl synthetase as an indicator of the identity of the amino acid.

18. The method of claim 17, wherein the amino acyl synthetase is bound to the amino acid and is specific for the amino acid.

19. The method of claim 17, wherein the change in the level of the reaction product comprises detecting a threshold voltage of the at least one chemFET.

20. The method of claim 17, wherein cleaving amino acids from the end of the polypeptide involves a protease conjugated to the amino acyl synthetase.

* * * * *